United States Patent
Wolfson et al.

(10) Patent No.: US 10,934,550 B2
(45) Date of Patent: Mar. 2, 2021

(54) IMMUNOTHERAPY OF CANCER

(71) Applicant: Phio Pharmaceuticals Corp., Marlborough, MA (US)

(72) Inventors: Alexey Wolfson, Westborough, MA (US); Alexey Eliseev, Boston, MA (US); Taisia Shmushkovich, Newton, MA (US)

(73) Assignee: Phio Pharmaceuticals Corp., Marlborough, MA (US)

( * ) Notice: Subject to any disclaimer, the term of this patent is extended or adjusted under 35 U.S.C. 154(b) by 0 days.

(21) Appl. No.: 15/100,536

(22) PCT Filed: Dec. 2, 2014

(86) PCT No.: PCT/US2014/068244
§ 371 (c)(1),
(2) Date: May 31, 2016

(87) PCT Pub. No.: WO2015/084897
PCT Pub. Date: Jun. 11, 2015

(65) Prior Publication Data
US 2016/0304873 A1    Oct. 20, 2016

Related U.S. Application Data

(60) Provisional application No. 61/910,728, filed on Dec. 2, 2013.

(51) Int. Cl.
| | | |
|---|---|---|
| C07H 21/04 | (2006.01) | |
| C12N 15/117 | (2010.01) | |
| A61K 39/00 | (2006.01) | |
| C12N 15/113 | (2010.01) | |

(52) U.S. Cl.
CPC ............ *C12N 15/117* (2013.01); *A61K 39/00* (2013.01); *C12N 15/113* (2013.01); *C12N 15/1135* (2013.01); *C12N 15/1137* (2013.01); *C12N 15/1138* (2013.01); *A61K 2039/5154* (2013.01); *A61K 2039/5156* (2013.01); *C12N 2310/14* (2013.01); *C12N 2310/17* (2013.01); *C12N 2310/321* (2013.01); *C12N 2310/3515* (2013.01); *C12N 2320/31* (2013.01); *C12N 2320/32* (2013.01); *C12N 2320/50* (2013.01); *Y02A 50/30* (2018.01)

(58) Field of Classification Search
USPC ...................................................... 536/24.5
See application file for complete search history.

(56) References Cited

U.S. PATENT DOCUMENTS

| | | |
|---|---|---|
| 3,687,808 A | 8/1972 | Merigan et al. |
| 4,201,860 A | 5/1980 | Naito et al. |
| 4,415,732 A | 11/1983 | Caruthers et al. |
| 4,426,330 A | 1/1984 | Sears |
| 4,897,355 A | 1/1990 | Eppstein et al. |
| 4,904,582 A | 2/1990 | Tullis |
| 4,958,013 A | 9/1990 | Letsinger |
| 5,023,243 A | 6/1991 | Tullis |
| 5,112,963 A | 5/1992 | Pieles et al. |
| 5,151,510 A | 9/1992 | Stec et al. |
| 5,188,897 A | 2/1993 | Suhadolnik et al. |
| 5,264,423 A | 11/1993 | Cohen et al. |
| 5,264,562 A | 11/1993 | Matteucci |
| 5,405,939 A | 4/1995 | Suhadolnik |
| 5,416,203 A | 5/1995 | Letsinger |
| 5,417,978 A | 5/1995 | Tan et al. |
| 5,432,272 A | 7/1995 | Benner |
| 5,453,496 A | 9/1995 | Caruthers et al. |
| 5,459,255 A | 10/1995 | Cook et al. |
| 5,466,786 A | 11/1995 | Buhr et al. |
| 5,470,967 A | 11/1995 | Huie et al. |
| 5,486,603 A | 1/1996 | Buhr |
| 5,489,677 A | 2/1996 | Sanghvi et al. |
| 5,495,009 A | 2/1996 | Matteucci et al. |
| 5,514,786 A | 5/1996 | Cook et al. |
| 5,527,528 A | 6/1996 | Allen et al. |
| 5,532,130 A | 7/1996 | Alul |
| 5,534,259 A | 7/1996 | Zalipsky et al. |
| 5,556,948 A | 9/1996 | Tagawa et al. |
| 5,561,225 A | 10/1996 | Maddry et al. |
| 5,578,718 A | 11/1996 | Cook et al. |
| 5,580,731 A | 12/1996 | Chang et al. |
| 5,580,972 A | 12/1996 | Tu et al. |
| 5,587,469 A | 12/1996 | Cook et al. |
| 5,591,721 A | 1/1997 | Agrawal et al. |
| 5,591,722 A | 1/1997 | Montgomery et al. |
| 5,591,843 A | 1/1997 | Eaton |

(Continued)

FOREIGN PATENT DOCUMENTS

| | | |
|---|---|---|
| AU | 2004206255 B2 | 8/2004 |
| CN | 1 568 373 A | 1/2005 |

(Continued)

OTHER PUBLICATIONS

Pardoll (Nature Apr. 2012; 252-264).*
Brenner et al. (Current Opinion in Immun. 2010: 251-257).*
[No Author Listed] RedChip Small-Cap Investor Conference. RXI Pharmaceuticals (Nasdaq RXII). Jun. 16, 2009 Presentation. 22 pages.
[No Author Listed] RXi Pharmaceutical Corporation. Ex 99.1. OTC: RXII. Mar. 2013. 38 pages.
[No Author Listed], Rxi Pharmaceuticals Presents Self-Delivering RNAi Data at Scar Club Meeting in France. Drugs.com. Mar. 26, 2010. http://www.drugs.com/clinical_trials/rxi-pharmaceuticals-presents-self-delivering-rnai-data-scar-club-meeting-france-9093.html [last accessed Aug. 19, 2014].

(Continued)

*Primary Examiner* — Kimberly Chong
(74) *Attorney, Agent, or Firm* — Wolf, Greenfield & Sacks, P.C.

(57) ABSTRACT

Immunogenic modulators and compositions comprising oligonucleotide agents capable of inhibiting suppression of immune response by reducing expression of one or more gene involved with an immune suppression mechanism.

18 Claims, 7 Drawing Sheets

Specification includes a Sequence Listing.

(56) References Cited

U.S. PATENT DOCUMENTS

| | | |
|---|---|---|
| 5,594,121 A | 1/1997 | Froehler et al. |
| 5,596,086 A | 1/1997 | Matteucci et al. |
| 5,596,091 A | 1/1997 | Switzer |
| 5,599,797 A | 2/1997 | Cook et al. |
| 5,602,240 A | 2/1997 | De Mesmaeker et al. |
| 5,607,923 A | 3/1997 | Cook et al. |
| 5,614,617 A | 3/1997 | Cook et al. |
| 5,614,621 A | 3/1997 | Ravikumar et al. |
| 5,623,070 A | 4/1997 | Cook et al. |
| 5,625,050 A | 4/1997 | Beaton et al. |
| 5,633,360 A | 5/1997 | Bischofberger et al. |
| 5,643,889 A | 7/1997 | Suhadolnik et al. |
| 5,646,126 A | 7/1997 | Cheng et al. |
| 5,646,265 A | 7/1997 | McGee |
| 5,658,731 A | 8/1997 | Sproat et al. |
| 5,661,134 A | 8/1997 | Cook et al. |
| 5,663,312 A | 9/1997 | Chaturvedula |
| 5,670,633 A | 9/1997 | Cook et al. |
| 5,672,695 A | 9/1997 | Eckstein et al. |
| 5,681,940 A | 10/1997 | Wang et al. |
| 5,681,941 A | 10/1997 | Cook et al. |
| 5,684,143 A | 11/1997 | Gryaznov et al. |
| 5,700,920 A | 12/1997 | Altmann et al. |
| 5,750,666 A | 5/1998 | Caruthers et al. |
| 5,770,713 A | 6/1998 | Imbach et al. |
| 5,777,153 A | 7/1998 | Lin et al. |
| 5,789,416 A | 8/1998 | Lum et al. |
| 5,792,847 A | 8/1998 | Buhr et al. |
| 5,808,023 A | 9/1998 | Sanghvi et al. |
| 5,817,781 A | 10/1998 | Swaminathan et al. |
| 5,830,430 A | 11/1998 | Unger et al. |
| 5,830,653 A | 11/1998 | Froehler et al. |
| 5,856,455 A | 1/1999 | Cook |
| 5,914,396 A | 6/1999 | Cook et al. |
| 5,945,521 A | 8/1999 | Just et al. |
| 5,948,767 A | 9/1999 | Scheule et al. |
| 5,969,116 A | 10/1999 | Martin |
| 5,976,567 A | 11/1999 | Wheeler et al. |
| 5,981,501 A | 11/1999 | Wheeler et al. |
| 5,986,083 A | 11/1999 | Dwyer et al. |
| 6,001,841 A | 12/1999 | Cook et al. |
| 6,005,096 A | 12/1999 | Matteucci et al. |
| 6,013,786 A | 1/2000 | Chen |
| 6,015,886 A | 1/2000 | Dale et al. |
| 6,020,475 A | 2/2000 | Capaldi et al. |
| 6,020,483 A | 2/2000 | Beckvermit et al. |
| 6,028,183 A | 2/2000 | Lin et al. |
| 6,043,352 A | 3/2000 | Manoharan et al. |
| 6,051,699 A | 4/2000 | Ravikumar |
| 6,107,094 A | 8/2000 | Crooke |
| 6,111,085 A | 8/2000 | Cook et al. |
| 6,121,437 A | 9/2000 | Guzaev |
| 6,153,737 A | 11/2000 | Manoharan et al. |
| 6,207,819 B1 | 3/2001 | Manoharan et al. |
| 6,248,878 B1 | 6/2001 | Matulic-Adamic et al. |
| 6,271,358 B1 | 8/2001 | Manoharan et al. |
| 6,326,358 B1 | 12/2001 | Manoharan |
| 6,331,617 B1 | 12/2001 | Weeks et al. |
| 6,333,152 B1 | 12/2001 | Vogelstein et al. |
| 6,335,434 B1 | 1/2002 | Guzaev et al. |
| 6,355,787 B1 | 3/2002 | Beckvermit et al. |
| 6,358,931 B1 | 3/2002 | Cook et al. |
| 6,395,492 B1 | 5/2002 | Manoharan et al. |
| 6,399,754 B1 | 6/2002 | Cook |
| 6,410,702 B1 | 6/2002 | Swaminathan et al. |
| 6,420,549 B1 | 7/2002 | Cook et al. |
| 6,432,963 B1 | 8/2002 | Hisamichi et al. |
| 6,440,943 B1 | 8/2002 | Cook et al. |
| 6,444,806 B1 | 9/2002 | Veerapanani et al. |
| 6,455,586 B1 | 9/2002 | Kaplan et al. |
| 6,465,628 B1 | 10/2002 | Ravikumar et al. |
| 6,476,205 B1 | 11/2002 | Buhr et al. |
| 6,506,559 B1 | 1/2003 | Fire et al. |
| 6,528,631 B1 | 3/2003 | Cook et al. |
| 6,531,584 B1 | 3/2003 | Cook et al. |
| 6,673,611 B2 | 1/2004 | Thompson et al. |
| 6,683,167 B2 | 1/2004 | Meteley et al. |
| 6,815,432 B2 | 11/2004 | Wheeler et al. |
| 6,849,726 B2 | 2/2005 | Usman et al. |
| 6,858,225 B2 | 2/2005 | Semple et al. |
| 7,041,824 B2 | 5/2006 | Bordon-Pallier et al. |
| 7,056,704 B2 | 6/2006 | Tuschl et al. |
| 7,078,196 B2 | 7/2006 | Tuschl et al. |
| 7,148,342 B2 | 12/2006 | Tolentino et al. |
| 7,205,297 B2 | 4/2007 | Beauchamp et al. |
| 7,432,250 B2 | 10/2008 | Crooke |
| 7,521,431 B2 | 4/2009 | Reich et al. |
| 7,538,095 B2 | 5/2009 | Fire et al. |
| 7,560,438 B2 | 7/2009 | Fire et al. |
| 7,595,387 B2 | 9/2009 | Leake et al. |
| 7,622,633 B2 | 11/2009 | Fire et al. |
| 7,629,321 B2 | 12/2009 | Crooke |
| 7,695,902 B2 | 4/2010 | Crooke |
| 7,745,608 B2 | 6/2010 | Manoharan et al. |
| 7,750,144 B2 | 7/2010 | Zamore et al. |
| 7,786,290 B2 | 8/2010 | Woppmann et al. |
| 7,789,841 B2 | 9/2010 | Huckle et al. |
| 7,829,693 B2 | 11/2010 | Kreutzer et al. |
| 8,110,674 B2 | 2/2012 | Manoharan et al. |
| 8,227,444 B2 | 7/2012 | Dejneka |
| 8,263,569 B2 | 9/2012 | Baukombe et al. |
| 8,470,792 B2 | 6/2013 | Frost et al. |
| 8,664,189 B2 | 3/2014 | Khvorova et al. |
| 8,796,443 B2 | 8/2014 | Khvorova et al. |
| 8,815,818 B2 | 8/2014 | Samarsky et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,222,092 B2 | 12/2015 | Giese et al. |
| 9,303,259 B2 | 4/2016 | Khvorova et al. |
| 9,340,786 B2 | 5/2016 | Khvorova et al. |
| 9,493,774 B2 | 11/2016 | Kamens |
| 9,745,574 B2 | 8/2017 | Woolf et al. |
| 9,938,530 B2 | 4/2018 | Khvorova et al. |
| 9,963,702 B2 | 5/2018 | Khvorova et al. |
| 10,041,073 B2 | 8/2018 | Khvorova et al. |
| 10,131,904 B2 | 11/2018 | Pavco et al. |
| 10,138,485 B2 | 11/2018 | Khvorova et al. |
| 10,167,471 B2 | 1/2019 | Kamens et al. |
| 10,184,124 B2 | 1/2019 | Libertine et al. |
| 10,240,149 B2 | 3/2019 | Khvorova et al. |
| 10,300,027 B2 | 5/2019 | Levis et al. |
| 10,479,992 B2 | 11/2019 | Woolf et al. |
| 10,633,654 B2 | 4/2020 | Pavco et al. |
| 10,662,430 B2 | 5/2020 | Libertine et al. |
| 10,774,330 B2 | 9/2020 | Khvorova et al. |
| 2002/0132788 A1 | 9/2002 | Lewis et al. |
| 2002/0147332 A1 | 10/2002 | Kaneko et al. |
| 2002/0160393 A1 | 10/2002 | Symonds et al. |
| 2002/0162126 A1 | 10/2002 | Beach et al. |
| 2003/0004325 A1 | 1/2003 | Cook et al. |
| 2003/0077829 A1 | 4/2003 | MacLachlan |
| 2003/0108923 A1 | 6/2003 | Tuschl et al. |
| 2003/0139585 A1 | 7/2003 | Uhlmann et al. |
| 2003/0157030 A1 | 8/2003 | Davis et al. |
| 2003/0158403 A1 | 8/2003 | Manoharan et al. |
| 2003/0166282 A1 | 9/2003 | Brown et al. |
| 2003/0175276 A1 | 9/2003 | Thorpe et al. |
| 2004/0009938 A1 | 1/2004 | Manoharan et al. |
| 2004/0014957 A1 | 1/2004 | Eldrup et al. |
| 2004/0018999 A1 | 1/2004 | Beach et al. |
| 2004/0054155 A1 | 3/2004 | Woolf et al. |
| 2004/0137471 A1 | 7/2004 | Vickers et al. |
| 2004/0167090 A1 | 8/2004 | Monahan et al. |
| 2004/0171033 A1 | 9/2004 | Baker et al. |
| 2004/0180351 A1 | 9/2004 | Giese et al. |
| 2004/0229266 A1 | 11/2004 | Tuschl et al. |
| 2004/0241845 A1 | 12/2004 | Desgroseillers et al. |
| 2004/0259247 A1 | 12/2004 | Tuschl et al. |
| 2005/0020521 A1 | 1/2005 | Rana et al. |
| 2005/0032733 A1 | 2/2005 | McSwiggen et al. |
| 2005/0080246 A1 | 4/2005 | Allerson et al. |
| 2005/0107325 A1 | 5/2005 | Manoharan et al. |

(56) References Cited

U.S. PATENT DOCUMENTS

| | | |
|---|---|---|
| 2005/0142535 A1 | 6/2005 | Damha et al. |
| 2005/0181382 A1 | 8/2005 | Zamore et al. |
| 2005/0245474 A1 | 11/2005 | Baker et al. |
| 2005/0246794 A1 | 11/2005 | Khvorova et al. |
| 2005/0255487 A1 | 11/2005 | Khvorova et al. |
| 2006/0009409 A1 | 1/2006 | Woolf |
| 2006/0069050 A1 | 3/2006 | Rana |
| 2006/0127891 A1 | 6/2006 | McSwiggen et al. |
| 2006/0142228 A1 | 6/2006 | Ford et al. |
| 2006/0160766 A1 | 7/2006 | Cheung |
| 2006/0178324 A1 | 8/2006 | Hadwiger et al. |
| 2006/0178327 A1 | 8/2006 | Yeung |
| 2006/0211766 A1 | 9/2006 | Kaplan et al. |
| 2007/0032441 A1 | 2/2007 | McSwiggen et al. |
| 2007/0166734 A1 | 7/2007 | Bhat et al. |
| 2007/0173476 A1 | 7/2007 | Leake et al. |
| 2007/0231392 A1 | 10/2007 | Wagner et al. |
| 2007/0248659 A1 | 10/2007 | Shanahan et al. |
| 2007/0254850 A1 | 11/2007 | Lieberman et al. |
| 2007/0269889 A1 | 11/2007 | Leake et al. |
| 2008/0071068 A1 | 3/2008 | Oba et al. |
| 2008/0085869 A1 | 4/2008 | Yamada et al. |
| 2008/0108583 A1 | 5/2008 | Feinstein et al. |
| 2008/0293593 A1 | 11/2008 | Khvorova et al. |
| 2008/0311040 A1 | 12/2008 | Berry et al. |
| 2009/0010948 A1 | 1/2009 | Huang et al. |
| 2009/0023216 A1 | 1/2009 | Woolf |
| 2009/0042828 A1 | 2/2009 | Xu et al. |
| 2009/0131360 A1 | 5/2009 | Woolf et al. |
| 2009/0208564 A1 | 8/2009 | Li et al. |
| 2009/0220582 A1 | 9/2009 | Min |
| 2009/0220583 A1 | 9/2009 | Pereswetoff-Morath et al. |
| 2009/0239814 A1 | 9/2009 | Manoharan et al. |
| 2010/0069620 A1 | 3/2010 | Zon |
| 2010/0136695 A1 | 6/2010 | Woolf |
| 2010/0286236 A1 | 11/2010 | Schlingensiepen et al. |
| 2010/0331812 A1 | 12/2010 | Friden et al. |
| 2011/0039914 A1 | 2/2011 | Pavco et al. |
| 2011/0237522 A1 | 9/2011 | Khvorova et al. |
| 2011/0251258 A1 | 10/2011 | Samarsky et al. |
| 2011/0263680 A1 | 10/2011 | Khvorova et al. |
| 2011/0268761 A1 | 11/2011 | Levis et al. |
| 2011/0294869 A1 | 12/2011 | Petersen |
| 2012/0046186 A1 | 2/2012 | Pelham et al. |
| 2012/0065243 A1 | 3/2012 | Woolf et al. |
| 2014/0030319 A1 | 1/2014 | Tocque et al. |
| 2014/0072613 A1 | 3/2014 | Lander et al. |
| 2015/0057362 A1 | 2/2015 | Levis et al. |
| 2016/0115482 A1 | 4/2016 | Libertine et al. |
| 2016/0115484 A1 | 4/2016 | Woolf et al. |
| 2016/0130578 A1 | 5/2016 | Khvorova et al. |
| 2016/0244765 A1 | 8/2016 | Khvorova et al. |
| 2016/0304875 A1 | 10/2016 | Cauwenbergh et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2017/0009239 A1 | 1/2017 | Khvorova et al. |
| 2017/0051288 A1 | 2/2017 | Byrne et al. |
| 2017/0051290 A1 | 2/2017 | Byrne et al. |
| 2017/0067056 A1 | 3/2017 | Khvorova et al. |
| 2017/0137823 A1 | 5/2017 | Kamens et al. |
| 2018/0030451 A1 | 2/2018 | Cauwenbergh |
| 2018/0155718 A1 | 6/2018 | Woolf et al. |
| 2018/0195066 A1 | 7/2018 | Byrne et al. |
| 2018/0195072 A1 | 7/2018 | Cardia et al. |
| 2018/0263925 A1 | 9/2018 | Cauwenbergh et al. |
| 2018/0327748 A1 | 11/2018 | Khvorova et al. |
| 2018/0371464 A1 | 12/2018 | Khvorova et al. |
| 2019/0029974 A1 | 1/2019 | Cauwenbergh et al. |
| 2019/0048341 A1 | 2/2019 | Cardia et al. |
| 2019/0161757 A1 | 5/2019 | Khvorova et al. |
| 2019/0169608 A1 | 6/2019 | Pavco et al. |
| 2019/0211337 A1 | 7/2019 | Khvorova et al. |
| 2019/0218557 A1 | 7/2019 | Kamens et al. |
| 2019/0233826 A1 | 8/2019 | Libertine et al. |
| 2020/0002701 A1 | 1/2020 | Khvorova et al. |
| 2020/0085764 A1 | 3/2020 | Maxwell et al. |
| 2020/0101028 A1 | 4/2020 | Levis et al. |
| 2020/0215113 A1 | 7/2020 | Eliseev |

FOREIGN PATENT DOCUMENTS

| | | |
|---|---|---|
| CN | 101663323 A | 3/2010 |
| CN | 103820454 A | 5/2014 |
| DE | 197 27 932 A1 | 1/1999 |
| DE | 19727932 A1 | 1/1999 |
| EP | 0 552 766 A2 | 7/1993 |
| EP | 1 214 945 A2 | 6/2002 |
| EP | 1 144 623 B9 | 3/2003 |
| EP | 1 352 061 B1 | 10/2003 |
| EP | 0 928 290 B9 | 3/2005 |
| EP | 1 407 044 B1 | 9/2007 |
| EP | 1 605 978 B1 | 9/2010 |
| JP | 2004-500846 | 1/2004 |
| JP | 4 095 895 B2 | 9/2004 |
| JP | 2007-525169 A | 9/2007 |
| JP | 2007-531520 A | 11/2007 |
| JP | 2008-536874 A | 9/2008 |
| JP | 2009-519033 | 5/2009 |
| RU | 2429246 C2 | 9/2011 |
| WO | WO 92/03464 A1 | 3/1992 |
| WO | 1992007065 A1 | 4/1992 |
| WO | 1993015187 A1 | 8/1993 |
| WO | WO 94/23028 A2 | 10/1994 |
| WO | WO 95/11910 A1 | 5/1995 |
| WO | WO 95/23162 A1 | 8/1995 |
| WO | WO 96/40964 A2 | 12/1996 |
| WO | WO 98/14172 A1 | 4/1998 |
| WO | WO 99/60012 A1 | 11/1999 |
| WO | WO 01/85941 A2 | 11/2001 |
| WO | WO 03/012052 A2 | 2/2003 |
| WO | WO 2003/064626 A2 | 8/2003 |
| WO | WO 2004/065600 A2 | 8/2004 |
| WO | WO 2004/065601 A2 | 8/2004 |
| WO | WO 2004/090105 A2 | 10/2004 |
| WO | WO 2005/019430 A2 | 3/2005 |
| WO | WO 2005/019453 A2 | 3/2005 |
| WO | WO 2005/079533 A2 | 9/2005 |
| WO | WO 2005/097992 A2 | 10/2005 |
| WO | WO 2006/019430 A2 | 2/2006 |
| WO | WO 2006/039656 A2 | 4/2006 |
| WO | WO 2006/065601 A2 | 6/2006 |
| WO | WO 2006/113679 A2 | 10/2006 |
| WO | WO 2006/128141 A2 | 11/2006 |
| WO | WO 2007/030167 A1 | 3/2007 |
| WO | WO 2007/069068 A2 | 6/2007 |
| WO | WO 2007/089607 A2 | 8/2007 |
| WO | WO 2008/011344 A2 | 1/2008 |
| WO | WO 2008/028965 A2 | 3/2008 |
| WO | WO 2008/028968 A2 | 3/2008 |
| WO | WO 2008/036825 A2 | 3/2008 |
| WO | WO 2008/109353 A1 | 9/2008 |
| WO | WO 2009/020344 A2 | 2/2009 |
| WO | WO 2009/029688 A3 | 3/2009 |
| WO | WO 2009/029690 A1 | 3/2009 |
| WO | WO 2009/044392 A2 | 4/2009 |
| WO | WO 2009/078685 A2 | 6/2009 |
| WO | WO 2010/006237 A2 | 1/2010 |
| WO | WO 2010/011346 A2 | 1/2010 |
| WO | WO 2010/027830 A2 | 3/2010 |
| WO | WO 2010/042281 A2 | 4/2010 |
| WO | 2011119852 A1 | 9/2011 |
| WO | WO 2011/119852 A1 | 9/2011 |
| WO | WO 2011/154542 A1 | 12/2011 |
| WO | 2012112079 A1 | 8/2012 |
| WO | WO 2012/112079 A1 | 8/2012 |
| WO | WO 2013/101436 A1 | 7/2013 |
| WO | WO 2015/024986 A1 | 2/2015 |

(56) References Cited

OTHER PUBLICATIONS

Alahari et al., Inhibition of expression of the multidrug resistance-associated P-glycoprotein of by phosphorothioate and 5' cholesterol-conjugated phosphorothioate antisense oligonucleotides. Mol Pharmacol. Oct. 1996;50(4):808-19.
Aleckovic et al., J RNAi Gene Silencing. May 27, 2008;4(1):266-8.
Baigude et al., Design and creation of new nanomaterials far therapeutic RNAi. ACS Chem Biol. Apr. 24, 2007;2(4):237-41.
Behlke, Progress towards in vivo use of siRNAs. Mal Ther. Apr. 2006;13(4):644-70. Epub Feb. 14, 2006.
Bjerke et at, Histone H3.3. mutations drive pediatric glioblastoma through upregulatian of MYCN. Cancer Discov. May 2013;3(5):512-9.
Borkner et al., RNA interference targeting programmed death receptor-1 improves immune functions of tumor-specific T cells. Cancer Immunol Immunother. Aug. 2010;59(8):1173-83. doi: 10.1007/s00262-010-0842-0. Epub Mar. 27, 2010.
Boutorin et al., Synthesis of alkylating oligonucleotide derivatives containing cholesterol or phenazinium residues at their 3'-terminus and their interaction with DNA within mammalian cells. FEBS Lett. Aug. 28, 1989;254(1-2):129-32.
Braasch et al., RNA interference in mammalian cells by chemically-modified RNA. Biochemistry. Jul. 8, 2003;42(26):7967-75.
Brown et al., RNAi off-targeting: Light at the end of the tunnel. J RNAi Gene Silencing. Jul. 28, 2006;2(2):175-7.
Cardia et al., Novel self-delivering RNAi compounds with enhanced cellular uptake and distribution properties. Keystone RNAi Silencing Conference. Jan. 14-19, 2010. Poster. 1 Page.
Chen et al., Nanoparticles modified with tumor-targeting scFv deliver siRNA and miRNA for cancer therapy. Mal Ther. Sep. 2010;18(9):1650-6. doi: 10.1038/mt.2010.136. Epub Jul. 6, 2010.
Choung et al., Chemical modification of siRNAs to improve serum stability without loss of efficacy. Biochem Biophys Res Commun. Apr. 14, 2003;342(3):919-27.
Chu et al., Potent RNAi by short RNA triggers. RNA. 2008;14:1714-9.
Czauderna et al., ., Structural variations and stabilising modifications of synthetic siRNAs in mammalian cells. Nucleic Acids Res. Jun. 1, 2003;31(11):2705-16.
De Smidt et al., Association of antisense oligonucleotides with lipoproteins prolongs the plasma half-life and modifies the tissue distribution. Nucleic Acids Res. Sep. 11, 1991;19(17):4695-700.
Debart et al., Chemical modifications to improve the cellular uptake of oligonucleotides. Curr Top Med Chem. 2007;7(7):727-37.
Dykxhoorn et al., The silent treatment: siRNAs as small molecule drugs. Gene Ther. Mar. 2006;13(6):541-52. Review.
Elbashir et al., Duplexes of 21-nucleotide RNAs mediate RNA interference in cultured mammalian cells. Nature. May 24, 2001;411(6836):494-8.
Elbashir et al., Functional anatomy of siRNAs for mediating efficient RNAi in *Drosophila melanogaster* embryo lysate. Embo J. Dec. 3, 2001;20(23):6877-88.
Fedorov et al., Off-target effects by siRNA can induce toxic phenotype. RNA. Jul. 2006;12(7):1188-96. Epub May 8, 2006.
Ferentz et al., Disulfide-crosslinked oligonucleotides. Journal of the American Chemical Society. 1991;113 (10): 4000-4002.
Fisher et al., Intracellular disposition and metabolism of fluorescently-labeled unmodified and modified oligonucleotides microinjected into mammalian cells. Nucleic Acids Res. Aug. 11, 1993;21(16):3857-65.
Ginobbi et al., Folic acid-polylysine carrier improves efficacy of c-myc antisense oligodeoxynucleotides on human melanoma (M14) cells. Anticancer Res. Jan.-Feb. 1997;17(1A):29-35.
Glaser, Oligonucleotide therapies move toward efficacy trials to treav HIV CMV, cancer. Genetic Engineering News 16, Feb. 1, 1996. 2 pages.
Heemskerk et al., T-cell receptor gene transfer for the treatment of leukemia and other tumors. Haematologica. Jan. 2010;95(1):15-9. doi: 10.3324/haematol.2009.016022.
Holmes et al., Syntheses and oligonucleotide incorporation of nucleoside analogues containing pendant imidazolyl or amino functionalities—the search for sequence-specific artificial ribonucleases. Eur J Org Chem. Apr. 13, 2005;5171-83. DOI; 10.1002/ejoc.20050413.
Hueng et al., Enhancing dendritic cell vaccine potency by combining a BAK/BAX siRNA-mesiated antiapoptotic strategy to prolong dendritic cell life with an intracellular strategy to target antigen to lysosomal compartments. Apr. 15, 2007. Medline Database Accession No. NLM17230516.
Iwakuma et al., MDM2, an introduction. Mol Cancer Res. Dec. 2003;1(14):993-1000.
Jackson et al., Position-specific chemical modification of siRNAs reduces "off-target" transcript silencing. RNA. Jul. 2006;12(7):1197-1205. Epub May 8, 2006.
Kamens et al., Novel, chemically modified RNAi compounds with improved potency, stability and specificity. Keystone RNAi Silencing: Mechanism, Biology and Application Conference. Jan. 14-19, 2010. Poster. 1 Page.
Kim et al., Systemic and specific delivery of small interfering RNAs to the liver mediated by apolipoprotein A-I. Mol Ther. Jun. 2007;15(6):1145-52. Epub Apr. 17, 2007.
Kraynack et al., Small interfering RNAs containing full 2'-O-methylribonucleotide-modified sense strands display Argonaute2/eIF2C2-dependent activity. RNA. Jan. 2006;12(1):163-76. Epub Nov. 21, 2005.
Kubo et al., Modified 27-nt dsRNAs with dramatically enhanced stability in serum and long-term RNAi activity. Oligonucleotides. 2007 Winter;17(4):445-64.
Layzer et al., In vivo activity of nuclease-resistant siRNAs. Rna. May 2004;10(5):766-71.
Lee et al., Contributions of 3'-overhang to the dissociation of small interfering RNAs from the PAZ domain: molecular dynamics simulation study. J Mal Graph Model. Mar. 2007;25(6):784-93. Epub Jul. 11, 2006.
Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.
Leuschner et al., Cleavage of the siRNA passenger strand during RISC assembly in human cells. EMBO Reports 2006;7(3):314-20.
Li et al., Surface-modified LPD nanoparticles for tumor targeting. Ann N Y Acad Sci. Oct. 2006;1082:1-8.
Manoharan et al., Chemical modifications to improve uptake and bioavailability of antisense oligonucleotides. Ann N Y Acad Sci. Oct. 28, 1992;660:306-9.
Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.
Martins et al., Sterol side chain length and structure affect the clearance of chylomicron-like lipid emulsions in rats and mice. J Lipid Res. Feb. 1998;39(2):302-12.
Mathews et al., Incorporating chemical modification constraints into a dynamic programming algorithm for prediction of RNA secondary structure. Proc Natl Acad Sci U S A. May 11, 2004;101(19):7287-92. Epub May 3, 2004.
McEvoy et al., Analysis of MDM2 and MDM4 single nucleotide polymorphisms, mRNA splicing and protein expression in retinoblastoma. PLoS One. 2012;7(8):e42739. doi: 10.1371/journal.pone.0042739. Epub Aug. 20, 2012.
Mescalchin et al., Cellular uptake and intracellular release are major obstacles to the therapeutic application of siRNA: novel options by phosphorothioate-stimulated delivery. Expert Opin Biol Ther. Oct. 2007;7(10):1531-8. Review.
Miska et al., Autoimmunity-mediated antitumor immunity: tumor as an immunoprivileged self. Eur J Immunol. Oct. 2012;42(10):2584-96. doi:10.1002/eji.201242590. Epub Aug. 10, 2012.
Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.
Overhoff et al., Phosphorothioate-stimulated uptake of short interfering RNA by human cells. Embo Rep. Dec. 2005;6(12):1176-81.

(56) References Cited

OTHER PUBLICATIONS

Parrish et al., Functional anatomy of a dsRNA trigger: differential requirement for the two trigger strands in RNA interference. Mal Cell. Nov. 2000;6(5):1077-87.
Pavco et al., Robust Intradermal efficacy with novel chemically modified self-delivering RNAi compounds. Keystone RNAi Silencing Conference: Mechanism, Biology and Application Conference. Jan. 14-19, 2010. Poster. 1 Page.
Peng et al., Vaccination with dendritic cells transfected with BAK and BAX siRNA enhances antigen-specific immune responses by prolonging dendritic cell life. Hum Gene Ther. May 200516(5):584-93.
Rajeev et al., 2'-modified-2-thiothymidine oligonucleotides. Org Lett. Aug. 21, 2003;5(17):3005-8.
Rozners et al., Expanding functionality of RNA: synthesis and properties of RNA containing imidazole modified tandem G-U wobble base pairs. Chem Commun (Camb). Dec. 14, 2005;(46):5778-80.
Rump et al., Preparation of conjugates of oligodeoxynucleotides and lipid structures and their interaction with low-density lipoprotein. Bioconjug Chem. May-Jun. 1998;9(3):341-9.
Salomon et al., Modified dsRNAs that are not processed by Dicer maintain potency and are incorporated into the RISC. Nucleic Acids Res. Jun. 2010;38(11):3771-9. doi: 10.1093/nar/gkq055. Epub Feb. 18, 2010.
Sato et al., Tumor targeting and imaging of intraperitoneal tumors by use of antisense oligo-DNA complexed with dendrimers and/or avidin in mice. Clin Cancer Res. Nov. 2001;7(11):3606-12.
Seela et al., Oligodeoxyribonucleotides containing 1,3-propanediol as nucleoside substitute. Nucleic Acids Res. Apr. 10, 1987;15(7):3113-29.
Shen, Advances in the development of siRNA-based therapeutics for cancer. IDrugs. Aug. 2008;11(8):572-8. Review.
Shi, Mammalian RNAi for the masses. Trends Genet. Jan. 2003;19(1):9-12.
Shi-Wen et al., Regulation and function of connective tissue growth factor/CCN2 in tissue repair, scarring and fibrosis. Cytokine Growth Factor Rev. Apr. 2008;19(2):133-44. doi: 10.1016/j.cytagfr.2008.01.002.
Snead et al., RNA interference trigger variants: getting the most out of RNA for RNA interference-based therapeutics. Nucleic Acid Ther. Jun. 2012;22(3):139-46. doi: 10.1089/nat.2012.0361. Review.
Soutschek et al., Therapeutic silencing of an endogenous gene by systemic administration of modified siRNAs. Nature. Nov. 11, 2004;432(7014):173-8.
Sun et al., Asymmetric RNA duplexes mediate RNA interference in mammalian cells. Nat Biotechnol. Dec. 2008;26(12):1379-82. doi: 10.1038/nbt.1512. Epub Nov. 23, 2008. 4 Pages.
Taylor et al., Curbing activation: proprotein convertases in homeostasis and pathology. FASEB J. Jul. 2003;17(10):1215-27.
Uhlmann et al., Antisense oligonucleotides: a new therapeutic principle. Chem Rev. 1990;90(4):543-84.
Ui-Tei, Letter to the Editor open access sdRNA: siRNA with a DNA seed for an efficienta nd target-gene specific ENA interference. Gene Technol. Jan. 1, 2012. Retrieved online via http://ui-tei.rnai.jp/assets/filed/pdf/GNT-1-102.pdf. DIO: 10.4172/gnt.100012.
Vaught et al., Expanding the chemistry of DNA for in vitro selection. J Am Chem Soc. Mar. 31, 2010;132(12):4141-51. doi: 10.1021/ja908035g.
Wolfrum et al., Mechanisms and optimization of in vivo delivery of lipophilic siRNAs. Nat Biteclmol. Oct. 2007;25(10):1149-57. Epub Sep. 16, 2007.
Yamada et al., Lysophosphatidic acid stimulates the proliferation and motility of malignant pleural mesothelioma cells through lysophosphatidic acid receptors, LPA1 and LPA2. Cancer Sci. Aug. 2008;99(8):1603-10.
Yamada et al., Synthesis and properties of oligonucleotides having a chemically stable 2-(trimethylsilyl)benzoyl group. Nucleic Acids Symp Ser (Oxf). 2008;(52):301-2. doi: 10.1093/nass/nrn152.

Correspondence associated with Gutkina inventorship claim. Dated Dec. 2, 2016 through Mar. 2, 2018. 187 pages.
[No Author Listed] RXi Pharmaceucticals Completes Apthera Acquisition. Press Release. BusinessWire. Apr. 14, 2011. 2 pages.
Genbank Submission; NIH/NCBI, Accession No. NM_000675.5. Rissanen et al., Dec. 1, 2003. 7 pages.
Genbank Submission; NIH/NCBI, Accession No. NM_002286.5. Li et al., Sep. 22, 2013. 6 pages.
Genbank Submission; NIH/NCBI, Accession No. NM_005018.2. Breton et al., Nov. 23, 2013. 6 pages.
Genbank Submission; NIH/NCBI, Accession No. NM_005214.4. Queirolo et al., Nov. 3, 2013. 7 pages.
Genbank Submission; NIH/NCBI, Accession No. NM_032782.4. Gao et al., Oct. 19, 2013. 6 pages.
Augustyns et al., Incorporation of hexose nucleoside analogues into oligonucleotides: synthesis, base-pairing properties and enzymatic stability. Nucleic Acids Res. Sep. 25, 1992;20(18):4711-6.
Chen et al., Functionalization of single-walled carbon nanotubes enables efficient intracellular delivery of siRNA targeting MDM2 to inhibit breast cancer cells growth. Biomed Pharmacother. Jul. 2012;66(5):334-8. doi: 10.1016/j.biopha.2011.12.005. Epub Feb. 17, 2012.
Chen et al., Mdm2 deficiency suppresses MYCN-Driven neuroblastoma tumorigenesis in vivo. Neoplasia. Aug. 2009;11(8):753-62.
Chiang et al., Antisense oligonucleotides inhibit intercellular adhesion molecule 1 expression by two distinct mechanisms. J Biol Chem. Sep. 25, 1991;266(27):18162-71.
Fabbri et al., MicroRNA-29 family reverts aberrant methylation in lung cancer by targeting DNA methyltransferases 3A and 3B. Proc Natl Acad Sci U S A. Oct. 2, 2007;104(40):15805-10. Epub Sep. 21, 2007.
Ortigão et al., Antisense effect of oligodeoxynucleotides with inverted terminal internucleotidic linkages: a minimal modification protecting against nucleolytic degradation. Antisense Res Dev. 1992 Summer;2(2):129-46.
Petukhova et al., Genome-wide association study in alopecia areata implicates both innate and adaptive immunity. Nature. Jul. 1, 2010;466(7302):113-7. doi: 10.1038/nature09114.
Stein et al., A specificity comparison of four antisense types: morpholino, 2'-O-methyl RNA, DNA, and phosphorothioate DNA. Antisense Nucleic Acid Drug Dev. Jun. 1997;7(3):151-7.
Summerton et al., Morpholino and phosphorothioate antisense oligomers compared in cell-free and in-cell systems. Antisense Nucleic Acid Drug Dev. Apr. 1997;7(2):63-70.
Kim et al., Blocking the immunosuppressive axis with small interfering RNA targeting interleukin (IL)-10 receptor enhances dendritic cell-based vaccine potency. Clin Exp Immunol. Aug. 2011;165(2):180-9. doi: 10.1111/j.1365-2249.2011.04410.x. Epub May 18, 2011.
Maxwell et al., Yhe Use of Self-delivering RNAi to Enhance NK Cell Cytotoxicity. Discovery on Target. Sep. 26, 2018. Poster. 1 Page.
U.S. Appl. No. 16/206,064, filed Nov. 30, 2018, Libertine et al.
U.S. Appl. No. 16/377,617, filed Apr. 3, 2018, Levis et al.
Byrne et al., Novel hydrophobically modified asymmetric RNAi compounds (sd-rxRNA) demonstrate robust efficacy in the eye. J Ocul Pharmacol Ther. Dec. 2013;29(10):855-64. doi: 10.1089/jop.2013.0148. Epub Nov. 1, 2013.
Freeley et al., Advances in siRNA delivery to T-cells: potential clinical applications for inflammatory disease, cancer and infection. Biochem J. Oct. 15, 2013;455(2):133-47. doi: 10.1042/BJ20130950.
Rose et al., Functional polarity is introduced by Dicer processing of short substrate RNAs. Nucleic Acids Res. Jul. 26, 2005;33(13):4140-56. Print 2005.
Shoeman et al., Fluorescence microscopic comparison of the binding of phosphodiester and phosphorothioate (antisense) oligodeoxyribonucleotides to subcellular structures, including intermediate filaments, the endoplasmic reticulum, and the nuclear interior. Antisense Nucleic Acid Drug Dev. Aug. 1997;7(4):291-308.
International Search Report from International Application No. PCT/US2014/068244, filed Dec. 2, 2014, dated Jun. 29, 2015.

(56) References Cited

OTHER PUBLICATIONS

Corsello, et al, Endocrine Side Effects Induced by Immune Checkpoint Inhibitors, J. Clin. Endocrinol. Metab., Apr. 2013, pp. 1361-1375, v. 98, No. 4.

Heemskerk, M., T-Cell Receptor Gene Transfer for the Treatment of Leukemia and other Tumors, Haematologica, 2010, pp. 15-19, vol. 95, No. 1.

Snead, N. M. et al, RNA Interference Trigger Variants: Getting the Most Out of RNA for RNA Interference-Based Therapeutics, Nucleic Acid Therapeutics, 2012, pp. 139-146, vol., 22, No. 3.

Ui-Tei, K., sdRNA: siRNA with a DNA Seed for an Efficient and Target-gene Specific RNA Interference, Gene Technology, 2012, pp. 1-6, vol. 1, No. 1.

Byrne, M. et al., Novel Hydrophobically Modified Asymmetric RNAi Compounds (sd-rxRNA) Demonstrate Robust Efficacy in the Eye, Journal of Ocular Pharmacology and Therapeutics, 2013.

Hodi, F. S., New Toxicities of Immune Checkpoint Modulators, Annals of Oncology, 2013, vol. 24 (Suppl 1), i7-i17.

U.S. Appl. No. 16/270,524, filed Feb. 7, 2019, Khvorova et al.
U.S. Appl. No. 16/377,617, filed Apr. 8, 2019, Levis et al.
U.S. Appl. No. 16/606,669, filed Oct. 18, 2019, Maxwell et al.
U.S. Appl. No. 16/637,514, filed Feb. 7, 2020, Eliseev.

Cardia et al., Self-Delivering RNAi Compounds. Drug Delivery Technology. Sep. 2010;10(7):1-4.

Chiu et al., siRNA function in RNAi: a chemical modification analysis. RNA. Sep. 2003;9(9):1034-48.

Vickers et al., Efficient reduction of target RNAs by small interfering RNA and RNase H-dependent antisense agents. A comparative analysis. J Biol Chem. Feb. 28, 2003;278(9):7108-18. Epub Dec. 23, 2002.

U.S. Appl. No. 16/153,424, filed Oct. 5, 2018, Pavco et al.
U.S. Appl. No. 16/191,396, filed Nov. 14, 2018, Kamens et al.
U.S. Appl. No. 16/159,590, filed Oct. 12, 2018, Khvorova et al.
U.S. Appl. No. 15/918,605, filed Mar. 12, 2018, Khvorova et al.
U.S. Appl. No. 16/022,652, filed Jun. 28, 2018, Khvorova et al.
U.S. Appl. No. 15/758,576, filed Mar. 8, 2018, Cauwenbergh et al.
U.S. Appl. No. 15/769,555, filed Apr. 18, 2018, Cardia et al.
U.S. Appl. No. 15/638,586, filed Jun. 30, 2017, Woolf et al.
U.S. Appl. No. 15/532,804, filed Jun. 2, 2017, Cauwenbergh et al.
U.S. Appl. No. 15/742,093, filed Jan. 5, 2018, Cardia et al.
U.S. Appl. No. 15/742,117, filed Jan. 5, 2018, Byrne et al.
U.S. Appl. No. 15/905,118, filed Feb. 26, 2018, Khvorova et al.

Correspondence associated with Gutkina inventorship claim. Dated Jun. 22, 2018 through Nov. 21, 2018. 78 pages.

Facciabene et al., T-regulatory cells: key players in tumor immune escape and angiogenesis. Cancer Res. May 1, 2012;72(9):2162-71. doi: 10.1158/0008-5472.CAN-11-3687.

Kandalaft et al., The emergence of immunomodulation: combinatorial immunochemotherapy opportunities for the next decade. Gynecol Oncol. Feb. 2010;116(2):222-33. doi: 10.1016/j.ygyno.2009.11.001. Epub Dec 2, 2009.

Kloss et al., Combinatorial antigen recognition with balanced signaling promotes selective tumor eradication by engineered T cells. Nat Biotechnol. Jan. 2013;31(1):71-5. doi: 10.1038/nbt.2459. Epub Dec. 16, 2012.

U.S. Appl. No. 16/680,101, filed Nov. 11, 2019, Woolf et al.
U.S. Appl. No. 16/850,912, filed Apr. 16, 2020, Cauwenbergh et al.
U.S. Appl. No. 16/852,328, filed Apr. 17, 2020, Byrne et al.
U.S. Appl. No. 15/930,377, filed May 12, 2020, Libertine et al.
U.S. Appl. No. 16/934,864, filed Jul. 21, 2020, Khvorova et al.

\* cited by examiner

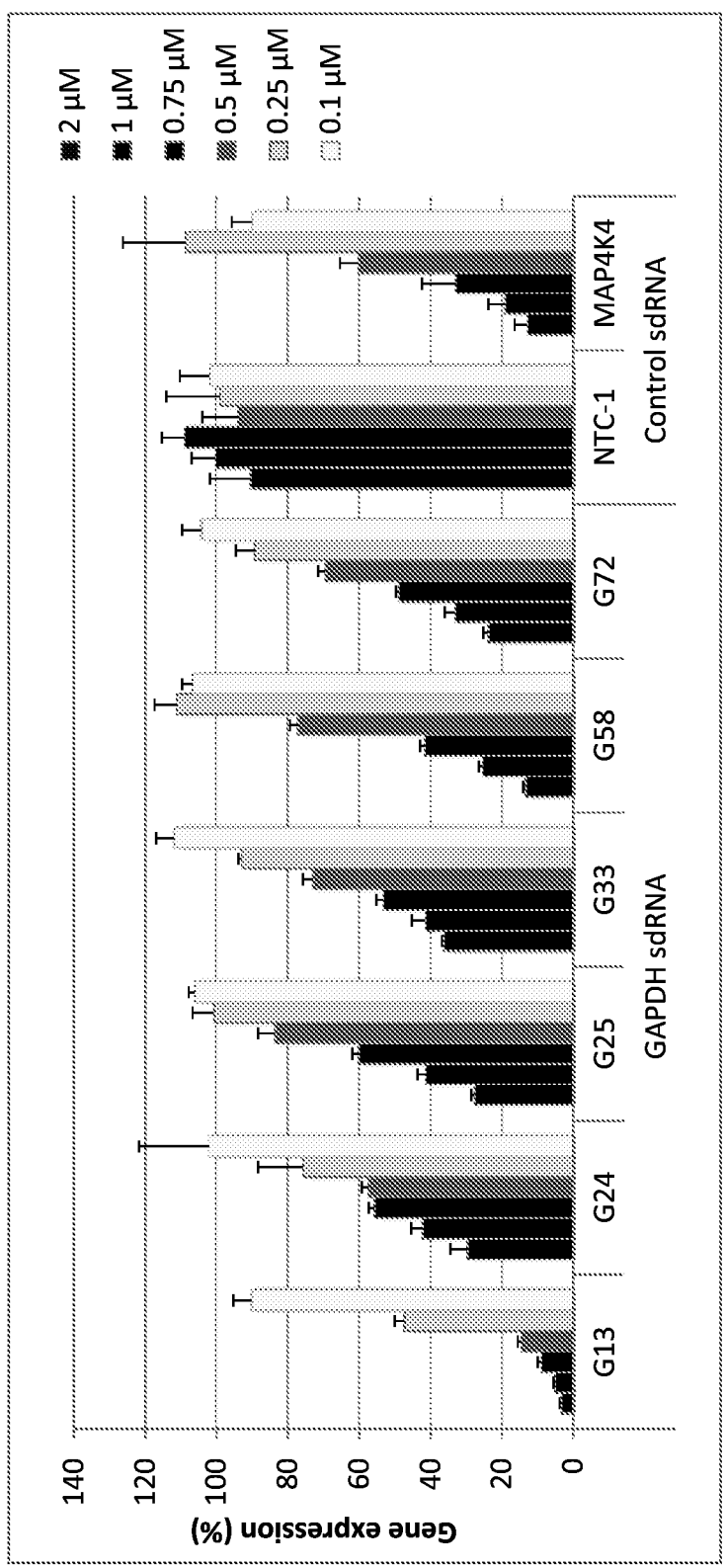
Fig.2. Silencing of target genes GAPDH and MAP4K4 in HeLa cells

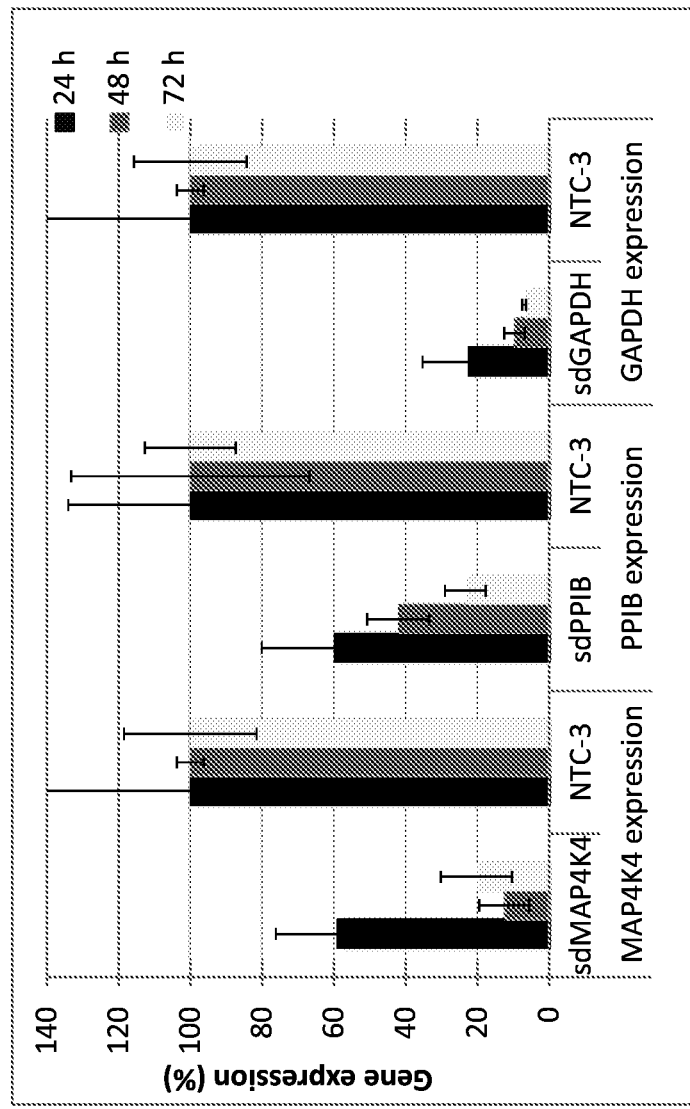
Fig. 3. Silencing of target genes MAP4K4, PPIB and GAPDH in NK-92 cells

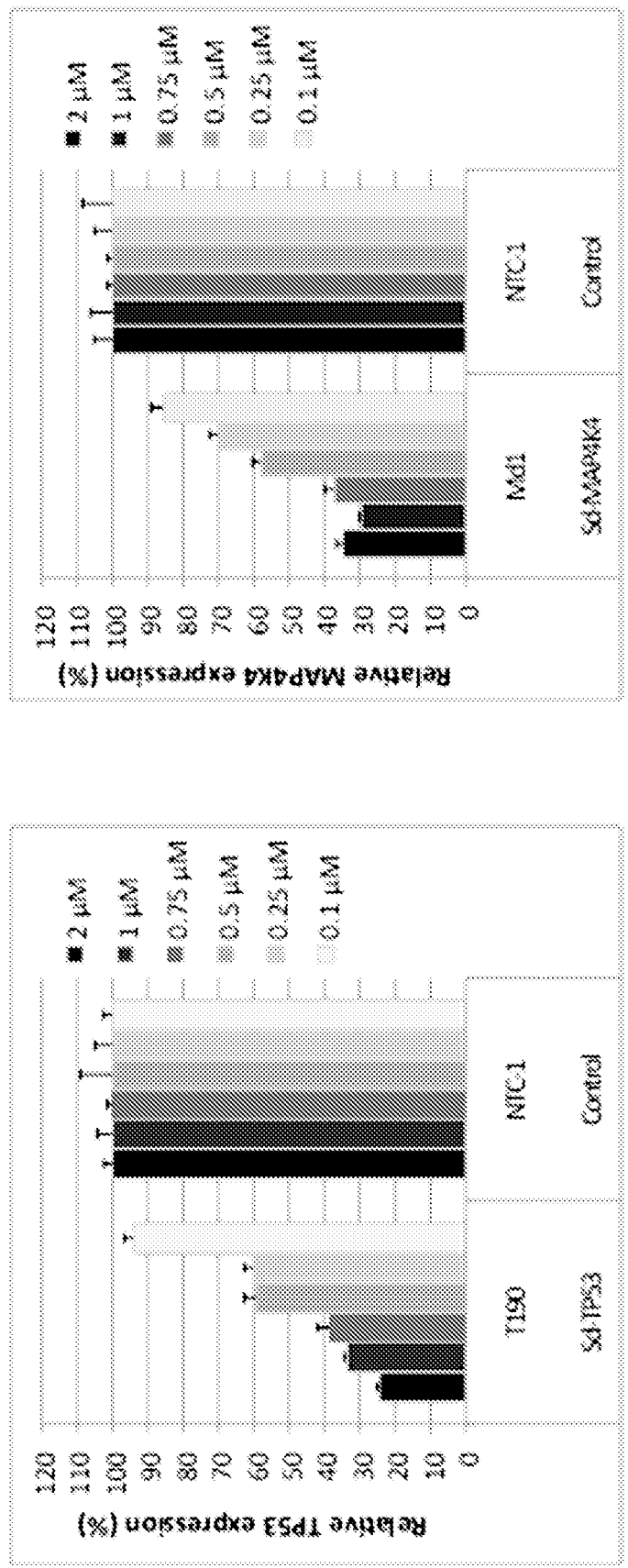
Fig. 4. Silencing of TP53 and MAP4K4 in Human Primary T cells

Fig. 5. Silencing of PDCD1 and CTLA-4 in activated Human Primary T cells
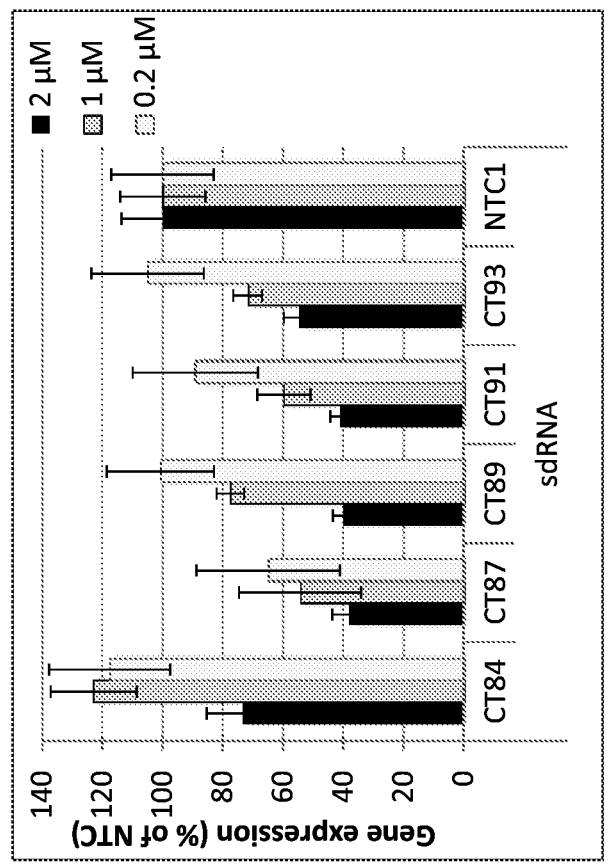
PDCD1:
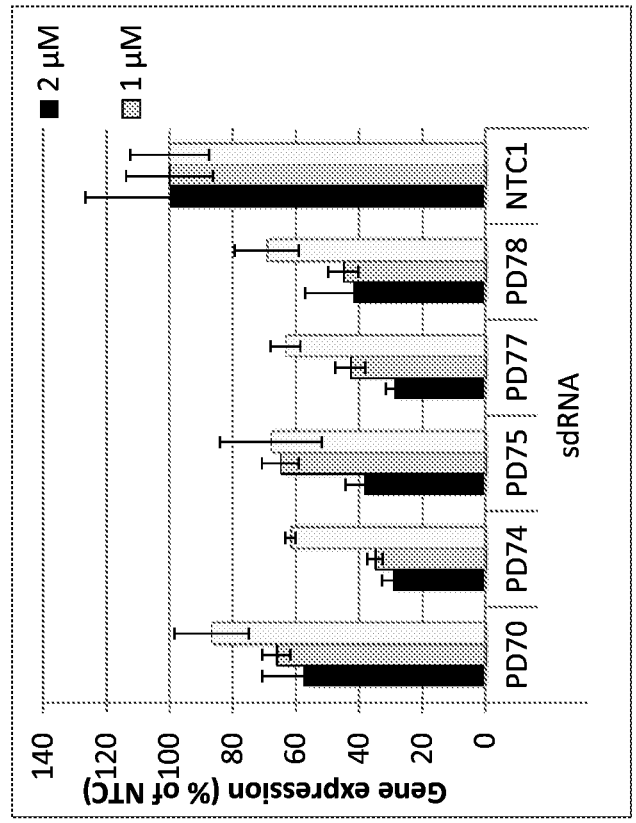
CTLA-4:

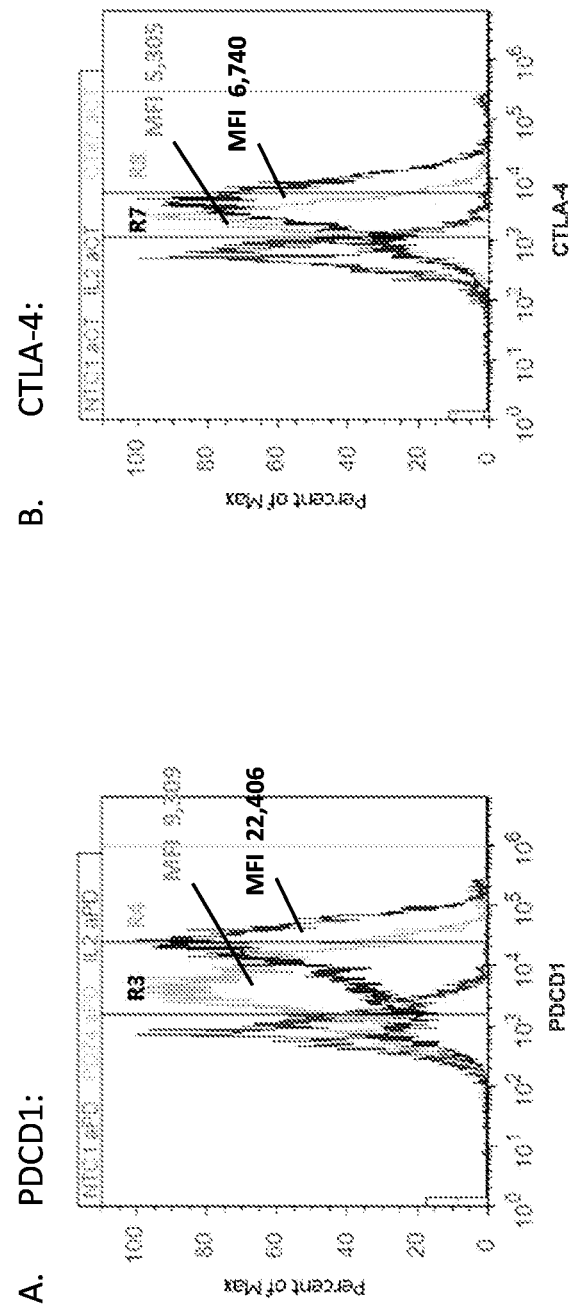
Fig.6. Reduction of PDCD1 and CTLA-4 surface expression by sdRNA in Human Primary T cells

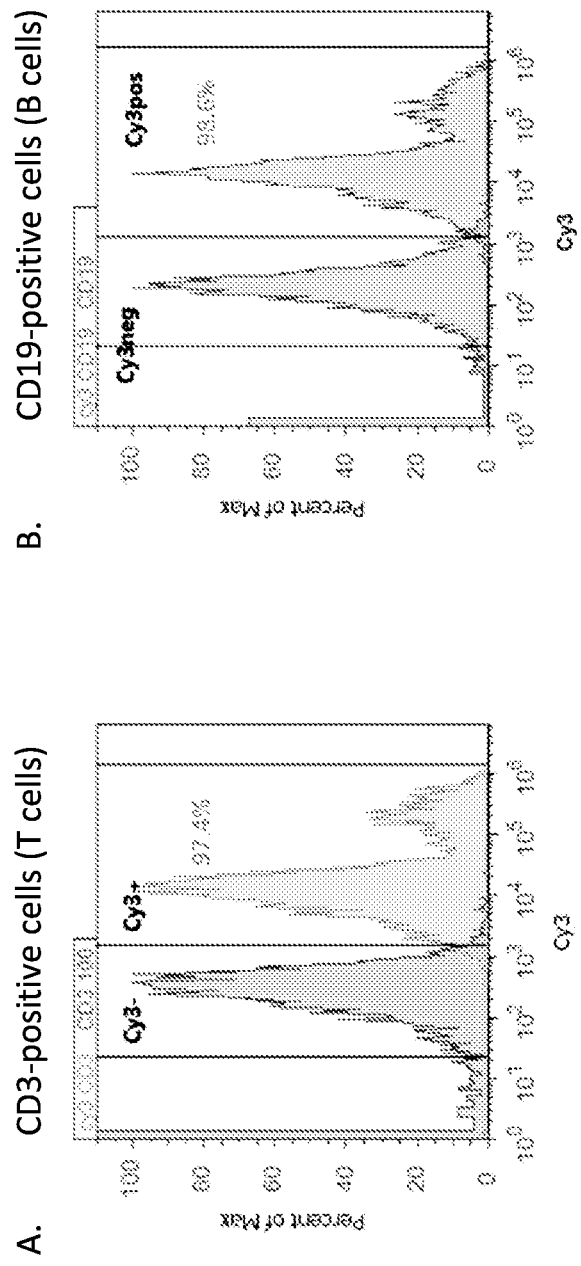
Fig. 7. MAP4K4-cy3 sdRNA delivery into T and B cells in human PBMCs

SEQUENCE LISTING

<160> NUMBER OF SEQ ID NOS: 1007

<210> SEQ ID NO 1
<211> LENGTH: 20
<212> TYPE: DNA
<213> ORGANISM: Homo sapiens

<400> SEQUENCE: 1
gaattgctca agttcattga                                              20

<210> SEQ ID NO 2
<211> LENGTH: 20
<212> TYPE: DNA
<213> ORGANISM: Homo sapiens

<400> SEQUENCE: 2
ttcatccagg atcgagcagg                                              20

<210> SEQ ID NO 3
<211> LENGTH: 20
<212> TYPE: DNA
<213> ORGANISM: Homo sapiens

<400> SEQUENCE: 3
atcatcagat gtggtctata                                              20

<210> SEQ ID NO 4
<211> LENGTH: 20
<212> TYPE: DNA
<213> ORGANISM: Homo sapiens

<400> SEQUENCE: 4
tactttgcca gcaaactggt                                              20

<210> SEQ ID NO 5
<211> LENGTH: 20
<212> TYPE: DNA
<213> ORGANISM: Homo sapiens

<400> SEQUENCE: 5
ggttgggtga gactcctcaa                                              20

<210> SEQ ID NO 6
<211> LENGTH: 20
<212> TYPE: DNA
<213> ORGANISM: Homo sapiens

<400> SEQUENCE: 6
ctactttgcc agcaaactgg                                              20

<210> SEQ ID NO 7
<211> LENGTH: 20
<212> TYPE: DNA
<213> ORGANISM: Homo sapiens

<400> SEQUENCE: 7
gcgttttcct tacgtgtctg                                              20

<210> SEQ ID NO 8
<211> LENGTH: 20
<212> TYPE: DNA
<213> ORGANISM: Homo sapiens

<400> SEQUENCE: 8
tacgtgtctg atcaatcccc                                              20

<210> SEQ ID NO 9
<211> LENGTH: 20
<212> TYPE: DNA
<213> ORGANISM: Homo sapiens

<400> SEQUENCE: 9
tcagggtttc atccaggatc                                              20

<210> SEQ ID NO 10
<211> LENGTH: 20
<212> TYPE: DNA
<213> ORGANISM: Homo sapiens

<400> SEQUENCE: 10
tgacggcaac ttcaactggg                                              20

<210> SEQ ID NO 11
<211> LENGTH: 20
<212> TYPE: DNA
<213> ORGANISM: Homo sapiens

<400> SEQUENCE: 11
cagctgacat gttttctgac                                              20

<210> SEQ ID NO 12
<211> LENGTH: 20
<212> TYPE: DNA
<213> ORGANISM: Homo sapiens

<400> SEQUENCE: 12
agctgacatg ttttctgacg                                              20

<210> SEQ ID NO 13
<211> LENGTH: 20
<212> TYPE: DNA
<213> ORGANISM: Homo sapiens

<400> SEQUENCE: 13
cactgtgacc ttgacttgat                                              20

<210> SEQ ID NO 14
<211> LENGTH: 20
<212> TYPE: DNA
<213> ORGANISM: Homo sapiens

<400> SEQUENCE: 14
tccttacgtg tctgatcaat                                              20

<210> SEQ ID NO 15
<211> LENGTH: 20
<212> TYPE: DNA
<213> ORGANISM: Homo sapiens

<400> SEQUENCE: 15
gatcagaacc atcatgggct                                              20

<210> SEQ ID NO 16
<211> LENGTH: 20
<212> TYPE: DNA
<213> ORGANISM: Homo sapiens

```
<400> SEQUENCE: 16
cttctggagc aggtcacagt                                          20

<210> SEQ ID NO 17
<211> LENGTH: 20
<212> TYPE: DNA
<213> ORGANISM: Homo sapiens

<400> SEQUENCE: 17
tgagcagatc atgaagacag                                          20

<210> SEQ ID NO 18
<211> LENGTH: 20
<212> TYPE: DNA
<213> ORGANISM: Homo sapiens

<400> SEQUENCE: 18
tataatgcgt tttccttacg                                          20

<210> SEQ ID NO 19
<211> LENGTH: 20
<212> TYPE: DNA
<213> ORGANISM: Homo sapiens

<400> SEQUENCE: 19
cccatcttca gatcatcaga                                          20

<210> SEQ ID NO 20
<211> LENGTH: 20
<212> TYPE: DNA
<213> ORGANISM: Homo sapiens

<400> SEQUENCE: 20
aggtgccgga actgatcaga                                          20

<210> SEQ ID NO 21
<211> LENGTH: 45
<212> TYPE: DNA
<213> ORGANISM: Homo sapiens

<400> SEQUENCE: 21
cctccactgc ctctggaatt gctcaagttc attgatgacc ctctg              45

<210> SEQ ID NO 22
<211> LENGTH: 45
<212> TYPE: DNA
<213> ORGANISM: Homo sapiens

<400> SEQUENCE: 22
cttttgcttc agggtttcat ccaggatcga gcagggcgaa tgggg              45

<210> SEQ ID NO 23
<211> LENGTH: 45
<212> TYPE: DNA
<213> ORGANISM: Homo sapiens

<400> SEQUENCE: 23
tctccccatc ttcagatcat cagatgtggt ctataatgcg ttttc              45

<210> SEQ ID NO 24
<211> LENGTH: 45
<212> TYPE: DNA
```

<400> SEQUENCE: 24
gttgtcgccc ttttctactt tgccagcaaa ctggtgctca aggcc                45

<210> SEQ ID NO 25
<211> LENGTH: 45
<212> TYPE: DNA
<213> ORGANISM: Homo sapiens

<400> SEQUENCE: 25
atccaagacc agggtggttg ggtgagactc ctcaagcctc ctcac                45

<210> SEQ ID NO 26
<211> LENGTH: 45
<212> TYPE: DNA
<213> ORGANISM: Homo sapiens

<400> SEQUENCE: 26
ggttgtcgcc cttttctact ttgccagcaa actggtgctc aaggc                45

<210> SEQ ID NO 27
<211> LENGTH: 45
<212> TYPE: DNA
<213> ORGANISM: Homo sapiens

<400> SEQUENCE: 27
gatgtggtct ataatgcgtt ttccttacgt gtctgatcaa tcccc                45

<210> SEQ ID NO 28
<211> LENGTH: 45
<212> TYPE: DNA
<213> ORGANISM: Homo sapiens

<400> SEQUENCE: 28
ataatgcgtt ttccttacgt gtctgatcaa tccccgattc atcta                45

<210> SEQ ID NO 29
<211> LENGTH: 45
<212> TYPE: DNA
<213> ORGANISM: Homo sapiens

<400> SEQUENCE: 29 aggggcccctt tgcttcagg gtttcatcca ggatcgagca gggcg                45

<210> SEQ ID NO 30
<211> LENGTH: 45
<212> TYPE: DNA
<213> ORGANISM: Homo sapiens

<400> SEQUENCE: 30
agctgacatg ttttctgacg gcaacttcaa ctggggccgg gttgt                45

<210> SEQ ID NO 31
<211> LENGTH: 45
<212> TYPE: DNA
<213> ORGANISM: Homo sapiens

<400> SEQUENCE: 31 tcttttttccg agtggcagct gacatgtttt ctgacggcaa cttca                45

<210> SEQ ID NO 32
<211> LENGTH: 45
<212> TYPE: DNA

<213> ORGANISM: Homo sapiens

<400> SEQUENCE: 32 cttttccga gtggcagctg acatgttttc tgacggcaac ttcaa    45

<210> SEQ ID NO 33
<211> LENGTH: 45
<212> TYPE: DNA
<213> ORGANISM: Homo sapiens

<400> SEQUENCE: 33
agtgacccct gacctcactg tgaccttgac ttgattagtg ccttc    45

<210> SEQ ID NO 34
<211> LENGTH: 45
<212> TYPE: DNA
<213> ORGANISM: Homo sapiens

<400> SEQUENCE: 34
gtctataatg cgttttcctt acgtgtctga tcaatcccg attca    45

<210> SEQ ID NO 35
<211> LENGTH: 45
<212> TYPE: DNA
<213> ORGANISM: Homo sapiens

<400> SEQUENCE: 35
caaggtgccg gaactgatca gaaccatcat gggctggaca ttgga    45

<210> SEQ ID NO 36
<211> LENGTH: 45
<212> TYPE: DNA
<213> ORGANISM: Homo sapiens

<400> SEQUENCE: 36
tctgggaccc tgggccttct ggagcaggtc acagtggtgc cctct    45

<210> SEQ ID NO 37
<211> LENGTH: 45
<212> TYPE: DNA
<213> ORGANISM: Homo sapiens

<400> SEQUENCE: 37
ggggcccacc agctctgagc agatcatgaa gacaggggcc ctttt    45

<210> SEQ ID NO 38
<211> LENGTH: 45
<212> TYPE: DNA
<213> ORGANISM: Homo sapiens

<400> SEQUENCE: 38
tcatcagatg tggtctataa tgcgttttcc ttacgtgtct gatca    45

<210> SEQ ID NO 39
<211> LENGTH: 45
<212> TYPE: DNA
<213> ORGANISM: Homo sapiens

<400> SEQUENCE: 39
cagtggtgcc ctctccccat cttcagatca tcagatgtgg tctat    45

<210> SEQ ID NO 40
<211> LENGTH: 45

<212> TYPE: DNA
<213> ORGANISM: Homo sapiens

<400> SEQUENCE: 40
aggccctgtg caccaaggtg ccggaactga tcagaaccat catgg    45

<210> SEQ ID NO 41
<211> LENGTH: 20
<212> TYPE: DNA
<213> ORGANISM: Homo sapiens

<400> SEQUENCE: 41
tggtttgtta tatcagggaa    20

<210> SEQ ID NO 42
<211> LENGTH: 20
<212> TYPE: DNA
<213> ORGANISM: Homo sapiens

<400> SEQUENCE: 42
tggtacgaag attcttcaaa    20

<210> SEQ ID NO 43
<211> LENGTH: 20
<212> TYPE: DNA
<213> ORGANISM: Homo sapiens

<400> SEQUENCE: 43
ttatatcagg gaaaggagt    20

<210> SEQ ID NO 44
<211> LENGTH: 20
<212> TYPE: DNA
<213> ORGANISM: Homo sapiens

<400> SEQUENCE: 44
tcccttcctc tctccttata    20

<210> SEQ ID NO 45
<211> LENGTH: 20
<212> TYPE: DNA
<213> ORGANISM: Homo sapiens

<400> SEQUENCE: 45
tcaaatcatg actcccaagg    20

<210> SEQ ID NO 46
<211> LENGTH: 20
<212> TYPE: DNA
<213> ORGANISM: Homo sapiens

<400> SEQUENCE: 46
tgttatatca gggaaaagga    20

<210> SEQ ID NO 47
<211> LENGTH: 20
<212> TYPE: DNA
<213> ORGANISM: Homo sapiens

<400> SEQUENCE: 47
acgaagattc ttcaaatcat    20

<210> SEQ ID NO 48

```
<211> LENGTH: 20
<212> TYPE: DNA
<213> ORGANISM: Homo sapiens

<400> SEQUENCE: 48
ggtacgaaga ttcttcaaat                                              20

<210> SEQ ID NO 49
<211> LENGTH: 20
<212> TYPE: DNA
<213> ORGANISM: Homo sapiens

<400> SEQUENCE: 49
gaagttcttg attcagccaa                                              20

<210> SEQ ID NO 50
<211> LENGTH: 20
<212> TYPE: DNA
<213> ORGANISM: Homo sapiens

<400> SEQUENCE: 50
cctatgagta cttcaccaag                                              20

<210> SEQ ID NO 51
<211> LENGTH: 20
<212> TYPE: DNA
<213> ORGANISM: Homo sapiens

<400> SEQUENCE: 51
tatcagggaa aaggagtagg                                              20

<210> SEQ ID NO 52
<211> LENGTH: 20
<212> TYPE: DNA
<213> ORGANISM: Homo sapiens

<400> SEQUENCE: 52
ctctccttat agacacttgc                                              20

<210> SEQ ID NO 53
<211> LENGTH: 20
<212> TYPE: DNA
<213> ORGANISM: Homo sapiens

<400> SEQUENCE: 53
acttggtttg ttatatcagg                                              20

<210> SEQ ID NO 54
<211> LENGTH: 20
<212> TYPE: DNA
<213> ORGANISM: Homo sapiens

<400> SEQUENCE: 54
aagatcagca ccctaagaga                                              20

<210> SEQ ID NO 55
<211> LENGTH: 20
<212> TYPE: DNA
<213> ORGANISM: Homo sapiens

<400> SEQUENCE: 55
gtttgagagt ggcatcaatt                                              20
```

```
<210> SEQ ID NO 56
<211> LENGTH: 20
<212> TYPE: DNA
<213> ORGANISM: Homo sapiens

<400> SEQUENCE: 56
gactatcaac accactagga                                            20

<210> SEQ ID NO 57
<211> LENGTH: 20
<212> TYPE: DNA
<213> ORGANISM: Homo sapiens

<400> SEQUENCE: 57
agctttagca agtgtgcact                                            20

<210> SEQ ID NO 58
<211> LENGTH: 20
<212> TYPE: DNA
<213> ORGANISM: Homo sapiens

<400> SEQUENCE: 58
ttcatctgga gggttctaag                                            20

<210> SEQ ID NO 59
<211> LENGTH: 20
<212> TYPE: DNA
<213> ORGANISM: Homo sapiens

<400> SEQUENCE: 59
aagttcttga ttcagccaaa                                            20

<210> SEQ ID NO 60
<211> LENGTH: 20
<212> TYPE: DNA
<213> ORGANISM: Homo sapiens

<400> SEQUENCE: 60
gttatatcag ggaaaaggag                                            20

<210> SEQ ID NO 61
<211> LENGTH: 45
<212> TYPE: DNA
<213> ORGANISM: Homo sapiens

<400> SEQUENCE: 61
acagggctta ggacttggtt tgttatatca gggaaaagga gtagg                45

<210> SEQ ID NO 62
<211> LENGTH: 45
<212> TYPE: DNA
<213> ORGANISM: Homo sapiens

<400> SEQUENCE: 62
tgttgggcca gtttgtggta cgaagattct tcaaatcatg actcc                45

<210> SEQ ID NO 63
<211> LENGTH: 45
<212> TYPE: DNA
<213> ORGANISM: Homo sapiens

<400> SEQUENCE: 63
ttaggacttg gtttgttata tcagggaaaa ggagtaggga gttca                45
```

```
<210> SEQ ID NO 64
<211> LENGTH: 45
<212> TYPE: DNA
<213> ORGANISM: Homo sapiens

<400> SEQUENCE: 64
gtcctctcag ttctctccct tcctctctcc ttatagacac ttgct            45

<210> SEQ ID NO 65
<211> LENGTH: 45
<212> TYPE: DNA
<213> ORGANISM: Homo sapiens

<400> SEQUENCE: 65
tggtacgaag attcttcaaa tcatgactcc caagggtgcc ctttg            45

<210> SEQ ID NO 66
<211> LENGTH: 45
<212> TYPE: DNA
<213> ORGANISM: Homo sapiens

<400> SEQUENCE: 66
gcttaggact tggtttgtta tatcagggaa aaggagtagg gagtt            45

<210> SEQ ID NO 67
<211> LENGTH: 45
<212> TYPE: DNA
<213> ORGANISM: Homo sapiens

<400> SEQUENCE: 67
gggccagttt gtggtacgaa gattcttcaa atcatgactc ccaag            45

<210> SEQ ID NO 68
<211> LENGTH: 45
<212> TYPE: DNA
<213> ORGANISM: Homo sapiens

<400> SEQUENCE: 68
gttgggccag tttgtggtac gaagattctt caaatcatga ctccc            45

<210> SEQ ID NO 69
<211> LENGTH: 45
<212> TYPE: DNA
<213> ORGANISM: Homo sapiens

<400> SEQUENCE: 69
gggggtcagg ggggagaagt tcttgattca gccaaatgca gggag            45

<210> SEQ ID NO 70
<211> LENGTH: 45
<212> TYPE: DNA
<213> ORGANISM: Homo sapiens

<400> SEQUENCE: 70
ccacggcaga gaatgcctat gagtacttca ccaagattgc cacca            45

<210> SEQ ID NO 71
<211> LENGTH: 45
<212> TYPE: DNA
<213> ORGANISM: Homo sapiens

<400> SEQUENCE: 71
ggacttggtt tgttatatca gggaaaagga gtagggagtt catct            45
```

<210> SEQ ID NO 72
<211> LENGTH: 45
<212> TYPE: DNA
<213> ORGANISM: Homo sapiens

<400> SEQUENCE: 72
gttctctccc ttcctctctc cttatagaca cttgctccca accca        45

<210> SEQ ID NO 73
<211> LENGTH: 45
<212> TYPE: DNA
<213> ORGANISM: Homo sapiens

<400> SEQUENCE: 73
actacagggc ttaggacttg gtttgttata tcagggaaaa ggagt        45

<210> SEQ ID NO 74
<211> LENGTH: 45
<212> TYPE: DNA
<213> ORGANISM: Homo sapiens

<400> SEQUENCE: 74
attcagctat tctggaagat cagcaccctaa agagatggga ctagg        45

<210> SEQ ID NO 75
<211> LENGTH: 45
<212> TYPE: DNA
<213> ORGANISM: Homo sapiens

<400> SEQUENCE: 75
gattgccacc agcctgtttg agagtggcat caattggggc cgtgt        45

<210> SEQ ID NO 76
<211> LENGTH: 45
<212> TYPE: DNA
<213> ORGANISM: Homo sapiens

<400> SEQUENCE: 76
tctaagtggg agaaggacta tcaacaccac taggaatccc agagg        45

<210> SEQ ID NO 77
<211> LENGTH: 45
<212> TYPE: DNA
<213> ORGANISM: Homo sapiens

<400> SEQUENCE: 77
cctcaagagt acagaagctt tagcaagtgt gcactccagc ttcgg        45

<210> SEQ ID NO 78
<211> LENGTH: 45
<212> TYPE: DNA
<213> ORGANISM: Homo sapiens

<400> SEQUENCE: 78
aaaaggagta gggagttcat ctggagggtt ctaagtggga gaagg        45

<210> SEQ ID NO 79
<211> LENGTH: 45
<212> TYPE: DNA
<213> ORGANISM: Homo sapiens

<400> SEQUENCE: 79
ggggtcaggg gggagaagtt cttgattcag ccaaatgcag ggagg 45

<210> SEQ ID NO 80
<211> LENGTH: 45
<212> TYPE: DNA
<213> ORGANISM: Homo sapiens

<400> SEQUENCE: 80
cttaggactt ggtttgttat atcagggaaa aggagtaggg agttc 45

<210> SEQ ID NO 81
<211> LENGTH: 20
<212> TYPE: DNA
<213> ORGANISM: Homo sapiens

<400> SEQUENCE: 81
tgtttgggag atgtaagaaa 20

<210> SEQ ID NO 82
<211> LENGTH: 20
<212> TYPE: DNA
<213> ORGANISM: Homo sapiens

<400> SEQUENCE: 82
gcattgtgag ggttaatgaa 20

<210> SEQ ID NO 83
<211> LENGTH: 20
<212> TYPE: DNA
<213> ORGANISM: Homo sapiens

<400> SEQUENCE: 83
tcgatctctt attttacaat 20

<210> SEQ ID NO 84
<211> LENGTH: 20
<212> TYPE: DNA
<213> ORGANISM: Homo sapiens

<400> SEQUENCE: 84
tgtgagggtt aatgaaataa 20

<210> SEQ ID NO 85
<211> LENGTH: 20
<212> TYPE: DNA
<213> ORGANISM: Homo sapiens

<400> SEQUENCE: 85
gagtatttgg atgacagaaa 20

<210> SEQ ID NO 86
<211> LENGTH: 20
<212> TYPE: DNA
<213> ORGANISM: Homo sapiens

<400> SEQUENCE: 86
ggatgtttgg gagatgtaag 20

<210> SEQ ID NO 87
<211> LENGTH: 20
<212> TYPE: DNA
<213> ORGANISM: Homo sapiens

<400> SEQUENCE: 87
gaaatgttct tgcagttaag                                                20

<210> SEQ ID NO 88
<211> LENGTH: 20
<212> TYPE: DNA
<213> ORGANISM: Homo sapiens

<400> SEQUENCE: 88
atgtacatct ggccttgaaa                                                20

<210> SEQ ID NO 89
<211> LENGTH: 20
<212> TYPE: DNA
<213> ORGANISM: Homo sapiens

<400> SEQUENCE: 89
agaaatgttc ttgcagttaa                                                20

<210> SEQ ID NO 90
<211> LENGTH: 20
<212> TYPE: DNA
<213> ORGANISM: Homo sapiens

<400> SEQUENCE: 90
ggtgaacctt agtacctaaa                                                20

<210> SEQ ID NO 91
<211> LENGTH: 20
<212> TYPE: DNA
<213> ORGANISM: Homo sapiens

<400> SEQUENCE: 91
taacttcaag gcccatatct                                                20

<210> SEQ ID NO 92
<211> LENGTH: 20
<212> TYPE: DNA
<213> ORGANISM: Homo sapiens

<400> SEQUENCE: 92
cttatccgag tggaaggaaa                                                20

<210> SEQ ID NO 93
<211> LENGTH: 20
<212> TYPE: DNA
<213> ORGANISM: Homo sapiens

<400> SEQUENCE: 93
atgatctgga tccaccaaga                                                20

<210> SEQ ID NO 94
<211> LENGTH: 20
<212> TYPE: DNA
<213> ORGANISM: Homo sapiens

<400> SEQUENCE: 94
aattttctct aacttcaagg                                                20

<210> SEQ ID NO 95
<211> LENGTH: 20
<212> TYPE: DNA
<213> ORGANISM: Homo sapiens

<400> SEQUENCE: 95
tctcttattt tacaataaaa                                           20

<210> SEQ ID NO 96
<211> LENGTH: 20
<212> TYPE: DNA
<213> ORGANISM: Homo sapiens

<400> SEQUENCE: 96
ttattttaca ataaaacttt                                           20

<210> SEQ ID NO 97
<211> LENGTH: 20
<212> TYPE: DNA
<213> ORGANISM: Homo sapiens

<400> SEQUENCE: 97
gccttgaaac caccttttat                                           20

<210> SEQ ID NO 98
<211> LENGTH: 20
<212> TYPE: DNA
<213> ORGANISM: Homo sapiens

<400> SEQUENCE: 98
tatatcgatc tcttatttta                                           20

<210> SEQ ID NO 99
<211> LENGTH: 20
<212> TYPE: DNA
<213> ORGANISM: Homo sapiens

<400> SEQUENCE: 99
ccttagtacc taaaaggaaa                                           20

<210> SEQ ID NO 100
<211> LENGTH: 20
<212> TYPE: DNA
<213> ORGANISM: Homo sapiens

<400> SEQUENCE: 100
cattgtgagg gttaatgaaa                                           20

<210> SEQ ID NO 101
<211> LENGTH: 45
<212> TYPE: DNA
<213> ORGANISM: Homo sapiens

<400> SEQUENCE: 101
ttttactgtg agggatgttt gggagatgta agaaatgttc ttgca               45

<210> SEQ ID NO 102
<211> LENGTH: 45
<212> TYPE: DNA
<213> ORGANISM: Homo sapiens

<400> SEQUENCE: 102
cctacctcac agagtgcatt gtgagggtta atgaaataat gtaca               45

<210> SEQ ID NO 103
<211> LENGTH: 45
<212> TYPE: DNA
<213> ORGANISM: Homo sapiens

```
<400> SEQUENCE: 103
tatcccattt ttatatcgat ctcttatttt acaataaaac tttgc              45

<210> SEQ ID NO 104
<211> LENGTH: 45
<212> TYPE: DNA
<213> ORGANISM: Homo sapiens

<400> SEQUENCE: 104
cctcacagag tgcattgtga gggttaatga aataatgtac atctg              45

<210> SEQ ID NO 105
<211> LENGTH: 45
<212> TYPE: DNA
<213> ORGANISM: Homo sapiens

<400> SEQUENCE: 105
ggaaatttgc gtgtggagta tttggatgac agaaacactt ttcga              45

<210> SEQ ID NO 106
<211> LENGTH: 45
<212> TYPE: DNA
<213> ORGANISM: Homo sapiens

<400> SEQUENCE: 106
ggtttttact gtgagggatg tttgggagat gtaagaaatg ttctt              45

<210> SEQ ID NO 107
<211> LENGTH: 45
<212> TYPE: DNA
<213> ORGANISM: Homo sapiens

<400> SEQUENCE: 107
gtttgggaga tgtaagaaat gttcttgcag ttaagggtta gttta              45

<210> SEQ ID NO 108
<211> LENGTH: 45
<212> TYPE: DNA
<213> ORGANISM: Homo sapiens

<400> SEQUENCE: 108
agggttaatg aaataatgta catctggcct tgaaaccacc tttta              45

<210> SEQ ID NO 109
<211> LENGTH: 45
<212> TYPE: DNA
<213> ORGANISM: Homo sapiens

<400> SEQUENCE: 109
tgtttgggag atgtaagaaa tgttcttgca gttaagggtt agttt              45

<210> SEQ ID NO 110
<211> LENGTH: 45
<212> TYPE: DNA
<213> ORGANISM: Homo sapiens

<400> SEQUENCE: 110
gtctgacaac ctcttggtga acctagtac ctaaaaggaa atctc              45

<210> SEQ ID NO 111
<211> LENGTH: 45
<212> TYPE: DNA
```

<213> ORGANISM: Homo sapiens

<400> SEQUENCE: 111
ctgttgaatt ttctctaact tcaaggccca tatctgtgaa atgct       45

<210> SEQ ID NO 112
<211> LENGTH: 45
<212> TYPE: DNA
<213> ORGANISM: Homo sapiens

<400> SEQUENCE: 112
gcccctcctc agcatcttat ccgagtggaa ggaaatttgc gtgtg       45

<210> SEQ ID NO 113
<211> LENGTH: 45
<212> TYPE: DNA
<213> ORGANISM: Homo sapiens

<400> SEQUENCE: 113
catctcttgt atatgatgat ctggatccac caagacttgt tttat       45

<210> SEQ ID NO 114
<211> LENGTH: 45
<212> TYPE: DNA
<213> ORGANISM: Homo sapiens

<400> SEQUENCE: 114
tgtccctcac tgttgaattt tctctaactt caaggcccat atctg       45

<210> SEQ ID NO 115
<211> LENGTH: 45
<212> TYPE: DNA
<213> ORGANISM: Homo sapiens

<400> SEQUENCE: 115
ccatttttat atcgatctct tattttacaa taaaactttg ctgcc       45

<210> SEQ ID NO 116
<211> LENGTH: 45
<212> TYPE: DNA
<213> ORGANISM: Homo sapiens

<400> SEQUENCE: 116
ttttatatcg atctcttatt ttacaataaa actttgctgc cacct       45

<210> SEQ ID NO 117
<211> LENGTH: 45
<212> TYPE: DNA
<213> ORGANISM: Homo sapiens

<400> SEQUENCE: 117
aataatgtac atctggcctt gaaaccacct tttattacat ggggt       45

<210> SEQ ID NO 118
<211> LENGTH: 45
<212> TYPE: DNA
<213> ORGANISM: Homo sapiens

<400> SEQUENCE: 118
tttatatccc attttatat cgatctctta ttttacaata aaact       45

<210> SEQ ID NO 119
<211> LENGTH: 45

<212> TYPE: DNA
<213> ORGANISM: Homo sapiens

<400> SEQUENCE: 119
caacctcttg gtgaacctta gtacctaaaa ggaaatctca cccca            45

<210> SEQ ID NO 120
<211> LENGTH: 45
<212> TYPE: DNA
<213> ORGANISM: Homo sapiens

<400> SEQUENCE: 120
ctacctcaca gagtgcattg tgagggttaa tgaaataatg tacat            45

<210> SEQ ID NO 121
<211> LENGTH: 20
<212> TYPE: DNA
<213> ORGANISM: Homo sapiens

<400> SEQUENCE: 121
ttaaatcatt aggaattaag            20

<210> SEQ ID NO 122
<211> LENGTH: 20
<212> TYPE: DNA
<213> ORGANISM: Homo sapiens

<400> SEQUENCE: 122
gaattaagtt atctttaaaa            20

<210> SEQ ID NO 123
<211> LENGTH: 20
<212> TYPE: DNA
<213> ORGANISM: Homo sapiens

<400> SEQUENCE: 123
aactttaatt ctctttcaaa            20

<210> SEQ ID NO 124
<211> LENGTH: 20
<212> TYPE: DNA
<213> ORGANISM: Homo sapiens

<400> SEQUENCE: 124
gactgaagtg aactatgaag            20

<210> SEQ ID NO 125
<211> LENGTH: 20
<212> TYPE: DNA
<213> ORGANISM: Homo sapiens

<400> SEQUENCE: 125
atattctcct gccttttaaa            20

<210> SEQ ID NO 126
<211> LENGTH: 20
<212> TYPE: DNA
<213> ORGANISM: Homo sapiens

<400> SEQUENCE: 126
agttatcttt aaaatttaag            20

<210> SEQ ID NO 127

-continued

```
<211> LENGTH: 20
<212> TYPE: DNA
<213> ORGANISM: Homo sapiens

<400> SEQUENCE: 127
tagattttct actttattaa                                                 20

<210> SEQ ID NO 128
<211> LENGTH: 20
<212> TYPE: DNA
<213> ORGANISM: Homo sapiens

<400> SEQUENCE: 128
ctgtgcccaa atcaacaaga                                                 20

<210> SEQ ID NO 129
<211> LENGTH: 20
<212> TYPE: DNA
<213> ORGANISM: Homo sapiens

<400> SEQUENCE: 129
agctggtggc aataaatacc                                                 20

<210> SEQ ID NO 130
<211> LENGTH: 20
<212> TYPE: DNA
<213> ORGANISM: Homo sapiens

<400> SEQUENCE: 130
tcctaccgaa accctgcaga                                                 20

<210> SEQ ID NO 131
<211> LENGTH: 20
<212> TYPE: DNA
<213> ORGANISM: Homo sapiens

<400> SEQUENCE: 131
tataagagct aaagttaaat                                                 20

<210> SEQ ID NO 132
<211> LENGTH: 20
<212> TYPE: DNA
<213> ORGANISM: Homo sapiens

<400> SEQUENCE: 132
cactatgttt atttactaat                                                 20

<210> SEQ ID NO 133
<211> LENGTH: 20
<212> TYPE: DNA
<213> ORGANISM: Homo sapiens

<400> SEQUENCE: 133
attgttatct atcaactata                                                 20

<210> SEQ ID NO 134
<211> LENGTH: 20
<212> TYPE: DNA
<213> ORGANISM: Homo sapiens

<400> SEQUENCE: 134
taactgtgtt tcctaccgaa                                                 20
```

```
<210> SEQ ID NO 135
<211> LENGTH: 20
<212> TYPE: DNA
<213> ORGANISM: Homo sapiens

<400> SEQUENCE: 135
taattctctt tcaaagctaa                                                    20

<210> SEQ ID NO 136
<211> LENGTH: 20
<212> TYPE: DNA
<213> ORGANISM: Homo sapiens

<400> SEQUENCE: 136
tatatgcttg gctaactata                                                    20

<210> SEQ ID NO 137
<211> LENGTH: 20
<212> TYPE: DNA
<213> ORGANISM: Homo sapiens

<400> SEQUENCE: 137
ctctgcttgg attattttaa                                                    20

<210> SEQ ID NO 138
<211> LENGTH: 20
<212> TYPE: DNA
<213> ORGANISM: Homo sapiens

<400> SEQUENCE: 138
atgcttggct aactatattt                                                    20

<210> SEQ ID NO 139
<211> LENGTH: 20
<212> TYPE: DNA
<213> ORGANISM: Homo sapiens

<400> SEQUENCE: 139
ataagagcta agttaaata                                                     20

<210> SEQ ID NO 140
<211> LENGTH: 20
<212> TYPE: DNA
<213> ORGANISM: Homo sapiens

<400> SEQUENCE: 140
atctttaaaa tttaagtatc                                                    20

<210> SEQ ID NO 141
<211> LENGTH: 45
<212> TYPE: DNA
<213> ORGANISM: Homo sapiens

<400> SEQUENCE: 141
tctgcttgga ttattttaaa tcattaggaa ttaagttatc tttaa                        45

<210> SEQ ID NO 142
<211> LENGTH: 45
<212> TYPE: DNA
<213> ORGANISM: Homo sapiens

<400> SEQUENCE: 142
attttaaatc attaggaatt aagttatctt taaaatttaa gtatc                        45
```

```
<210> SEQ ID NO 143
<211> LENGTH: 45
<212> TYPE: DNA
<213> ORGANISM: Homo sapiens

<400> SEQUENCE: 143
tgttaatatt ctattaactt taattctctt tcaaagctaa attcc            45

<210> SEQ ID NO 144
<211> LENGTH: 45
<212> TYPE: DNA
<213> ORGANISM: Homo sapiens

<400> SEQUENCE: 144
tattctcacc atcctgactg aagtgaacta tgaagtaagc aacaa            45

<210> SEQ ID NO 145
<211> LENGTH: 45
<212> TYPE: DNA
<213> ORGANISM: Homo sapiens

<400> SEQUENCE: 145
gggaatattg agattatatt ctcctgcctt ttaaaaagat ggact            45

<210> SEQ ID NO 146
<211> LENGTH: 45
<212> TYPE: DNA
<213> ORGANISM: Homo sapiens

<400> SEQUENCE: 146
aatcattagg aattaagtta tctttaaaat ttaagtatct ttttt            45

<210> SEQ ID NO 147
<211> LENGTH: 45
<212> TYPE: DNA
<213> ORGANISM: Homo sapiens

<400> SEQUENCE: 147
tatttactaa ttttctagat tttctacttt attaattgtt ttgca            45

<210> SEQ ID NO 148
<211> LENGTH: 45
<212> TYPE: DNA
<213> ORGANISM: Homo sapiens

<400> SEQUENCE: 148
catcctgaaa agagtctgtg cccaaatcaa caagagcctg ctgaa            45

<210> SEQ ID NO 149
<211> LENGTH: 45
<212> TYPE: DNA
<213> ORGANISM: Homo sapiens

<400> SEQUENCE: 149
tttgggaatg ttttagctg gtggcaataa ataccagaca cgtac             45

<210> SEQ ID NO 150
<211> LENGTH: 45
<212> TYPE: DNA
<213> ORGANISM: Homo sapiens

<400> SEQUENCE: 150
gtgaataact gtgtttccta ccgaaaccct gcagagggaa cctgg            45
```

<210> SEQ ID NO 151
<211> LENGTH: 45
<212> TYPE: DNA
<213> ORGANISM: Homo sapiens

<400> SEQUENCE: 151
tgttttgcac tttttataa gagctaaagt taaataggat attaa    45

<210> SEQ ID NO 152
<211> LENGTH: 45
<212> TYPE: DNA
<213> ORGANISM: Homo sapiens

<400> SEQUENCE: 152
actatttaga tataacacta tgtttattta ctaattttct agatt    45

<210> SEQ ID NO 153
<211> LENGTH: 45
<212> TYPE: DNA
<213> ORGANISM: Homo sapiens

<400> SEQUENCE: 153
gggcttatga ttcagattgt tatctatcaa ctataagccc actgt    45

<210> SEQ ID NO 154
<211> LENGTH: 45
<212> TYPE: DNA
<213> ORGANISM: Homo sapiens

<400> SEQUENCE: 154
gatggccact gtgaataact gtgtttccta ccgaaaccct gcaga    45

<210> SEQ ID NO 155
<211> LENGTH: 45
<212> TYPE: DNA
<213> ORGANISM: Homo sapiens

<400> SEQUENCE: 155
atattctatt aactttaatt ctctttcaaa gctaaattcc acact    45

<210> SEQ ID NO 156
<211> LENGTH: 45
<212> TYPE: DNA
<213> ORGANISM: Homo sapiens

<400> SEQUENCE: 156
tgcttttatg atatatatat gcttggctaa ctatatttgc ttttt    45

<210> SEQ ID NO 157
<211> LENGTH: 45
<212> TYPE: DNA
<213> ORGANISM: Homo sapiens

<400> SEQUENCE: 157
catttgctct ttcatctctg cttggattat tttaaatcat tagga    45

<210> SEQ ID NO 158
<211> LENGTH: 45
<212> TYPE: DNA
<213> ORGANISM: Homo sapiens

<400> SEQUENCE: 158

```
tttttatgata tatatatgct tggctaacta tatttgcttt ttgct                45

<210> SEQ ID NO 159
<211> LENGTH: 45
<212> TYPE: DNA
<213> ORGANISM: Homo sapiens

<400> SEQUENCE: 159
gttttgcact tttttataag agctaaagtt aaataggata ttaac                45

<210> SEQ ID NO 160
<211> LENGTH: 45
<212> TYPE: DNA
<213> ORGANISM: Homo sapiens

<400> SEQUENCE: 160
attaggaatt aagttatctt taaaatttaa gtatcttttt tcaaa                45

<210> SEQ ID NO 161
<211> LENGTH: 20
<212> TYPE: DNA
<213> ORGANISM: Homo sapiens

<400> SEQUENCE: 161
taactgcctt tccttctaaa                                            20

<210> SEQ ID NO 162
<211> LENGTH: 20
<212> TYPE: DNA
<213> ORGANISM: Homo sapiens

<400> SEQUENCE: 162
ttccttctaa agggaatgtt                                            20

<210> SEQ ID NO 163
<211> LENGTH: 20
<212> TYPE: DNA
<213> ORGANISM: Homo sapiens

<400> SEQUENCE: 163
gcctttcctt ctaaagggaa                                            20

<210> SEQ ID NO 164
<211> LENGTH: 20
<212> TYPE: DNA
<213> ORGANISM: Homo sapiens

<400> SEQUENCE: 164
ttttctgaga taaaataaaa                                            20

<210> SEQ ID NO 165
<211> LENGTH: 20
<212> TYPE: DNA
<213> ORGANISM: Homo sapiens

<400> SEQUENCE: 165
catctcttgg agtgacaaag                                            20

<210> SEQ ID NO 166
<211> LENGTH: 20
<212> TYPE: DNA
<213> ORGANISM: Homo sapiens

<400> SEQUENCE: 166
```
catggtgtac ttcaacttct    20

<210> SEQ ID NO 167
<211> LENGTH: 20
<212> TYPE: DNA
<213> ORGANISM: Homo sapiens

<400> SEQUENCE: 167
ctaactgcct ttccttctaa    20

<210> SEQ ID NO 168
<211> LENGTH: 20
<212> TYPE: DNA
<213> ORGANISM: Homo sapiens

<400> SEQUENCE: 168
ctgatgattc atggagtttg    20

<210> SEQ ID NO 169
<211> LENGTH: 20
<212> TYPE: DNA
<213> ORGANISM: Homo sapiens

<400> SEQUENCE: 169
ctcagagtcc tctgtgaaaa    20

<210> SEQ ID NO 170
<211> LENGTH: 20
<212> TYPE: DNA
<213> ORGANISM: Homo sapiens

<400> SEQUENCE: 170
aacgagccac atcgtgtttt    20

<210> SEQ ID NO 171
<211> LENGTH: 20
<212> TYPE: DNA
<213> ORGANISM: Homo sapiens

<400> SEQUENCE: 171
tccttctaaa gggaatgttt    20

<210> SEQ ID NO 172
<211> LENGTH: 20
<212> TYPE: DNA
<213> ORGANISM: Homo sapiens

<400> SEQUENCE: 172
catgaactac atggtgtact    20

<210> SEQ ID NO 173
<211> LENGTH: 20
<212> TYPE: DNA
<213> ORGANISM: Homo sapiens

<400> SEQUENCE: 173
aactgccttt ccttctaaag    20

<210> SEQ ID NO 174
<211> LENGTH: 20
<212> TYPE: DNA
<213> ORGANISM: Homo sapiens

<400> SEQUENCE: 174
cagatgtttc atgctgtgag                                            20

<210> SEQ ID NO 175
<211> LENGTH: 20
<212> TYPE: DNA
<213> ORGANISM: Homo sapiens

<400> SEQUENCE: 175
cccatgaact acatggtgta                                            20

<210> SEQ ID NO 176
<211> LENGTH: 20
<212> TYPE: DNA
<213> ORGANISM: Homo sapiens

<400> SEQUENCE: 176
aggcagcaag aacctttcaa                                            20

<210> SEQ ID NO 177
<211> LENGTH: 20
<212> TYPE: DNA
<213> ORGANISM: Homo sapiens

<400> SEQUENCE: 177
gtcctgatga ttcatggagt                                            20

<210> SEQ ID NO 178
<211> LENGTH: 20
<212> TYPE: DNA
<213> ORGANISM: Homo sapiens

<400> SEQUENCE: 178
gtacttcaac ttctttgcct                                            20

<210> SEQ ID NO 179
<211> LENGTH: 20
<212> TYPE: DNA
<213> ORGANISM: Homo sapiens

<400> SEQUENCE: 179
tgtaagtgtg aggaaaccct                                            20

<210> SEQ ID NO 180
<211> LENGTH: 20
<212> TYPE: DNA
<213> ORGANISM: Homo sapiens

<400> SEQUENCE: 180
cctactttgg actgagagaa                                            20

<210> SEQ ID NO 181
<211> LENGTH: 45
<212> TYPE: DNA
<213> ORGANISM: Homo sapiens

<400> SEQUENCE: 181
gtgagaggcc ttgtctaact gcctttcctt ctaagggaa tgttt                 45

<210> SEQ ID NO 182
<211> LENGTH: 45
<212> TYPE: DNA
<213> ORGANISM: Homo sapiens -continued

<400> SEQUENCE: 182
cttgtctaac tgcctttcct tctaaaggga atgttttttt ctgag    45

<210> SEQ ID NO 183
<211> LENGTH: 45
<212> TYPE: DNA
<213> ORGANISM: Homo sapiens

<400> SEQUENCE: 183
aggccttgtc taactgcctt tccttctaaa gggaatgttt tttttc    45

<210> SEQ ID NO 184
<211> LENGTH: 45
<212> TYPE: DNA
<213> ORGANISM: Homo sapiens

<400> SEQUENCE: 184
ctaaagggaa tgttttttc tgagataaaa taaaaacgag ccaca    45

<210> SEQ ID NO 185
<211> LENGTH: 45
<212> TYPE: DNA
<213> ORGANISM: Homo sapiens

<400> SEQUENCE: 185
tctcagtccc agggccatct cttggagtga caaagctggg atcaa    45

<210> SEQ ID NO 186
<211> LENGTH: 45
<212> TYPE: DNA
<213> ORGANISM: Homo sapiens

<400> SEQUENCE: 186
ggtccccatg aactacatgg tgtacttcaa cttctttgcc tgtgt    45

<210> SEQ ID NO 187
<211> LENGTH: 45
<212> TYPE: DNA
<213> ORGANISM: Homo sapiens

<400> SEQUENCE: 187
agtgagaggc cttgtctaac tgcctttcct tctaaaggga atgtt    45

<210> SEQ ID NO 188
<211> LENGTH: 45
<212> TYPE: DNA
<213> ORGANISM: Homo sapiens

<400> SEQUENCE: 188
tggagcagga gtgtcctgat gattcatgga gtttgcccct tccta    45

<210> SEQ ID NO 189
<211> LENGTH: 45
<212> TYPE: DNA
<213> ORGANISM: Homo sapiens

<400> SEQUENCE: 189
cctggtttca ggagactcag agtcctctgt gaaaaagccc ttgga    45

<210> SEQ ID NO 190
<211> LENGTH: 45
<212> TYPE: DNA

<213> ORGANISM: Homo sapiens

<400> SEQUENCE: 190
ctgagataaa ataaaaacga gccacatcgt gttttaagct tgtcc         45

<210> SEQ ID NO 191
<211> LENGTH: 45
<212> TYPE: DNA
<213> ORGANISM: Homo sapiens

<400> SEQUENCE: 191
ttgtctaact gcctttcctt ctaaagggaa tgttttttc tgaga          45

<210> SEQ ID NO 192
<211> LENGTH: 45
<212> TYPE: DNA
<213> ORGANISM: Homo sapiens

<400> SEQUENCE: 192
tgaggatgtg gtccccatga actacatggt gtacttcaac ttctt         45

<210> SEQ ID NO 193
<211> LENGTH: 45
<212> TYPE: DNA
<213> ORGANISM: Homo sapiens

<400> SEQUENCE: 193
tgagaggcct tgtctaactg cctttccttc taaagggaat gtttt         45

<210> SEQ ID NO 194
<211> LENGTH: 45
<212> TYPE: DNA
<213> ORGANISM: Homo sapiens

<400> SEQUENCE: 194
tgggttctga ggaagcagat gtttcatgct gtgaggcctt gcacc         45

<210> SEQ ID NO 195
<211> LENGTH: 45
<212> TYPE: DNA
<213> ORGANISM: Homo sapiens

<400> SEQUENCE: 195
tttgaggatg tggtccccat gaactacatg gtgtacttca acttc         45

<210> SEQ ID NO 196
<211> LENGTH: 45
<212> TYPE: DNA
<213> ORGANISM: Homo sapiens

<400> SEQUENCE: 196
cgcagccacg tcctgaggca gcaagaacct ttcaaggcag ctggc         45

<210> SEQ ID NO 197
<211> LENGTH: 45
<212> TYPE: DNA
<213> ORGANISM: Homo sapiens

<400> SEQUENCE: 197
ggatggagca ggagtgtcct gatgattcat ggagtttgcc ccttc         45

<210> SEQ ID NO 198
<211> LENGTH: 45

```
<212> TYPE: DNA
<213> ORGANISM: Homo sapiens

<400> SEQUENCE: 198
catgaactac atggtgtact tcaacttctt tgcctgtgtg ctggt          45

<210> SEQ ID NO 199
<211> LENGTH: 45
<212> TYPE: DNA
<213> ORGANISM: Homo sapiens

<400> SEQUENCE: 199
tttttccagg aaaaatgtaa gtgtgaggaa acccttttta tttta          45

<210> SEQ ID NO 200
<211> LENGTH: 45
<212> TYPE: DNA
<213> ORGANISM: Homo sapiens

<400> SEQUENCE: 200
tgagggcagc cggttcctac tttggactga gagaagggag cccca          45

<210> SEQ ID NO 201
<211> LENGTH: 20
<212> TYPE: DNA
<213> ORGANISM: Homo sapiens

<400> SEQUENCE: 201
tgattctgtg tgggttcaaa                                       20

<210> SEQ ID NO 202
<211> LENGTH: 20
<212> TYPE: DNA
<213> ORGANISM: Homo sapiens

<400> SEQUENCE: 202
ttatttgttt gtgcatttgg                                       20

<210> SEQ ID NO 203
<211> LENGTH: 20
<212> TYPE: DNA
<213> ORGANISM: Homo sapiens

<400> SEQUENCE: 203
tgattacatc aaggcttcaa                                       20

<210> SEQ ID NO 204
<211> LENGTH: 20
<212> TYPE: DNA
<213> ORGANISM: Homo sapiens

<400> SEQUENCE: 204
gatgtgggtc aaggaattaa                                       20

<210> SEQ ID NO 205
<211> LENGTH: 20
<212> TYPE: DNA
<213> ORGANISM: Homo sapiens

<400> SEQUENCE: 205 cctttattt cttaaacaaa                                        20

<210> SEQ ID NO 206
```

```
<211> LENGTH: 20
<212> TYPE: DNA
<213> ORGANISM: Homo sapiens

<400> SEQUENCE: 206
gattacatca aggcttcaaa                                            20

<210> SEQ ID NO 207
<211> LENGTH: 20
<212> TYPE: DNA
<213> ORGANISM: Homo sapiens

<400> SEQUENCE: 207
tctgtgtggg ttcaaacaca                                            20

<210> SEQ ID NO 208
<211> LENGTH: 20
<212> TYPE: DNA
<213> ORGANISM: Homo sapiens

<400> SEQUENCE: 208
ttgatagtat tgtgcataga                                            20

<210> SEQ ID NO 209
<211> LENGTH: 20
<212> TYPE: DNA
<213> ORGANISM: Homo sapiens

<400> SEQUENCE: 209 tgcctttat ttcttaaaca                                             20

<210> SEQ ID NO 210
<211> LENGTH: 20
<212> TYPE: DNA
<213> ORGANISM: Homo sapiens

<400> SEQUENCE: 210
tccatgaaaa tgcaacaaca                                            20

<210> SEQ ID NO 211
<211> LENGTH: 20
<212> TYPE: DNA
<213> ORGANISM: Homo sapiens

<400> SEQUENCE: 211
ttatttctta aacaaatgta                                            20

<210> SEQ ID NO 212
<211> LENGTH: 20
<212> TYPE: DNA
<213> ORGANISM: Homo sapiens

<400> SEQUENCE: 212
ttaatggttt gaatataaac                                            20

<210> SEQ ID NO 213
<211> LENGTH: 20
<212> TYPE: DNA
<213> ORGANISM: Homo sapiens

<400> SEQUENCE: 213
atgtgggtca aggaattaag                                            20
```

```
<210> SEQ ID NO 214
<211> LENGTH: 20
<212> TYPE: DNA
<213> ORGANISM: Homo sapiens

<400> SEQUENCE: 214
agccgaaatg atcttttcaa                                              20

<210> SEQ ID NO 215
<211> LENGTH: 20
<212> TYPE: DNA
<213> ORGANISM: Homo sapiens

<400> SEQUENCE: 215
gtttgaatat aaacactata                                              20

<210> SEQ ID NO 216
<211> LENGTH: 20
<212> TYPE: DNA
<213> ORGANISM: Homo sapiens

<400> SEQUENCE: 216
tatgcctttt atttcttaaa                                              20

<210> SEQ ID NO 217
<211> LENGTH: 20
<212> TYPE: DNA
<213> ORGANISM: Homo sapiens

<400> SEQUENCE: 217
ttccatgaaa atgcaacaac                                              20

<210> SEQ ID NO 218
<211> LENGTH: 20
<212> TYPE: DNA
<213> ORGANISM: Homo sapiens

<400> SEQUENCE: 218
catctctctt taatataaag                                              20

<210> SEQ ID NO 219
<211> LENGTH: 20
<212> TYPE: DNA
<213> ORGANISM: Homo sapiens

<400> SEQUENCE: 219
ggaattcatc tctctttaat                                              20

<210> SEQ ID NO 220
<211> LENGTH: 20
<212> TYPE: DNA
<213> ORGANISM: Homo sapiens

<400> SEQUENCE: 220
atctatataa agtccttgat                                              20

<210> SEQ ID NO 221
<211> LENGTH: 45
<212> TYPE: DNA
<213> ORGANISM: Homo sapiens

<400> SEQUENCE: 221
tctatataaa gtccttgatt ctgtgtgggt tcaaacacat ttcaa                  45
```

<210> SEQ ID NO 222
<211> LENGTH: 45
<212> TYPE: DNA
<213> ORGANISM: Homo sapiens

<400> SEQUENCE: 222
gctatccagc tattttttatt tgtttgtgca tttgggggga attca                45

<210> SEQ ID NO 223
<211> LENGTH: 45
<212> TYPE: DNA
<213> ORGANISM: Homo sapiens

<400> SEQUENCE: 223
tcttaaacaa atgtatgatt acatcaaggc ttcaaaaata ctcac                45

<210> SEQ ID NO 224
<211> LENGTH: 45
<212> TYPE: DNA
<213> ORGANISM: Homo sapiens

<400> SEQUENCE: 224
gggatgcagc attatgatgt gggtcaagga attaagttag ggaat                45

<210> SEQ ID NO 225
<211> LENGTH: 45
<212> TYPE: DNA
<213> ORGANISM: Homo sapiens

<400> SEQUENCE: 225
aagttaaatt ttatgccttt tatttcttaa acaaatgtat gatta                45

<210> SEQ ID NO 226
<211> LENGTH: 45
<212> TYPE: DNA
<213> ORGANISM: Homo sapiens

<400> SEQUENCE: 226
cttaaacaaa tgtatgatta catcaaggct tcaaaaatac tcaca                45

<210> SEQ ID NO 227
<211> LENGTH: 45
<212> TYPE: DNA
<213> ORGANISM: Homo sapiens

<400> SEQUENCE: 227
tataaagtcc ttgattctgt gtgggttcaa acacatttca aagct                45

<210> SEQ ID NO 228
<211> LENGTH: 45
<212> TYPE: DNA
<213> ORGANISM: Homo sapiens

<400> SEQUENCE: 228
tatatatatt ttaatttgat agtattgtgc atagagccac gtatg                45

<210> SEQ ID NO 229
<211> LENGTH: 45
<212> TYPE: DNA
<213> ORGANISM: Homo sapiens

<400> SEQUENCE: 229
tcaagttaaa ttttatgcct tttatttctt aaacaaatgt atgat                45

<210> SEQ ID NO 230
<211> LENGTH: 45
<212> TYPE: DNA
<213> ORGANISM: Homo sapiens

<400> SEQUENCE: 230
tttaactcaa tattttccat gaaaatgcaa caacatgtat aatat    45

<210> SEQ ID NO 231
<211> LENGTH: 45
<212> TYPE: DNA
<213> ORGANISM: Homo sapiens

<400> SEQUENCE: 231
taaattttat gccttttatt tcttaaacaa atgtatgatt acatc    45

<210> SEQ ID NO 232
<211> LENGTH: 45
<212> TYPE: DNA
<213> ORGANISM: Homo sapiens

<400> SEQUENCE: 232 gttttttgtgt atttgttaat ggtttgaata taaacactat atggc    45

<210> SEQ ID NO 233
<211> LENGTH: 45
<212> TYPE: DNA
<213> ORGANISM: Homo sapiens

<400> SEQUENCE: 233
ggatgcagca ttatgatgtg ggtcaaggaa ttaagttagg gaatg    45

<210> SEQ ID NO 234
<211> LENGTH: 45
<212> TYPE: DNA
<213> ORGANISM: Homo sapiens

<400> SEQUENCE: 234
gtatgagacg tttatagccg aaatgatctt ttcaagttaa atttt    45

<210> SEQ ID NO 235
<211> LENGTH: 45
<212> TYPE: DNA
<213> ORGANISM: Homo sapiens

<400> SEQUENCE: 235
gtgtatttgt taatggtttg aatataaaca ctatatggca gtgtc    45

<210> SEQ ID NO 236
<211> LENGTH: 45
<212> TYPE: DNA
<213> ORGANISM: Homo sapiens

<400> SEQUENCE: 236
tttcaagtta aattttatgc cttttatttc ttaaacaaat gtatg    45

<210> SEQ ID NO 237
<211> LENGTH: 45
<212> TYPE: DNA
<213> ORGANISM: Homo sapiens

<400> SEQUENCE: 237

```
ttttaactca atattttcca tgaaaatgca acaacatgta taata          45

<210> SEQ ID NO 238
<211> LENGTH: 45
<212> TYPE: DNA
<213> ORGANISM: Homo sapiens

<400> SEQUENCE: 238
catttggggg gaattcatct ctctttaata taaagttgga tgcgg          45

<210> SEQ ID NO 239
<211> LENGTH: 45
<212> TYPE: DNA
<213> ORGANISM: Homo sapiens

<400> SEQUENCE: 239
tttgtgcatt tgggggggaat tcatctctct ttaatataaa gttgg         45

<210> SEQ ID NO 240
<211> LENGTH: 45
<212> TYPE: DNA
<213> ORGANISM: Homo sapiens

<400> SEQUENCE: 240
tctgggatca aagctatcta tataaagtcc ttgattctgt gtggg          45

<210> SEQ ID NO 241
<211> LENGTH: 20
<212> TYPE: DNA
<213> ORGANISM: Homo sapiens

<400> SEQUENCE: 241
gactttaccc ttcgactaga                                       20

<210> SEQ ID NO 242
<211> LENGTH: 20
<212> TYPE: DNA
<213> ORGANISM: Homo sapiens

<400> SEQUENCE: 242
caacgtctcc atcatgtata                                       20

<210> SEQ ID NO 243
<211> LENGTH: 20
<212> TYPE: DNA
<213> ORGANISM: Homo sapiens

<400> SEQUENCE: 243
gtcctttctc tgctcctttt                                       20

<210> SEQ ID NO 244
<211> LENGTH: 20
<212> TYPE: DNA
<213> ORGANISM: Homo sapiens

<400> SEQUENCE: 244
tccagtatct ggacaagaac                                       20

<210> SEQ ID NO 245
<211> LENGTH: 20
<212> TYPE: DNA
<213> ORGANISM: Homo sapiens

<400> SEQUENCE: 245
```
attttctgcc ttagagcaag                                                    20

<210> SEQ ID NO 246
<211> LENGTH: 20
<212> TYPE: DNA
<213> ORGANISM: Homo sapiens

<400> SEQUENCE: 246
tttcaccttt ggagaagaca                                                    20

<210> SEQ ID NO 247
<211> LENGTH: 20
<212> TYPE: DNA
<213> ORGANISM: Homo sapiens

<400> SEQUENCE: 247
cattttgaac tgctccttca                                                    20

<210> SEQ ID NO 248
<211> LENGTH: 20
<212> TYPE: DNA
<213> ORGANISM: Homo sapiens

<400> SEQUENCE: 248
tcatcacagt gactcccaaa                                                    20

<210> SEQ ID NO 249
<211> LENGTH: 20
<212> TYPE: DNA
<213> ORGANISM: Homo sapiens

<400> SEQUENCE: 249
gctttcacct ttggagaaga                                                    20

<210> SEQ ID NO 250
<211> LENGTH: 20
<212> TYPE: DNA
<213> ORGANISM: Homo sapiens

<400> SEQUENCE: 250
ctttggcttt cacctttgga                                                    20

<210> SEQ ID NO 251
<211> LENGTH: 20
<212> TYPE: DNA
<213> ORGANISM: Homo sapiens

<400> SEQUENCE: 251
attttgaact gctccttcag                                                    20

<210> SEQ ID NO 252
<211> LENGTH: 20
<212> TYPE: DNA
<213> ORGANISM: Homo sapiens

<400> SEQUENCE: 252
cacattggca atcatcacag                                                    20

<210> SEQ ID NO 253
<211> LENGTH: 20
<212> TYPE: DNA
<213> ORGANISM: Homo sapiens

```
<400> SEQUENCE: 253
tttctgacct cctttggag                                          20

<210> SEQ ID NO 254
<211> LENGTH: 20
<212> TYPE: DNA
<213> ORGANISM: Homo sapiens

<400> SEQUENCE: 254
cgactgggtc attttgaact                                         20

<210> SEQ ID NO 255
<211> LENGTH: 20
<212> TYPE: DNA
<213> ORGANISM: Homo sapiens

<400> SEQUENCE: 255
tacttcacag agctgtctag                                         20

<210> SEQ ID NO 256
<211> LENGTH: 20
<212> TYPE: DNA
<213> ORGANISM: Homo sapiens

<400> SEQUENCE: 256
attggcaatc atcacagtga                                         20

<210> SEQ ID NO 257
<211> LENGTH: 20
<212> TYPE: DNA
<213> ORGANISM: Homo sapiens

<400> SEQUENCE: 257
ctgtttctca tccttggtgt                                         20

<210> SEQ ID NO 258
<211> LENGTH: 20
<212> TYPE: DNA
<213> ORGANISM: Homo sapiens

<400> SEQUENCE: 258
ttgtgaggtg actccagtat                                         20

<210> SEQ ID NO 259
<211> LENGTH: 20
<212> TYPE: DNA
<213> ORGANISM: Homo sapiens

<400> SEQUENCE: 259
tttggctttc acctttggag                                         20

<210> SEQ ID NO 260
<211> LENGTH: 20
<212> TYPE: DNA
<213> ORGANISM: Homo sapiens

<400> SEQUENCE: 260
tggagacaat ggcgacttta                                         20

<210> SEQ ID NO 261
<211> LENGTH: 45
<212> TYPE: DNA
<213> ORGANISM: Homo sapiens
```

<400> SEQUENCE: 261
actggagaca atggcgactt taccctttcga ctagaggatg tgagc                45

<210> SEQ ID NO 262
<211> LENGTH: 45
<212> TYPE: DNA
<213> ORGANISM: Homo sapiens

<400> SEQUENCE: 262
ctacagagat ggcttcaacg tctccatcat gtataacctc actgt                45

<210> SEQ ID NO 263
<211> LENGTH: 45
<212> TYPE: DNA
<213> ORGANISM: Homo sapiens

<400> SEQUENCE: 263
tttctcatcc ttggtgtcct ttctctgctc cttttggtga ctgga                45

<210> SEQ ID NO 264
<211> LENGTH: 45
<212> TYPE: DNA
<213> ORGANISM: Homo sapiens

<400> SEQUENCE: 264
gctttgtgag gtgactccag tatctggaca agaacgcttt gtgtg                45

<210> SEQ ID NO 265
<211> LENGTH: 45
<212> TYPE: DNA
<213> ORGANISM: Homo sapiens

<400> SEQUENCE: 265
gtggcgacca agacgatttt ctgccttaga gcaagggatt caccc                45

<210> SEQ ID NO 266
<211> LENGTH: 45
<212> TYPE: DNA
<213> ORGANISM: Homo sapiens

<400> SEQUENCE: 266
actggagcct ttggctttca cctttggaga agacagtggc gacca                45

<210> SEQ ID NO 267
<211> LENGTH: 45
<212> TYPE: DNA
<213> ORGANISM: Homo sapiens

<400> SEQUENCE: 267
agcctccgac tgggtcattt tgaactgctc cttcagccgc cctga                45

<210> SEQ ID NO 268
<211> LENGTH: 45
<212> TYPE: DNA
<213> ORGANISM: Homo sapiens

<400> SEQUENCE: 268
ctgtcacatt ggcaatcatc acagtgactc ccaaatcctt tgggt                45

<210> SEQ ID NO 269
<211> LENGTH: 45
<212> TYPE: DNA

<213> ORGANISM: Homo sapiens

<400> SEQUENCE: 269
tgactggagc ctttggcttt cacctttgga gaagacagtg gcgac    45

<210> SEQ ID NO 270
<211> LENGTH: 45
<212> TYPE: DNA
<213> ORGANISM: Homo sapiens

<400> SEQUENCE: 270
tttggtgact ggagcctttg gctttcacct ttggagaaga cagtg    45

<210> SEQ ID NO 271
<211> LENGTH: 45
<212> TYPE: DNA
<213> ORGANISM: Homo sapiens

<400> SEQUENCE: 271
gcctccgact gggtcatttt gaactgctcc ttcagccgcc ctgac    45

<210> SEQ ID NO 272
<211> LENGTH: 45
<212> TYPE: DNA
<213> ORGANISM: Homo sapiens

<400> SEQUENCE: 272
gctcaatgcc actgtcacat tggcaatcat cacagtgact cccaa    45

<210> SEQ ID NO 273
<211> LENGTH: 45
<212> TYPE: DNA
<213> ORGANISM: Homo sapiens

<400> SEQUENCE: 273
actgccccct ttccttttct gacctccttt tggagggctc agcgc    45

<210> SEQ ID NO 274
<211> LENGTH: 45
<212> TYPE: DNA
<213> ORGANISM: Homo sapiens

<400> SEQUENCE: 274
atctctcaga gcctccgact gggtcatttt gaactgctcc ttcag    45

<210> SEQ ID NO 275
<211> LENGTH: 45
<212> TYPE: DNA
<213> ORGANISM: Homo sapiens

<400> SEQUENCE: 275
cttggagcag cagtgtactt cacagagctg tctagcccag gtgcc    45

<210> SEQ ID NO 276
<211> LENGTH: 45
<212> TYPE: DNA
<213> ORGANISM: Homo sapiens

<400> SEQUENCE: 276
caatgccact gtcacattgg caatcatcac agtgactccc aaatc    45

<210> SEQ ID NO 277
<211> LENGTH: 45

```
<212> TYPE: DNA
<213> ORGANISM: Homo sapiens

<400> SEQUENCE: 277
gcaggccacc tcctgctgtt tctcatcctt ggtgtccttt ctctg         45

<210> SEQ ID NO 278
<211> LENGTH: 45
<212> TYPE: DNA
<213> ORGANISM: Homo sapiens

<400> SEQUENCE: 278
cctggggaag ctgctttgtg aggtgactcc agtatctgga caaga         45

<210> SEQ ID NO 279
<211> LENGTH: 45
<212> TYPE: DNA
<213> ORGANISM: Homo sapiens

<400> SEQUENCE: 279
ttggtgactg gagcctttgg ctttcacctt tggagaagac agtgg         45

<210> SEQ ID NO 280
<211> LENGTH: 45
<212> TYPE: DNA
<213> ORGANISM: Homo sapiens

<400> SEQUENCE: 280
tgacctcctg gtgactggag acaatggcga ctttacccct cgact         45

<210> SEQ ID NO 281
<211> LENGTH: 20
<212> TYPE: DNA
<213> ORGANISM: Homo sapiens

<400> SEQUENCE: 281
tattatatta taattataat                                     20

<210> SEQ ID NO 282
<211> LENGTH: 20
<212> TYPE: DNA
<213> ORGANISM: Homo sapiens

<400> SEQUENCE: 282
tctattatat tataattata                                     20

<210> SEQ ID NO 283
<211> LENGTH: 20
<212> TYPE: DNA
<213> ORGANISM: Homo sapiens

<400> SEQUENCE: 283
cattcctgaa attatttaaa                                     20

<210> SEQ ID NO 284
<211> LENGTH: 20
<212> TYPE: DNA
<213> ORGANISM: Homo sapiens

<400> SEQUENCE: 284
ctattatatt ataattataa                                     20

<210> SEQ ID NO 285
```

```
<211> LENGTH: 20
<212> TYPE: DNA
<213> ORGANISM: Homo sapiens

<400> SEQUENCE: 285
agtttcaggg aaggtcagaa                                              20

<210> SEQ ID NO 286
<211> LENGTH: 20
<212> TYPE: DNA
<213> ORGANISM: Homo sapiens

<400> SEQUENCE: 286
tgtggttcta ttatattata                                              20

<210> SEQ ID NO 287
<211> LENGTH: 20
<212> TYPE: DNA
<213> ORGANISM: Homo sapiens

<400> SEQUENCE: 287
tgtgttctct gtggactatg                                              20

<210> SEQ ID NO 288
<211> LENGTH: 20
<212> TYPE: DNA
<213> ORGANISM: Homo sapiens

<400> SEQUENCE: 288
cccattcctg aaattattta                                              20

<210> SEQ ID NO 289
<211> LENGTH: 20
<212> TYPE: DNA
<213> ORGANISM: Homo sapiens

<400> SEQUENCE: 289
tgccaccatt gtctttccta                                              20

<210> SEQ ID NO 290
<211> LENGTH: 20
<212> TYPE: DNA
<213> ORGANISM: Homo sapiens

<400> SEQUENCE: 290
aagtttcagg gaaggtcaga                                              20

<210> SEQ ID NO 291
<211> LENGTH: 20
<212> TYPE: DNA
<213> ORGANISM: Homo sapiens

<400> SEQUENCE: 291
ctgtggttct attatattat                                              20

<210> SEQ ID NO 292
<211> LENGTH: 20
<212> TYPE: DNA
<213> ORGANISM: Homo sapiens

<400> SEQUENCE: 292
ttctattata ttataattat                                              20
```

```
<210> SEQ ID NO 293
<211> LENGTH: 20
<212> TYPE: DNA
<213> ORGANISM: Homo sapiens

<400> SEQUENCE: 293
tttcagggaa ggtcagaaga                                              20

<210> SEQ ID NO 294
<211> LENGTH: 20
<212> TYPE: DNA
<213> ORGANISM: Homo sapiens

<400> SEQUENCE: 294
cttggaaccc attcctgaaa                                              20

<210> SEQ ID NO 295
<211> LENGTH: 20
<212> TYPE: DNA
<213> ORGANISM: Homo sapiens

<400> SEQUENCE: 295
tccctgtggt tctattatat                                              20

<210> SEQ ID NO 296
<211> LENGTH: 20
<212> TYPE: DNA
<213> ORGANISM: Homo sapiens

<400> SEQUENCE: 296
cctgtggttc tattatatta                                              20

<210> SEQ ID NO 297
<211> LENGTH: 20
<212> TYPE: DNA
<213> ORGANISM: Homo sapiens

<400> SEQUENCE: 297
tggaacccat tcctgaaatt                                              20

<210> SEQ ID NO 298
<211> LENGTH: 20
<212> TYPE: DNA
<213> ORGANISM: Homo sapiens

<400> SEQUENCE: 298
ccttccctgt ggttctatta                                              20

<210> SEQ ID NO 299
<211> LENGTH: 20
<212> TYPE: DNA
<213> ORGANISM: Homo sapiens

<400> SEQUENCE: 299
ttccctgtgg ttctattata                                              20

<210> SEQ ID NO 300
<211> LENGTH: 20
<212> TYPE: DNA
<213> ORGANISM: Homo sapiens

<400> SEQUENCE: 300
cacaggactc atgtctcaat                                              20
```

<210> SEQ ID NO 301
<211> LENGTH: 45
<212> TYPE: DNA
<213> ORGANISM: Homo sapiens

<400> SEQUENCE: 301
ccttccctgt ggttctatta tattataatt ataattaaat atgag					45

<210> SEQ ID NO 302
<211> LENGTH: 45
<212> TYPE: DNA
<213> ORGANISM: Homo sapiens

<400> SEQUENCE: 302 cccccttccct gtggttctat tatattataa ttataattaa atatg					45

<210> SEQ ID NO 303
<211> LENGTH: 45
<212> TYPE: DNA
<213> ORGANISM: Homo sapiens

<400> SEQUENCE: 303
gctctccttg gaacccattc ctgaaattat ttaaaggggt tggcc					45

<210> SEQ ID NO 304
<211> LENGTH: 45
<212> TYPE: DNA
<213> ORGANISM: Homo sapiens

<400> SEQUENCE: 304
cccttccctg tggttctatt atattataat tataattaaa tatga					45

<210> SEQ ID NO 305
<211> LENGTH: 45
<212> TYPE: DNA
<213> ORGANISM: Homo sapiens

<400> SEQUENCE: 305
ctgcaggcct agagaagttt cagggaaggt cagaagagct cctgg					45

<210> SEQ ID NO 306
<211> LENGTH: 45
<212> TYPE: DNA
<213> ORGANISM: Homo sapiens

<400> SEQUENCE: 306
gggatccccc ttccctgtgg ttctattata ttataattat aatta					45

<210> SEQ ID NO 307
<211> LENGTH: 45
<212> TYPE: DNA
<213> ORGANISM: Homo sapiens

<400> SEQUENCE: 307
cccctcagcc gtgcctgtgt tctctgtgga ctatggggag ctgga					45

<210> SEQ ID NO 308
<211> LENGTH: 45
<212> TYPE: DNA
<213> ORGANISM: Homo sapiens

<400> SEQUENCE: 308
gagctctcct tggaacccat tcctgaaatt atttaaaggg gttgg					45

<210> SEQ ID NO 309
<211> LENGTH: 45
<212> TYPE: DNA
<213> ORGANISM: Homo sapiens

<400> SEQUENCE: 309
tgagcagacg gagtatgcca ccattgtctt tcctagcgga atggg    45

<210> SEQ ID NO 310
<211> LENGTH: 45
<212> TYPE: DNA
<213> ORGANISM: Homo sapiens

<400> SEQUENCE: 310
cctgcaggcc tagagaagtt tcagggaagg tcagaagagc tcctg    45

<210> SEQ ID NO 311
<211> LENGTH: 45
<212> TYPE: DNA
<213> ORGANISM: Homo sapiens

<400> SEQUENCE: 311
agggatcccc cttccctgtg gttctattat attataatta taatt    45

<210> SEQ ID NO 312
<211> LENGTH: 45
<212> TYPE: DNA
<213> ORGANISM: Homo sapiens

<400> SEQUENCE: 312
cccccttccc tgtggttcta ttatattata attataatta aatat    45

<210> SEQ ID NO 313
<211> LENGTH: 45
<212> TYPE: DNA
<213> ORGANISM: Homo sapiens

<400> SEQUENCE: 313
gcaggcctag agaagtttca gggaaggtca gaagagctcc tggct    45

<210> SEQ ID NO 314
<211> LENGTH: 45
<212> TYPE: DNA
<213> ORGANISM: Homo sapiens

<400> SEQUENCE: 314
accctgggag ctctccttgg aacccattcc tgaaattatt taaag    45

<210> SEQ ID NO 315
<211> LENGTH: 45
<212> TYPE: DNA
<213> ORGANISM: Homo sapiens

<400> SEQUENCE: 315
acaagggatc cccttccct gtggttctat tatattataa ttata    45

<210> SEQ ID NO 316
<211> LENGTH: 45
<212> TYPE: DNA
<213> ORGANISM: Homo sapiens

<400> SEQUENCE: 316
aagggatccc ccttccctgt ggttctatta tattataatt ataat          45

<210> SEQ ID NO 317
<211> LENGTH: 45
<212> TYPE: DNA
<213> ORGANISM: Homo sapiens

<400> SEQUENCE: 317
cctgggagct ctccttggaa cccattcctg aaattattta aaggg          45

<210> SEQ ID NO 318
<211> LENGTH: 45
<212> TYPE: DNA
<213> ORGANISM: Homo sapiens

<400> SEQUENCE: 318
gggacaaggg atccccttc cctgtggttc tattatatta taatt           45

<210> SEQ ID NO 319
<211> LENGTH: 45
<212> TYPE: DNA
<213> ORGANISM: Homo sapiens

<400> SEQUENCE: 319
gacaagggat ccccttccc tgtggttcta ttatattata attat           45

<210> SEQ ID NO 320
<211> LENGTH: 45
<212> TYPE: DNA
<213> ORGANISM: Homo sapiens

<400> SEQUENCE: 320
caggcacagc cccaccacag gactcatgtc tcaatgccca cagtg          45

<210> SEQ ID NO 321
<211> LENGTH: 20
<212> TYPE: DNA
<213> ORGANISM: Homo sapiens

<400> SEQUENCE: 321
cctgtttatt acaacttaaa                                      20

<210> SEQ ID NO 322
<211> LENGTH: 20
<212> TYPE: DNA
<213> ORGANISM: Homo sapiens

<400> SEQUENCE: 322
ccattggtgg aattcatgaa                                      20

<210> SEQ ID NO 323
<211> LENGTH: 20
<212> TYPE: DNA
<213> ORGANISM: Homo sapiens

<400> SEQUENCE: 323
ttttccttat aacaaagaca                                      20

<210> SEQ ID NO 324
<211> LENGTH: 20
<212> TYPE: DNA
<213> ORGANISM: Homo sapiens

<400> SEQUENCE: 324
tgtattactt gtttaataat                                              20

<210> SEQ ID NO 325
<211> LENGTH: 20
<212> TYPE: DNA
<213> ORGANISM: Homo sapiens

<400> SEQUENCE: 325
ttattgaatc aaagattgag                                              20

<210> SEQ ID NO 326
<211> LENGTH: 20
<212> TYPE: DNA
<213> ORGANISM: Homo sapiens

<400> SEQUENCE: 326
ttcttaccta agtggataaa                                              20

<210> SEQ ID NO 327
<211> LENGTH: 20
<212> TYPE: DNA
<213> ORGANISM: Homo sapiens

<400> SEQUENCE: 327
atgttgctca gttactcaaa                                              20

<210> SEQ ID NO 328
<211> LENGTH: 20
<212> TYPE: DNA
<213> ORGANISM: Homo sapiens

<400> SEQUENCE: 328
atatttgtac cccaaataac                                              20

<210> SEQ ID NO 329
<211> LENGTH: 20
<212> TYPE: DNA
<213> ORGANISM: Homo sapiens

<400> SEQUENCE: 329
tgtaaatgta aacttctaaa                                              20

<210> SEQ ID NO 330
<211> LENGTH: 20
<212> TYPE: DNA
<213> ORGANISM: Homo sapiens

<400> SEQUENCE: 330
agaatgagtg acatattaca                                              20

<210> SEQ ID NO 331
<211> LENGTH: 20
<212> TYPE: DNA
<213> ORGANISM: Homo sapiens

<400> SEQUENCE: 331
ccatttctaa gcctaccaga                                              20

<210> SEQ ID NO 332
<211> LENGTH: 20
<212> TYPE: DNA
<213> ORGANISM: Homo sapiens

<400> SEQUENCE: 332
atattccaaa agaatgtaaa                                           20

<210> SEQ ID NO 333
<211> LENGTH: 20
<212> TYPE: DNA
<213> ORGANISM: Homo sapiens

<400> SEQUENCE: 333
ttacttccaa tgctatgaag                                           20

<210> SEQ ID NO 334
<211> LENGTH: 20
<212> TYPE: DNA
<213> ORGANISM: Homo sapiens

<400> SEQUENCE: 334
tctttatctg ttcaaagact                                           20

<210> SEQ ID NO 335
<211> LENGTH: 20
<212> TYPE: DNA
<213> ORGANISM: Homo sapiens

<400> SEQUENCE: 335
gtctaagtat acttttaaaa                                           20

<210> SEQ ID NO 336
<211> LENGTH: 20
<212> TYPE: DNA
<213> ORGANISM: Homo sapiens

<400> SEQUENCE: 336
atctttggac atgtactgca                                           20

<210> SEQ ID NO 337
<211> LENGTH: 20
<212> TYPE: DNA
<213> ORGANISM: Homo sapiens

<400> SEQUENCE: 337
gtgttgtatt acttgtttaa                                           20

<210> SEQ ID NO 338
<211> LENGTH: 20
<212> TYPE: DNA
<213> ORGANISM: Homo sapiens

<400> SEQUENCE: 338
tgctgtagat ggcaactaga                                           20

<210> SEQ ID NO 339
<211> LENGTH: 20
<212> TYPE: DNA
<213> ORGANISM: Homo sapiens

<400> SEQUENCE: 339
tctttcactt attcagaaca                                           20

<210> SEQ ID NO 340
<211> LENGTH: 20
<212> TYPE: DNA
<213> ORGANISM: Homo sapiens -continued

<400> SEQUENCE: 340
gtatttgtag taatattcca                                               20

<210> SEQ ID NO 341
<211> LENGTH: 45
<212> TYPE: DNA
<213> ORGANISM: Homo sapiens

<400> SEQUENCE: 341
gttaataaca ttcaacctgt ttattacaac ttaaaaggaa cttca                   45

<210> SEQ ID NO 342
<211> LENGTH: 45
<212> TYPE: DNA
<213> ORGANISM: Homo sapiens

<400> SEQUENCE: 342
ttgctcgacg atgttccatt ggtggaattc atgaagatta ccaac                   45

<210> SEQ ID NO 343
<211> LENGTH: 45
<212> TYPE: DNA
<213> ORGANISM: Homo sapiens

<400> SEQUENCE: 343
tttagggatt tttttttttc cttataacaa agacatcacc aggat                   45

<210> SEQ ID NO 344
<211> LENGTH: 45
<212> TYPE: DNA
<213> ORGANISM: Homo sapiens

<400> SEQUENCE: 344
tttttatagt tgtgttgtat tacttgttta ataataatct ctaat                   45

<210> SEQ ID NO 345
<211> LENGTH: 45
<212> TYPE: DNA
<213> ORGANISM: Homo sapiens

<400> SEQUENCE: 345
tgctgaagat attttttatt gaatcaaaga ttgagttaca attat                   45

<210> SEQ ID NO 346
<211> LENGTH: 45
<212> TYPE: DNA
<213> ORGANISM: Homo sapiens

<400> SEQUENCE: 346
gttacaatta tactttttctt acctaagtgg ataaaatgta cttt                   45

<210> SEQ ID NO 347
<211> LENGTH: 45
<212> TYPE: DNA
<213> ORGANISM: Homo sapiens

<400> SEQUENCE: 347
taaagtatgg gtattatgtt gctcagttac tcaaatggta ctgta                   45

<210> SEQ ID NO 348
<211> LENGTH: 45
<212> TYPE: DNA

<213> ORGANISM: Homo sapiens

<400> SEQUENCE: 348
ggtactgtat tgtttatatt tgtaccccaa ataacatcgt ctgta       45

<210> SEQ ID NO 349
<211> LENGTH: 45
<212> TYPE: DNA
<213> ORGANISM: Homo sapiens

<400> SEQUENCE: 349
ttatgcaatc ttgtttgtaa atgtaaactt ctaaaaatat ggtta       45

<210> SEQ ID NO 350
<211> LENGTH: 45
<212> TYPE: DNA
<213> ORGANISM: Homo sapiens

<400> SEQUENCE: 350
aaccaaagta attttagaat gagtgacata ttacatagga attta       45

<210> SEQ ID NO 351
<211> LENGTH: 45
<212> TYPE: DNA
<213> ORGANISM: Homo sapiens

<400> SEQUENCE: 351
gttgttgttt ttgggccatt tctaagccta ccagatctgc tttat       45

<210> SEQ ID NO 352
<211> LENGTH: 45
<212> TYPE: DNA
<213> ORGANISM: Homo sapiens

<400> SEQUENCE: 352
attgtatttg tagtaatatt ccaaaagaat gtaaatagga aatag       45

<210> SEQ ID NO 353
<211> LENGTH: 45
<212> TYPE: DNA
<213> ORGANISM: Homo sapiens

<400> SEQUENCE: 353
tataataact ggttttact tccaatgcta tgaagtctct gcagg       45

<210> SEQ ID NO 354
<211> LENGTH: 45
<212> TYPE: DNA
<213> ORGANISM: Homo sapiens

<400> SEQUENCE: 354
tgtaagccat ttttttcttt atctgttcaa agacttattt tttaa       45

<210> SEQ ID NO 355
<211> LENGTH: 45
<212> TYPE: DNA
<213> ORGANISM: Homo sapiens

<400> SEQUENCE: 355
cattttaatt gtgttgtcta agtatacttt taaaaaatca gtgg       45

<210> SEQ ID NO 356
<211> LENGTH: 45

```
<212> TYPE: DNA
<213> ORGANISM: Homo sapiens

<400> SEQUENCE: 356
gagatactaa ggattatctt tggacatgta ctgcagcttc ttgtc              45

<210> SEQ ID NO 357
<211> LENGTH: 45
<212> TYPE: DNA
<213> ORGANISM: Homo sapiens

<400> SEQUENCE: 357
tttgttttta tagttgtgtt gtattacttg tttaataata atctc              45

<210> SEQ ID NO 358
<211> LENGTH: 45
<212> TYPE: DNA
<213> ORGANISM: Homo sapiens

<400> SEQUENCE: 358
catgccatat gtagttgctg tagatggcaa ctagaacctt tgagt              45

<210> SEQ ID NO 359
<211> LENGTH: 45
<212> TYPE: DNA
<213> ORGANISM: Homo sapiens

<400> SEQUENCE: 359
gtatactatt attgttcttt cacttattca gaacattaca tgcct              45

<210> SEQ ID NO 360
<211> LENGTH: 45
<212> TYPE: DNA
<213> ORGANISM: Homo sapiens

<400> SEQUENCE: 360
tttaaattgt atattgtatt tgtagtaata ttccaaaaga atgta              45

<210> SEQ ID NO 361
<211> LENGTH: 20
<212> TYPE: DNA
<213> ORGANISM: Homo sapiens

<400> SEQUENCE: 361
ctcatagcaa agagaagata                                           20

<210> SEQ ID NO 362
<211> LENGTH: 20
<212> TYPE: DNA
<213> ORGANISM: Homo sapiens

<400> SEQUENCE: 362
gtattctcat agcaaagaga                                           20

<210> SEQ ID NO 363
<211> LENGTH: 20
<212> TYPE: DNA
<213> ORGANISM: Homo sapiens

<400> SEQUENCE: 363
ttgcttgttg tgtgcttgaa                                           20

<210> SEQ ID NO 364
```

```
<211> LENGTH: 20
<212> TYPE: DNA
<213> ORGANISM: Homo sapiens

<400> SEQUENCE: 364
tattcgtgga ccaaactgaa                                               20

<210> SEQ ID NO 365
<211> LENGTH: 20
<212> TYPE: DNA
<213> ORGANISM: Homo sapiens

<400> SEQUENCE: 365
attgtggagt agacagttgg                                               20

<210> SEQ ID NO 366
<211> LENGTH: 20
<212> TYPE: DNA
<213> ORGANISM: Homo sapiens

<400> SEQUENCE: 366
gttgtgtgct tgaaagaaaa                                               20

<210> SEQ ID NO 367
<211> LENGTH: 20
<212> TYPE: DNA
<213> ORGANISM: Homo sapiens

<400> SEQUENCE: 367
tgttgtgtgc ttgaaagaaa                                               20

<210> SEQ ID NO 368
<211> LENGTH: 20
<212> TYPE: DNA
<213> ORGANISM: Homo sapiens

<400> SEQUENCE: 368
ccctaaactt aaatttcaag                                               20

<210> SEQ ID NO 369
<211> LENGTH: 20
<212> TYPE: DNA
<213> ORGANISM: Homo sapiens

<400> SEQUENCE: 369
acatccagat actggctaaa                                               20

<210> SEQ ID NO 370
<211> LENGTH: 20
<212> TYPE: DNA
<213> ORGANISM: Homo sapiens

<400> SEQUENCE: 370
cattttcaga agataatgac                                               20

<210> SEQ ID NO 371
<211> LENGTH: 20
<212> TYPE: DNA
<213> ORGANISM: Homo sapiens

<400> SEQUENCE: 371
cacattggcc aatgagttac                                               20
```

-continued

```
<210> SEQ ID NO 372
<211> LENGTH: 20
<212> TYPE: DNA
<213> ORGANISM: Homo sapiens

<400> SEQUENCE: 372
tgcttgttgt gtgcttgaaa                                               20

<210> SEQ ID NO 373
<211> LENGTH: 20
<212> TYPE: DNA
<213> ORGANISM: Homo sapiens

<400> SEQUENCE: 373
gagtagacag ttggaagaag                                               20

<210> SEQ ID NO 374
<211> LENGTH: 20
<212> TYPE: DNA
<213> ORGANISM: Homo sapiens

<400> SEQUENCE: 374
ttgttgtgtg cttgaaagaa                                               20

<210> SEQ ID NO 375
<211> LENGTH: 20
<212> TYPE: DNA
<213> ORGANISM: Homo sapiens

<400> SEQUENCE: 375
cggcgcttta attttcaaat                                               20

<210> SEQ ID NO 376
<211> LENGTH: 20
<212> TYPE: DNA
<213> ORGANISM: Homo sapiens

<400> SEQUENCE: 376
tttggcacag aaagtctaaa                                               20

<210> SEQ ID NO 377
<211> LENGTH: 20
<212> TYPE: DNA
<213> ORGANISM: Homo sapiens

<400> SEQUENCE: 377
gatctgtctt gcttattgtt                                               20

<210> SEQ ID NO 378
<211> LENGTH: 20
<212> TYPE: DNA
<213> ORGANISM: Homo sapiens

<400> SEQUENCE: 378
ggtgtgtatt ggccaagttt                                               20

<210> SEQ ID NO 379
<211> LENGTH: 20
<212> TYPE: DNA
<213> ORGANISM: Homo sapiens

<400> SEQUENCE: 379
cccatttcca gaagataatg                                               20
```

<210> SEQ ID NO 380
<211> LENGTH: 20
<212> TYPE: DNA
<213> ORGANISM: Homo sapiens

<400> SEQUENCE: 380
tggcacagaa agtctaaagg                                           20

<210> SEQ ID NO 381
<211> LENGTH: 45
<212> TYPE: DNA
<213> ORGANISM: Homo sapiens

<400> SEQUENCE: 381
ttttcaaatg gtattctcat agcaaagaga agatacagaa tttaa               45

<210> SEQ ID NO 382
<211> LENGTH: 45
<212> TYPE: DNA
<213> ORGANISM: Homo sapiens

<400> SEQUENCE: 382
tttaattttc aaatggtatt ctcatagcaa agagaagata cagaa               45

<210> SEQ ID NO 383
<211> LENGTH: 45
<212> TYPE: DNA
<213> ORGANISM: Homo sapiens

<400> SEQUENCE: 383
tgtattggcc aagttttgct tgttgtgtgc ttgaaagaaa atatc               45

<210> SEQ ID NO 384
<211> LENGTH: 45
<212> TYPE: DNA
<213> ORGANISM: Homo sapiens

<400> SEQUENCE: 384
tctgaccaac ttctgtattc gtggaccaaa ctgaagctat atttt               45

<210> SEQ ID NO 385
<211> LENGTH: 45
<212> TYPE: DNA
<213> ORGANISM: Homo sapiens

<400> SEQUENCE: 385
gctactgctc atgtgattgt ggagtagaca gttggaagaa gtacc               45

<210> SEQ ID NO 386
<211> LENGTH: 45
<212> TYPE: DNA
<213> ORGANISM: Homo sapiens

<400> SEQUENCE: 386
ggccaagttt tgcttgttgt gtgcttgaaa gaaaatatct ctgac               45

<210> SEQ ID NO 387
<211> LENGTH: 45
<212> TYPE: DNA
<213> ORGANISM: Homo sapiens

<400> SEQUENCE: 387
tggccaagtt ttgcttgttg tgtgcttgaa agaaaatatc tctga               45

<210> SEQ ID NO 388
<211> LENGTH: 45
<212> TYPE: DNA
<213> ORGANISM: Homo sapiens

<400> SEQUENCE: 388
ttgacagaga gtggtcccta aacttaaatt tcaagacggt atagg          45

<210> SEQ ID NO 389
<211> LENGTH: 45
<212> TYPE: DNA
<213> ORGANISM: Homo sapiens

<400> SEQUENCE: 389
gatgtgaatt attggacatc cagatactgg ctaaatgggg atttc          45

<210> SEQ ID NO 390
<211> LENGTH: 45
<212> TYPE: DNA
<213> ORGANISM: Homo sapiens

<400> SEQUENCE: 390
ggagcagagt tttcccattt tcagaagata atgactcaca tggga          45

<210> SEQ ID NO 391
<211> LENGTH: 45
<212> TYPE: DNA
<213> ORGANISM: Homo sapiens

<400> SEQUENCE: 391
tctaacacaa atatccacat tggccaatga gttacgggac tctag          45

<210> SEQ ID NO 392
<211> LENGTH: 45
<212> TYPE: DNA
<213> ORGANISM: Homo sapiens

<400> SEQUENCE: 392
gtattggcca agttttgctt gttgtgtgct tgaaagaaaa tatct          45

<210> SEQ ID NO 393
<211> LENGTH: 45
<212> TYPE: DNA
<213> ORGANISM: Homo sapiens

<400> SEQUENCE: 393
gctcatgtga ttgtggagta gacagttgga agaagtaccc agtcc          45

<210> SEQ ID NO 394
<211> LENGTH: 45
<212> TYPE: DNA
<213> ORGANISM: Homo sapiens

<400> SEQUENCE: 394
ttggccaagt tttgcttgtt gtgtgcttga aagaaaatat ctctg          45

<210> SEQ ID NO 395
<211> LENGTH: 45
<212> TYPE: DNA
<213> ORGANISM: Homo sapiens

<400> SEQUENCE: 395
tctggctctt atcttcggcg ctttaattt caaatggtat tctca                45

<210> SEQ ID NO 396
<211> LENGTH: 45
<212> TYPE: DNA
<213> ORGANISM: Homo sapiens

<400> SEQUENCE: 396
tgaaagcata acttttttgg cacagaaagt ctaaaggggc cactg                45

<210> SEQ ID NO 397
<211> LENGTH: 45
<212> TYPE: DNA
<213> ORGANISM: Homo sapiens

<400> SEQUENCE: 397
agacggtata ggcttgatct gtcttgctta ttgttgcccc ctgcg                45

<210> SEQ ID NO 398
<211> LENGTH: 45
<212> TYPE: DNA
<213> ORGANISM: Homo sapiens

<400> SEQUENCE: 398
gaagtgcatt tgattggtgt gtattggcca agttttgctt gttgt                45

<210> SEQ ID NO 399
<211> LENGTH: 45
<212> TYPE: DNA
<213> ORGANISM: Homo sapiens

<400> SEQUENCE: 399
atggagcaga gttttcccat tttcagaaga taatgactca catgg                45

<210> SEQ ID NO 400
<211> LENGTH: 45
<212> TYPE: DNA
<213> ORGANISM: Homo sapiens

<400> SEQUENCE: 400
aaagcataac tttttggca cagaaagtct aaggggcca ctgat                45

<210> SEQ ID NO 401
<211> LENGTH: 20
<212> TYPE: DNA
<213> ORGANISM: Homo sapiens

<400> SEQUENCE: 401
aaatacctgc aaagccttga                                            20

<210> SEQ ID NO 402
<211> LENGTH: 20
<212> TYPE: DNA
<213> ORGANISM: Homo sapiens

<400> SEQUENCE: 402
ttttgtaact gtgcagggca                                            20

<210> SEQ ID NO 403
<211> LENGTH: 20
<212> TYPE: DNA
<213> ORGANISM: Homo sapiens

<400> SEQUENCE: 403

```
agagtgaaga atgcagttaa                                          20

<210> SEQ ID NO 404
<211> LENGTH: 20
<212> TYPE: DNA
<213> ORGANISM: Homo sapiens

<400> SEQUENCE: 404
aagccttgag aggtcttgaa                                          20

<210> SEQ ID NO 405
<211> LENGTH: 20
<212> TYPE: DNA
<213> ORGANISM: Homo sapiens

<400> SEQUENCE: 405
aatacctgca aagccttgag                                          20

<210> SEQ ID NO 406
<211> LENGTH: 20
<212> TYPE: DNA
<213> ORGANISM: Homo sapiens

<400> SEQUENCE: 406
tgcagttaaa tacctgcaaa                                          20

<210> SEQ ID NO 407
<211> LENGTH: 20
<212> TYPE: DNA
<213> ORGANISM: Homo sapiens

<400> SEQUENCE: 407
caacaacaag agagtgaaga                                          20

<210> SEQ ID NO 408
<211> LENGTH: 20
<212> TYPE: DNA
<213> ORGANISM: Homo sapiens

<400> SEQUENCE: 408
ctgaattcaa aaccagggtg                                          20

<210> SEQ ID NO 409
<211> LENGTH: 20
<212> TYPE: DNA
<213> ORGANISM: Homo sapiens

<400> SEQUENCE: 409
atacctgcaa agccttgaga                                          20

<210> SEQ ID NO 410
<211> LENGTH: 20
<212> TYPE: DNA
<213> ORGANISM: Homo sapiens

<400> SEQUENCE: 410
ttccccttag aaagctgaag                                          20

<210> SEQ ID NO 411
<211> LENGTH: 20
<212> TYPE: DNA
<213> ORGANISM: Homo sapiens
```

```
<400> SEQUENCE: 411
ggagagctga attcaaaacc                                               20

<210> SEQ ID NO 412
<211> LENGTH: 20
<212> TYPE: DNA
<213> ORGANISM: Homo sapiens

<400> SEQUENCE: 412
gcagttaaat acctgcaaag                                               20

<210> SEQ ID NO 413
<211> LENGTH: 20
<212> TYPE: DNA
<213> ORGANISM: Homo sapiens

<400> SEQUENCE: 413
gaagaatgca gttaaatacc                                               20

<210> SEQ ID NO 414
<211> LENGTH: 20
<212> TYPE: DNA
<213> ORGANISM: Homo sapiens

<400> SEQUENCE: 414
atgcagttaa atacctgcaa                                               20

<210> SEQ ID NO 415
<211> LENGTH: 20
<212> TYPE: DNA
<213> ORGANISM: Homo sapiens

<400> SEQUENCE: 415
cattcccctt agaaagctga                                               20

<210> SEQ ID NO 416
<211> LENGTH: 20
<212> TYPE: DNA
<213> ORGANISM: Homo sapiens

<400> SEQUENCE: 416
agagctgaat tcaaaaccag                                               20

<210> SEQ ID NO 417
<211> LENGTH: 20
<212> TYPE: DNA
<213> ORGANISM: Homo sapiens

<400> SEQUENCE: 417
gatgggagag ctgaattcaa                                               20

<210> SEQ ID NO 418
<211> LENGTH: 20
<212> TYPE: DNA
<213> ORGANISM: Homo sapiens

<400> SEQUENCE: 418
tgatgggaga gctgaattca                                               20

<210> SEQ ID NO 419
<211> LENGTH: 20
<212> TYPE: DNA
<213> ORGANISM: Homo sapiens
```

```
<400> SEQUENCE: 419
actttgagct cacagtgtca                                          20

<210> SEQ ID NO 420
<211> LENGTH: 20
<212> TYPE: DNA
<213> ORGANISM: Homo sapiens

<400> SEQUENCE: 420
gagtgaagaa tgcagttaaa                                          20

<210> SEQ ID NO 421
<211> LENGTH: 45
<212> TYPE: DNA
<213> ORGANISM: Homo sapiens

<400> SEQUENCE: 421
gtgaagaatg cagttaaata cctgcaaagc cttgagaggt cttga              45

<210> SEQ ID NO 422
<211> LENGTH: 45
<212> TYPE: DNA
<213> ORGANISM: Homo sapiens

<400> SEQUENCE: 422
cagggatgcc atcgtttttg taactgtgca gggcagggcc atctg              45

<210> SEQ ID NO 423
<211> LENGTH: 45
<212> TYPE: DNA
<213> ORGANISM: Homo sapiens

<400> SEQUENCE: 423
gaccccaaca acaagagagt gaagaatgca gttaaatacc tgcaa              45

<210> SEQ ID NO 424
<211> LENGTH: 45
<212> TYPE: DNA
<213> ORGANISM: Homo sapiens

<400> SEQUENCE: 424
agttaaatac ctgcaaagcc ttgagaggtc ttgaagcctc ctcac              45

<210> SEQ ID NO 425
<211> LENGTH: 45
<212> TYPE: DNA
<213> ORGANISM: Homo sapiens

<400> SEQUENCE: 425
tgaagaatgc agttaaatac ctgcaaagcc ttgagaggtc ttgaa              45

<210> SEQ ID NO 426
<211> LENGTH: 45
<212> TYPE: DNA
<213> ORGANISM: Homo sapiens

<400> SEQUENCE: 426
caagagagtg aagaatgcag ttaaatacct gcaaagcctt gagag              45

<210> SEQ ID NO 427
<211> LENGTH: 45
<212> TYPE: DNA
```

<213> ORGANISM: Homo sapiens

<400> SEQUENCE: 427
catctgttcg acccccaaca acaagagagt gaagaatgca gttaa     45

<210> SEQ ID NO 428
<211> LENGTH: 45
<212> TYPE: DNA
<213> ORGANISM: Homo sapiens

<400> SEQUENCE: 428
ctgctgatgg gagagctgaa ttcaaaacca gggtgtctcc ctgag     45

<210> SEQ ID NO 429
<211> LENGTH: 45
<212> TYPE: DNA
<213> ORGANISM: Homo sapiens

<400> SEQUENCE: 429
gaagaatgca gttaaatacc tgcaaagcct tgagaggtct tgaag     45

<210> SEQ ID NO 430
<211> LENGTH: 45
<212> TYPE: DNA
<213> ORGANISM: Homo sapiens

<400> SEQUENCE: 430
acttcaaggg agccattccc cttagaaagc tgaagacgtg gtacc     45

<210> SEQ ID NO 431
<211> LENGTH: 45
<212> TYPE: DNA
<213> ORGANISM: Homo sapiens

<400> SEQUENCE: 431
caccgcctgc tgatgggaga gctgaattca aaaccagggt gtctc     45

<210> SEQ ID NO 432
<211> LENGTH: 45
<212> TYPE: DNA
<213> ORGANISM: Homo sapiens

<400> SEQUENCE: 432
aagagagtga agaatgcagt taaatacctg caaagccttg agagg     45

<210> SEQ ID NO 433
<211> LENGTH: 45
<212> TYPE: DNA
<213> ORGANISM: Homo sapiens

<400> SEQUENCE: 433
caacaacaag agagtgaaga atgcagttaa atacctgcaa agcct     45

<210> SEQ ID NO 434
<211> LENGTH: 45
<212> TYPE: DNA
<213> ORGANISM: Homo sapiens

<400> SEQUENCE: 434
acaagagagt gaagaatgca gttaaatacc tgcaaagcct tgaga     45

<210> SEQ ID NO 435
<211> LENGTH: 45

```
<212> TYPE: DNA
<213> ORGANISM: Homo sapiens

<400> SEQUENCE: 435
gtacttcaag ggagccattc cccttagaaa gctgaagacg tggta          45

<210> SEQ ID NO 436
<211> LENGTH: 45
<212> TYPE: DNA
<213> ORGANISM: Homo sapiens

<400> SEQUENCE: 436
ccgcctgctg atgggagagc tgaattcaaa accagggtgt ctccc          45

<210> SEQ ID NO 437
<211> LENGTH: 45
<212> TYPE: DNA
<213> ORGANISM: Homo sapiens

<400> SEQUENCE: 437
gtgtcaccgc ctgctgatgg gagagctgaa ttcaaaacca gggtg          45

<210> SEQ ID NO 438
<211> LENGTH: 45
<212> TYPE: DNA
<213> ORGANISM: Homo sapiens

<400> SEQUENCE: 438
agtgtcaccg cctgctgatg ggagagctga attcaaaacc aggt           45

<210> SEQ ID NO 439
<211> LENGTH: 45
<212> TYPE: DNA
<213> ORGANISM: Homo sapiens

<400> SEQUENCE: 439
gctcagagag aagtgacttt gagctcacag tgtcaccgcc tgctg          45

<210> SEQ ID NO 440
<211> LENGTH: 45
<212> TYPE: DNA
<213> ORGANISM: Homo sapiens

<400> SEQUENCE: 440
accccaacaa caagagagtg aagaatgcag ttaaatacct gcaaa          45

<210> SEQ ID NO 441
<211> LENGTH: 20
<212> TYPE: DNA
<213> ORGANISM: Homo sapiens

<400> SEQUENCE: 441
gtatttgaaa acagagtaaa                                      20

<210> SEQ ID NO 442
<211> LENGTH: 20
<212> TYPE: DNA
<213> ORGANISM: Homo sapiens

<400> SEQUENCE: 442
caataagctg agccaatgaa                                      20

<210> SEQ ID NO 443
```

-continued

```
<211> LENGTH: 20
<212> TYPE: DNA
<213> ORGANISM: Homo sapiens

<400> SEQUENCE: 443
tacttaagag gccaaataga                                                    20

<210> SEQ ID NO 444
<211> LENGTH: 20
<212> TYPE: DNA
<213> ORGANISM: Homo sapiens

<400> SEQUENCE: 444
atgtatttga aaacagagta                                                    20

<210> SEQ ID NO 445
<211> LENGTH: 20
<212> TYPE: DNA
<213> ORGANISM: Homo sapiens

<400> SEQUENCE: 445
ttcatacagc aagtatggga                                                    20

<210> SEQ ID NO 446
<211> LENGTH: 20
<212> TYPE: DNA
<213> ORGANISM: Homo sapiens

<400> SEQUENCE: 446
ctgcagacaa aatcaataaa                                                    20

<210> SEQ ID NO 447
<211> LENGTH: 20
<212> TYPE: DNA
<213> ORGANISM: Homo sapiens

<400> SEQUENCE: 447
tgcagacaaa atcaataaaa                                                    20

<210> SEQ ID NO 448
<211> LENGTH: 20
<212> TYPE: DNA
<213> ORGANISM: Homo sapiens

<400> SEQUENCE: 448
ggccaaatag atgaatggaa                                                    20

<210> SEQ ID NO 449
<211> LENGTH: 20
<212> TYPE: DNA
<213> ORGANISM: Homo sapiens

<400> SEQUENCE: 449
aataagctga gccaatgaag                                                    20

<210> SEQ ID NO 450
<211> LENGTH: 20
<212> TYPE: DNA
<213> ORGANISM: Homo sapiens

<400> SEQUENCE: 450
aagaggccaa atagatgaat                                                    20
```

```
<210> SEQ ID NO 451
<211> LENGTH: 20
<212> TYPE: DNA
<213> ORGANISM: Homo sapiens

<400> SEQUENCE: 451
aaatagatga atggaagaat                                               20

<210> SEQ ID NO 452
<211> LENGTH: 20
<212> TYPE: DNA
<213> ORGANISM: Homo sapiens

<400> SEQUENCE: 452
aaacagagta aatacttaag                                               20

<210> SEQ ID NO 453
<211> LENGTH: 20
<212> TYPE: DNA
<213> ORGANISM: Homo sapiens

<400> SEQUENCE: 453
agctggagtt atatatgtat                                               20

<210> SEQ ID NO 454
<211> LENGTH: 20
<212> TYPE: DNA
<213> ORGANISM: Homo sapiens

<400> SEQUENCE: 454
acctttgact tggtattata                                               20

<210> SEQ ID NO 455
<211> LENGTH: 20
<212> TYPE: DNA
<213> ORGANISM: Homo sapiens

<400> SEQUENCE: 455
aaccttcagg gataaggaga                                               20

<210> SEQ ID NO 456
<211> LENGTH: 20
<212> TYPE: DNA
<213> ORGANISM: Homo sapiens

<400> SEQUENCE: 456
gtgaaagact acctttgact                                               20

<210> SEQ ID NO 457
<211> LENGTH: 20
<212> TYPE: DNA
<213> ORGANISM: Homo sapiens

<400> SEQUENCE: 457
ctatggtgtg aaagactacc                                               20

<210> SEQ ID NO 458
<211> LENGTH: 20
<212> TYPE: DNA
<213> ORGANISM: Homo sapiens

<400> SEQUENCE: 458
cactacggct ggctaatttt                                               20
```

<210> SEQ ID NO 459
<211> LENGTH: 20
<212> TYPE: DNA
<213> ORGANISM: Homo sapiens

<400> SEQUENCE: 459
ggagttatat atgtatttga                                          20

<210> SEQ ID NO 460
<211> LENGTH: 20
<212> TYPE: DNA
<213> ORGANISM: Homo sapiens

<400> SEQUENCE: 460
atatcaatac agagactcaa                                          20

<210> SEQ ID NO 461
<211> LENGTH: 45
<212> TYPE: DNA
<213> ORGANISM: Homo sapiens

<400> SEQUENCE: 461
gctggagtta tatatgtatt tgaaaacaga gtaaatactt aagag               45

<210> SEQ ID NO 462
<211> LENGTH: 45
<212> TYPE: DNA
<213> ORGANISM: Homo sapiens

<400> SEQUENCE: 462
ggtgaagatg attctcaata agctgagcca atgaagagcc tactc               45

<210> SEQ ID NO 463
<211> LENGTH: 45
<212> TYPE: DNA
<213> ORGANISM: Homo sapiens

<400> SEQUENCE: 463
tgaaaacaga gtaaatactt aagaggccaa atagatgaat ggaag               45

<210> SEQ ID NO 464
<211> LENGTH: 45
<212> TYPE: DNA
<213> ORGANISM: Homo sapiens

<400> SEQUENCE: 464
aagctggagt tatatatgta tttgaaaaca gagtaaatac ttaag               45

<210> SEQ ID NO 465
<211> LENGTH: 45
<212> TYPE: DNA
<213> ORGANISM: Homo sapiens

<400> SEQUENCE: 465
ttgagaaata ttcttttcat acagcaagta tgggacagca gtgtc               45

<210> SEQ ID NO 466
<211> LENGTH: 45
<212> TYPE: DNA
<213> ORGANISM: Homo sapiens

<400> SEQUENCE: 466
gagcccagaa agtggctgca gacaaaatca ataaaactaa tgtcc               45

```
<210> SEQ ID NO 467
<211> LENGTH: 45
<212> TYPE: DNA
<213> ORGANISM: Homo sapiens

<400> SEQUENCE: 467
agcccagaaa gtggctgcag acaaaatcaa taaaactaat gtccc            45

<210> SEQ ID NO 468
<211> LENGTH: 45
<212> TYPE: DNA
<213> ORGANISM: Homo sapiens

<400> SEQUENCE: 468
agtaaatact taagaggcca aatagatgaa tggaagaatt ttagg            45

<210> SEQ ID NO 469
<211> LENGTH: 45
<212> TYPE: DNA
<213> ORGANISM: Homo sapiens

<400> SEQUENCE: 469
gtgaagatga ttctcaataa gctgagccaa tgaagagcct actct            45

<210> SEQ ID NO 470
<211> LENGTH: 45
<212> TYPE: DNA
<213> ORGANISM: Homo sapiens

<400> SEQUENCE: 470
acagagtaaa tacttaagag gccaaataga tgaatggaag aattt            45

<210> SEQ ID NO 471
<211> LENGTH: 45
<212> TYPE: DNA
<213> ORGANISM: Homo sapiens

<400> SEQUENCE: 471
aatacttaag aggccaaata gatgaatgga agaattttag gaact            45

<210> SEQ ID NO 472
<211> LENGTH: 45
<212> TYPE: DNA
<213> ORGANISM: Homo sapiens

<400> SEQUENCE: 472
tatatatgta tttgaaaaca gagtaaatac ttaagaggcc aaata            45

<210> SEQ ID NO 473
<211> LENGTH: 45
<212> TYPE: DNA
<213> ORGANISM: Homo sapiens

<400> SEQUENCE: 473
tgacttggta ttataagctg gagttatata tgtatttgaa aacag            45

<210> SEQ ID NO 474
<211> LENGTH: 45
<212> TYPE: DNA
<213> ORGANISM: Homo sapiens

<400> SEQUENCE: 474
```

```
atggtgtgaa agactacctt tgacttggta ttataagctg gagtt            45

<210> SEQ ID NO 475
<211> LENGTH: 45
<212> TYPE: DNA
<213> ORGANISM: Homo sapiens

<400> SEQUENCE: 475
tggcgtggtg ttgctaacct tcagggataa ggagatctgt gccga            45

<210> SEQ ID NO 476
<211> LENGTH: 45
<212> TYPE: DNA
<213> ORGANISM: Homo sapiens

<400> SEQUENCE: 476
aattcatgct atggtgtgaa agactacctt tgacttggta ttata            45

<210> SEQ ID NO 477
<211> LENGTH: 45
<212> TYPE: DNA
<213> ORGANISM: Homo sapiens

<400> SEQUENCE: 477
acaatcaaat tcatgctatg gtgtgaaaga ctacctttga cttgg            45

<210> SEQ ID NO 478
<211> LENGTH: 45
<212> TYPE: DNA
<213> ORGANISM: Homo sapiens

<400> SEQUENCE: 478
attacaggtg tgtgccacta cggctggcta attttttgtat ttta            45

<210> SEQ ID NO 479
<211> LENGTH: 45
<212> TYPE: DNA
<213> ORGANISM: Homo sapiens

<400> SEQUENCE: 479
ttggtattat aagctggagt tatatatgta tttgaaaaca gagta            45

<210> SEQ ID NO 480
<211> LENGTH: 45
<212> TYPE: DNA
<213> ORGANISM: Homo sapiens

<400> SEQUENCE: 480
ccaaaaggca gttacatatc aatacagaga ctcaaggtca ctaga            45

<210> SEQ ID NO 481
<211> LENGTH: 20
<212> TYPE: DNA
<213> ORGANISM: Homo sapiens

<400> SEQUENCE: 481
ctgttttgtt aatgaagaaa                                        20

<210> SEQ ID NO 482
<211> LENGTH: 20
<212> TYPE: DNA
<213> ORGANISM: Homo sapiens

<400> SEQUENCE: 482
```
ttgtatataa atgtatttat                                           20

<210> SEQ ID NO 483
<211> LENGTH: 20
<212> TYPE: DNA
<213> ORGANISM: Homo sapiens

<400> SEQUENCE: 483
tgttttgtta atgaagaaat                                           20

<210> SEQ ID NO 484
<211> LENGTH: 20
<212> TYPE: DNA
<213> ORGANISM: Homo sapiens

<400> SEQUENCE: 484
aattttggta aatatgtaca                                           20

<210> SEQ ID NO 485
<211> LENGTH: 20
<212> TYPE: DNA
<213> ORGANISM: Homo sapiens

<400> SEQUENCE: 485
aaattttatg aatgacaaaa                                           20

<210> SEQ ID NO 486
<211> LENGTH: 20
<212> TYPE: DNA
<213> ORGANISM: Homo sapiens

<400> SEQUENCE: 486
tttatggaat attgtgcaaa                                           20

<210> SEQ ID NO 487
<211> LENGTH: 20
<212> TYPE: DNA
<213> ORGANISM: Homo sapiens

<400> SEQUENCE: 487
ttactgtttt gttaatgaag                                           20

<210> SEQ ID NO 488
<211> LENGTH: 20
<212> TYPE: DNA
<213> ORGANISM: Homo sapiens

<400> SEQUENCE: 488
ttcttgaatt agaaacacaa                                           20

<210> SEQ ID NO 489
<211> LENGTH: 20
<212> TYPE: DNA
<213> ORGANISM: Homo sapiens

<400> SEQUENCE: 489
cagttgctct taagagaata                                           20

<210> SEQ ID NO 490
<211> LENGTH: 20
<212> TYPE: DNA
<213> ORGANISM: Homo sapiens

```
<400> SEQUENCE: 490
caacttcaaa agacaccaag                                               20

<210> SEQ ID NO 491
<211> LENGTH: 20
<212> TYPE: DNA
<213> ORGANISM: Homo sapiens

<400> SEQUENCE: 491
tccaaaataa attttatgaa                                               20

<210> SEQ ID NO 492
<211> LENGTH: 20
<212> TYPE: DNA
<213> ORGANISM: Homo sapiens

<400> SEQUENCE: 492
gaactgaatt acgcataaga                                               20

<210> SEQ ID NO 493
<211> LENGTH: 20
<212> TYPE: DNA
<213> ORGANISM: Homo sapiens

<400> SEQUENCE: 493
ggattttgtg acaaaccagg                                               20

<210> SEQ ID NO 494
<211> LENGTH: 20
<212> TYPE: DNA
<213> ORGANISM: Homo sapiens

<400> SEQUENCE: 494
tactgttttg ttaatgaaga                                               20

<210> SEQ ID NO 495
<211> LENGTH: 20
<212> TYPE: DNA
<213> ORGANISM: Homo sapiens

<400> SEQUENCE: 495
tttggtaaat atgtacaaag                                               20

<210> SEQ ID NO 496
<211> LENGTH: 20
<212> TYPE: DNA
<213> ORGANISM: Homo sapiens

<400> SEQUENCE: 496
ccaaaataaa ttttatgaat                                               20

<210> SEQ ID NO 497
<211> LENGTH: 20
<212> TYPE: DNA
<213> ORGANISM: Homo sapiens

<400> SEQUENCE: 497
ataatttaaa ttttggtaaa                                               20

<210> SEQ ID NO 498
<211> LENGTH: 20
<212> TYPE: DNA
<213> ORGANISM: Homo sapiens
```

```
<400> SEQUENCE: 498
aaatgggtga actgaattac                                               20

<210> SEQ ID NO 499
<211> LENGTH: 20
<212> TYPE: DNA
<213> ORGANISM: Homo sapiens

<400> SEQUENCE: 499
ttcgggtcta tgtgactata                                               20

<210> SEQ ID NO 500
<211> LENGTH: 20
<212> TYPE: DNA
<213> ORGANISM: Homo sapiens

<400> SEQUENCE: 500
actgttttgt taatgaagaa                                               20

<210> SEQ ID NO 501
<211> LENGTH: 45
<212> TYPE: DNA
<213> ORGANISM: Homo sapiens

<400> SEQUENCE: 501
tatttgagtt ttttactgtt ttgttaatga agaaattcct tttta                   45

<210> SEQ ID NO 502
<211> LENGTH: 45
<212> TYPE: DNA
<213> ORGANISM: Homo sapiens

<400> SEQUENCE: 502
tgtgactata tttttttgta tataaatgta tttatggaat attgt                   45

<210> SEQ ID NO 503
<211> LENGTH: 45
<212> TYPE: DNA
<213> ORGANISM: Homo sapiens

<400> SEQUENCE: 503
atttgagttt tttactgttt tgttaatgaa gaaattcctt tttaa                   45

<210> SEQ ID NO 504
<211> LENGTH: 45
<212> TYPE: DNA
<213> ORGANISM: Homo sapiens

<400> SEQUENCE: 504 gtttttata atttaaattt tggtaaatat gtacaaaggc acttc                    45

<210> SEQ ID NO 505
<211> LENGTH: 45
<212> TYPE: DNA
<213> ORGANISM: Homo sapiens

<400> SEQUENCE: 505 atattttttcc aaaataaatt ttatgaatga caaaaaaaaa aaaaa                  45

<210> SEQ ID NO 506
<211> LENGTH: 45
<212> TYPE: DNA
```

<213> ORGANISM: Homo sapiens

<400> SEQUENCE: 506
ttgtatataa atgtatttat ggaatattgt gcaaatgtta tttga         45

<210> SEQ ID NO 507
<211> LENGTH: 45
<212> TYPE: DNA
<213> ORGANISM: Homo sapiens

<400> SEQUENCE: 507
tgttatttga gtttttact gttttgttaa tgaagaaatt ccttt         45

<210> SEQ ID NO 508
<211> LENGTH: 45
<212> TYPE: DNA
<213> ORGANISM: Homo sapiens

<400> SEQUENCE: 508
ttatgagcca gtctttctt gaattagaaa cacaaacact gcctt         45

<210> SEQ ID NO 509
<211> LENGTH: 45
<212> TYPE: DNA
<213> ORGANISM: Homo sapiens

<400> SEQUENCE: 509
ccgttgcact atggacagtt gctcttaaga gaatatatat ttaaa         45

<210> SEQ ID NO 510
<211> LENGTH: 45
<212> TYPE: DNA
<213> ORGANISM: Homo sapiens

<400> SEQUENCE: 510
cggactcggg ctgttcaact tcaaaagaca ccaagtacca gtcgg         45

<210> SEQ ID NO 511
<211> LENGTH: 45
<212> TYPE: DNA
<213> ORGANISM: Homo sapiens

<400> SEQUENCE: 511
tttttaaaat attttccaa aataaatttt atgaatgaca aaaaa         45

<210> SEQ ID NO 512
<211> LENGTH: 45
<212> TYPE: DNA
<213> ORGANISM: Homo sapiens

<400> SEQUENCE: 512
tatatttaaa tgggtgaact gaattacgca taagaagcat gcact         45

<210> SEQ ID NO 513
<211> LENGTH: 45
<212> TYPE: DNA
<213> ORGANISM: Homo sapiens

<400> SEQUENCE: 513
tgtgatgagc agcatggatt ttgtgacaaa ccaggggaat gcaag         45

<210> SEQ ID NO 514
<211> LENGTH: 45

```
<212> TYPE: DNA
<213> ORGANISM: Homo sapiens

<400> SEQUENCE: 514
gttatttgag ttttttactg ttttgttaat gaagaaattc ctttt            45

<210> SEQ ID NO 515
<211> LENGTH: 45
<212> TYPE: DNA
<213> ORGANISM: Homo sapiens

<400> SEQUENCE: 515
ttttataatt taaattttgg taaatatgta caaaggcact tcggg            45

<210> SEQ ID NO 516
<211> LENGTH: 45
<212> TYPE: DNA
<213> ORGANISM: Homo sapiens

<400> SEQUENCE: 516
ttttaaaata tttttccaaa ataaatttta tgaatgacaa aaaaa            45

<210> SEQ ID NO 517
<211> LENGTH: 45
<212> TYPE: DNA
<213> ORGANISM: Homo sapiens

<400> SEQUENCE: 517
tgatgttcgt tttttataat ttaaattttg gtaaatatgt acaaa            45

<210> SEQ ID NO 518
<211> LENGTH: 45
<212> TYPE: DNA
<213> ORGANISM: Homo sapiens

<400> SEQUENCE: 518
agagaatata tatttaaatg ggtgaactga attacgcata agaag            45

<210> SEQ ID NO 519
<211> LENGTH: 45
<212> TYPE: DNA
<213> ORGANISM: Homo sapiens

<400> SEQUENCE: 519
tatgtacaaa ggcacttcgg gtctatgtga ctatattttt ttgta            45

<210> SEQ ID NO 520
<211> LENGTH: 45
<212> TYPE: DNA
<213> ORGANISM: Homo sapiens

<400> SEQUENCE: 520
ttatttgagt ttttactgt tttgttaatg aagaaattcc ttttt             45

<210> SEQ ID NO 521
<211> LENGTH: 20
<212> TYPE: DNA
<213> ORGANISM: Homo sapiens

<400> SEQUENCE: 521
tagctcctca actcacctaa                                        20

<210> SEQ ID NO 522
```

```
<211> LENGTH: 20
<212> TYPE: DNA
<213> ORGANISM: Homo sapiens

<400> SEQUENCE: 522
atgttttcct ataatataat                                               20

<210> SEQ ID NO 523
<211> LENGTH: 20
<212> TYPE: DNA
<213> ORGANISM: Homo sapiens

<400> SEQUENCE: 523
ttttcctata atataataaa                                               20

<210> SEQ ID NO 524
<211> LENGTH: 20
<212> TYPE: DNA
<213> ORGANISM: Homo sapiens

<400> SEQUENCE: 524
ttcctataat ataataaata                                               20

<210> SEQ ID NO 525
<211> LENGTH: 20
<212> TYPE: DNA
<213> ORGANISM: Homo sapiens

<400> SEQUENCE: 525
tgcatttgag gtcaagtaag                                               20

<210> SEQ ID NO 526
<211> LENGTH: 20
<212> TYPE: DNA
<213> ORGANISM: Homo sapiens

<400> SEQUENCE: 526
attgattgtc agctactaat                                               20

<210> SEQ ID NO 527
<211> LENGTH: 20
<212> TYPE: DNA
<213> ORGANISM: Homo sapiens

<400> SEQUENCE: 527
aaatgaaaac atgtaataaa                                               20

<210> SEQ ID NO 528
<211> LENGTH: 20
<212> TYPE: DNA
<213> ORGANISM: Homo sapiens

<400> SEQUENCE: 528
attgtgaagt acatattagg                                               20

<210> SEQ ID NO 529
<211> LENGTH: 20
<212> TYPE: DNA
<213> ORGANISM: Homo sapiens

<400> SEQUENCE: 529
gctttctgga gtgaagtata                                               20
```

```
<210> SEQ ID NO 530
<211> LENGTH: 20
<212> TYPE: DNA
<213> ORGANISM: Homo sapiens

<400> SEQUENCE: 530
catttggtca agattttgaa                                              20

<210> SEQ ID NO 531
<211> LENGTH: 20
<212> TYPE: DNA
<213> ORGANISM: Homo sapiens

<400> SEQUENCE: 531
ggcttatata agctctaaga                                              20

<210> SEQ ID NO 532
<211> LENGTH: 20
<212> TYPE: DNA
<213> ORGANISM: Homo sapiens

<400> SEQUENCE: 532
accagtgctg atcatttata                                              20

<210> SEQ ID NO 533
<211> LENGTH: 20
<212> TYPE: DNA
<213> ORGANISM: Homo sapiens

<400> SEQUENCE: 533
ccatttaaca ggcaagtcca                                              20

<210> SEQ ID NO 534
<211> LENGTH: 20
<212> TYPE: DNA
<213> ORGANISM: Homo sapiens

<400> SEQUENCE: 534
aagtacatat taggaaaata                                              20

<210> SEQ ID NO 535
<211> LENGTH: 20
<212> TYPE: DNA
<213> ORGANISM: Homo sapiens

<400> SEQUENCE: 535
tgtgtgtgtg tatgactaaa                                              20

<210> SEQ ID NO 536
<211> LENGTH: 20
<212> TYPE: DNA
<213> ORGANISM: Homo sapiens

<400> SEQUENCE: 536
aagagggaga agcatgaaaa                                              20

<210> SEQ ID NO 537
<211> LENGTH: 20
<212> TYPE: DNA
<213> ORGANISM: Homo sapiens

<400> SEQUENCE: 537
gtgtatgact aaagagagaa                                              20
```

<210> SEQ ID NO 538
<211> LENGTH: 20
<212> TYPE: DNA
<213> ORGANISM: Homo sapiens

<400> SEQUENCE: 538
gtatttccag tgcaattgta                                           20

<210> SEQ ID NO 539
<211> LENGTH: 20
<212> TYPE: DNA
<213> ORGANISM: Homo sapiens

<400> SEQUENCE: 539
caactctaat agtgcttaaa                                           20

<210> SEQ ID NO 540
<211> LENGTH: 20
<212> TYPE: DNA
<213> ORGANISM: Homo sapiens

<400> SEQUENCE: 540
gtgtgtgtgt atgactaaag                                           20

<210> SEQ ID NO 541
<211> LENGTH: 45
<212> TYPE: DNA
<213> ORGANISM: Homo sapiens

<400> SEQUENCE: 541
ggttcaaaat gtctgtagct cctcaactca cctaatgttt atgag               45

<210> SEQ ID NO 542
<211> LENGTH: 45
<212> TYPE: DNA
<213> ORGANISM: Homo sapiens

<400> SEQUENCE: 542
tgtcagctac taatgatgtt ttcctataat ataataaata tttat               45

<210> SEQ ID NO 543
<211> LENGTH: 45
<212> TYPE: DNA
<213> ORGANISM: Homo sapiens

<400> SEQUENCE: 543
cagctactaa tgatgttttc ctataatata ataaatattt atgta               45

<210> SEQ ID NO 544
<211> LENGTH: 45
<212> TYPE: DNA
<213> ORGANISM: Homo sapiens

<400> SEQUENCE: 544
gctactaatg atgttttcct ataatataat aaatatttat gtaga               45

<210> SEQ ID NO 545
<211> LENGTH: 45
<212> TYPE: DNA
<213> ORGANISM: Homo sapiens

<400> SEQUENCE: 545
gagggtcttc ttacatgcat ttgaggtcaa gtaagaagac atgaa               45

-continued

<210> SEQ ID NO 546
<211> LENGTH: 45
<212> TYPE: DNA
<213> ORGANISM: Homo sapiens

<400> SEQUENCE: 546
tagtgcttaa aaatcattga ttgtcagcta ctaatgatgt tttcc                45

<210> SEQ ID NO 547
<211> LENGTH: 45
<212> TYPE: DNA
<213> ORGANISM: Homo sapiens

<400> SEQUENCE: 547
atgtgcattt ttgtgaaatg aaaacatgta ataaaaagta tatgt                45

<210> SEQ ID NO 548
<211> LENGTH: 45
<212> TYPE: DNA
<213> ORGANISM: Homo sapiens

<400> SEQUENCE: 548
agagagaatg tagatattgt gaagtacata ttaggaaaat atggg                45

<210> SEQ ID NO 549
<211> LENGTH: 45
<212> TYPE: DNA
<213> ORGANISM: Homo sapiens

<400> SEQUENCE: 549
ctatggaatt gtcctgcttt ctggagtgaa gtataagaag ggtgg                45

<210> SEQ ID NO 550
<211> LENGTH: 45
<212> TYPE: DNA
<213> ORGANISM: Homo sapiens

<400> SEQUENCE: 550
ggaaaatatg ggttgcattt ggtcaagatt ttgaatgctt cctga                45

<210> SEQ ID NO 551
<211> LENGTH: 45
<212> TYPE: DNA
<213> ORGANISM: Homo sapiens

<400> SEQUENCE: 551
tctcagacgt ttttcggctt atataagctc taagagaagc acttt                45

<210> SEQ ID NO 552
<211> LENGTH: 45
<212> TYPE: DNA
<213> ORGANISM: Homo sapiens

<400> SEQUENCE: 552
gcagtgttca atcttaccag tgctgatcat ttatatgtca acgta                45

<210> SEQ ID NO 553
<211> LENGTH: 45
<212> TYPE: DNA
<213> ORGANISM: Homo sapiens

<400> SEQUENCE: 553
gctgaggaaa gtggcccatt taacaggcaa gtccaactca aggtc                45

<210> SEQ ID NO 554
<211> LENGTH: 45
<212> TYPE: DNA
<213> ORGANISM: Homo sapiens

<400> SEQUENCE: 554
aatgtagata ttgtgaagta catattagga aaatatgggt tgcat                45

<210> SEQ ID NO 555
<211> LENGTH: 45
<212> TYPE: DNA
<213> ORGANISM: Homo sapiens

<400> SEQUENCE: 555
gtgtgtgtgt gtgtgtgtgt gtgtgtatga ctaaagagag aatgt                45

<210> SEQ ID NO 556
<211> LENGTH: 45
<212> TYPE: DNA
<213> ORGANISM: Homo sapiens

<400> SEQUENCE: 556
ctgggctgcc atgtgaagag ggagaagcat gaaaaagcag ctacc                45

<210> SEQ ID NO 557
<211> LENGTH: 45
<212> TYPE: DNA
<213> ORGANISM: Homo sapiens

<400> SEQUENCE: 557
tgtgtgtgtg tgtgtgtgta tgactaaaga gagaatgtag atatt                45

<210> SEQ ID NO 558
<211> LENGTH: 45
<212> TYPE: DNA
<213> ORGANISM: Homo sapiens

<400> SEQUENCE: 558
cctaacacag catgtgtatt tccagtgcaa ttgtaggggt gtgtg                45

<210> SEQ ID NO 559
<211> LENGTH: 45
<212> TYPE: DNA
<213> ORGANISM: Homo sapiens

<400> SEQUENCE: 559
atgcttcctg acaatcaact ctaatagtgc ttaaaaatca ttgat                45

<210> SEQ ID NO 560
<211> LENGTH: 45
<212> TYPE: DNA
<213> ORGANISM: Homo sapiens

<400> SEQUENCE: 560
tgtgtgtgtg tgtgtgtgtg tgtgtatgac taaagagaga atgta                45

<210> SEQ ID NO 561
<211> LENGTH: 20
<212> TYPE: DNA
<213> ORGANISM: Homo sapiens

<400> SEQUENCE: 561

```
acctgcatta atttaataaa                                                 20

<210> SEQ ID NO 562
<211> LENGTH: 20
<212> TYPE: DNA
<213> ORGANISM: Homo sapiens

<400> SEQUENCE: 562
aacttgccca aaccagtaaa                                                 20

<210> SEQ ID NO 563
<211> LENGTH: 20
<212> TYPE: DNA
<213> ORGANISM: Homo sapiens

<400> SEQUENCE: 563
atttgctcac atctagtaaa                                                 20

<210> SEQ ID NO 564
<211> LENGTH: 20
<212> TYPE: DNA
<213> ORGANISM: Homo sapiens

<400> SEQUENCE: 564
cctttgccat ataatctaat                                                 20

<210> SEQ ID NO 565
<211> LENGTH: 20
<212> TYPE: DNA
<213> ORGANISM: Homo sapiens

<400> SEQUENCE: 565
atatagcaga tggaatgaat                                                 20

<210> SEQ ID NO 566
<211> LENGTH: 20
<212> TYPE: DNA
<213> ORGANISM: Homo sapiens

<400> SEQUENCE: 566
gcctttgcca tataatctaa                                                 20

<210> SEQ ID NO 567
<211> LENGTH: 20
<212> TYPE: DNA
<213> ORGANISM: Homo sapiens

<400> SEQUENCE: 567
gatttgcctt tgccatataa                                                 20

<210> SEQ ID NO 568
<211> LENGTH: 20
<212> TYPE: DNA
<213> ORGANISM: Homo sapiens

<400> SEQUENCE: 568
aattttcatt tacaaagaga                                                 20

<210> SEQ ID NO 569
<211> LENGTH: 20
<212> TYPE: DNA
<213> ORGANISM: Homo sapiens
```

```
<400> SEQUENCE: 569
agtgtttctt atatagcaga                                              20

<210> SEQ ID NO 570
<211> LENGTH: 20
<212> TYPE: DNA
<213> ORGANISM: Homo sapiens

<400> SEQUENCE: 570
gctttctgtc aagtataaac                                              20

<210> SEQ ID NO 571
<211> LENGTH: 20
<212> TYPE: DNA
<213> ORGANISM: Homo sapiens

<400> SEQUENCE: 571
catttggaaa tgtatgttaa                                              20

<210> SEQ ID NO 572
<211> LENGTH: 20
<212> TYPE: DNA
<213> ORGANISM: Homo sapiens

<400> SEQUENCE: 572
ttattttagt gtttcttata                                              20

<210> SEQ ID NO 573
<211> LENGTH: 20
<212> TYPE: DNA
<213> ORGANISM: Homo sapiens

<400> SEQUENCE: 573
gtggtagcct acacacataa                                              20

<210> SEQ ID NO 574
<211> LENGTH: 20
<212> TYPE: DNA
<213> ORGANISM: Homo sapiens

<400> SEQUENCE: 574
atgaggagat taacaagaaa                                              20

<210> SEQ ID NO 575
<211> LENGTH: 20
<212> TYPE: DNA
<213> ORGANISM: Homo sapiens

<400> SEQUENCE: 575
caattttgtc gccaaactaa                                              20

<210> SEQ ID NO 576
<211> LENGTH: 20
<212> TYPE: DNA
<213> ORGANISM: Homo sapiens

<400> SEQUENCE: 576
tatatagcag atggaatgaa                                              20

<210> SEQ ID NO 577
<211> LENGTH: 20
<212> TYPE: DNA
<213> ORGANISM: Homo sapiens
```

```
<400> SEQUENCE: 577
aaatgccact aaattttaaa                                              20

<210> SEQ ID NO 578
<211> LENGTH: 20
<212> TYPE: DNA
<213> ORGANISM: Homo sapiens

<400> SEQUENCE: 578
tctttcccat agcttttcat                                              20

<210> SEQ ID NO 579
<211> LENGTH: 20
<212> TYPE: DNA
<213> ORGANISM: Homo sapiens

<400> SEQUENCE: 579
tatattcatg acctactggc                                              20

<210> SEQ ID NO 580
<211> LENGTH: 20
<212> TYPE: DNA
<213> ORGANISM: Homo sapiens

<400> SEQUENCE: 580
gtccagtgtc atagcataag                                              20

<210> SEQ ID NO 581
<211> LENGTH: 45
<212> TYPE: DNA
<213> ORGANISM: Homo sapiens

<400> SEQUENCE: 581
attgtcactt tttgtacctg cattaattta ataaaatatt cttat                  45

<210> SEQ ID NO 582
<211> LENGTH: 45
<212> TYPE: DNA
<213> ORGANISM: Homo sapiens

<400> SEQUENCE: 582
gcaaacagat taagtaactt gcccaaacca gtaaatagca gacct                  45

<210> SEQ ID NO 583
<211> LENGTH: 45
<212> TYPE: DNA
<213> ORGANISM: Homo sapiens

<400> SEQUENCE: 583
acttgctgct taatgatttg ctcacatcta gtaaaacatg gagta                  45

<210> SEQ ID NO 584
<211> LENGTH: 45
<212> TYPE: DNA
<213> ORGANISM: Homo sapiens

<400> SEQUENCE: 584
tttattcctg atttgccttt gccatataat ctaatgcttg tttat                  45

<210> SEQ ID NO 585
<211> LENGTH: 45
<212> TYPE: DNA
```

<213> ORGANISM: Homo sapiens

<400> SEQUENCE: 585
attttagtgt tcttatata gcagatggaa tgaatttgaa gttcc    45

<210> SEQ ID NO 586
<211> LENGTH: 45
<212> TYPE: DNA
<213> ORGANISM: Homo sapiens

<400> SEQUENCE: 586
atttattcct gatttgcctt tgccatataa tctaatgctt gttta    45

<210> SEQ ID NO 587
<211> LENGTH: 45
<212> TYPE: DNA
<213> ORGANISM: Homo sapiens

<400> SEQUENCE: 587
attatattta ttcctgattt gcctttgcca tataatctaa tgctt    45

<210> SEQ ID NO 588
<211> LENGTH: 45
<212> TYPE: DNA
<213> ORGANISM: Homo sapiens

<400> SEQUENCE: 588
cttaataatc agagtaattt tcatttacaa agagaggtcg gtact    45

<210> SEQ ID NO 589
<211> LENGTH: 45
<212> TYPE: DNA
<213> ORGANISM: Homo sapiens

<400> SEQUENCE: 589
atttttattt attttagtgt tcttatata gcagatggaa tgaat    45

<210> SEQ ID NO 590
<211> LENGTH: 45
<212> TYPE: DNA
<213> ORGANISM: Homo sapiens

<400> SEQUENCE: 590
gaacttttgt tttctgcttt ctgtcaagta taaacttcac tttga    45

<210> SEQ ID NO 591
<211> LENGTH: 45
<212> TYPE: DNA
<213> ORGANISM: Homo sapiens

<400> SEQUENCE: 591
tctaaagata gtctacattt ggaaatgtat gttaaaagca cgtat    45

<210> SEQ ID NO 592
<211> LENGTH: 45
<212> TYPE: DNA
<213> ORGANISM: Homo sapiens

<400> SEQUENCE: 592
ctttgctatt tttatttatt ttagtgtttc ttatatagca gatgg    45

<210> SEQ ID NO 593
<211> LENGTH: 45

```
<212> TYPE: DNA
<213> ORGANISM: Homo sapiens

<400> SEQUENCE: 593
cagctttaca attatgtggt agcctacaca cataatctca tttca            45

<210> SEQ ID NO 594
<211> LENGTH: 45
<212> TYPE: DNA
<213> ORGANISM: Homo sapiens

<400> SEQUENCE: 594
ggagctcata gtataatgag gagattaaca agaaaatgta ttatt            45

<210> SEQ ID NO 595
<211> LENGTH: 45
<212> TYPE: DNA
<213> ORGANISM: Homo sapiens

<400> SEQUENCE: 595
ttgtagtaga tgttacaatt ttgtcgccaa actaaacttg ctgct            45

<210> SEQ ID NO 596
<211> LENGTH: 45
<212> TYPE: DNA
<213> ORGANISM: Homo sapiens

<400> SEQUENCE: 596
tattttagtg tttcttatat agcagatgga atgaatttga agttc            45

<210> SEQ ID NO 597
<211> LENGTH: 45
<212> TYPE: DNA
<213> ORGANISM: Homo sapiens

<400> SEQUENCE: 597
ctgtcttttc tatttaaatg ccactaaatt ttaaattcat acctt            45

<210> SEQ ID NO 598
<211> LENGTH: 45
<212> TYPE: DNA
<213> ORGANISM: Homo sapiens

<400> SEQUENCE: 598
tttgtttcta agttatcttt cccatagctt ttcattatct ttcat            45

<210> SEQ ID NO 599
<211> LENGTH: 45
<212> TYPE: DNA
<213> ORGANISM: Homo sapiens

<400> SEQUENCE: 599
gatatttgct gtctttatat tcatgaccta ctggcatttg ctgaa            45

<210> SEQ ID NO 600
<211> LENGTH: 45
<212> TYPE: DNA
<213> ORGANISM: Homo sapiens

<400> SEQUENCE: 600
tattattaca atttagtcca gtgtcatagc ataaggatga tgcga            45

<210> SEQ ID NO 601
```

```
<211> LENGTH: 20
<212> TYPE: DNA
<213> ORGANISM: Homo sapiens

<400> SEQUENCE: 601
attctgtcat aataaataaa                                                    20

<210> SEQ ID NO 602
<211> LENGTH: 20
<212> TYPE: DNA
<213> ORGANISM: Homo sapiens

<400> SEQUENCE: 602
tatcttatca ttggaataaa                                                    20

<210> SEQ ID NO 603
<211> LENGTH: 20
<212> TYPE: DNA
<213> ORGANISM: Homo sapiens

<400> SEQUENCE: 603
gtgatggaga ctgcagtaaa                                                    20

<210> SEQ ID NO 604
<211> LENGTH: 20
<212> TYPE: DNA
<213> ORGANISM: Homo sapiens

<400> SEQUENCE: 604
ttctgtcata ataaataaaa                                                    20

<210> SEQ ID NO 605
<211> LENGTH: 20
<212> TYPE: DNA
<213> ORGANISM: Homo sapiens

<400> SEQUENCE: 605
cttgtaggaa aacaacaaaa                                                    20

<210> SEQ ID NO 606
<211> LENGTH: 20
<212> TYPE: DNA
<213> ORGANISM: Homo sapiens

<400> SEQUENCE: 606
ataaaatgac attcaataaa                                                    20

<210> SEQ ID NO 607
<211> LENGTH: 20
<212> TYPE: DNA
<213> ORGANISM: Homo sapiens

<400> SEQUENCE: 607
cgtaaggtct tgccaagaaa                                                    20

<210> SEQ ID NO 608
<211> LENGTH: 20
<212> TYPE: DNA
<213> ORGANISM: Homo sapiens

<400> SEQUENCE: 608
tcttgtagga aacaacaaa                                                     20
```

```
<210> SEQ ID NO 609
<211> LENGTH: 20
<212> TYPE: DNA
<213> ORGANISM: Homo sapiens

<400> SEQUENCE: 609
aactggaggc actgatttaa                                               20

<210> SEQ ID NO 610
<211> LENGTH: 20
<212> TYPE: DNA
<213> ORGANISM: Homo sapiens

<400> SEQUENCE: 610
caatacaaaa gacctcaaaa                                               20

<210> SEQ ID NO 611
<211> LENGTH: 20
<212> TYPE: DNA
<213> ORGANISM: Homo sapiens

<400> SEQUENCE: 611
tgcttctgca atcaaagtaa                                               20

<210> SEQ ID NO 612
<211> LENGTH: 20
<212> TYPE: DNA
<213> ORGANISM: Homo sapiens

<400> SEQUENCE: 612
aatgacattc aataaataaa                                               20

<210> SEQ ID NO 613
<211> LENGTH: 20
<212> TYPE: DNA
<213> ORGANISM: Homo sapiens

<400> SEQUENCE: 613
atcattggaa taaatgaca                                                20

<210> SEQ ID NO 614
<211> LENGTH: 20
<212> TYPE: DNA
<213> ORGANISM: Homo sapiens

<400> SEQUENCE: 614
accaataatg caatacaaaa                                               20

<210> SEQ ID NO 615
<211> LENGTH: 20
<212> TYPE: DNA
<213> ORGANISM: Homo sapiens

<400> SEQUENCE: 615
atctgtatct tatcattgga                                               20

<210> SEQ ID NO 616
<211> LENGTH: 20
<212> TYPE: DNA
<213> ORGANISM: Homo sapiens

<400> SEQUENCE: 616
atcttatcat tggaataaaa                                               20
```

<210> SEQ ID NO 617
<211> LENGTH: 20
<212> TYPE: DNA
<213> ORGANISM: Homo sapiens

<400> SEQUENCE: 617
cagctgcttc tgcaatcaaa                                                    20

<210> SEQ ID NO 618
<211> LENGTH: 20
<212> TYPE: DNA
<213> ORGANISM: Homo sapiens

<400> SEQUENCE: 618
gcaatacaaa agacctcaaa                                                    20

<210> SEQ ID NO 619
<211> LENGTH: 20
<212> TYPE: DNA
<213> ORGANISM: Homo sapiens

<400> SEQUENCE: 619
tcctactgta ttcaaggcaa                                                    20

<210> SEQ ID NO 620
<211> LENGTH: 20
<212> TYPE: DNA
<213> ORGANISM: Homo sapiens

<400> SEQUENCE: 620
cagagccaca aactaatact                                                    20

<210> SEQ ID NO 621
<211> LENGTH: 45
<212> TYPE: DNA
<213> ORGANISM: Homo sapiens

<400> SEQUENCE: 621
aaaaaaaaaa gatatattct gtcataataa ataaaaatgc ataag                        45

<210> SEQ ID NO 622
<211> LENGTH: 45
<212> TYPE: DNA
<213> ORGANISM: Homo sapiens

<400> SEQUENCE: 622
aagttttgta atctgtatct tatcattgga ataaaatgac attca                        45

<210> SEQ ID NO 623
<211> LENGTH: 45
<212> TYPE: DNA
<213> ORGANISM: Homo sapiens

<400> SEQUENCE: 623
ttttgttctc atttcgtgat ggagactgca gtaaaggatt cttcc                        45

<210> SEQ ID NO 624
<211> LENGTH: 45
<212> TYPE: DNA
<213> ORGANISM: Homo sapiens

<400> SEQUENCE: 624
aaaaaaaaag atatattctg tcataataaa taaaaatgca taaga                        45

<210> SEQ ID NO 625
<211> LENGTH: 45
<212> TYPE: DNA
<213> ORGANISM: Homo sapiens

<400> SEQUENCE: 625
aatacctgtg catttcttgt aggaaaacaa caaaaggtaa ttatg            45

<210> SEQ ID NO 626
<211> LENGTH: 45
<212> TYPE: DNA
<213> ORGANISM: Homo sapiens

<400> SEQUENCE: 626
tatcttatca ttggaataaa atgcattca ataaataaaa atgca             45

<210> SEQ ID NO 627
<211> LENGTH: 45
<212> TYPE: DNA
<213> ORGANISM: Homo sapiens

<400> SEQUENCE: 627
ggtcatggag atgtccgtaa ggtcttgcca agaaatattg ctgtt            45

<210> SEQ ID NO 628
<211> LENGTH: 45
<212> TYPE: DNA
<213> ORGANISM: Homo sapiens

<400> SEQUENCE: 628
aaatacctgt gcatttcttg taggaaaaca acaaaggta attat             45

<210> SEQ ID NO 629
<211> LENGTH: 45
<212> TYPE: DNA
<213> ORGANISM: Homo sapiens

<400> SEQUENCE: 629
actggaagcc aaaggaactg gaggcactga tttaatgaat ttcct            45

<210> SEQ ID NO 630
<211> LENGTH: 45
<212> TYPE: DNA
<213> ORGANISM: Homo sapiens

<400> SEQUENCE: 630
gttttaccaa taatgcaata caaaagacct caaaatacct gtgca            45

<210> SEQ ID NO 631
<211> LENGTH: 45
<212> TYPE: DNA
<213> ORGANISM: Homo sapiens

<400> SEQUENCE: 631
ggtggaaata gcagctgctt ctgcaatcaa agtaattcct actgt            45

<210> SEQ ID NO 632
<211> LENGTH: 45
<212> TYPE: DNA
<213> ORGANISM: Homo sapiens

<400> SEQUENCE: 632

```
ttatcattgg aataaaatga cattcaataa ataaaaatgc ataag          45

<210> SEQ ID NO 633
<211> LENGTH: 45
<212> TYPE: DNA
<213> ORGANISM: Homo sapiens

<400> SEQUENCE: 633
tgtaatctgt atcttatcat tggaataaaa tgacattcaa taaat          45

<210> SEQ ID NO 634
<211> LENGTH: 45
<212> TYPE: DNA
<213> ORGANISM: Homo sapiens

<400> SEQUENCE: 634
actatgcaat gttttaccaa taatgcaata caaaagacct caaaa          45

<210> SEQ ID NO 635
<211> LENGTH: 45
<212> TYPE: DNA
<213> ORGANISM: Homo sapiens

<400> SEQUENCE: 635
actagaagtt ttgtaatctg tatcttatca ttggaataaa atgac          45

<210> SEQ ID NO 636
<211> LENGTH: 45
<212> TYPE: DNA
<213> ORGANISM: Homo sapiens

<400> SEQUENCE: 636
agttttgtaa tctgtatctt atcattggaa taaaatgaca ttcaa          45

<210> SEQ ID NO 637
<211> LENGTH: 45
<212> TYPE: DNA
<213> ORGANISM: Homo sapiens

<400> SEQUENCE: 637
tattggtgga aatagcagct gcttctgcaa tcaaagtaat tccta          45

<210> SEQ ID NO 638
<211> LENGTH: 45
<212> TYPE: DNA
<213> ORGANISM: Homo sapiens

<400> SEQUENCE: 638
tgttttacca ataatgcaat acaaaagacc tcaaaatacc tgtgc          45

<210> SEQ ID NO 639
<211> LENGTH: 45
<212> TYPE: DNA
<213> ORGANISM: Homo sapiens

<400> SEQUENCE: 639
tgcaatcaaa gtaattccta ctgtattcaa ggcaatgcaa atgca          45

<210> SEQ ID NO 640
<211> LENGTH: 45
<212> TYPE: DNA
<213> ORGANISM: Homo sapiens

<400> SEQUENCE: 640
```
cattacccat tgtaacagag ccacaaacta atactatgca atgtt         45

<210> SEQ ID NO 641
<211> LENGTH: 20
<212> TYPE: DNA
<213> ORGANISM: Homo sapiens

<400> SEQUENCE: 641
ttgttcattt atttattgga         20

<210> SEQ ID NO 642
<211> LENGTH: 20
<212> TYPE: DNA
<213> ORGANISM: Homo sapiens

<400> SEQUENCE: 642
ttattccaat aaattgtcaa         20

<210> SEQ ID NO 643
<211> LENGTH: 20
<212> TYPE: DNA
<213> ORGANISM: Homo sapiens

<400> SEQUENCE: 643
tattttctgg acactcaaac         20

<210> SEQ ID NO 644
<211> LENGTH: 20
<212> TYPE: DNA
<213> ORGANISM: Homo sapiens

<400> SEQUENCE: 644
tttattggag aggcagcatt         20

<210> SEQ ID NO 645
<211> LENGTH: 20
<212> TYPE: DNA
<213> ORGANISM: Homo sapiens

<400> SEQUENCE: 645
accttggaga agtcacttat         20

<210> SEQ ID NO 646
<211> LENGTH: 20
<212> TYPE: DNA
<213> ORGANISM: Homo sapiens

<400> SEQUENCE: 646
ttatttattt attttgttca         20

<210> SEQ ID NO 647
<211> LENGTH: 20
<212> TYPE: DNA
<213> ORGANISM: Homo sapiens

<400> SEQUENCE: 647 ctcttttcctg tatcataaag         20

<210> SEQ ID NO 648
<211> LENGTH: 20
<212> TYPE: DNA
<213> ORGANISM: Homo sapiens

```
<400> SEQUENCE: 648
ctgaggaaat gggtatgaat                                               20

<210> SEQ ID NO 649
<211> LENGTH: 20
<212> TYPE: DNA
<213> ORGANISM: Homo sapiens

<400> SEQUENCE: 649
gaatgtgcct tgaacacaaa                                               20

<210> SEQ ID NO 650
<211> LENGTH: 20
<212> TYPE: DNA
<213> ORGANISM: Homo sapiens

<400> SEQUENCE: 650
ggacactcaa acacatcata                                               20

<210> SEQ ID NO 651
<211> LENGTH: 20
<212> TYPE: DNA
<213> ORGANISM: Homo sapiens

<400> SEQUENCE: 651
ctgtatcata aaggattatt                                               20

<210> SEQ ID NO 652
<211> LENGTH: 20
<212> TYPE: DNA
<213> ORGANISM: Homo sapiens

<400> SEQUENCE: 652
tcacttccga gagtatgaga                                               20

<210> SEQ ID NO 653
<211> LENGTH: 20
<212> TYPE: DNA
<213> ORGANISM: Homo sapiens

<400> SEQUENCE: 653
tctctggagc attctgaaaa                                               20

<210> SEQ ID NO 654
<211> LENGTH: 20
<212> TYPE: DNA
<213> ORGANISM: Homo sapiens

<400> SEQUENCE: 654
ttatgccaga ggctaacaga                                               20

<210> SEQ ID NO 655
<211> LENGTH: 20
<212> TYPE: DNA
<213> ORGANISM: Homo sapiens

<400> SEQUENCE: 655
agtggcattg acttagttca                                               20

<210> SEQ ID NO 656
<211> LENGTH: 20
<212> TYPE: DNA
<213> ORGANISM: Homo sapiens
```

```
<400> SEQUENCE: 656
tttctggaca ctcaaacaca                                              20

<210> SEQ ID NO 657
<211> LENGTH: 20
<212> TYPE: DNA
<213> ORGANISM: Homo sapiens

<400> SEQUENCE: 657
gcattgcaca gtgaaagaat                                              20

<210> SEQ ID NO 658
<211> LENGTH: 20
<212> TYPE: DNA
<213> ORGANISM: Homo sapiens

<400> SEQUENCE: 658
gaccttggag aagtcactta                                              20

<210> SEQ ID NO 659
<211> LENGTH: 20
<212> TYPE: DNA
<213> ORGANISM: Homo sapiens

<400> SEQUENCE: 659
tcacgttcac acacaagaaa                                              20

<210> SEQ ID NO 660
<211> LENGTH: 20
<212> TYPE: DNA
<213> ORGANISM: Homo sapiens

<400> SEQUENCE: 660
actttgctgt ttccagtggt                                              20

<210> SEQ ID NO 661
<211> LENGTH: 45
<212> TYPE: DNA
<213> ORGANISM: Homo sapiens

<400> SEQUENCE: 661
ctttatttat ttattttgtt catttattta ttggagaggc agcat                  45

<210> SEQ ID NO 662
<211> LENGTH: 45
<212> TYPE: DNA
<213> ORGANISM: Homo sapiens

<400> SEQUENCE: 662
agtgatacat gtttttttatt ccaataaatt gtcaagacca cagga                 45

<210> SEQ ID NO 663
<211> LENGTH: 45
<212> TYPE: DNA
<213> ORGANISM: Homo sapiens

<400> SEQUENCE: 663
agatcttaag gtatatattt tctggacact caaacacatc ataat                  45

<210> SEQ ID NO 664
<211> LENGTH: 45
<212> TYPE: DNA
```

<213> ORGANISM: Homo sapiens

<400> SEQUENCE: 664
tattttgttc atttatttat tggagaggca gcattgcaca gtgaa    45

<210> SEQ ID NO 665
<211> LENGTH: 45
<212> TYPE: DNA
<213> ORGANISM: Homo sapiens

<400> SEQUENCE: 665
gtttccagtg gtatgacctt ggagaagtca cttatcctct tggag    45

<210> SEQ ID NO 666
<211> LENGTH: 45
<212> TYPE: DNA
<213> ORGANISM: Homo sapiens

<400> SEQUENCE: 666
gttcccttga aagctttatt tatttatttt gttcatttat ttatt    45

<210> SEQ ID NO 667
<211> LENGTH: 45
<212> TYPE: DNA
<213> ORGANISM: Homo sapiens

<400> SEQUENCE: 667
tctccctcct aggaactctt tcctgtatca taaaggatta tttgc    45

<210> SEQ ID NO 668
<211> LENGTH: 45
<212> TYPE: DNA
<213> ORGANISM: Homo sapiens

<400> SEQUENCE: 668
ggatgtgagg ttctgctgag gaaatgggta tgaatgtgcc ttgaa    45

<210> SEQ ID NO 669
<211> LENGTH: 45
<212> TYPE: DNA
<213> ORGANISM: Homo sapiens

<400> SEQUENCE: 669
tgaggaaatg ggtatgaatg tgccttgaac acaaagctct gtcaa    45

<210> SEQ ID NO 670
<211> LENGTH: 45
<212> TYPE: DNA
<213> ORGANISM: Homo sapiens

<400> SEQUENCE: 670
aggtatatat tttctggaca ctcaaacaca tcataatgga ttcac    45

<210> SEQ ID NO 671
<211> LENGTH: 45
<212> TYPE: DNA
<213> ORGANISM: Homo sapiens

<400> SEQUENCE: 671
cctaggaact ctttcctgta tcataaagga ttatttgctc agggg    45

<210> SEQ ID NO 672
<211> LENGTH: 45

<212> TYPE: DNA
<213> ORGANISM: Homo sapiens

<400> SEQUENCE: 672
tgaaagcatc ttcagtcact tccgagagta tgagattgcc attcg          45

<210> SEQ ID NO 673
<211> LENGTH: 45
<212> TYPE: DNA
<213> ORGANISM: Homo sapiens

<400> SEQUENCE: 673
tctcagccct gcctttctct ggagcattct gaaaacagat attct          45

<210> SEQ ID NO 674
<211> LENGTH: 45
<212> TYPE: DNA
<213> ORGANISM: Homo sapiens

<400> SEQUENCE: 674
aagctggctt gtttcttatg ccagaggcta acagatccaa tggga          45

<210> SEQ ID NO 675
<211> LENGTH: 45
<212> TYPE: DNA
<213> ORGANISM: Homo sapiens

<400> SEQUENCE: 675
aggggccagg atgacagtgg cattgactta gttcaaaact ctgag          45

<210> SEQ ID NO 676
<211> LENGTH: 45
<212> TYPE: DNA
<213> ORGANISM: Homo sapiens

<400> SEQUENCE: 676
tcttaaggta tatttttct ggacactcaa acacatcata atgga           45

<210> SEQ ID NO 677
<211> LENGTH: 45
<212> TYPE: DNA
<213> ORGANISM: Homo sapiens

<400> SEQUENCE: 677
tttattggag aggcagcatt gcacagtgaa agaattctgg atatc          45

<210> SEQ ID NO 678
<211> LENGTH: 45
<212> TYPE: DNA
<213> ORGANISM: Homo sapiens

<400> SEQUENCE: 678
tgtttccagt ggtatgacct tggagaagtc acttatcctc ttgga          45

<210> SEQ ID NO 679
<211> LENGTH: 45
<212> TYPE: DNA
<213> ORGANISM: Homo sapiens

<400> SEQUENCE: 679
aggtgccggg aaacttcacg ttcacacaca agaaagtaaa acatg          45

<210> SEQ ID NO 680

```
<211> LENGTH: 45
<212> TYPE: DNA
<213> ORGANISM: Homo sapiens

<400> SEQUENCE: 680
gaaattctag ctctgacttt gctgtttcca gtggtatgac cttgg           45

<210> SEQ ID NO 681
<211> LENGTH: 20
<212> TYPE: DNA
<213> ORGANISM: Homo sapiens

<400> SEQUENCE: 681
tatttgattt attaacttaa                                        20

<210> SEQ ID NO 682
<211> LENGTH: 20
<212> TYPE: DNA
<213> ORGANISM: Homo sapiens

<400> SEQUENCE: 682
gaaaagtaat atttattaaa                                        20

<210> SEQ ID NO 683
<211> LENGTH: 20
<212> TYPE: DNA
<213> ORGANISM: Homo sapiens

<400> SEQUENCE: 683
actttgtata gttatgtaaa                                        20

<210> SEQ ID NO 684
<211> LENGTH: 20
<212> TYPE: DNA
<213> ORGANISM: Homo sapiens

<400> SEQUENCE: 684
gaatacttga accataaaat                                        20

<210> SEQ ID NO 685
<211> LENGTH: 20
<212> TYPE: DNA
<213> ORGANISM: Homo sapiens

<400> SEQUENCE: 685
tcttggcaat aaattttgaa                                        20

<210> SEQ ID NO 686
<211> LENGTH: 20
<212> TYPE: DNA
<213> ORGANISM: Homo sapiens

<400> SEQUENCE: 686
tttctgcttt agacttgaaa                                        20

<210> SEQ ID NO 687
<211> LENGTH: 20
<212> TYPE: DNA
<213> ORGANISM: Homo sapiens

<400> SEQUENCE: 687
tatatttatt gactcttgag                                        20
```

```
<210> SEQ ID NO 688
<211> LENGTH: 20
<212> TYPE: DNA
<213> ORGANISM: Homo sapiens

<400> SEQUENCE: 688
tatgatgacg tacaagtagt                                              20

<210> SEQ ID NO 689
<211> LENGTH: 20
<212> TYPE: DNA
<213> ORGANISM: Homo sapiens

<400> SEQUENCE: 689
gtgttgttct tggcaataaa                                              20

<210> SEQ ID NO 690
<211> LENGTH: 20
<212> TYPE: DNA
<213> ORGANISM: Homo sapiens

<400> SEQUENCE: 690
ctgatctaaa agggaataaa                                              20

<210> SEQ ID NO 691
<211> LENGTH: 20
<212> TYPE: DNA
<213> ORGANISM: Homo sapiens

<400> SEQUENCE: 691
tacgacgtca gatgtttaaa                                              20

<210> SEQ ID NO 692
<211> LENGTH: 20
<212> TYPE: DNA
<213> ORGANISM: Homo sapiens

<400> SEQUENCE: 692
aataatcaag agccttaaaa                                              20

<210> SEQ ID NO 693
<211> LENGTH: 20
<212> TYPE: DNA
<213> ORGANISM: Homo sapiens

<400> SEQUENCE: 693
gtatgaaaac atggaacagt                                              20

<210> SEQ ID NO 694
<211> LENGTH: 20
<212> TYPE: DNA
<213> ORGANISM: Homo sapiens

<400> SEQUENCE: 694
tggttttatg atgacgtaca                                              20

<210> SEQ ID NO 695
<211> LENGTH: 20
<212> TYPE: DNA
<213> ORGANISM: Homo sapiens

<400> SEQUENCE: 695
ttctgcttta gacttgaaaa                                              20
```

```
<210> SEQ ID NO 696
<211> LENGTH: 20
<212> TYPE: DNA
<213> ORGANISM: Homo sapiens

<400> SEQUENCE: 696
cttggcaata aattttgaaa                                                    20

<210> SEQ ID NO 697
<211> LENGTH: 20
<212> TYPE: DNA
<213> ORGANISM: Homo sapiens

<400> SEQUENCE: 697
tttaatctac tgcatttagg                                                    20

<210> SEQ ID NO 698
<211> LENGTH: 20
<212> TYPE: DNA
<213> ORGANISM: Homo sapiens

<400> SEQUENCE: 698
tgtatagtta tgtaaataat                                                    20

<210> SEQ ID NO 699
<211> LENGTH: 20
<212> TYPE: DNA
<213> ORGANISM: Homo sapiens

<400> SEQUENCE: 699
atttatattt attgactctt                                                    20

<210> SEQ ID NO 700
<211> LENGTH: 20
<212> TYPE: DNA
<213> ORGANISM: Homo sapiens

<400> SEQUENCE: 700
cttttcacca ttcgtacata                                                    20

<210> SEQ ID NO 701
<211> LENGTH: 45
<212> TYPE: DNA
<213> ORGANISM: Homo sapiens

<400> SEQUENCE: 701
attaatcact gtgtatattt gatttattaa cttaataatc aagag                        45

<210> SEQ ID NO 702
<211> LENGTH: 45
<212> TYPE: DNA
<213> ORGANISM: Homo sapiens

<400> SEQUENCE: 702
ttggcaataa attttgaaaa gtaatattta ttaaattttt ttgta                        45

<210> SEQ ID NO 703
<211> LENGTH: 45
<212> TYPE: DNA
<213> ORGANISM: Homo sapiens

<400> SEQUENCE: 703
aatgtcaaaa gtagaacttt gtatagttat gtaaataatt cttttt                       45
```

<210> SEQ ID NO 704
<211> LENGTH: 45
<212> TYPE: DNA
<213> ORGANISM: Homo sapiens

<400> SEQUENCE: 704
tctaataagc tagttgaata cttgaaccat aaaatgtcca gtaag    45

<210> SEQ ID NO 705
<211> LENGTH: 45
<212> TYPE: DNA
<213> ORGANISM: Homo sapiens

<400> SEQUENCE: 705
tctttgatgt gttgttcttg gcaataaatt ttgaaaagta atatt    45

<210> SEQ ID NO 706
<211> LENGTH: 45
<212> TYPE: DNA
<213> ORGANISM: Homo sapiens

<400> SEQUENCE: 706
tgtttgtttt ttgttttttct gctttagact tgaaaagaga caggc    45

<210> SEQ ID NO 707
<211> LENGTH: 45
<212> TYPE: DNA
<213> ORGANISM: Homo sapiens

<400> SEQUENCE: 707
gatcatagtt ttatttatat ttattgactc ttgagttgtt tttgt    45

<210> SEQ ID NO 708
<211> LENGTH: 45
<212> TYPE: DNA
<213> ORGANISM: Homo sapiens

<400> SEQUENCE: 708
tttgtatatt ggttttatga tgacgtacaa gtagttctgt atttg    45

<210> SEQ ID NO 709
<211> LENGTH: 45
<212> TYPE: DNA
<213> ORGANISM: Homo sapiens

<400> SEQUENCE: 709
aaatgcatct ttgatgtgtt gttcttggca ataaattttg aaaag    45

<210> SEQ ID NO 710
<211> LENGTH: 45
<212> TYPE: DNA
<213> ORGANISM: Homo sapiens

<400> SEQUENCE: 710
cctttttcca tgcagctgat ctaaaaggga ataaaaggct gcgca    45

<210> SEQ ID NO 711
<211> LENGTH: 45
<212> TYPE: DNA
<213> ORGANISM: Homo sapiens

<400> SEQUENCE: 711

```
gatggaattt ttttgtacga cgtcagatgt ttaaaacacc ttcta            45

<210> SEQ ID NO 712
<211> LENGTH: 45
<212> TYPE: DNA
<213> ORGANISM: Homo sapiens

<400> SEQUENCE: 712
ttgatttatt aacttaataa tcaagagcct taaaacatca ttcct            45

<210> SEQ ID NO 713
<211> LENGTH: 45
<212> TYPE: DNA
<213> ORGANISM: Homo sapiens

<400> SEQUENCE: 713
ttattaaatt tttttgtatg aaaacatgga acagtgtggc ctctt            45

<210> SEQ ID NO 714
<211> LENGTH: 45
<212> TYPE: DNA
<213> ORGANISM: Homo sapiens

<400> SEQUENCE: 714 gttgttttg tatattggtt ttatgatgac gtacaagtag ttctg             45

<210> SEQ ID NO 715
<211> LENGTH: 45
<212> TYPE: DNA
<213> ORGANISM: Homo sapiens

<400> SEQUENCE: 715
gtttgttttt tgtttttctg ctttagactt gaaaagagac aggca            45

<210> SEQ ID NO 716
<211> LENGTH: 45
<212> TYPE: DNA
<213> ORGANISM: Homo sapiens

<400> SEQUENCE: 716
ctttgatgtg ttgttcttgg caataaattt tgaaaagtaa tattt            45

<210> SEQ ID NO 717
<211> LENGTH: 45
<212> TYPE: DNA
<213> ORGANISM: Homo sapiens

<400> SEQUENCE: 717
gatttgattt ttttttttaa tctactgcat ttagggagta ttcta            45

<210> SEQ ID NO 718
<211> LENGTH: 45
<212> TYPE: DNA
<213> ORGANISM: Homo sapiens

<400> SEQUENCE: 718
tcaaaagtag aactttgtat agttatgtaa ataattcttt tttat            45

<210> SEQ ID NO 719
<211> LENGTH: 45
<212> TYPE: DNA
<213> ORGANISM: Homo sapiens

<400> SEQUENCE: 719
```
ttagatcata gttttattta tatttattga ctcttgagtt gtttt            45

<210> SEQ ID NO 720
<211> LENGTH: 45
<212> TYPE: DNA
<213> ORGANISM: Homo sapiens

<400> SEQUENCE: 720
tgtaaattct gatttctttt caccattcgt acataatact gaacc            45

<210> SEQ ID NO 721
<211> LENGTH: 20
<212> TYPE: DNA
<213> ORGANISM: Homo sapiens

<400> SEQUENCE: 721
cgtttcttta accttgtata                                        20

<210> SEQ ID NO 722
<211> LENGTH: 20
<212> TYPE: DNA
<213> ORGANISM: Homo sapiens

<400> SEQUENCE: 722
taaatgaatg aacgaataaa                                        20

<210> SEQ ID NO 723
<211> LENGTH: 20
<212> TYPE: DNA
<213> ORGANISM: Homo sapiens

<400> SEQUENCE: 723
tcattcattt attcctttgt                                        20

<210> SEQ ID NO 724
<211> LENGTH: 20
<212> TYPE: DNA
<213> ORGANISM: Homo sapiens

<400> SEQUENCE: 724
gtaaatgtgt acatattaaa                                        20

<210> SEQ ID NO 725
<211> LENGTH: 20
<212> TYPE: DNA
<213> ORGANISM: Homo sapiens

<400> SEQUENCE: 725
acccacgaat acgtatcaag                                        20

<210> SEQ ID NO 726
<211> LENGTH: 20
<212> TYPE: DNA
<213> ORGANISM: Homo sapiens

<400> SEQUENCE: 726
gttttataaa atagtataaa                                        20

<210> SEQ ID NO 727
<211> LENGTH: 20
<212> TYPE: DNA
<213> ORGANISM: Homo sapiens

```
<400> SEQUENCE: 727
caactgagtc aaggagcaaa                                              20

<210> SEQ ID NO 728
<211> LENGTH: 20
<212> TYPE: DNA
<213> ORGANISM: Homo sapiens

<400> SEQUENCE: 728
atgtgtacat attaaaggaa                                              20

<210> SEQ ID NO 729
<211> LENGTH: 20
<212> TYPE: DNA
<213> ORGANISM: Homo sapiens

<400> SEQUENCE: 729
ttctttaacc ttgtataaat                                              20

<210> SEQ ID NO 730
<211> LENGTH: 20
<212> TYPE: DNA
<213> ORGANISM: Homo sapiens

<400> SEQUENCE: 730
attttctacg tttctttaac                                              20

<210> SEQ ID NO 731
<211> LENGTH: 20
<212> TYPE: DNA
<213> ORGANISM: Homo sapiens

<400> SEQUENCE: 731
cagttttata aaatagtata                                              20

<210> SEQ ID NO 732
<211> LENGTH: 20
<212> TYPE: DNA
<213> ORGANISM: Homo sapiens

<400> SEQUENCE: 732
gcacaggcag aacaaatgaa                                              20

<210> SEQ ID NO 733
<211> LENGTH: 20
<212> TYPE: DNA
<213> ORGANISM: Homo sapiens

<400> SEQUENCE: 733
tcaggctgaa aacaatggag                                              20

<210> SEQ ID NO 734
<211> LENGTH: 20
<212> TYPE: DNA
<213> ORGANISM: Homo sapiens

<400> SEQUENCE: 734
taaaattgct tacccacgaa                                              20

<210> SEQ ID NO 735
<211> LENGTH: 20
<212> TYPE: DNA
<213> ORGANISM: Homo sapiens
```

<400> SEQUENCE: 735
gtcaggctga aaacaatgga                                                20

<210> SEQ ID NO 736
<211> LENGTH: 20
<212> TYPE: DNA
<213> ORGANISM: Homo sapiens

<400> SEQUENCE: 736
aaatgtgtac atattaaagg                                                20

<210> SEQ ID NO 737
<211> LENGTH: 20
<212> TYPE: DNA
<213> ORGANISM: Homo sapiens

<400> SEQUENCE: 737
cagtaactgt caggctgaaa                                                20

<210> SEQ ID NO 738
<211> LENGTH: 20
<212> TYPE: DNA
<213> ORGANISM: Homo sapiens

<400> SEQUENCE: 738
gtattctcgg atagttgcta                                                20

<210> SEQ ID NO 739
<211> LENGTH: 20
<212> TYPE: DNA
<213> ORGANISM: Homo sapiens

<400> SEQUENCE: 739
tctcacacaa attcaccaaa                                                20

<210> SEQ ID NO 740
<211> LENGTH: 20
<212> TYPE: DNA
<213> ORGANISM: Homo sapiens

<400> SEQUENCE: 740
ttgttttgct tggtcattca                                                20

<210> SEQ ID NO 741
<211> LENGTH: 45
<212> TYPE: DNA
<213> ORGANISM: Homo sapiens

<400> SEQUENCE: 741
aatgtttatt ttctacgttt ctttaacctt gtataaatta ttcag                    45

<210> SEQ ID NO 742
<211> LENGTH: 45
<212> TYPE: DNA
<213> ORGANISM: Homo sapiens

<400> SEQUENCE: 742
ggcagaacaa atgaataaat gaatgaacga ataaaaattt tgacc                    45

<210> SEQ ID NO 743
<211> LENGTH: 45
<212> TYPE: DNA

<213> ORGANISM: Homo sapiens

<400> SEQUENCE: 743
ggtcaaaatt tttattcatt catttattcc tttgttttgc ttggt               45

<210> SEQ ID NO 744
<211> LENGTH: 45
<212> TYPE: DNA
<213> ORGANISM: Homo sapiens

<400> SEQUENCE: 744
tgaaagtgca tttttgtaaa tgtgtacata ttaaaggaag cactc               45

<210> SEQ ID NO 745
<211> LENGTH: 45
<212> TYPE: DNA
<213> ORGANISM: Homo sapiens

<400> SEQUENCE: 745
agtataaaat tgcttaccca cgaatacgta tcaaggtctt aagga               45

<210> SEQ ID NO 746
<211> LENGTH: 45
<212> TYPE: DNA
<213> ORGANISM: Homo sapiens

<400> SEQUENCE: 746
aaacagctga aaacagtttt ataaatagt ataaaattgc ttacc                45

<210> SEQ ID NO 747
<211> LENGTH: 45
<212> TYPE: DNA
<213> ORGANISM: Homo sapiens

<400> SEQUENCE: 747 tgagggtag gaggtcaact gagtcaagga gcaaagccaa gaacc                45

<210> SEQ ID NO 748
<211> LENGTH: 45
<212> TYPE: DNA
<213> ORGANISM: Homo sapiens

<400> SEQUENCE: 748
agtgcatttt tgtaaatgtg tacatattaa aggaagcact ctgta               45

<210> SEQ ID NO 749
<211> LENGTH: 45
<212> TYPE: DNA
<213> ORGANISM: Homo sapiens

<400> SEQUENCE: 749
gtttattttc tacgtttctt taaccttgta taaattattc agtaa               45

<210> SEQ ID NO 750
<211> LENGTH: 45
<212> TYPE: DNA
<213> ORGANISM: Homo sapiens

<400> SEQUENCE: 750
aaaaaccaaa tgtttatttt ctacgtttct ttaaccttgt ataaa               45

<210> SEQ ID NO 751
<211> LENGTH: 45

<212> TYPE: DNA
<213> ORGANISM: Homo sapiens

<400> SEQUENCE: 751
taaaacagct gaaaacagtt ttataaaata gtataaaatt gctta                45

<210> SEQ ID NO 752
<211> LENGTH: 45
<212> TYPE: DNA
<213> ORGANISM: Homo sapiens

<400> SEQUENCE: 752
gagtgaggct gccttgcaca ggcagaacaa atgaataaat gaatg                45

<210> SEQ ID NO 753
<211> LENGTH: 45
<212> TYPE: DNA
<213> ORGANISM: Homo sapiens

<400> SEQUENCE: 753
attattcagt aactgtcagg ctgaaaacaa tggagtattc tcgga                45

<210> SEQ ID NO 754
<211> LENGTH: 45
<212> TYPE: DNA
<213> ORGANISM: Homo sapiens

<400> SEQUENCE: 754
ttttataaaa tagtataaaa ttgcttaccc acgaatacgt atcaa                45

<210> SEQ ID NO 755
<211> LENGTH: 45
<212> TYPE: DNA
<213> ORGANISM: Homo sapiens

<400> SEQUENCE: 755
aattattcag taactgtcag gctgaaaaca atggagtatt ctcgg                45

<210> SEQ ID NO 756
<211> LENGTH: 45
<212> TYPE: DNA
<213> ORGANISM: Homo sapiens

<400> SEQUENCE: 756
aaagtgcatt tttgtaaatg tgtacatatt aaaggaagca ctctg                45

<210> SEQ ID NO 757
<211> LENGTH: 45
<212> TYPE: DNA
<213> ORGANISM: Homo sapiens

<400> SEQUENCE: 757
cttgtataaa ttattcagta actgtcaggc tgaaaacaat ggagt                45

<210> SEQ ID NO 758
<211> LENGTH: 45
<212> TYPE: DNA
<213> ORGANISM: Homo sapiens

<400> SEQUENCE: 758
gctgaaaaca atggagtatt ctcggatagt tgctattttt gtaaa                45

<210> SEQ ID NO 759

```
<211> LENGTH: 45
<212> TYPE: DNA
<213> ORGANISM: Homo sapiens

<400> SEQUENCE: 759
aggcggagaa gttcctctca cacaaattca ccaaagatcc tggcc            45

<210> SEQ ID NO 760
<211> LENGTH: 45
<212> TYPE: DNA
<213> ORGANISM: Homo sapiens

<400> SEQUENCE: 760
cattcattta ttcctttgtt ttgcttggtc attcagaggc aaggt            45

<210> SEQ ID NO 761
<211> LENGTH: 20
<212> TYPE: DNA
<213> ORGANISM: Homo sapiens

<400> SEQUENCE: 761
tcatgcgaaa agaacctaca                                        20

<210> SEQ ID NO 762
<211> LENGTH: 20
<212> TYPE: DNA
<213> ORGANISM: Homo sapiens

<400> SEQUENCE: 762
aaatgtcaga agcttacaga                                        20

<210> SEQ ID NO 763
<211> LENGTH: 20
<212> TYPE: DNA
<213> ORGANISM: Homo sapiens

<400> SEQUENCE: 763
aaacatatga aacatgaaaa                                        20

<210> SEQ ID NO 764
<211> LENGTH: 20
<212> TYPE: DNA
<213> ORGANISM: Homo sapiens

<400> SEQUENCE: 764
cagttcctta tctaccaaat                                        20

<210> SEQ ID NO 765
<211> LENGTH: 20
<212> TYPE: DNA
<213> ORGANISM: Homo sapiens

<400> SEQUENCE: 765
tcctggtaca gaccatatta                                        20

<210> SEQ ID NO 766
<211> LENGTH: 20
<212> TYPE: DNA
<213> ORGANISM: Homo sapiens

<400> SEQUENCE: 766
ttccttatct accaaattct                                        20
```

```
<210> SEQ ID NO 767
<211> LENGTH: 20
<212> TYPE: DNA
<213> ORGANISM: Homo sapiens

<400> SEQUENCE: 767
ttcctggtac agaccatatt                                              20

<210> SEQ ID NO 768
<211> LENGTH: 20
<212> TYPE: DNA
<213> ORGANISM: Homo sapiens

<400> SEQUENCE: 768
aagtatatac attcagctga                                              20

<210> SEQ ID NO 769
<211> LENGTH: 20
<212> TYPE: DNA
<213> ORGANISM: Homo sapiens

<400> SEQUENCE: 769
cattacaacc agacagttga                                              20

<210> SEQ ID NO 770
<211> LENGTH: 20
<212> TYPE: DNA
<213> ORGANISM: Homo sapiens

<400> SEQUENCE: 770
agggacctaa aacctagtaa                                              20

<210> SEQ ID NO 771
<211> LENGTH: 20
<212> TYPE: DNA
<213> ORGANISM: Homo sapiens

<400> SEQUENCE: 771
ctctggagga attcaatgat                                              20

<210> SEQ ID NO 772
<211> LENGTH: 20
<212> TYPE: DNA
<213> ORGANISM: Homo sapiens

<400> SEQUENCE: 772
taaacatatg aaacatgaaa                                              20

<210> SEQ ID NO 773
<211> LENGTH: 20
<212> TYPE: DNA
<213> ORGANISM: Homo sapiens

<400> SEQUENCE: 773
gatctgaaca acattgtgaa                                              20

<210> SEQ ID NO 774
<211> LENGTH: 20
<212> TYPE: DNA
<213> ORGANISM: Homo sapiens

<400> SEQUENCE: 774
tcagttcctt atctaccaaa                                              20
```

```
<210> SEQ ID NO 775
<211> LENGTH: 20
<212> TYPE: DNA
<213> ORGANISM: Homo sapiens

<400> SEQUENCE: 775
ataattcaca gggacctaaa                                              20

<210> SEQ ID NO 776
<211> LENGTH: 20
<212> TYPE: DNA
<213> ORGANISM: Homo sapiens

<400> SEQUENCE: 776
cgaggtctaa agtatataca                                              20

<210> SEQ ID NO 777
<211> LENGTH: 20
<212> TYPE: DNA
<213> ORGANISM: Homo sapiens

<400> SEQUENCE: 777
gaaatgtcag aagcttacag                                              20

<210> SEQ ID NO 778
<211> LENGTH: 20
<212> TYPE: DNA
<213> ORGANISM: Homo sapiens

<400> SEQUENCE: 778
agctgttgac tggaagaaca                                              20

<210> SEQ ID NO 779
<211> LENGTH: 20
<212> TYPE: DNA
<213> ORGANISM: Homo sapiens

<400> SEQUENCE: 779
aaattctccg aggtctaaag                                              20

<210> SEQ ID NO 780
<211> LENGTH: 20
<212> TYPE: DNA
<213> ORGANISM: Homo sapiens

<400> SEQUENCE: 780
aatgtgattg gtctgttgga                                              20

<210> SEQ ID NO 781
<211> LENGTH: 45
<212> TYPE: DNA
<213> ORGANISM: Homo sapiens

<400> SEQUENCE: 781
atttcagtcc atcattcatg cgaaaagaac ctacagagaa ctgcg                  45

<210> SEQ ID NO 782
<211> LENGTH: 45
<212> TYPE: DNA
<213> ORGANISM: Homo sapiens

<400> SEQUENCE: 782
ctgaacaaca ttgtgaaatg tcagaagctt acagatgacc atgtt                  45
```

<210> SEQ ID NO 783
<211> LENGTH: 45
<212> TYPE: DNA
<213> ORGANISM: Homo sapiens

<400> SEQUENCE: 783
gaactgcggt tacttaaaca tatgaaacat gaaaatgtga ttggt            45

<210> SEQ ID NO 784
<211> LENGTH: 45
<212> TYPE: DNA
<213> ORGANISM: Homo sapiens

<400> SEQUENCE: 784
acagatgacc atgttcagtt ccttatctac caaattctcc gaggt            45

<210> SEQ ID NO 785
<211> LENGTH: 45
<212> TYPE: DNA
<213> ORGANISM: Homo sapiens

<400> SEQUENCE: 785
tggaagaaca ttgtttcctg gtacagacca tattaaccag cttca            45

<210> SEQ ID NO 786
<211> LENGTH: 45
<212> TYPE: DNA
<213> ORGANISM: Homo sapiens

<400> SEQUENCE: 786
gatgaccatg ttcagttcct tatctaccaa attctccgag gtcta            45

<210> SEQ ID NO 787
<211> LENGTH: 45
<212> TYPE: DNA
<213> ORGANISM: Homo sapiens

<400> SEQUENCE: 787
ctggaagaac attgtttcct ggtacagacc atattaacca gcttc            45

<210> SEQ ID NO 788
<211> LENGTH: 45
<212> TYPE: DNA
<213> ORGANISM: Homo sapiens

<400> SEQUENCE: 788
attctccgag gtctaaagta tatacattca gctgacataa ttcac            45

<210> SEQ ID NO 789
<211> LENGTH: 45
<212> TYPE: DNA
<213> ORGANISM: Homo sapiens

<400> SEQUENCE: 789
atgctgaact ggatgcatta caaccagaca gttgatattt ggtca            45

<210> SEQ ID NO 790
<211> LENGTH: 45
<212> TYPE: DNA
<213> ORGANISM: Homo sapiens

<400> SEQUENCE: 790

```
gctgacataa ttcacaggga cctaaaacct agtaatctag ctgtg            45

<210> SEQ ID NO 791
<211> LENGTH: 45
<212> TYPE: DNA
<213> ORGANISM: Homo sapiens

<400> SEQUENCE: 791
ttacacctgc aaggtctctg gaggaattca atgatgtgta tctgg            45

<210> SEQ ID NO 792
<211> LENGTH: 45
<212> TYPE: DNA
<213> ORGANISM: Homo sapiens

<400> SEQUENCE: 792
agaactgcgg ttacttaaac atatgaaaca tgaaaatgtg attgg            45

<210> SEQ ID NO 793
<211> LENGTH: 45
<212> TYPE: DNA
<213> ORGANISM: Homo sapiens

<400> SEQUENCE: 793
catctcatgg gggcagatct gaacaacatt gtgaaatgtc agaag            45

<210> SEQ ID NO 794
<211> LENGTH: 45
<212> TYPE: DNA
<213> ORGANISM: Homo sapiens

<400> SEQUENCE: 794
tacagatgac catgttcagt tccttatcta ccaaattctc cgagg            45

<210> SEQ ID NO 795
<211> LENGTH: 45
<212> TYPE: DNA
<213> ORGANISM: Homo sapiens

<400> SEQUENCE: 795
atacattcag ctgacataat tcacagggac ctaaaaccta gtaat            45

<210> SEQ ID NO 796
<211> LENGTH: 45
<212> TYPE: DNA
<213> ORGANISM: Homo sapiens

<400> SEQUENCE: 796
atctaccaaa ttctccgagg tctaaagtat atacattcag ctgac            45

<210> SEQ ID NO 797
<211> LENGTH: 45
<212> TYPE: DNA
<213> ORGANISM: Homo sapiens

<400> SEQUENCE: 797
tctgaacaac attgtgaaat gtcagaagct tacagatgac catgt            45

<210> SEQ ID NO 798
<211> LENGTH: 45
<212> TYPE: DNA
<213> ORGANISM: Homo sapiens

<400> SEQUENCE: 798
```

```
gatgcataat ggccgagctg ttgactggaa gaacattgtt tcctg          45
```

<210> SEQ ID NO 799
<211> LENGTH: 45
<212> TYPE: DNA
<213> ORGANISM: Homo sapiens

<400> SEQUENCE: 799

```
agttccttat ctaccaaatt ctccgaggtc taaagtatat acatt          45
```

<210> SEQ ID NO 800
<211> LENGTH: 45
<212> TYPE: DNA
<213> ORGANISM: Homo sapiens

<400> SEQUENCE: 800

```
catatgaaac atgaaaatgt gattggtctg ttggacgttt ttaca          45
```

<210> SEQ ID NO 801
<211> LENGTH: 20
<212> TYPE: DNA
<213> ORGANISM: Homo sapiens

<400> SEQUENCE: 801

```
ctgctgtgca gaatcctatt                                      20
```

<210> SEQ ID NO 802
<211> LENGTH: 20
<212> TYPE: DNA
<213> ORGANISM: Homo sapiens

<400> SEQUENCE: 802

```
gctgtgcaga atcctatttt                                      20
```

<210> SEQ ID NO 803
<211> LENGTH: 20
<212> TYPE: DNA
<213> ORGANISM: Homo sapiens

<400> SEQUENCE: 803

```
ttaaagtcag tttaggtaat                                      20
```

<210> SEQ ID NO 804
<211> LENGTH: 20
<212> TYPE: DNA
<213> ORGANISM: Homo sapiens

<400> SEQUENCE: 804

```
ctgtgcagaa tcctatttta                                      20
```

<210> SEQ ID NO 805
<211> LENGTH: 20
<212> TYPE: DNA
<213> ORGANISM: Homo sapiens

<400> SEQUENCE: 805

```
gtttacatat acccagtatc                                      20
```

<210> SEQ ID NO 806
<211> LENGTH: 20
<212> TYPE: DNA
<213> ORGANISM: Homo sapiens

```
<400> SEQUENCE: 806
attttgttat tacttgcctg                                              20

<210> SEQ ID NO 807
<211> LENGTH: 20
<212> TYPE: DNA
<213> ORGANISM: Homo sapiens

<400> SEQUENCE: 807
taactgggat gccgtgttat                                              20

<210> SEQ ID NO 808
<211> LENGTH: 20
<212> TYPE: DNA
<213> ORGANISM: Homo sapiens

<400> SEQUENCE: 808
tgttattact tgcctggaac                                              20

<210> SEQ ID NO 809
<211> LENGTH: 20
<212> TYPE: DNA
<213> ORGANISM: Homo sapiens

<400> SEQUENCE: 809
tttctgctgt gcagaatcct                                              20

<210> SEQ ID NO 810
<211> LENGTH: 20
<212> TYPE: DNA
<213> ORGANISM: Homo sapiens

<400> SEQUENCE: 810
cgtgttattt tgttattact                                              20

<210> SEQ ID NO 811
<211> LENGTH: 20
<212> TYPE: DNA
<213> ORGANISM: Homo sapiens

<400> SEQUENCE: 811
ttttaaagtc agtttaggta                                              20

<210> SEQ ID NO 812
<211> LENGTH: 20
<212> TYPE: DNA
<213> ORGANISM: Homo sapiens

<400> SEQUENCE: 812
tgctgtgcag aatcctattt                                              20

<210> SEQ ID NO 813
<211> LENGTH: 20
<212> TYPE: DNA
<213> ORGANISM: Homo sapiens

<400> SEQUENCE: 813
ggatgccgtg ttattttgtt                                              20

<210> SEQ ID NO 814
<211> LENGTH: 20
<212> TYPE: DNA
<213> ORGANISM: Homo sapiens
```

```
<400> SEQUENCE: 814
tttaaagtca gtttaggtaa                                              20

<210> SEQ ID NO 815
<211> LENGTH: 20
<212> TYPE: DNA
<213> ORGANISM: Homo sapiens

<400> SEQUENCE: 815
taaagtcagt ttaggtaata                                              20

<210> SEQ ID NO 816
<211> LENGTH: 20
<212> TYPE: DNA
<213> ORGANISM: Homo sapiens

<400> SEQUENCE: 816
tctgctgtgc agaatcctat                                              20

<210> SEQ ID NO 817
<211> LENGTH: 20
<212> TYPE: DNA
<213> ORGANISM: Homo sapiens

<400> SEQUENCE: 817
atatacccag tatctttgca                                              20

<210> SEQ ID NO 818
<211> LENGTH: 20
<212> TYPE: DNA
<213> ORGANISM: Homo sapiens

<400> SEQUENCE: 818
agaatcctat tttatatttt                                              20

<210> SEQ ID NO 819
<211> LENGTH: 20
<212> TYPE: DNA
<213> ORGANISM: Homo sapiens

<400> SEQUENCE: 819
ggttgttgta gcagcttaac                                              20

<210> SEQ ID NO 820
<211> LENGTH: 20
<212> TYPE: DNA
<213> ORGANISM: Homo sapiens

<400> SEQUENCE: 820
cccagtatct ttgcacaaac                                              20

<210> SEQ ID NO 821
<211> LENGTH: 45
<212> TYPE: DNA
<213> ORGANISM: Homo sapiens

<400> SEQUENCE: 821
tctggcttta tttttctgct gtgcagaatc ctatttata ttttt                   45

<210> SEQ ID NO 822
<211> LENGTH: 45
<212> TYPE: DNA
```

<213> ORGANISM: Homo sapiens

<400> SEQUENCE: 822
tggctttatt tttctgctgt gcagaatcct attttatatt tttta          45

<210> SEQ ID NO 823
<211> LENGTH: 45
<212> TYPE: DNA
<213> ORGANISM: Homo sapiens

<400> SEQUENCE: 823
cctattttat atttttaaa gtcagtttag gtaataaact ttatt          45

<210> SEQ ID NO 824
<211> LENGTH: 45
<212> TYPE: DNA
<213> ORGANISM: Homo sapiens

<400> SEQUENCE: 824
ggctttattt ttctgctgtg cagaatccta ttttatattt tttaa          45

<210> SEQ ID NO 825
<211> LENGTH: 45
<212> TYPE: DNA
<213> ORGANISM: Homo sapiens

<400> SEQUENCE: 825
ctcctacctc ttcatgttta catataccca gtatctttgc acaaa          45

<210> SEQ ID NO 826
<211> LENGTH: 45
<212> TYPE: DNA
<213> ORGANISM: Homo sapiens

<400> SEQUENCE: 826
ctgggatgcc gtgttatttt gttattactt gcctggaacc atgtg          45

<210> SEQ ID NO 827
<211> LENGTH: 45
<212> TYPE: DNA
<213> ORGANISM: Homo sapiens

<400> SEQUENCE: 827
ccgtgcacgc agcattaact gggatgccgt gttattttgt tatta          45

<210> SEQ ID NO 828
<211> LENGTH: 45
<212> TYPE: DNA
<213> ORGANISM: Homo sapiens

<400> SEQUENCE: 828
gatgccgtgt tattttgtta ttacttgcct ggaaccatgt gggta          45

<210> SEQ ID NO 829
<211> LENGTH: 45
<212> TYPE: DNA
<213> ORGANISM: Homo sapiens

<400> SEQUENCE: 829
gtctctggct ttatttttct gctgtgcaga atcctatttt atatt          45

<210> SEQ ID NO 830
<211> LENGTH: 45

<212> TYPE: DNA
<213> ORGANISM: Homo sapiens

<400> SEQUENCE: 830
cattaactgg gatgccgtgt tattttgtta ttacttgcct ggaac     45

<210> SEQ ID NO 831
<211> LENGTH: 45
<212> TYPE: DNA
<213> ORGANISM: Homo sapiens

<400> SEQUENCE: 831
atcctatttt atatttttta aagtcagttt aggtaataaa cttta     45

<210> SEQ ID NO 832
<211> LENGTH: 45
<212> TYPE: DNA
<213> ORGANISM: Homo sapiens

<400> SEQUENCE: 832
ctggctttat ttttctgctg tgcagaatcc tattttatat ttttt     45

<210> SEQ ID NO 833
<211> LENGTH: 45
<212> TYPE: DNA
<213> ORGANISM: Homo sapiens

<400> SEQUENCE: 833
acgcagcatt aactgggatg ccgtgttatt ttgttattac ttgcc     45

<210> SEQ ID NO 834
<211> LENGTH: 45
<212> TYPE: DNA
<213> ORGANISM: Homo sapiens

<400> SEQUENCE: 834
tcctatttta tattttttaa agtcagttta ggtaataaac tttat     45

<210> SEQ ID NO 835
<211> LENGTH: 45
<212> TYPE: DNA
<213> ORGANISM: Homo sapiens

<400> SEQUENCE: 835 ctatttt ata tttttt aaag tcagtttagg taataaactt tatta     45

<210> SEQ ID NO 836
<211> LENGTH: 45
<212> TYPE: DNA
<213> ORGANISM: Homo sapiens

<400> SEQUENCE: 836
ctctggcttt attttctgc tgtgcagaat cctattttat atttt     45

<210> SEQ ID NO 837
<211> LENGTH: 45
<212> TYPE: DNA
<213> ORGANISM: Homo sapiens

<400> SEQUENCE: 837
cctcttcatg tttacatata cccagtatct ttgcacaaac caggg     45

<210> SEQ ID NO 838

```
<211> LENGTH: 45
<212> TYPE: DNA
<213> ORGANISM: Homo sapiens

<400> SEQUENCE: 838 attttctgc tgtgcagaat cctattttat atttttaaa gtcag          45

<210> SEQ ID NO 839
<211> LENGTH: 45
<212> TYPE: DNA
<213> ORGANISM: Homo sapiens

<400> SEQUENCE: 839
cctctgggtc cccctggttg ttgtagcagc ttaactgtat ctgga         45

<210> SEQ ID NO 840
<211> LENGTH: 45
<212> TYPE: DNA
<213> ORGANISM: Homo sapiens

<400> SEQUENCE: 840
tcatgtttac atatacccag tatctttgca caaaccaggg gttgg         45

<210> SEQ ID NO 841
<211> LENGTH: 20
<212> TYPE: DNA
<213> ORGANISM: Homo sapiens

<400> SEQUENCE: 841
atattgctgt atctacttta                                     20

<210> SEQ ID NO 842
<211> LENGTH: 20
<212> TYPE: DNA
<213> ORGANISM: Homo sapiens

<400> SEQUENCE: 842
tgtttgttaa atcaaattag                                     20

<210> SEQ ID NO 843
<211> LENGTH: 20
<212> TYPE: DNA
<213> ORGANISM: Homo sapiens

<400> SEQUENCE: 843
tttatctaaa tgcaaataag                                     20

<210> SEQ ID NO 844
<211> LENGTH: 20
<212> TYPE: DNA
<213> ORGANISM: Homo sapiens

<400> SEQUENCE: 844
attttccttt gtaatgtatt                                     20

<210> SEQ ID NO 845
<211> LENGTH: 20
<212> TYPE: DNA
<213> ORGANISM: Homo sapiens

<400> SEQUENCE: 845
tatcagcaca atctacgaag                                     20
```

```
<210> SEQ ID NO 846
<211> LENGTH: 20
<212> TYPE: DNA
<213> ORGANISM: Homo sapiens

<400> SEQUENCE: 846
agcttaactg ataaacagaa                                              20

<210> SEQ ID NO 847
<211> LENGTH: 20
<212> TYPE: DNA
<213> ORGANISM: Homo sapiens

<400> SEQUENCE: 847
gttgttgttg ttcttagaca                                              20

<210> SEQ ID NO 848
<211> LENGTH: 20
<212> TYPE: DNA
<213> ORGANISM: Homo sapiens

<400> SEQUENCE: 848
gttgttgttc ttagacaagt                                              20

<210> SEQ ID NO 849
<211> LENGTH: 20
<212> TYPE: DNA
<213> ORGANISM: Homo sapiens

<400> SEQUENCE: 849
tctgtattta agaaacttaa                                              20

<210> SEQ ID NO 850
<211> LENGTH: 20
<212> TYPE: DNA
<213> ORGANISM: Homo sapiens

<400> SEQUENCE: 850
ttattttcct ttgtaatgta                                              20

<210> SEQ ID NO 851
<211> LENGTH: 20
<212> TYPE: DNA
<213> ORGANISM: Homo sapiens

<400> SEQUENCE: 851
taactgataa acagaatatt                                              20

<210> SEQ ID NO 852
<211> LENGTH: 20
<212> TYPE: DNA
<213> ORGANISM: Homo sapiens

<400> SEQUENCE: 852
acattctggg cacaaacaca                                              20

<210> SEQ ID NO 853
<211> LENGTH: 20
<212> TYPE: DNA
<213> ORGANISM: Homo sapiens

<400> SEQUENCE: 853
gtgatctgct tttatctaaa                                              20
```

```
<210> SEQ ID NO 854
<211> LENGTH: 20
<212> TYPE: DNA
<213> ORGANISM: Homo sapiens

<400> SEQUENCE: 854
cagacccgtc aacaaattaa                                              20

<210> SEQ ID NO 855
<211> LENGTH: 20
<212> TYPE: DNA
<213> ORGANISM: Homo sapiens

<400> SEQUENCE: 855
ggagctgttt agaaacttaa                                              20

<210> SEQ ID NO 856
<211> LENGTH: 20
<212> TYPE: DNA
<213> ORGANISM: Homo sapiens

<400> SEQUENCE: 856
accattgggt ttaaatcata                                              20

<210> SEQ ID NO 857
<211> LENGTH: 20
<212> TYPE: DNA
<213> ORGANISM: Homo sapiens

<400> SEQUENCE: 857
ggagaatcta agcattttag                                              20

<210> SEQ ID NO 858
<211> LENGTH: 20
<212> TYPE: DNA
<213> ORGANISM: Homo sapiens

<400> SEQUENCE: 858
ccttgctgac atccaaatag                                              20

<210> SEQ ID NO 859
<211> LENGTH: 20
<212> TYPE: DNA
<213> ORGANISM: Homo sapiens

<400> SEQUENCE: 859
aaattaagaa ataataacaa                                              20

<210> SEQ ID NO 860
<211> LENGTH: 20
<212> TYPE: DNA
<213> ORGANISM: Homo sapiens

<400> SEQUENCE: 860
ttttaaatta agaaataata                                              20

<210> SEQ ID NO 861
<211> LENGTH: 45
<212> TYPE: DNA
<213> ORGANISM: Homo sapiens

<400> SEQUENCE: 861
tttttttttt ttggtatatt gctgtatcta ctttaacttc cagaa                  45
```

<210> SEQ ID NO 862
<211> LENGTH: 45
<212> TYPE: DNA
<213> ORGANISM: Homo sapiens

<400> SEQUENCE: 862
gtttctgtgg aattctgttt gttaaatcaa attagctggt ctctg            45

<210> SEQ ID NO 863
<211> LENGTH: 45
<212> TYPE: DNA
<213> ORGANISM: Homo sapiens

<400> SEQUENCE: 863
tgtgggtgat ctgctttat ctaaatgcaa ataaggatgt gttct            45

<210> SEQ ID NO 864
<211> LENGTH: 45
<212> TYPE: DNA
<213> ORGANISM: Homo sapiens

<400> SEQUENCE: 864
tttataaata gacttatttt cctttgtaat gtattggcct tttag            45

<210> SEQ ID NO 865
<211> LENGTH: 45
<212> TYPE: DNA
<213> ORGANISM: Homo sapiens

<400> SEQUENCE: 865
gagtcgaatg ttctctatca gcacaatcta cgaagaatca agcag            45

<210> SEQ ID NO 866
<211> LENGTH: 45
<212> TYPE: DNA
<213> ORGANISM: Homo sapiens

<400> SEQUENCE: 866
cttcagtaca taataagctt aactgataaa cagaatattt agaaa            45

<210> SEQ ID NO 867
<211> LENGTH: 45
<212> TYPE: DNA
<213> ORGANISM: Homo sapiens

<400> SEQUENCE: 867 cagcttttg ttattgttgt tgttgttctt agacaagtgc ctcct            45

<210> SEQ ID NO 868
<211> LENGTH: 45
<212> TYPE: DNA
<213> ORGANISM: Homo sapiens

<400> SEQUENCE: 868 cttttgtta ttgttgttgt tgttcttaga caagtgcctc ctggt            45

<210> SEQ ID NO 869
<211> LENGTH: 45
<212> TYPE: DNA
<213> ORGANISM: Homo sapiens

<400> SEQUENCE: 869

```
tatcagcata gcctttctgt atttaagaaa cttaagcagc cgggc                45

<210> SEQ ID NO 870
<211> LENGTH: 45
<212> TYPE: DNA
<213> ORGANISM: Homo sapiens

<400> SEQUENCE: 870
tttttataaa tagacttatt ttcctttgta atgtattggc ctttt                45

<210> SEQ ID NO 871
<211> LENGTH: 45
<212> TYPE: DNA
<213> ORGANISM: Homo sapiens

<400> SEQUENCE: 871
agtacataat aagcttaact gataaacaga atatttagaa aggtg                45

<210> SEQ ID NO 872
<211> LENGTH: 45
<212> TYPE: DNA
<213> ORGANISM: Homo sapiens

<400> SEQUENCE: 872
gatcccggaa atttaacatt ctgggcacaa acacaaaagt gatga                45

<210> SEQ ID NO 873
<211> LENGTH: 45
<212> TYPE: DNA
<213> ORGANISM: Homo sapiens

<400> SEQUENCE: 873
aatgagtgaa tgtgggtgat ctgcttttat ctaaatgcaa ataag                45

<210> SEQ ID NO 874
<211> LENGTH: 45
<212> TYPE: DNA
<213> ORGANISM: Homo sapiens

<400> SEQUENCE: 874
gcagaatctc aacttcagac ccgtcaacaa attaagaaac tggag                45

<210> SEQ ID NO 875
<211> LENGTH: 45
<212> TYPE: DNA
<213> ORGANISM: Homo sapiens

<400> SEQUENCE: 875
ggaggagaga atcgtggagc tgtttagaaa cttaatgaaa agtgc                45

<210> SEQ ID NO 876
<211> LENGTH: 45
<212> TYPE: DNA
<213> ORGANISM: Homo sapiens

<400> SEQUENCE: 876
gtgagacttg ggcttaccat tgggtttaaa tcatagggac ctagg                45

<210> SEQ ID NO 877
<211> LENGTH: 45
<212> TYPE: DNA
<213> ORGANISM: Homo sapiens

<400> SEQUENCE: 877
```

-continued aataggaagg tttaaggaga atctaagcat tttagacttt ttttt                45

<210> SEQ ID NO 878
<211> LENGTH: 45
<212> TYPE: DNA
<213> ORGANISM: Homo sapiens

<400> SEQUENCE: 878
cattgcactt tttaaccttg ctgacatcca aatagaagat aggac                45

<210> SEQ ID NO 879
<211> LENGTH: 45
<212> TYPE: DNA
<213> ORGANISM: Homo sapiens

<400> SEQUENCE: 879
cctaggtttc ttttaaatt aagaaataat aacaattaaa gggca                 45

<210> SEQ ID NO 880
<211> LENGTH: 45
<212> TYPE: DNA
<213> ORGANISM: Homo sapiens

<400> SEQUENCE: 880
aagccctagg tttcttttta aattaagaaa taataacaat taaag                45

<210> SEQ ID NO 881
<211> LENGTH: 20
<212> TYPE: DNA
<213> ORGANISM: Homo sapiens

<400> SEQUENCE: 881
agcttgaact gaggagtaaa                                            20

<210> SEQ ID NO 882
<211> LENGTH: 20
<212> TYPE: DNA
<213> ORGANISM: Homo sapiens

<400> SEQUENCE: 882
cctttgcaac atcctcagaa                                            20

<210> SEQ ID NO 883
<211> LENGTH: 20
<212> TYPE: DNA
<213> ORGANISM: Homo sapiens

<400> SEQUENCE: 883
ttctttccaa agataccaaa                                            20

<210> SEQ ID NO 884
<211> LENGTH: 20
<212> TYPE: DNA
<213> ORGANISM: Homo sapiens

<400> SEQUENCE: 884
ttattttatt acaaacttca                                            20

<210> SEQ ID NO 885
<211> LENGTH: 20
<212> TYPE: DNA
<213> ORGANISM: Homo sapiens

```
<400> SEQUENCE: 885
tatttatact tattataaaa                                          20

<210> SEQ ID NO 886
<211> LENGTH: 20
<212> TYPE: DNA
<213> ORGANISM: Homo sapiens

<400> SEQUENCE: 886
catttcagac aaaatgctaa                                          20

<210> SEQ ID NO 887
<211> LENGTH: 20
<212> TYPE: DNA
<213> ORGANISM: Homo sapiens

<400> SEQUENCE: 887
atgaaggaga agctcttaaa                                          20

<210> SEQ ID NO 888
<211> LENGTH: 20
<212> TYPE: DNA
<213> ORGANISM: Homo sapiens

<400> SEQUENCE: 888
attttgtgtt gatcattatt                                          20

<210> SEQ ID NO 889
<211> LENGTH: 20
<212> TYPE: DNA
<213> ORGANISM: Homo sapiens

<400> SEQUENCE: 889
ttcatcgagt acagagaaaa                                          20

<210> SEQ ID NO 890
<211> LENGTH: 20
<212> TYPE: DNA
<213> ORGANISM: Homo sapiens

<400> SEQUENCE: 890
ttactgggaa gacgtgtaac                                          20

<210> SEQ ID NO 891
<211> LENGTH: 20
<212> TYPE: DNA
<213> ORGANISM: Homo sapiens

<400> SEQUENCE: 891
tcattgaagc tcagaatcag                                          20

<210> SEQ ID NO 892
<211> LENGTH: 20
<212> TYPE: DNA
<213> ORGANISM: Homo sapiens

<400> SEQUENCE: 892
ttccattctt aatgtgaaaa                                          20

<210> SEQ ID NO 893
<211> LENGTH: 20
<212> TYPE: DNA
<213> ORGANISM: Homo sapiens
```

-continued

```
<400> SEQUENCE: 893
tgaaggatac tgccagaagt                                               20

<210> SEQ ID NO 894
<211> LENGTH: 20
<212> TYPE: DNA
<213> ORGANISM: Homo sapiens

<400> SEQUENCE: 894
cacaagagtc aacattaaaa                                               20

<210> SEQ ID NO 895
<211> LENGTH: 20
<212> TYPE: DNA
<213> ORGANISM: Homo sapiens

<400> SEQUENCE: 895
aattatttat acttattata                                               20

<210> SEQ ID NO 896
<211> LENGTH: 20
<212> TYPE: DNA
<213> ORGANISM: Homo sapiens

<400> SEQUENCE: 896
ttcgtgcttc tccttatgaa                                               20

<210> SEQ ID NO 897
<211> LENGTH: 20
<212> TYPE: DNA
<213> ORGANISM: Homo sapiens

<400> SEQUENCE: 897
tattttatta caaacttcaa                                               20

<210> SEQ ID NO 898
<211> LENGTH: 20
<212> TYPE: DNA
<213> ORGANISM: Homo sapiens

<400> SEQUENCE: 898
tattacaaac ttcaagatta                                               20

<210> SEQ ID NO 899
<211> LENGTH: 20
<212> TYPE: DNA
<213> ORGANISM: Homo sapiens

<400> SEQUENCE: 899
ctcttaaagt tgatatctta                                               20

<210> SEQ ID NO 900
<211> LENGTH: 20
<212> TYPE: DNA
<213> ORGANISM: Homo sapiens

<400> SEQUENCE: 900
ttccaaagat accaaataaa                                               20

<210> SEQ ID NO 901
<211> LENGTH: 45
<212> TYPE: DNA
```

<213> ORGANISM: Homo sapiens

<400> SEQUENCE: 901
acttctaaag aagttagctt gaactgagga gtaaaagtgt gtaca  45

<210> SEQ ID NO 902
<211> LENGTH: 45
<212> TYPE: DNA
<213> ORGANISM: Homo sapiens

<400> SEQUENCE: 902
aatacacata tttgtccttt gcaacatcct cagaaggcca atcat  45

<210> SEQ ID NO 903
<211> LENGTH: 45
<212> TYPE: DNA
<213> ORGANISM: Homo sapiens

<400> SEQUENCE: 903
acgaatcttt ataatttctt tccaaagata ccaataaac ttcag  45

<210> SEQ ID NO 904
<211> LENGTH: 45
<212> TYPE: DNA
<213> ORGANISM: Homo sapiens

<400> SEQUENCE: 904
tgtaattcac tttatttatt ttattacaaa cttcaagatt attta  45

<210> SEQ ID NO 905
<211> LENGTH: 45
<212> TYPE: DNA
<213> ORGANISM: Homo sapiens

<400> SEQUENCE: 905
gtgaaaaaaa gtaattattt atacttatta taaaaagtat ttgaa  45

<210> SEQ ID NO 906
<211> LENGTH: 45
<212> TYPE: DNA
<213> ORGANISM: Homo sapiens

<400> SEQUENCE: 906
aaggccaatc attgtcattt cagacaaaat gctaagaagt ttgga  45

<210> SEQ ID NO 907
<211> LENGTH: 45
<212> TYPE: DNA
<213> ORGANISM: Homo sapiens

<400> SEQUENCE: 907
gatcctgaaa atgagatgaa ggagaagctc ttaaaagagt actta  45

<210> SEQ ID NO 908
<211> LENGTH: 45
<212> TYPE: DNA
<213> ORGANISM: Homo sapiens

<400> SEQUENCE: 908
agttgatatc ttaatatttt gtgttgatca ttatttccat tctta  45

<210> SEQ ID NO 909
<211> LENGTH: 45

```
<212> TYPE: DNA
<213> ORGANISM: Homo sapiens

<400> SEQUENCE: 909
ttttgcacac tgtgtttcat cgagtacaga gaaaacaaac atttt            45

<210> SEQ ID NO 910
<211> LENGTH: 45
<212> TYPE: DNA
<213> ORGANISM: Homo sapiens

<400> SEQUENCE: 910
aaaaattaga atattttact gggaagacgt gtaactcttt gggtt            45

<210> SEQ ID NO 911
<211> LENGTH: 45
<212> TYPE: DNA
<213> ORGANISM: Homo sapiens

<400> SEQUENCE: 911
actgccagaa gtgtttcatt gaagctcaga atcagagatt tcatg            45

<210> SEQ ID NO 912
<211> LENGTH: 45
<212> TYPE: DNA
<213> ORGANISM: Homo sapiens

<400> SEQUENCE: 912
tgtgttgatc attatttcca ttcttaatgt gaaaaaagt aatta             45

<210> SEQ ID NO 913
<211> LENGTH: 45
<212> TYPE: DNA
<213> ORGANISM: Homo sapiens

<400> SEQUENCE: 913
tggaagcacc atgtttgaag gatactgcca gaagtgtttc attga            45

<210> SEQ ID NO 914
<211> LENGTH: 45
<212> TYPE: DNA
<213> ORGANISM: Homo sapiens

<400> SEQUENCE: 914
ataaatgtaa cttttcacaa gagtcaacat taaaaaataa attat            45

<210> SEQ ID NO 915
<211> LENGTH: 45
<212> TYPE: DNA
<213> ORGANISM: Homo sapiens

<400> SEQUENCE: 915
aatgtgaaaa aaagtaatta tttatactta ttataaaaag tattt            45

<210> SEQ ID NO 916
<211> LENGTH: 45
<212> TYPE: DNA
<213> ORGANISM: Homo sapiens

<400> SEQUENCE: 916
catattcatc gatgtttcgt gcttctcctt atgaaactcc agcta            45

<210> SEQ ID NO 917
```

```
<211> LENGTH: 45
<212> TYPE: DNA
<213> ORGANISM: Homo sapiens

<400> SEQUENCE: 917
gtaattcact ttatttattt tattacaaac ttcaagatta tttaa            45

<210> SEQ ID NO 918
<211> LENGTH: 45
<212> TYPE: DNA
<213> ORGANISM: Homo sapiens

<400> SEQUENCE: 918
tcactttatt tattttatta caaacttcaa gattatttaa gtgaa            45

<210> SEQ ID NO 919
<211> LENGTH: 45
<212> TYPE: DNA
<213> ORGANISM: Homo sapiens

<400> SEQUENCE: 919
tgttttcatc taattctctt aaagttgata tcttaatatt ttgtg            45

<210> SEQ ID NO 920
<211> LENGTH: 45
<212> TYPE: DNA
<213> ORGANISM: Homo sapiens

<400> SEQUENCE: 920
atctttataa tttctttcca aagataccaa ataaacttca gtgtt            45

<210> SEQ ID NO 921
<211> LENGTH: 20
<212> TYPE: DNA
<213> ORGANISM: Homo sapiens

<400> SEQUENCE: 921
aatttgactt agccactaac                                        20

<210> SEQ ID NO 922
<211> LENGTH: 20
<212> TYPE: DNA
<213> ORGANISM: Homo sapiens

<400> SEQUENCE: 922
gatattaata atatagttaa                                        20

<210> SEQ ID NO 923
<211> LENGTH: 20
<212> TYPE: DNA
<213> ORGANISM: Homo sapiens

<400> SEQUENCE: 923
ctgtgaatgc acatattaaa                                        20

<210> SEQ ID NO 924
<211> LENGTH: 20
<212> TYPE: DNA
<213> ORGANISM: Homo sapiens

<400> SEQUENCE: 924
gttttctatt tcctcttaag                                        20
```

```
<210> SEQ ID NO 925
<211> LENGTH: 20
<212> TYPE: DNA
<213> ORGANISM: Homo sapiens

<400> SEQUENCE: 925
aaatagcact aagaagttat                                               20

<210> SEQ ID NO 926
<211> LENGTH: 20
<212> TYPE: DNA
<213> ORGANISM: Homo sapiens

<400> SEQUENCE: 926
ccaatcccga tccaaatcat                                               20

<210> SEQ ID NO 927
<211> LENGTH: 20
<212> TYPE: DNA
<213> ORGANISM: Homo sapiens

<400> SEQUENCE: 927
ctatttagag aatgcttaag                                               20

<210> SEQ ID NO 928
<211> LENGTH: 20
<212> TYPE: DNA
<213> ORGANISM: Homo sapiens

<400> SEQUENCE: 928
cagtttgcat attgcctaaa                                               20

<210> SEQ ID NO 929
<211> LENGTH: 20
<212> TYPE: DNA
<213> ORGANISM: Homo sapiens

<400> SEQUENCE: 929
ctcgaattca aagtatcaaa                                               20

<210> SEQ ID NO 930
<211> LENGTH: 20
<212> TYPE: DNA
<213> ORGANISM: Homo sapiens

<400> SEQUENCE: 930
atctgtgaat gcacatatta                                               20

<210> SEQ ID NO 931
<211> LENGTH: 20
<212> TYPE: DNA
<213> ORGANISM: Homo sapiens

<400> SEQUENCE: 931
tttgtgggaa aagaattgaa                                               20

<210> SEQ ID NO 932
<211> LENGTH: 20
<212> TYPE: DNA
<213> ORGANISM: Homo sapiens

<400> SEQUENCE: 932
attgaccatg ttctgcaaaa                                               20
```

<210> SEQ ID NO 933
<211> LENGTH: 20
<212> TYPE: DNA
<213> ORGANISM: Homo sapiens

<400> SEQUENCE: 933
gattcttcat tgcaagtgaa                                           20

<210> SEQ ID NO 934
<211> LENGTH: 20
<212> TYPE: DNA
<213> ORGANISM: Homo sapiens

<400> SEQUENCE: 934
gatgtcaaat agcactaaga                                           20

<210> SEQ ID NO 935
<211> LENGTH: 20
<212> TYPE: DNA
<213> ORGANISM: Homo sapiens

<400> SEQUENCE: 935
gtatacaggg agagtgagat                                           20

<210> SEQ ID NO 936
<211> LENGTH: 20
<212> TYPE: DNA
<213> ORGANISM: Homo sapiens

<400> SEQUENCE: 936
gttgctatga gtcaaggagt                                           20

<210> SEQ ID NO 937
<211> LENGTH: 20
<212> TYPE: DNA
<213> ORGANISM: Homo sapiens

<400> SEQUENCE: 937
tagttgaaat gtccccttaa                                           20

<210> SEQ ID NO 938
<211> LENGTH: 20
<212> TYPE: DNA
<213> ORGANISM: Homo sapiens

<400> SEQUENCE: 938
ctctgtgcca aaccttttat                                           20

<210> SEQ ID NO 939
<211> LENGTH: 20
<212> TYPE: DNA
<213> ORGANISM: Homo sapiens

<400> SEQUENCE: 939
ctctgtctag aaataccata                                           20

<210> SEQ ID NO 940
<211> LENGTH: 20
<212> TYPE: DNA
<213> ORGANISM: Homo sapiens

<400> SEQUENCE: 940
ggtttcaaga aatgaggtga                                           20

<210> SEQ ID NO 941
<211> LENGTH: 45
<212> TYPE: DNA
<213> ORGANISM: Homo sapiens

<400> SEQUENCE: 941
gagatcagaa ttttaaattt gacttagcca ctaactagcc atgta    45

<210> SEQ ID NO 942
<211> LENGTH: 45
<212> TYPE: DNA
<213> ORGANISM: Homo sapiens

<400> SEQUENCE: 942
gagagtatta atattgatat taataatata gttaatagta atatt    45

<210> SEQ ID NO 943
<211> LENGTH: 45
<212> TYPE: DNA
<213> ORGANISM: Homo sapiens

<400> SEQUENCE: 943
tgcttacagt gttatctgtg aatgcacata ttaaatgtct atgtt    45

<210> SEQ ID NO 944
<211> LENGTH: 45
<212> TYPE: DNA
<213> ORGANISM: Homo sapiens

<400> SEQUENCE: 944
ggattttttt ttcctgtttt ctatttcctc ttaagtacac cttca    45

<210> SEQ ID NO 945
<211> LENGTH: 45
<212> TYPE: DNA
<213> ORGANISM: Homo sapiens

<400> SEQUENCE: 945
attcaatctg atgtcaaata gcactaagaa gttattgtgc cttat    45

<210> SEQ ID NO 946
<211> LENGTH: 45
<212> TYPE: DNA
<213> ORGANISM: Homo sapiens

<400> SEQUENCE: 946
aatgcttaag ggattccaat cccgatccaa atcataattt gttct    45

<210> SEQ ID NO 947
<211> LENGTH: 45
<212> TYPE: DNA
<213> ORGANISM: Homo sapiens

<400> SEQUENCE: 947
ttagttagat attttctatt tagagaatgc ttaagggatt ccaat    45

<210> SEQ ID NO 948
<211> LENGTH: 45
<212> TYPE: DNA
<213> ORGANISM: Homo sapiens

<400> SEQUENCE: 948
aggttaaatt gattgcagtt tgcatattgc ctaaatttaa acttt         45

<210> SEQ ID NO 949
<211> LENGTH: 45
<212> TYPE: DNA
<213> ORGANISM: Homo sapiens

<400> SEQUENCE: 949
tatcacatcg gtatcctcga attcaaagta tcaaagtaca attta         45

<210> SEQ ID NO 950
<211> LENGTH: 45
<212> TYPE: DNA
<213> ORGANISM: Homo sapiens

<400> SEQUENCE: 950
tatgcttaca gtgttatctg tgaatgcaca tattaaatgt ctatg         45

<210> SEQ ID NO 951
<211> LENGTH: 45
<212> TYPE: DNA
<213> ORGANISM: Homo sapiens

<400> SEQUENCE: 951
tatacatggc agagttttgt gggaaaagaa ttgaatgaaa agtca         45

<210> SEQ ID NO 952
<211> LENGTH: 45
<212> TYPE: DNA
<213> ORGANISM: Homo sapiens

<400> SEQUENCE: 952
atttcacttt ttgttattga ccatgttctg caaaattgca gttac         45

<210> SEQ ID NO 953
<211> LENGTH: 45
<212> TYPE: DNA
<213> ORGANISM: Homo sapiens

<400> SEQUENCE: 953
ggtggacagg gcatggattc ttcattgcaa gtgaaggagc ctccc         45

<210> SEQ ID NO 954
<211> LENGTH: 45
<212> TYPE: DNA
<213> ORGANISM: Homo sapiens

<400> SEQUENCE: 954
tatcaaattc aatctgatgt caaatagcac taagaagtta ttgtg         45

<210> SEQ ID NO 955
<211> LENGTH: 45
<212> TYPE: DNA
<213> ORGANISM: Homo sapiens

<400> SEQUENCE: 955
aagagagatt ttcttgtata cagggagagt gagataactt attgt         45

<210> SEQ ID NO 956
<211> LENGTH: 45
<212> TYPE: DNA
<213> ORGANISM: Homo sapiens

<400> SEQUENCE: 956

```
aatgtctatg ttcttgttgc tatgagtcaa ggagtgtaac cttct                45

<210> SEQ ID NO 957
<211> LENGTH: 45
<212> TYPE: DNA
<213> ORGANISM: Homo sapiens

<400> SEQUENCE: 957 gtatccccctt atgtttagtt gaaatgtccc cttaacttga tataa               45

<210> SEQ ID NO 958
<211> LENGTH: 45
<212> TYPE: DNA
<213> ORGANISM: Homo sapiens

<400> SEQUENCE: 958
gatgatttgt aacttctctg tgccaaacct tttataaaca taaat                45

<210> SEQ ID NO 959
<211> LENGTH: 45
<212> TYPE: DNA
<213> ORGANISM: Homo sapiens

<400> SEQUENCE: 959
atgaaaaata atgatctctg tctagaaata ccatagacca tatat                45

<210> SEQ ID NO 960
<211> LENGTH: 45
<212> TYPE: DNA
<213> ORGANISM: Homo sapiens

<400> SEQUENCE: 960
cacagaaaca ttgctggttt caagaaatga ggtgatccta ttatc                45

<210> SEQ ID NO 961
<211> LENGTH: 20
<212> TYPE: DNA
<213> ORGANISM: Homo sapiens

<400> SEQUENCE: 961
agttgctgtt taaaatagaa                                            20

<210> SEQ ID NO 962
<211> LENGTH: 20
<212> TYPE: DNA
<213> ORGANISM: Homo sapiens

<400> SEQUENCE: 962
ctgtttaaaa tagaaataaa                                            20

<210> SEQ ID NO 963
<211> LENGTH: 20
<212> TYPE: DNA
<213> ORGANISM: Homo sapiens

<400> SEQUENCE: 963
ggcatcagcg atgaactaaa                                            20

<210> SEQ ID NO 964
<211> LENGTH: 20
<212> TYPE: DNA
<213> ORGANISM: Homo sapiens
```

```
<400> SEQUENCE: 964
aatatcctaa gactaacaaa                                            20

<210> SEQ ID NO 965
<211> LENGTH: 20
<212> TYPE: DNA
<213> ORGANISM: Homo sapiens

<400> SEQUENCE: 965
gttgctgttt aaaatagaaa                                            20

<210> SEQ ID NO 966
<211> LENGTH: 20
<212> TYPE: DNA
<213> ORGANISM: Homo sapiens

<400> SEQUENCE: 966
aaaatagaaa taaaattgaa                                            20

<210> SEQ ID NO 967
<211> LENGTH: 20
<212> TYPE: DNA
<213> ORGANISM: Homo sapiens

<400> SEQUENCE: 967
ctgtgaagct cacaacctaa                                            20

<210> SEQ ID NO 968
<211> LENGTH: 20
<212> TYPE: DNA
<213> ORGANISM: Homo sapiens

<400> SEQUENCE: 968
ttgaagacta aagacctaaa                                            20

<210> SEQ ID NO 969
<211> LENGTH: 20
<212> TYPE: DNA
<213> ORGANISM: Homo sapiens

<400> SEQUENCE: 969
tcctaagact aacaaaggca                                            20

<210> SEQ ID NO 970
<211> LENGTH: 20
<212> TYPE: DNA
<213> ORGANISM: Homo sapiens

<400> SEQUENCE: 970
ggacatttcc aagctgttag                                            20

<210> SEQ ID NO 971
<211> LENGTH: 20
<212> TYPE: DNA
<213> ORGANISM: Homo sapiens

<400> SEQUENCE: 971 atgttttccat ggttaccatg                                           20

<210> SEQ ID NO 972
<211> LENGTH: 20
<212> TYPE: DNA
<213> ORGANISM: Homo sapiens
```

-continued

```
<400> SEQUENCE: 972
tagttgctgt ttaaaataga                                              20

<210> SEQ ID NO 973
<211> LENGTH: 20
<212> TYPE: DNA
<213> ORGANISM: Homo sapiens

<400> SEQUENCE: 973
aaaattgaag actaaagacc                                              20

<210> SEQ ID NO 974
<211> LENGTH: 20
<212> TYPE: DNA
<213> ORGANISM: Homo sapiens

<400> SEQUENCE: 974
agctgttagg gacatttcca                                              20

<210> SEQ ID NO 975
<211> LENGTH: 20
<212> TYPE: DNA
<213> ORGANISM: Homo sapiens

<400> SEQUENCE: 975
gaggacgtgt atgatctcat                                              20

<210> SEQ ID NO 976
<211> LENGTH: 20
<212> TYPE: DNA
<213> ORGANISM: Homo sapiens

<400> SEQUENCE: 976
ttttaggtga gggttggtaa                                              20

<210> SEQ ID NO 977
<211> LENGTH: 20
<212> TYPE: DNA
<213> ORGANISM: Homo sapiens

<400> SEQUENCE: 977
agctgacatc attgcctcaa                                              20

<210> SEQ ID NO 978
<211> LENGTH: 20
<212> TYPE: DNA
<213> ORGANISM: Homo sapiens

<400> SEQUENCE: 978
aaatctcaaa atatcctaag                                              20

<210> SEQ ID NO 979
<211> LENGTH: 20
<212> TYPE: DNA
<213> ORGANISM: Homo sapiens

<400> SEQUENCE: 979
aagctgttag ttgctgttta                                              20

<210> SEQ ID NO 980
<211> LENGTH: 20
<212> TYPE: DNA
```

<213> ORGANISM: Homo sapiens

<400> SEQUENCE: 980
tccttgtaat attcccttt 20

<210> SEQ ID NO 981
<211> LENGTH: 45
<212> TYPE: DNA
<213> ORGANISM: Homo sapiens

<400> SEQUENCE: 981
catttccaag ctgttagttg ctgtttaaaa tagaaataaa attga 45

<210> SEQ ID NO 982
<211> LENGTH: 45
<212> TYPE: DNA
<213> ORGANISM: Homo sapiens

<400> SEQUENCE: 982
ccaagctgtt agttgctgtt taaatagaa ataaaattga agact 45

<210> SEQ ID NO 983
<211> LENGTH: 45
<212> TYPE: DNA
<213> ORGANISM: Homo sapiens

<400> SEQUENCE: 983
acattggaca gcttgggcat cagcgatgaa ctaaaggaaa aactg 45

<210> SEQ ID NO 984
<211> LENGTH: 45
<212> TYPE: DNA
<213> ORGANISM: Homo sapiens

<400> SEQUENCE: 984
gctaccaaat ctcaaaatat cctaagacta acaaaggcag ctgtg 45

<210> SEQ ID NO 985
<211> LENGTH: 45
<212> TYPE: DNA
<213> ORGANISM: Homo sapiens

<400> SEQUENCE: 985
atttccaagc tgttagttgc tgtttaaaat agaaataaaa ttgaa 45

<210> SEQ ID NO 986
<211> LENGTH: 45
<212> TYPE: DNA
<213> ORGANISM: Homo sapiens

<400> SEQUENCE: 986
tgttagttgc tgtttaaaat agaaataaaa ttgaagacta aagac 45

<210> SEQ ID NO 987
<211> LENGTH: 45
<212> TYPE: DNA
<213> ORGANISM: Homo sapiens

<400> SEQUENCE: 987
gagcaccatg ttttcctgtg aagctcacaa cctaaaaggc ctggc 45

<210> SEQ ID NO 988
<211> LENGTH: 45

```
<212> TYPE: DNA
<213> ORGANISM: Homo sapiens

<400> SEQUENCE: 988
aaaatagaaa taaaattgaa gactaaagac ctaaaaaaaa aaaaa              45

<210> SEQ ID NO 989
<211> LENGTH: 45
<212> TYPE: DNA
<213> ORGANISM: Homo sapiens

<400> SEQUENCE: 989
ccaaatctca aaatatccta agactaacaa aggcagctgt gtctg              45

<210> SEQ ID NO 990
<211> LENGTH: 45
<212> TYPE: DNA
<213> ORGANISM: Homo sapiens

<400> SEQUENCE: 990
ggtcctagct gttagggaca tttccaagct gttagttgct gttta              45

<210> SEQ ID NO 991
<211> LENGTH: 45
<212> TYPE: DNA
<213> ORGANISM: Homo sapiens

<400> SEQUENCE: 991
aggagtgggg tggttatgtt tccatggtta ccatgggtgt ggatg              45

<210> SEQ ID NO 992
<211> LENGTH: 45
<212> TYPE: DNA
<213> ORGANISM: Homo sapiens

<400> SEQUENCE: 992
acatttccaa gctgttagtt gctgtttaaa atagaaataa aattg              45

<210> SEQ ID NO 993
<211> LENGTH: 45
<212> TYPE: DNA
<213> ORGANISM: Homo sapiens

<400> SEQUENCE: 993
gtttaaaata gaaataaaat tgaagactaa agacctaaaa aaaaa              45

<210> SEQ ID NO 994
<211> LENGTH: 45
<212> TYPE: DNA
<213> ORGANISM: Homo sapiens

<400> SEQUENCE: 994
catggggcgg gtcctagctg ttagggacat ttccaagctg ttagt              45

<210> SEQ ID NO 995
<211> LENGTH: 45
<212> TYPE: DNA
<213> ORGANISM: Homo sapiens

<400> SEQUENCE: 995
cctccggagt gtatggagga cgtgtatgat ctcatgtacc agtgc              45

<210> SEQ ID NO 996
```

<211> LENGTH: 45
<212> TYPE: DNA
<213> ORGANISM: Homo sapiens

<400> SEQUENCE: 996
ccttgtaata ttccctttta ggtgagggtt ggtaaggggt tggta    45

<210> SEQ ID NO 997
<211> LENGTH: 45
<212> TYPE: DNA
<213> ORGANISM: Homo sapiens

<400> SEQUENCE: 997
tgtgaagatg ctgaaagctg acatcattgc ctcaagcgac attga    45

<210> SEQ ID NO 998
<211> LENGTH: 45
<212> TYPE: DNA
<213> ORGANISM: Homo sapiens

<400> SEQUENCE: 998
tctgagcacg ctaccaaatc tcaaaatatc ctaagactaa caaag    45

<210> SEQ ID NO 999
<211> LENGTH: 45
<212> TYPE: DNA
<213> ORGANISM: Homo sapiens

<400> SEQUENCE: 999
gttagggaca tttccaagct gttagttgct gtttaaaata gaaat    45

<210> SEQ ID NO 1000
<211> LENGTH: 45
<212> TYPE: DNA
<213> ORGANISM: Homo sapiens

<400> SEQUENCE: 1000
agtcacaaag agatgtcctt gtaatattcc cttttaggtg aggt    45

<210> SEQ ID NO 1001
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1001
gagtaggaca taccagctta    20

<210> SEQ ID NO 1002
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 1002
agagttctgt ggaagtcta    19

<210> SEQ ID NO 1003
<211> LENGTH: 19
<212> TYPE: DNA
<213> ORGANISM: Artificial Sequence
<220> FEATURE:
<223> OTHER INFORMATION: Synthetic polynucleotide

```
<400> SEQUENCE: 1003
agagttctgt ggaagtcta                                              19

<210> SEQ ID NO 1004
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 1004
agagttctgt ggaagtcta                                              19

<210> SEQ ID NO 1005
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 1005
acagcaaatt ccatcgtgt                                              19

<210> SEQ ID NO 1006
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1006
ctggtaaagt ggatattgtt                                             20

<210> SEQ ID NO 1007
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 1007
agagttctgt ggaagtcta                                              19
```

IMMUNOTHERAPY OF CANCER

CROSS REFERENCE

This application is a national stage filing under 35 U.S.C. § 371 of International Application No. PCT/US2014/068244, filed Dec. 2, 2014, which was published under PCT Article 21(2) in English and claims priority to U.S. Provisional Application No. 61/910,728, filed Dec. 2, 2013, each of which is herein incorporated by reference in its entirety.

TECHNICAL FIELD

The present invention relates to immunogenic compositions, method of making immunogenic compositions, and methods of using immunogenic compositions for the treatment of cell proliferative disorders or infectious disease, including, for example, cancer and autoimmune disorders.

More particularly, the invention provides cells that are treated with oligonucleotides specifically designed to modulate expression of target genes involved in tumor immune resistance mechanisms.

BACKGROUND

Immunotherapy is the "treatment of disease by inducing, enhancing, or suppressing an immune response". Immunotherapies designed to elicit or amplify an immune response are activation immunotherapies, while immunotherapies that reduce or suppress immune response are classified as suppression immunotherapies.

Immunotherapy of cancer has become increasingly important in clinical practice over recent decades. The primary approach in today's standard of care is passive immunotherapy through the use of recombinant monoclonal antibodies (mAbs). MAbs act through a mechanisms relevant to the body's own humoral immune response, by binding to key antigens involved in the tumor development and causing moderate forms of cell-mediated immunity, such as antibody-dependent cell-mediated cytotoxicity (ADCC).

Another group of emerging immunotherapeutic approaches is based on the administration of cells capable of destroying tumor cells. The administered cells may be the patient's own tumor-infiltrating lymphocytes (TIL), isolated and expanded ex-vivo. In some cases, TIL are capable of recognizing a variety of tumor associated antigens (TAA), while in other cases TIL can be reactivated and expanded in vitro to recognize specific antigens. The TIL-based therapeutic approaches are commonly referred to as "adoptive cell transfer" (ACT).

Further developments of ACT involve genetic modifications of T-cells to express receptors that recognize specific tumor-associated antigens (TAA). Such modifications may induce the expression of a specific T-cell receptor (TCR) or of a chimeric antigen receptor (CAR) consisting of TAA-specific antibody fused to CD3/co-stimulatory molecule transmembrane and cytoplasmic domains.

The ACT methods may also be considered as passive immunotherapeutic approaches in that they act directly on the tumor cells without invoking an extended immune response. However, unlike mAbs, ACT agents are capable of fully destroying the tumor cells, as opposed to the blockade of selected receptors and moderate cellular responses such as ADCC.

There is ongoing development of numerous methods of active immunotherapy, which restore the ability of body's own immune system to generate antitumor response. Active immunotherapeutic agents are often called therapeutic cancer vaccines, or just cancer vaccines. Many cancer vaccines are currently in clinical trials, and sipuleucell-T has recently become the first such vaccine approved by the United States FDA.

There are several classes of cancer vaccines using different antigens and different mechanisms of generating cell-mediated immune response. One class of vaccines is based on peptide fragments of antigens selectively expressed by tumor cells. The peptides are administered alone or in combination with immune-stimulatory agents, which may include adjuvants and cytokines, such as granulocyte-macrophage colony-stimulating factor (GM-CSF).

Another class of cancer vaccines is based on modified (e.g. sub-lethally irradiated) tumor cells used as antigens, also in combinations with immuno-stimulatory agents. Vaccines of this type currently in clinical trials are based both on autologous (e.g. OncoVAX, LipoNova) and allogeneic (e.g. Canvaxin, Onyvax-P, GVAX) tumor cell lines.

Yet another class of cancer vaccines uses dendritic cells. By their nature, dendritic cells (DC) are "professional" antigen-presenting cells capable of generating of a strong antigen-dependent cell-mediated immune response and eliciting therapeutic T-cells in vivo. DC-based cancer vaccines usually comprise DCs isolated from patients or generated ex vivo by culturing patient's hematopoietic progenitor cells or monocytes. DCs are further loaded with tumor antigens and sometimes combined with immune-stimulating agents, such as GM-CSF. A large number of DC-vaccines are now in clinical trials, and the first FDA-approved vaccine sipuleucell-T is based on DC.

Mechanisms of Immunosuppression and Therapeutic Approaches to its Mitigation

One of the key physiologic functions of the immune system is to recognize and eliminate neoplastic cells, therefore an essential part of any tumor progression is the development of immune resistance mechanisms. Once developed, these mechanisms not only prevent the natural immune system from effecting the tumor growth, but also limit the efficacy of any immunotherapeutic approaches to cancer. An important immune resistance mechanism involves immune-inhibitory pathways, sometimes referred to as immune checkpoints. The immune-inhibitory pathways play particularly important role in the interaction between tumor cells and CD8+ cytotoxic T-lymphocytes, including ACT therapeutic agents. Among important immune checkpoints are inhibitory receptors expressed on the T-cell surface, such as CTLA-4, PD1 and LAGS, among others.

The importance of the attenuation of immune checkpoints has been recognized by the scientific and medical community. One way to mitigate immunosuppression is to block the immune checkpoints by specially designed agents. The CTLA-4-blocking-antibody, ipilimumab, has recently been approved by the FDA. Several molecules blocking PD1 are currently in clinical development.

Immunosuppression mechanisms also negatively affect the function of dendritic cells and, as a consequence, the efficacy of DC-based cancer vaccines. Immunosuppressive mechanisms can inhibit the ability of DC to present tumor antigens through the MHC class I pathway and to prime naïve CD8+ T-cells for antitumor immunity. Among the important molecules responsible for the immunosuppression mechanisms in DC are ubiquitin ligase A20 and the broadly immune-suppressive protein SOCS1.

The efficacy of immunotherapeutic approaches to cancer can be augmented by combining them with inhibitors of immune checkpoints. Numerous ongoing preclinical and clinical studies are exploring potential synergies between cancer vaccines and other immunotherapeutic agents and checkpoint blocking agents, for example, ipilimumab. Such combination approaches have the potential to result in significantly improved clinical outcomes.

However, there are a number of drawbacks of using cancer immunotherapeutic agents in combination with checkpoint inhibitors. For example, immune checkpoint blockade can lead to the breaking of immune self-tolerance, thereby inducing a novel syndrome of autoimmune/auto-inflammatory side effects, designated "immune related adverse events," mainly including rash, colitis, hepatitis and endocrinopathies (Corsello, et al. *J. Clin. Endocrinol. Metab.,* 2013, 98:1361).

Reported toxicity profiles of checkpoint inhibitors are different than the toxicity profiles reported for other classes of oncologic agents. Those involve inflammatory events in multiple organ systems, including skin, gastrointestinal, endocrine, pulmonary, hepatic, ocular, and nervous system. (Hodi, 2013, *Annals of Oncology,* 24: Suppl, i7).

In view of the above, there is a need for new cancer therapeutic agents that can be used in combination with checkpoint inhibitors as well as other classes of oncolytic agents without risk of adverse inflammatory events in multiple organ systems previously reported for checkpoint inhibitors. The immunotherapeutic cells of the invention, prepared by treating cells with a combination oligonucleotide agents targeting genes associated with tumor or infections disease resistance mechanisms, as well as methods of producing such therapeutic cells and methods of treating disease with the produced therapeutic cells, satisfy this long felt need.

SUMMARY OF EMBODIMENTS OF THE INVENTION

The efficacy of immunotherapeutic approaches to cell proliferation disorders and infectious diseases can be augmented by combining them with inhibitors of immune checkpoints. Numerous synergies between cancer vaccines and other immunotherapeutic agents and checkpoint blocking agents provide opportunities for combination approaches that may significantly improve clinical outcomes for example, in proliferative cell disorders and immune diseases.

Various embodiments of the inventions disclosed herein include compositions comprising therapeutic cells obtained by treating cells ex vivo with oligonucleotides to modulate expression of target genes involved in immune suppression mechanisms. The oligonucleotide agent may be an antisense oliogonucleotide (ASO), including locked nucleic acids (LNAs), methoxyethyl gapmers, and the like, or an siRNA, miRNA, miRNA-inhibitor, morpholino, PNA, and the like. The oligonucleotide is preferably a self-delivered (sd) RNAi agent. The oligonucleotides may be chemically modified, for example, including at least one 2-O-methyl modification, 2'-Fluro modification, and/or phosphorothioate modification. The oligonucleotides may include one or more hydrophobic modification, for example, one or more sterol, cholesterol, vitamin D, Naphtyl, isobutyl, benzyl, indol, tryptophane, or phenyl hydrophobic modification. The oligonucleotide may be a hydrophobically-modified siRNA-antisense hybrid. The oligonucleotides may be used in combination with transmembrane delivery systems, such as delivery systems comprising lipids.

In an embodiment, the cells are obtained and/or derived from a cancer or infectious disease patient, and may be, for example, tumor infiltrating lymphocytes (TIL) and/or T-cells, antigen presenting cells such as dendritic cells, natural killer cells, induced-pluripotent stem cells, stem central memory T-cells, and the like. The T-cells and NK-cells are preferably genetically engineered to express high-affinity T-Cell receptors (TCR) and/or chimeric antibody or antibody-fragment—T-Cell receptors (CAR). In an embodiment, the chimeric antibody/antibody fragment is preferably capable of binding to antigens expressed on tumor cells. Immune cells may be engineered by transfection with plasmid, viral delivery vehicles, or mRNAs.

In an embodiment, the chimeric antibody or fragment is capable of binding CD19 receptors of B-cells and/or binding to antigens expressed on tumors, such as melanoma tumors. Such melanoma-expressed antigens include, for example, GD2, GD3, HMW-MAA, VEGF-R2, and the like.

Target genes identified herein for modification include: cytotoxic T-cell antigen 4 (CTLA4), programmed cell death protein 1 (PD1), tumor growth factor receptor beta (TGFR-beta), LAG3, TIM3, and adenosine A2a receptor; anti-apoptotic genes including, but not limited to: BAX, BAC, Casp8, and P53; A20 ubiquitine ligase (TNFAIP3, SOCS1 (suppressor of cytokine signaling), IDO (indolamine-2,3-dioxygenase; tryptophan-degrading enzyme), PD-L1 (CD274)(surface receptor, binder to PD1 on Tcells), Notch ligand Delta1 (DLL1), Jagged 1, Jagged 2, FasL (pro-apoptotic surface molecule), CCL17, CCL22 (secreted chemokines that attract Treg cells), IL10 receptor (IL10RA), p38 (MAPK14), STAT3, TNFSF4 (OX40L), MicroRNA miR-155, miR-146a, anti-apoptotic genes including but not limited to BAX, BAC, Casp8 and P53, and the like genes, and combinations thereof. Representative target sequences are listed in Table 1.

The engineered therapeutic cells are treated with RNAi agents designed to inhibit expression of one or more of the targeted genes. The RNAi agent may comprise a guide sequence that hybridizes to a target gene and inhibits expression of the target gene through an RNA interference mechanism, where the target region is selected from the group listed in Table 1. The RNA agent can be chemically modified, and preferably includes at least one 2'-O-methyl, 2'-O-Fluoro, and/or phosphorothioate modification, as well as at least one hydrophobic modification such as cholesterol, and the like.

The immunogenic compositions described herein are useful for the treatment of proliferative disorders, including cancers, and/or infectious disease and are produced by the ex-vivo treatment of cells with oligonucleotides to modulate the expression of target genes involved in tumor immune resistance mechanisms. The ex vivo treatment of cells includes administering to the cells an oligonucleotide capable of targeting and inhibiting expression of a gene involved in a tumor suppressor mechanism, such as the genes listed in Table 1. The oligonucleotide can be used in combination with a transmembrane delivery system that may comprise one or more of: lipid(s) and vector, such as a viral vector.

The invention includes a method of treating a cell proliferative disorder or infectious disease by administering to a subject in need thereof, an immunogenic composition comprising cells that have been treated with one or more oligonucleotide to modulate the expression of one or more target gene involved in tumor immune resistance mechanisms, for example, one or more of the target genes of Table 1.

The invention preferably includes immunogenic cells treated with a plurality of oligonucleotide agents targeting a combination of target genes described herein. The combination may target a plurality of suppressor receptor genes, cytokine receptor genes, regulatory genes, and/or apoptotic factors in order to inhibit tumor immune resistance mechanisms.

The present invention is directed to novel immunotherapeutic cells, methods of generating the immunotherapeutic cells, and therapeutic methods employing such cells.

A new method of immune checkpoint inhibition is described herein, applicable to a broad variety of cell-based immunotherapies, including, but not limited to adaptive cell transfer, for example, based on TIL, TCR, CAR, and other cell types, as well as dendritic cell-based cancer vaccines. Self-deliverable RNAi technology provides efficient transfection of short oligonucleotides in any cell type, including immune cells, providing increased efficacy of immunotherapeutic treatments. In addition, the activated immune cells can be protected by preventing apoptosis via inhibition of key activators of the apoptotic pathway, such as BAC, BAX, Casp8, and P53, among others.

The activated immune cells modified by oligonucleotide transfer for a single therapeutic agent for administration to a subject, providing a number of advantages as compared to separately administered combinations of vaccines and immunotherapeutics and separately administered checkpoint inhibitors. These advantages include lack of side effects associated with the checkpoint inhibitors in a single therapeutic agent (activated immune cells modified by oligonucleotides targeting immune resistance genes).

The claimed immunotherapeutic cells, method of producing immunotherapeutic cells by introduction of oligonucleotide molecules targeting immune resistance pathways, and methods of treating proliferative and infectious disease, improves upon any known immunotherapeutic cells and methods of producing immunotherapeutic cells because it provides:

1) a single therapeutic composition providing a combination of checkpoint inhibitors and other immune resistance mechanism inhibitors;
2) with reduced toxicity; and
3) increased efficacy as compared with other compositions.

BRIEF DESCRIPTION OF THE FIGURES

The foregoing features of embodiments will be more readily understood by reference to the following detailed description, taken with reference to the accompanying drawings, in which:

FIG. 2 is a graph showing sdRNA-induced silencing of GAPDH and MAP4K4 in HeLa cells.

FIG. 3 is a graph showing sdRNA-induced knock-down of multiple targets using sdRNA agents directed to three genes in NK-92 cells.

FIG. 4 is a graph showing the knock-down of gene expression in Human Primary T cells by sdRNA agents targeting TP53 and MAP4K4.

FIG. 5 is a graph showing sdRNA-induced knock-down of CTLA4 and PD1 in Human Primary T cells.

FIG. 6 is a graph showing the reduction of PDCD1 and CTLA-4 surface expression by sdRNA in Human Primary T cells.

FIG. 7 is a graph showing MAP4K4-cy3 sdRNA delivery into T and B cells in human PBMCs.

DETAILED DESCRIPTION OF SPECIFIC EMBODIMENTS

Figure 1:
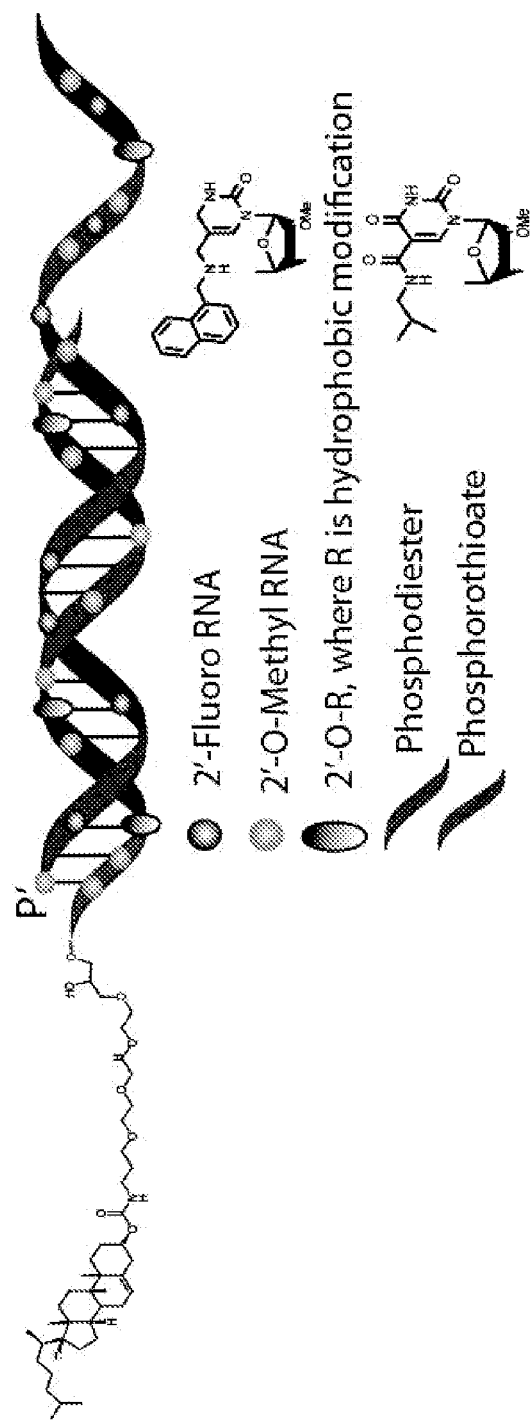
FIG. 1 is a schematic diagram showing the structure of an sdRNA molecule.

The invention is defined by the claims, and includes oligonucleotides specifically designed and selected to reduce and/or inhibit expression of suppressors of immune resistance (inhibitory oligonucleotides), compositions comprising cells modified by treatment with such inhibitory oligonucleotides, methods of making such compositions, and methods of using the compositions to treat proliferation and/or infectious diseases. In particular, cells are treated with a combination of oligonucleotide agents, each agent particularly designed to interfere with and reduce the activity of a targeted immune suppressor.

Preferably, the combination of oligonucleotide agents targets multiple immune suppressor genes selected from checkpoint inhibitor genes such as CTLA4, PD-1/PD-1L, BTLA (B and T-lymphocyte attenuator), KIR (killer immunoglobulin-like receptors), B7-H3, B7-H4 receptors, and TGF beta type 2 receptor; cytokine receptors that inactivate immune cells, such as TGF-beta receptor A and IL-10 receptor; regulatory genes/transcription factors modulating cytokine production by immune cells, such as STAT-3 and P38, miR-155, miR-146a; and apoptotic factors involved in cascades leading to cell death, such as p53 and Cacp8.

Most preferably the oligonucleotide agent is a self-deliverable RNAi agent, which is a hydrophobically modified siRNA-antisense hybrid molecule, comprising a double-stranded region of about 13-22 base pairs, with or without a 3'-overhang on each of the sense and antisense strands, and a 3' single-stranded tail on the antisense strand of about 2-9 nucleotides. The oligonucleotide contains at least one 2'-O-Methyl modification, at least one 2'-O-Fluoro modification, and at least one phosphorothioate modification, as well as at least one hydrophobic modification selected from sterol, cholesterol, vitamin D, napthyl, isobutyl, benzyl, indol, tryptophane, phenyl, and the like hydrophobic modifiers (see FIG. 1). The oligonucleotide may contain a plurality of such modifications.

Definitions

As used in this description and the accompanying claims, the following terms shall have the meanings indicated, unless the context requires otherwise:

Proliferative disease, as used herein, includes diseases and disorders characterized by excessive proliferation of cells and turnover of cellular matrix, including cancer, atherlorosclerosis, rheumatoid arthritis, psoriasis, idiopathic pulmonary fibrosis, scleroderma, cirrhosis of the liver, and the like. Cancers include but are not limited to, one or more of: small cell lung cancer, colon cancer, breast cancer, lung cancer, prostate cancer, ovarian cancer, pancreatic cancer, melanoma, hematological malignancy such as chronic myeloid leukemia, and the like cancers where immunotherapeutic intervention to suppress tumor related immune resistance is needed.

Immune target genes can be grouped into at least four general categories: (1) checkpoint inhibitors; (2) cytokine receptors that inactivate immune cells, (3) anti-apoptotic genes; and (4) regulator genes, for example, transcription factors.

Immune Checkpoint inhibitors (ICI), as used herein, include immunotherapeutic agents that bind to certain checkpoint proteins, such as cytotoxic T lymphocyte antigen-4 (CTLA-4) and programmed death-1 (PD-1) and its ligand PD-L1 to block and disable inhibitory proteins that prevent the immune system from attacking diseased cells such as cancer cells, liberating tumor-specific T cells to exert their effector function against tumor cells.

Tumor related immune resistance genes, as used herein, include genes involved in checkpoint inhibition of immune response, such as CTLA-4 and PD-1/PD-L1; TGF-beta, LAG3, Tim3, adenosine A2a receptor;

Regulator genes, as used herein, include transcription factors and the like that modulate cytokine production by immune cells, and include p38, STAT3, microRNAs miR-155, miR-146a;

Anti-apoptotic genes, as used herein, include BAX, BAC, Casp8, P53 and the like; and combinations thereof.

Infectious diseases, as used herein, include, but are not limited to, diseases caused by pathogenic microorganisms, including, but not limited to, one or more of bacteria, viruses, parasites, or fungi, where immunotherapeutic intervention to suppress pathogen related immune resistance and/or overactive immune response.

Immunogenic composition, as used herein, includes cells treated with one or more oligonucleotide agent, wherein the cells comprise T-cells. The T-cells may be genetically engineered, for example, to express high affinity T-cell receptors (TCR), chimeric antibody—T-cell receptors (CAR), where the chimeric antibody fragments are capable of binding to CD19 receptors of B-cells and/or to antigens expressed on tumor cells. In one embodiment, the chimeric antibody fragments bind antigens expressed on melanoma tumors, selected from GD2, GD3, HMW-MAA, and VEGF-R2.

Immunogenic compositions described herein include cells comprising antigen-presenting cells, dendritic cells, engineered T-cells, natural killer cells, stem cells, including induced pluripotent stem cells, and stem central memory T-cells. The treated cell also comprises one or a plurality of oligonucleotide agents, preferably sdRNAi agents specifically targeting a gene involved in an immune suppression mechanism, where the oligonucleotide agent inhibits expression of said target gene.

In one embodiment, the target gene is selected from A20 ubiquitin ligase such as TNFAIP3, SOCS1 (suppressor of cytokine signaling), Tyro3/Ax1/Mer (suppressors of TLR signaling), IDO (indolamine-2,3-dioxygenase, tryptophan-degrading enzyme), PD-L1/CD274 (surface receptor, binds PD1 on T-cells), Notch ligand Delta (DLL1), Jagged 1, Jagged 2, FasL (pro-apoptotic surface molecule), CCL17, CCL22 (secreted chemokines that attract Treg cells), IL-10 receptor (IL10Ra), p38 (MAPK14), STAT3, TNFSF4 (OX40L), microRNA miR-155, miR-146a, anti-apoptotic genes, including but not limited to BAX, BAC, Casp8, and P53; and combinations thereof.

Particularly preferred target genes are those shown in Table 1.

Ex-vivo treatment, as used herein, includes cells treated with oligonucleotide agents that modulate expression of target genes involved in immune suppression mechanisms. The oligonucleotide agent may be an antisense oligonucleotide, including, for example, locked nucleotide analogs, methyoxyethyl gapmers, cyclo-ethyl-B nucleic acids, siRNAs, miRNAs, miRNA inhibitors, morpholinos, PNAs, and the like. Preferably, the oligonucleotide agent is an sdRNAi agent targeting a gene involved in an immune suppression mechanism. The cells treated in vitro by the oligonucleotide agent may be immune cells expanded in vitro, and can be cells obtained from a subject having a proliferative or infectious disease. Alternatively, the cells or tissue may be treated in vivo, for example by in situ injection and/or intravenous injection.

Oligonucleotide or oligonucleotide agent, as used herein, refers to a molecule containing a plurality of "nucleotides" including deoxyribonucleotides, ribonucleotides, or modified nucleotides, and polymers thereof in single- or double-stranded form. The term encompasses nucleotides containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Nucleotide, as used herein to include those with natural bases (standard), and modified bases well known in the art. The nucleotides can be unmodified or modified at the sugar, phosphate and/or base moiety, (also referred to interchangeably as nucleotide analogs, modified nucleotides, non-natural nucleotides, non-standard nucleotides and other; see, for example, PCT Publications No. WO 92/07065 and WO 93/15187. Non-limiting examples of base modifications that can be introduced into nucleic acid molecules include, hypoxanthine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine and pseudouridine), propyne, and others. The phrase "modified bases" includes nucleotide bases other than adenine, guanine, cytosine, and uracil, modified for example, at the 1' position or their equivalents.

As used herein, the term "deoxyribonucleotide" encompasses natural and synthetic, unmodified and modified deoxyribonucleotides. Modifications include changes to the sugar moiety, to the base moiety and/or to the linkages between deoxyribonucleotide in the oligonucleotide.

As used herein, the term "RNA" defines a molecule comprising at least one ribonucleotide residue. The term "ribonucleotide" defines a nucleotide with a hydroxyl group at the 2' position of a □-D-ribofuranose moiety. The term RNA includes double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Nucleotides of the RNA molecules described herein may also comprise non-standard nucleotides, such as non-naturally occurring nucleotides or chemically synthesized nucleotides or deoxynucleotides. These altered RNAs can be referred to as analogs or analogs of naturally-occurring RNA.

As used herein, "modified nucleotide" refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate.

Modifications include those naturally-occurring that result from modification by enzymes that modify nucleotides, such as methyltransferases.

Modified nucleotides also include synthetic or non-naturally occurring nucleotides. Synthetic or non-naturally occurring modifications in nucleotides include those with 2' modifications, e.g., 2'-O-methyl, 2'-methoxyethoxy, 2'-fluoro, 2'-allyl, 2'-O-[2-(methylamino)-2-oxoethyl], 4'-thio, 4'-CH2-O-2'-bridge, 4'-(CH2) 2-O-2'-bridge, 2'-LNA, and 2'-O—(N-methylcarbamate) or those comprising base analogs. In connection with 2'-modified nucleotides as described for the present disclosure, by "amino" is meant 2'-NH2 or 2'-O—NH2, which can be modified or unmodified. Such modified groups are described, for example, in U.S. Pat. Nos. 5,672,695 and 6,248,878.

As used herein, "microRNA" or "miRNA" refers to a nucleic acid that forms a single-stranded RNA, which single-stranded RNA has the ability to alter the expression (reduce or inhibit expression; modulate expression; directly or indirectly enhance expression) of a gene or target gene when the miRNA is expressed in the same cell as the gene or target gene. In one embodiment, a miRNA refers to a nucleic acid that has substantial or complete identity to a target gene and forms a single-stranded miRNA. In some embodiments miRNA may be in the form of pre-miRNA, wherein the pre-miRNA is double-stranded RNA. The sequence of the miRNA can correspond to the full length target gene, or a subsequence thereof. Typically, the miRNA is at least about 15-50 nucleotides in length (e.g., each sequence of the single-stranded miRNA is 15-50 nucleotides in length, and the double stranded pre-miRNA is about 15-50 base pairs in length). In some embodiments the miRNA is 20-30 base nucleotides. In some embodiments the miRNA is 20-25 nucleotides in length. In some embodiments the miRNA is 20, 21, 22, 23, 24, 25, 26, 27, 28, 29, or 30 nucleotides in length.

Target gene, as used herein, includes genes known or identified as modulating the expression of a gene involved in an immune resistance mechanism, and can be one of several groups of genes, such as suppressor receptors, for example, CTLA4 and PD1; cytokine receptors that inactivate immune cells, for example, TGF-beta receptor, LAG3, Tim3, adenosine A2a receptor, and IL10 receptor; regulatory genes for example, STAT3, p38, mir155 and mir146a; and apoptosis factors involved in cascades leading to cell death, for example, P53, Casp8, BAX, BAC, and combinations thereof. See also preferred target genes listed in Table 1.

As used herein, small interfering RNA (siRNA), sometimes known as short interfering RNA or silencing RNA, defines a group of double-stranded RNA molecules, comprising sense and antisense RNA strands, each generally of about 1022 nucleotides in length, optionally including a 3' overhang of 1-3 nucleotides. siRNA is active in the RNA interference (RNAi) pathway, and interferes with expression of specific target genes with complementary nucleotide sequences.

As used herein, sdRNA refers to "self-deliverable" RNAi agents, that are formed as an asymmetric double-stranded RNA-antisense oligonucleotide hybrid. The double stranded RNA includes a guide (sense) strand of about 19-25 nucleotides and a passenger (antisense) strand of about 10-19 nucleotides with a duplex formation that results in a single-stranded phosphorothiolated tail of about 5-9 nucleotides. The RNA sequences may be modified with stabilizing and hydrophobic modifications such as sterols, for example, cholesterol, vitamin D, naphtyl, isobutyl, benzyl, indol, tryptophane, and phenyl, which confer stability and efficient cellular uptake in the absence of any transfection reagent or formulation. Immune response assays testing for IFN-induced proteins indicate sdRNAs produce a reduced immunostimulatory profile as compared other RNAi agents. See, for example, Byrne et al., December 2013, *J. Ocular Pharmacology and Therapeutics*, 29(10): 855-864.

Cell-Based Immunotherapeutics

In general, cells are obtained from subjects with proliferative disease such as cancer, or an infectious disease such as viral infection. The obtained cells are treated directly as obtained or may be expanded in cell culture prior to treatment with oligonucleotides. The cells may also be genetically modified to express receptors that recognize specific antigens expressed on the tumor cell surface (CAR) or intracellular tumor antigens presented on MHC class I (TCR).

Oligonucleotide Agents

Antisense Oligonucleotides

Small interfering RNA (siRNA), sometimes known as short interfering RNA or silencing RNA, is a double stranded RNA molecule, generally 19-25 base pairs in length. siRNA is used in RNA interference (RNAi), where it interferes with expression of specific genes with complementary nucleotide sequences.

Double stranded DNA (dsRNA) can be generally used to define any molecule comprising a pair of complementary strands of RNA, generally a sense (passenger) and antisense (guide) strands, and may include single-stranded overhang regions. The term dsRNA, contrasted with siRNA, generally refers to a precursor molecule that includes the sequence of an siRNA molecule which is released from the larger dsRNA molecule by the action of cleavage enzyme systems, including Dicer.

sdRNA (self-deliverable) are a new class of covalently modified RNAi compounds that do not require a delivery vehicle to enter cells and have improved pharmacology compared to traditional siRNAs. "Self-deliverable RNA" or sdRNA is a hydrophobically modified RNA interfering-antisense hybrid, demonstrated to be highly efficacious in vitro in primary cells and in vivo upon local administration. Robust uptake and/or silencing without toxicity has been demonstrated in several tissues including dermal, muscle, tumors, alveolar macrophages, spinal cord, and retina cells and tissues. In dermal layer and retina, intradermal and intra-vitreal injection of sdRNA at mg doses induced potent and long lasting silencing.

While sdRNA is a superior functional genomics tool, enabling RNAi in primary cells and in vivo, it has a relatively low hit rate as compared to conventional siRNAs. While the need to screen large number of sequences per gene is not a limiting factor for therapeutic applications, it severely limits the applicability of sdRNA technology to functional genomics, where cost effective compound selection against thousands of genes is required. To optimize sdRNA structure, chemistry, targeting position, sequence preferences, and the like, a proprietary algorithm has been developed and utilized for sdRNA potency prediction. Availability of sdRNA reagents that are active in all cell types ex vivo and in vivo enables functional genomics and target stratification/validation studies.

Proprietary Algorithm

SdRNA sequences were selected based on a proprietary selection algorithm, designed on the basis of a functional screen of over 500 sdRNA sequences in the luciferase reporter assay of HeLa cells. Regression analysis of was used to establish a correlation between the frequency of occurrence of specific nucleotide and modification at any specific position in sdRNA duplex and its functionality in gene suppression assay. This algorithm allows prediction of functional sdRNA sequences, defined as having over 70% knockdown µM concentration, with a probability over 40%.

Table 1 shows predictive gene targets identified using the proprietary algorithm and useful in the cellular immunotherapeutic compositions and methods described herein.

Delivery of RNAi Agents

BTLA (B and T-lymphocyte attenuator), KIR (killer immunoglobulin-like receptors), B7-H3 and B7-H4 receptors and TGFbeta type 2 receptor; Applic BTLA (B and T-lymphocyte attenuator), KIR (killer immunoglobulin-like receptors), B7-H3 and B7-H4 receptors and TGFbeta type 2 receptor; ation of RNAi technology to functional genomics studies in prim BTLA (B and T-lymphocyte attenuator), KIR (killer immunoglobulin-like receptors), B7-H3 and B7-H4 receptors and TGFbeta type 2 receptor; ary cells and in vivo is limited by requirements to formulate siRNAs into lipids or use of other cell delivery techniques. To circumvent delivery problems, the self-deliverable RNAi technology provides a method of directly transfecting cells with the RNAi agent, without the need for additional formulations or techniques. The ability to transfect hard-to-transfect cell lines, high in vivo activity, and simplicity of use, are characteristics of the compositions and methods that present significant functional advantages over traditional siRNA-based techniques. The sdRNAi technology allows direct delivery of chemically synthesized compounds to a wide range of primary cells and tissues, both ex-vivo and in vivo.

To enable BTLA (B and T-lymphocyte attenuator), KIR (killer immunoglobulin-like receptors), B7-H3 and B7-H4 receptors and TGFbeta type 2 receptor; self-delivery, traditional siRNA molecules require a substantial reduction in size and the introduction of extensive chemical modifications which are not well tolerated by RNAi machinery, resulting in extremely low probability of finding active molecules (low hit rate). In contrast, the sdRNA technology allows efficient RNAi delivery to primary cells and tissues in vitro and in vivo, with demonstrated silencing efficiency in humans.

The general structure of sdRNA molecules is shown in FIG. 1. sdRNA are formed as hydrophobically-modified siRNA-antisense oligonucleotide hybrid structures, and are disclosed, for example in Byrne et al., Dec. 2013, *J. Ocular Pharmacology and Therapeutics*, 29(10): 855-864.

Oligonucleotide Modifications: 2'-O-Methyl, 2'-O-Fluro, Phosphorothioate

The oligonucleotide agents preferably comprise one or more modification to increase stability and/or effectiveness of the therapeutic agent, and to effect efficient delivery of the oligonucleotide to the cells or tissue to be treated. Such modifications include at least one BTLA (B and T-lymphocyte attenuator), KIR (killer immunoglobulin-like receptors), B7-H3 and B7-H4 receptors and TGFbeta type 2 receptor; BTLA (B and T-lymphocyte attenuator), KIR (killer immunoglobulin-like receptors), B7-H3 and B7-H4 receptors and TGFbeta type 2 receptor; 2'-O-methyl modification, at least one 2'-O-Fluro modification, and at least one diphosphorothioate modification. Additionally, the oligonucleotide is modified to include one or more hydrophobic modification selected from sterol, cholesterol, vitamin D, naphtyl, isobutyl, benzyl, indol, tryptophane, and phenyl. The hydrophobic modification is preferably a sterol.

Delivery of Oligonucleotide Agents to Cells

The oligonucleotides may be delivered to the cells in combination with a transmembrane delivery system, preferably comprising lipids, viral vectors, and the like. Most preferably, the oligonucleotide agent is a self-delivery RNAi agent, that does not require any delivery agents.

Combination Therapy

Most preferred for this invention, e.g. particular combinations of elements and/or alternatives for specific needs. This objective is accomplished by determining the appropriate genes to be targeted by the oligonucleotide in order to silence immune suppressor genes and using the proprietary algorithm to select the most appropriate target sequence.

It is preferred that the immunotherapeutic cell be modified to include multiple oligonucleotide agents targeting a variety of genes involved in immune suppression and appropriate for the selected target disease and genes. For example, a preferred immunotherapeutic cell is a T-Cell modified to knock-down both CTLA-4 and PD-1

Additional combinations of oligonucleotides to related genes involved in immune suppression include varied combinations of the selected target sequences of Table 1.

BTLA (B and T-lymphocyte attenuator), KIR (killer immunoglobulin-like receptors), B7-H3 and B7-H4 receptors and TGFbeta type 2 receptor; (B and T-lymphocyte attenuator), KIR (killer immunoglobulin-like receptors), B7-H3 and B7-H4 receptors and TGFbeta type 2 receptor; Preferred BTLA (B and T-lymphocyte attenuator), KIR (killer immunoglobulin-like receptors), B7-H3 and B7-H4 receptors and TGFbeta type 2 receptor; therapeutic combinations include cells engineered to knock down gene expression of the following target genes:
  a) CTLA4 and PD1
  b) STAT3 and p38
  c) PD1 and BaxPD1, CTLA4, Lag-1, ILM-3, and TP53
  d) PD1 and Casp8
  e) PD1 and IL10R The therapeutic compositions described herein are useful to treat a subject suffering from a proliferation disorder or infectious disease. In particular, the immunotherapeutic composition is useful to treat disease characterized by suppression of the subjects immune mechanisms. The sdRNA agents described herein are specifically designed to target genes involved in diseases-associated immune suppression pathways.

Methods of treating a subject comprise administering to a subject in need thereof, an immunogenic composition comprising an sdRNAi agent capable of inhibiting expression of genes involved in immune suppression mechanisms, for example, any of the genes listed in Table 1 or otherwise described herein.

EXAMPLES

The embodiments of the invention described above are intended to be merely exemplary; numerous variations and modifications will be apparent to those skilled in the art. All such variations and modifications are intended to be within the scope of the present invention as defined in any appended claims.

Example 1

Self-Deliverable RNAi Immunotherapeutic Agents

Immunotherapeutic agents described herein were produced by treating cells with particular sdRNA agents designed to target and knock down specific genes involved in immune suppression mechanisms. In particular, the following cells and cell lines have been successfully treated with sdRNA and were shown to knock down at least 70% of targeted gene expression in the specified human cells.

These studies demonstrated utility of these immunogenic agents to suppress expression of target genes in cells normally very resistant to transfection, and suggests the agents are capable of reducing expression of target cells in any cell type.

TABLE 2

| Cell Type | Target Gene | sdRNA target sequence | % Knock Down | |
|---|---|---|---|---|
| Primary human T-cells | TP53 (P53) | GAGTAGGACATACCAGCTTA (SEQ ID NO: 1001) | >70% | 2 uM |
| Primary human T-cells | MAP4K4 | AGAGTTCTGTGGAAGTCTA (SEQ ID NO: 1002) | >70% | 2 uM |
| Jurkat T-lymphoma cells | MAP4K4 | AGAGTTCTGTGGAAGTCTA (SEQ ID NO: 1003) | 100% | 1 uM 72h |
| NK-92 cells | MAP4K4 | AGAGTTCTGTGGAAGTCTA (SEQ ID NO: 1004) | 80% | 2 uM 72h |
| NK-92 cells | PPIB | ACAGCAAATTCCATCGTGT (SEQ ID NO: 1005) | >75% | 2 uM 72h |
| NK-92 cells | GADPH | CTGGTAAAGTGGATATTGTT (SEQ ID NO: 1006) | >90% | 2 uM 72h |
| HeLa Cells | MAP4K4 | AGAGTTCTGTGGAAGTCTA (SEQ ID NO: 1007) | >80% | 2 uM 72h |

Example 2

Oligonucleotide Sequences for Inhibiting Expression of Target Genes

A number of human genes were selected as candidate target genes due to involvement in immune suppression mechanisms, including the following genes shown in Table 3:

| | | |
|---|---|---|
| BAX (NM_004324) | BAK1 (NM_001188) | CASP8 (NM_001228) |
| ADORA2A (NM_000675) | CTLA4 (NM_005214) | LAG3 (NM002286) |
| PDCD1 (NM_NM005018) | TGFBR1 (NM-004612) | HAVCR2 (NM_032782) |
| CCL17 (NM_002987) | CCL22 (NM_002990) | DLL2 (NM_005618) |
| FASLG (NM_000639) | CD274 (NM_001267706) | IDO1 (NM_002164) |
| IL10RA (NM_001558) | JAG1 (NM_000214) | JAG2 (NM_002226) |
| MAPK14 (NM_001315) | SOCS1 (NM_003745) | STAT3 (NM_003150) |
| TNFA1P3 (NM_006290) | TNFSF4 (NM_003326) | TYRO2 (NM_006293) |
| TP53 (NM_000546) | | |

Each of the genes listed above was analyzed using a proprietary algorithm to identify preferred sdRNA targeting sequences and target regions for each gene for prevention of immunosuppression of antigen-presenting cells and T-cells. Results are shown in Table 1.

Example 3

Knock-Down of Target Gene (GAPDH) by sdRNA in HeLa Cells

HeLa cells (ATCC CRM-CCL-2) were subcultured 24 hours before transfection and kept log phase. The efficacy of several GAPDH sdRNAs was tested by qRT-PCR, including G13 sdRNA listed in the Table 1.

Solutions of GAPDH, MAP4K4 (positive control) and NTC (non-targeting control) sdRNA with twice the required concentration were prepared in serum-free EMEM medium, by diluting 100 μM oligonucleotides to 0.2-4 μM.

The total volume of medium for each oligo concentration point was calculated as [50 μl/well]×[number of replicates for each serum point]. Oligonucleotides were dispensed into a 96 well plate at 50 μl/well.

Cells were collected for transfection by trypsinization in a 50 ml tube, washed twice with medium containing 10% FBS without antibiotics, spun down at 200×g for 5 minutes at room temperature and resuspended in EMEM medium containing twice the required amount of FBS for the experiment (6%) and without antibiotics. The concentration of the cells was adjusted to 120,000/ml to yield a final concentration of 6,000 cells/50 μl/well. The cells were dispensed at 50 μl/well into the 96-well plate with pre-diluted oligos and placed in the incubator for 48 hours.

Gene Expression Analysis in HeLa Cells Using qRT-PCR

RNA was isolated from transfected HeLa cells using the PureLink™ Pro96 total RNA purification Kit (Ambion, Cat. No. 12173-011A), with Quanta qScript XLT One-Step RT-qPCR ToughMix, ROX (VWR, 89236672). The isolated RNA was analyzed for gene expression using the Human MAP4K4-FAM (Taqman Hs0377405_m1) and Human GAPDH-VIC (Applied Biosystems, Cat. No. 4326317E) gene expression assays.

The incubated plate was spun down and washed once with 100 μl/well PBS and lysed with 60 μl/well buffer provided in the kit. RNA isolation was conducted according to the manufacturer's instructions, and the RNA was eluted with 100 µl RNase-free water, and used undiluted for one-step qRT-PCR.

Dilutions of non-transfected (NT) cells of 1:5 and 1:25 were prepared for the standard curve using RNase-free water. qRT-PCR was performed by dispensing 9 µl/well into a low profile PCR plate and adding 1 µl RNA/well from the earlier prepared RNA samples. After brief centrifugation, the samples were placed in the real-time cycler and amplified using the settings recommended by the manufacturer.

GAPDH gene expression was measured by qPCR, normalized to MAP4K4 and plotted as percent of expression in the presence of non-targeting sdRNA. The results were compared to the normalized according to the standard curve. As shown in FIG. 2, several sdRNA agents targeting GAPDH or MAP4K4 significantly reduced their mRNA levels leading to more than 80-90% knock-down with 1 µM sdRNA. (See FIG. 2).

Example 4

Silencing of Multiple Targets by sdRNA in NK-92 Cells

NK-92 cells were obtained from Conqwest and subjected to one-step RT-PCR analysis without RNA purification using the FastLane Cell Multiplex Kit (Qiagen, Cat. No. 216513). For transfection, NK-92 cells were collected by centrifugation and diluted with RPMI medium containing 4% FBS and IL2 1000 U/ml and adjusted to 1,000,000 cells/ml.

Multiple sdRNA agents targeting MAP4K4, PPIB or GADPH were diluted separately in serum-free RPMI medium to 4 µM and individually aliquoted at 50 µl/well into a 96-well plate. The prepared cells were then added at 50 µl cells/well to the wells with either MAP4K4, PPIB or GAPDH sdRNAs. Cells were incubated for 24, 48, or 72 hours.

At the specified timepoints, the plated transfected cells were washed once with 100 µl/well PBS and once with FCW buffer. After removal of supernatant, cell processing mix of 23.5 µl FCPL and 1.5 µl gDNA wipeout solution was added to each well and incubated for five minutes at room temperature. Lysates were then transferred to PCR strips and heated at 75° C. for five minutes.

To setup qRT-PCR, the lysates were mixed with Quanti-Tect reagents from the FastLane Cell Multiplex Kit and with primer probe mix for MAP4K4-FAM/GAPDH-VIC or PPIB-FAM/GAPDH-VIC. The following Taqman gene expression assays were used: human MAP4K4-FAM (Taqman, Hs00377405_m1), human PPIB-FAM (Taqman, Hs00168719_m1) and human GAPDH-VIC (Applied Biosystems, cat. No 4326317E).

A volume of 9 µl/well of each reaction mix was dispensed into a low profile PCR plate. One µl lysate per well was added from the previously prepared lysates. The samples were amplified using the settings recommended by the manufacturer.

Results shown in FIG. 3 demonstrate significant silencing of each of the multiple targets, MAP4K4, PPIB, and GADPH by sdRNA agents transfected into NK-92 cells, including greater than 75% inhibition of expression of each target within 24 to 72 hours of incubation.

Example 5

Silencing of TP53 and MAP4K4 by sdRNA in Human Primary T-Cells

Primary human T-cells were obtained from AllCells (CA) and cultured in complete RPMI medium containing 1000 IU/ml IL2. Cells were activated with anti-CD3/CD28 Dynabeads (Gibco, 11131) according to the manufacturer's instructions for at least 4 days prior to the transfection. Cells were collected by brief vortexing to dislodge the beads from cells and separating them using the designated magnet.

sdRNA agents targeting TP53 or MAP4K4 were prepared by separately diluting the sdRNAs to 0.2-4 µM in serum-free RPMI per sample (well) and individually aliquoted at 100 µl/well of 96-well plate. Cells were prepared in RPMI medium containing 4% FBS and IL2 2000 U/ml at 1,000,000 cells/ml and seeded at 100 µl/well into the 96-well plate with pre-diluted sdRNAs.

At the end of the transfection incubation period, the plated transfected cells were washed once with 100 µl/well PBS and processed with FastLane Cell Multiplex Kit reagents essentially as described for the Example 4 and according to the manufacturer's instructions. Taqman gene expression assays were used in the following combinations: human MAP4K4-FAM/GAPDH-VIC or human TP53-FAM (Taqman, Hs01034249 m1)/GAPDH-VIC. A volume of 18 µl/well of each reaction mix was combined with 2 µl lysates per well from the previously prepared lysates. The samples were amplified as before (see Example 4).

Results shown in FIG. 4 demonstrate significant silencing of both MAP4K4 and TP53 by sdRNA agents transfected into T-cells, reaching 70-80% inhibition of gene expression with 1-2 µM sdRNA.

Example 6

Immunotherapeutic Combination of sdRNAs for Treating Melanoma

Melanomas utilize at least two particular pathways to suppress immune function of T-cells, and each involves both PD1 and CTLA4. Melanoma tumors expressing the PD1 ligand, PD1L, can be targeted with T-cells pretreated ex-vivo with sd-RNAi agents specifically designed to target PD1 and interfere with PD1 expression. PD1 is also known as PDCD1, and particular targeting sequences and gene regions identified and predicted to be particularly functional in sdRNA mediated suppression, are shown in Table 1 for PDCD1 (NM_005018) and for CTLA4 (NM005214).

Treatment of melanoma tumors can be effected by providing to melanoma cells T-cells, such as tumor-infiltrating lymphocytes, pretreated ex-vivo with a combination of sdRNAs targeting PD1/PDCD1 and CTLA4, for example, targeting one or more of the twenty target sequences listed for PD1/PDCD1 and/or CTLA4. A combination of sdRNAs targeting PD1/PDCD1 and FASLG (NM_000639) and/or CTLA4, can increase T-cell toxicity in tumors expressing both PD1L and FAS.

In addition to and in combination with anti-CTLA-4 and anti-PD1 sdRNAs, T-cells used for the immunotherapy of melanoma can also be treated with sdRNA targeting other genes implicated in immunosuppression by the tumor. These receptors include, but are not limited to TGF-beta type 1 and 2 receptors, BTLA (binder of herpes virus entry indicator (HVEM) expressed on melanoma cells), and receptors of integrins expressed by myeloid derived suppressor cells (MDSC), such as CD11b, CD18, and CD29.

For tumors whose profile of expressed suppressive proteins is unknown, any combination of sdRNAs targeting PD1/PDCD1 and any one of know suppressing receptors may be helpful to reduce immune suppression and increase therapeutic efficacy.

Example 7

Combination of sdRNAs for Mitigating Immune Cell Suppression

T-cell or dendritic cell suppression may be modulated by various cytokines, such as IL10 and/or TGF beta. Suppressing corresponding receptors in T-cells and dendritic cells may be beneficial for their activity. For example, providing a combination of anti-PD1 with anti-IL10R sdRNAs is expected to mitigate cytokine induced suppression of T-cells and dendritic cells, as compared with anti-PD1 alone.

Example 8

Combination of sdRNAs for Mitigating Immune Cell Suppression

When the mechanism of tumor suppression of immune cells may be not known, use of sdRNA agents to suppress genes involved in apoptosis (programmed cell death), such as p53, Casp8 or other gene activating apoptosis may be beneficial to increase immune cell activity. Combination of an anti-receptor sdRNAs with sdRNAs against pro-apoptotic genes can additionally reduce death of immune cells and thus increase their activity. For example, combination of anti-PD1 with anti-p53 sdRNAs may additionally protect T-cells from suppression by blocking activation of apoptosis.

Example 9

Silencing of CTLA-4 and PDCD1 by sdRNA in Human Primary T-Cells

Primary human T-cells were cultured and activated essentially as described in Example 5. sdRNA agents targeting PDCD1 and CTLA-4 were prepared by separately diluting the sdRNAs to 0.4-4 µM in serum-free RPMI per sample (well) and aliquoted at 100 µl/well of 96-well plate. Cells were prepared in RPMI medium containing 4% FBS and IL2 2000 U/ml at 1,000,000 cells/ml and seeded at 100 µl/well into the 96-well plate with pre-diluted sdRNAs.

72 h later, the transfected cells were washed once with 100 µl/well PBS and processed with FastLane Cell Multiplex Kit reagents essentially as described for the Example 4 and according to the manufacturer's instructions. Taqman gene expression assays were used in the following combinations: human PDCD1-FAM (Taqman, Hs01550088_ml)/ GAPDH-VIC or human CTLA4-FAM (Taqman, Hs03044418_ml)/GAPDH-VIC. A volume of 18 µl/well of each reaction mix was combined with 2 µl lysates per well from the previously prepared lysates. The samples were amplified as before (see Example 4).

Results shown in FIG. 5 demonstrate significant silencing of PDCD1 and CTLA-4 by using combined sdRNA agents delivered to T-cells, obtaining greater than 60-70% inhibition of gene expression with 2 µM sdRNA.

Example 10

Reduction of CTLA-4 and PDCD1 Surface Expression by sdRNA in Human Primary T-Cells Primary human T-cells were cultured and activated essentially as described in Example 5.

sdRNA agents targeting CTLA-4 or PD1 were separately diluted to 5 µM in serum-free RPMI per sample (well) and aliquoted at 250 µl/well to 24-well plates. Cells mixed with magnetic beads were collected and adjusted to 500,000 cells in 250 µl RPMI medium containing 4% FBS and IL2 2000 IU/ml. Cells were seeded at 250 µl/well to the prepared plate containing pre-diluted sdRNAs. 24 hours later FBS was added to the cells to obtain 10% final concentration.

After 72 hours of incubation, the transfected cells were collected, separated from the activation beads using the magnet, as described in Example 5. Cells were washed with PBS, spun down and resuspended in blocking buffer (PBS with 3% BSA) at 200,000 cells/50 µl/sample.

Antibody dilutions were prepared in the blocking buffer. The antibodies were mixed in two combinations: anti-PD1/ anti-CD3 (1:100 dilutions for both antibodies) and anti-CTLA4/anti-CD3 (10 µl/106 cells for anti-CTLA4; 1:100 for CD3). The following antibodies were used: rabbit monoclonal [SP7] to CD3 (Abcam, ab16669); mouse monoclonal [BNI3] to CTLA4 (Abcam, ab33320) and mouse monoclonal [NAT105] to PD1 (Abcam, ab52587). Cells were mixed with the diluted antibodies and incubated 30 minutes on ice. Cells were then washed twice with PBS containing 0.2% Tween-20 and 0.1% sodium azide.

Secondary antibodies were diluted in blocking buffer and mixed together resulting in a final dilution 1:500 for anti-mouse Cy5 (Abcam, ab97037) and 1:2000 for anti-rabbit Alexa-488 (Abcam, ab150077). Cells were mixed with the diluted antibodies at 1:1 ratio and incubated 30 minutes on ice. Cells were washed as before, and diluted in 500 µl PBS per tube. The data was acquired immediately on the Attune Acoustic Focusing Cytometer (Applied Biosystems).

As shown in FIG. 6, sdRNA efficiently reduced surface expression of CTLA-4 and PD1 in activated Human Primary T cells.

Example 11

MAP4K4 sdRNA Delivery into CD3- and CD19-Positive Subsets of Human Peripheral Blood Mononuclear Cells (PBMCs)

PBMCs were cultured in complete RPMI supplemented with 1.5% PHA solution and 500 U/ml IL2. For transfection, PBMCs were collected by centrifugation and diluted with RPMI medium containing 4% FBS and IL2 1000 U/ml and seeded to 24-well plate at 500,000 cells/well.

MAP4K4 sdRNA labeled with cy3 was added to the cells at 0.1 µM final concentration. After 72 hours of incubation, the transfected cells were collected, washed with PBS, spun down and diluted in blocking buffer (PBS with 3% BSA) at 200,000 cells/50 µl/sample.

Antibody dilutions were prepared in the blocking buffer as following: 1:100 final dilution anti-CD3 (Abcam, ab16669) and anti-CD19 at 10 µl/1,000,000 cells (Abcam, ab31947). Cells were mixed with the diluted antibodies and incubated 30 min on ice. Cells were then washed twice with PBS containing 0.2% Tween-20 and 0.1% sodium azide.

Secondary antibodies were diluted in the blocking buffer in a final dilution 1:500 for anti-mouse Cy5 (Abcam, ab97037) and 1:2000 for anti-rabbit Alexa-488 (Abcam, ab150077). Cells were mixed with the diluted antibodies at 1:1 ratio and incubated 30 min on ice. Cells were washed as before, and diluted in 500 µl PBS per tube. The data was acquired immediately on the Attune Acoustic Focusing Cytometer (Applied Biosystems).

FIG. 7 shows efficient transfection over 97% of CD3-positive (t cells) and over 98% CD19-positive (B-cells) subsets in Human Peripheral Blood Mononuclear Cells (PBMCs).

TABLE 1

Targeting sequences and gene regions of genes targeted with sdRNAs to prevent immunosuppression of antigen-presenting cells and T-cells.

Accession: NM_004324
HUGO gene symbol: BAX

| Oligo_count | Oligo_ID | targeting sequence | SEQ ID NO: | Gene_region | SEQ ID NO: |
|---|---|---|---|---|---|
| 1 | BAX_NM_004324_human_835 | GAATTGCTCAAGTTCATTGA | 1 | CCTCCACTGCCTCTGGAATTGCTCAAG TTCATTGATGACCCTCTG | 21 |
| 2 | BAX_NM_004324_human_157 | TTCATCCAGGATCGAGCAGG | 2 | CTTTTGCTTCAGGGTTTCATCCAGGAT CGAGCAGGGCGAATGGGG | 22 |
| 3 | BAX_NM_004324_human_684 | ATCATCAGATGTGGTCTATA | 3 | TCTCCCCATCTTCAGATCATCAGATGT GGTCTATAATGCGTTTTC | 23 |
| 4 | BAX_NM_004324_human_412 | TACTTTGCCAGCAAACTGGT | 4 | GTTGTCGCCCTTTTCTACTTTGCCAGCA AACTGGTGCTCAAGGCC | 24 |
| 5 | BAX_NM_004324_human_538 | GGTTGGGTGAGACTCCTCAA | 5 | ATCCAAGACCAGGGTGGTTGGGTGAG ACTCCTCAAGCCTCCTCAC | 25 |
| 6 | BAX_NM_004324_human_411 | CTACTTTGCCAGCAAACTGG | 6 | GGTTGTCGCCCTTTTCTACTTTGCCAGC AAACTGGTGCTCAAGGC | 26 |
| 7 | BAX_NM_004324_human_706 | GCGTTTTCCTTACGTGTCTG | 7 | GATGTGGTCTATAATGCGTTTTCCTTA CGTGTCTGATCAATCCCC | 27 |
| 8 | BAX_NM_004324_human_716 | TACGTGTCTGATCAATCCCC | 8 | ATAATGCGTTTTCCTTACGTGTCTGATC AATCCCGATTCATCTA | 28 |
| 9 | BAX_NM_004324_human_150 | TCAGGGTTTCATCCAGGATC | 9 | AGGGGCCCTTTTGCTTCAGGGTTTCAT CCAGGATCGAGCAGGGCG | 29 |
| 10 | BAX_NM_004324_human_372_ | TGACGGCAACTTCAACTGGG | 10 | AGCTGACATGTTTTCTGACGGCAACTT CAACTGGGCCGGGTTGT | 30 |
| 11 | BAX_NM_004324_human_356 | CAGCTGACATGTTTTCTGAC | 11 | TCTTTTTCCGAGTGGCAGCTGACATGT TTTCTGACGGCAACTTCA | 31 |
| 12 | BAX_NM_004324_human_357 | AGCTGACATGTTTTCTGACG | 12 | CTTTTTCCGAGTGGCAGCTGACATGTT TTCTGACGGCAACTTCAA | 32 |
| 13 | BAX_NM_004324_human_776 | CACTGTGACCTTGACTTGAT | 13 | AGTGACCCCTGACCTCACTGTGACCTT GACTTGATTAGTGCCTTC | 33 |
| 14 | BAX_NM_004324_human_712 | TCCTTACGTGTCTGATCAAT | 14 | GTCTATAATGCGTTTTCCTTACGTGTCT GATCAATCCCCGATTCA | 34 |
| 15 | BAX_NM_004324_human_465 | GATCAGAACCATCATGGGCT | 15 | CAAGGTGCCGGAACTGATCAGAACCA TCATGGGCTGGACATTGGA | 35 |
| 16 | BAX_NM_004324_human_642 | CTTCTGGAGCAGGTCACAGT | 16 | TCTGGGACCCTGGCCTTCTGGAGCA GGTCACAGTGGTGCCCTCT | 36 |
| 17 | BAX_NM_004324_human_117 | TGAGCAGATCATGAAGACAG | 17 | GGGGCCCACCAGCTCTGAGCAGATCA TGAAGACAGGGGCCCTTTT | 37 |
| 18 | BAX_NM_004324_human_700 | TATAATGCGTTTTCCTTACG | 18 | TCATCAGATGTGGTCTATAATGCGTTT TCCTTACGTGTCTGATCA | 38 |

TABLE 1-continued

Targeting sequences and gene regions of genes targeted with sdRNAs to prevent immunosuppression of antigen-presenting cells and T-cells.

| | | | | | |
|---|---|---|---|---|---|
| 19 | BAX_NM_004324_human_673 | CCCATCTTCAGATCATCAGA | 19 | CAGTGGTGCCCTCTCCCCATCTTCAGA TCATCAGATGTGGTCTAT | 39 |
| 20 | BAX_NM_004324_human_452 | AGGTGCCGGAACTGATCAGA | 20 | AGGCCCTGTGCACCAAGGTGCCGGAA CTGATCAGAACCATCATGG | 40 |

Accession: NM_001188
HUGO gene symbol: BAK1

| Oligo_count | Oligo_ID | targeting sequence | SEQ ID NO: | Gene_region | SEQ ID NO: |
|---|---|---|---|---|---|
| 1 | BAK1_NM_001188_human_1813 | TGGTTTGTTATATCAGGGAA | 41 | ACAGGGCTTAGGACTTGGTTTGTTA TATCAGGGAAAAGGAGTAGG | 61 |
| 2 | BAK1_NM_001188_human_911 | TGGTACGAAGATTCTTCAAA | 42 | TGTTGGGCCAGTTTGTGGTACGAAG ATTCTTCAAATCATGACTCC | 62 |
| 3 | BAK1_NM_001188_human_1820 | TTATATCAGGGAAAAGGAGT | 43 | TTAGGACTTGGTTTGTTATATCAGG GAAAAGGAGTAGGGAGTTCA | 63 |
| 4 | BAK1_NM_001188_human_1678 | TCCCTTCCTCTCTCCTTATA | 44 | GTCCTCTCAGTTCTCTCCCTTCCTCTC TCCTTATAGACACTTGCT | 64 |
| 5 | BAK1_NM_001188_human_926 | TCAAATCATGACTCCCAAGG | 45 | TGGTACGAAGATTCTTCAAATCATG ACTCCCAAGGGTGCCCTTTG | 65 |
| 6 | BAK1_NM_001188_human_1818 | TGTTATATCAGGGAAAAGGA | 46 | GCTTAGGACTTGGTTTGTTATATCA GGGAAAAGGAGTAGGGAGTT | 66 |
| 7 | BAK1_NM_001188_human_915 | ACGAAGATTCTTCAAATCAT | 47 | GGGCCAGTTTGTGGTACGAAGATTC TTCAAATCATGACTCCCAAG | 67 |
| 8 | BAK1_NM_001188_human_912 | GGTACGAAGATTCTTCAAAT | 48 | GTTGGGCCAGTTTGTGGTACGAAGA TTCTTCAAATCATGACTCCC | 68 |
| 9 | BAK1_NM_001188_human_2086 | GAAGTTCTTGATTCAGCCAA | 49 | GGGGGTCAGGGGGAGAAGTTCTT GATTCAGCCAAATGCAGGGAG | 69 |
| 10 | BAK1_NM_001188_human_620 | CCTATGAGTACTTCACCAAG | 50 | CCACGGCAGAGAATGCCTATGAGTA CTTCACCAAGATTGCCACCA | 70 |
| 11 | BAK1_NM_001188_human_1823 | TATCAGGGAAAAGGAGTAGG | 51 | GGACTTGGTTTGTTATATCAGGGAA AAGGAGTAGGGAGTTCATCT | 71 |
| 12 | BAK1_NM_001188_human_1687 | CTCTCCTTATAGACACTTGC | 52 | GTTCTCTCCCTTCCTCTCTCCTTATAG ACACTTGCTCCCAACCCA | 72 |
| 13 | BAK1_NM_001188_human_1810 | ACTTGGTTTGTTATATCAGG | 53 | ACTACAGGGCTTAGGACTTGGTTTG TTATATCAGGGAAAAGGAGT | 73 |
| 14 | BAK1_NM_001188_human_1399 | AAGATCAGCACCCTAAGAGA | 54 | ATTCAGCTATTCTGGAAGATCAGCA CCCTAAGAGATGGGACTAGG | 74 |
| 15 | BAK1_NM_001188_human_654 | GTTTGAGAGTGGCATCAATT | 55 | GATTGCCACCAGCCTGTTTGAGAGT GGCATCAATTGGGGCCGTGT | 75 |
| 16 | BAK1_NM_001188_human_1875 | GACTATCAACACCACTAGGA | 56 | TCTAAGTGGGAGAAGGACTATCAAC ACCACTAGGAATCCCAGAGG | 76 |
| 17 | BAK1_NM_001188_human_1043 | AGCTTTAGCAAGTGTGCACT | 57 | CCTCAAGAGTACAGAAGCTTTAGCA AGTGTGCACTCCAGCTTCGG | 77 |
| 18 | BAK1_NM_001188_human_1846 | TTCATCTGGAGGGTTCTAAG | 58 | AAAAGGAGTAGGGAGTTCATCTGG AGGGTTCTAAGTGGGAGAAGG | 78 |
| 19 | BAK1_NM_001188_human_2087 | AAGTTCTTGATTCAGCCAAA | 59 | GGGGTCAGGGGGAGAAGTTCTTG ATTCAGCCAAATGCAGGGAGG | 79 |
| 20 | BAK1_NM_001188_human_1819 | GTTATATCAGGGAAAAGGAG | 60 | CTTAGGACTTGGTTTGTTATATCAG GGAAAAGGAGTAGGGAGTTC | 80 |

TABLE 1-continued

Targeting sequences and gene regions of genes targeted with sdRNAs to prevent
immunosuppression of antigen-presenting cells and T-cells.

Accession: NM_001228
HUGO gene symbol: CASP8

| Oligo_count | Oligo_ID | targeting sequence | SEQ ID NO: | Gene_region | SEQ ID NO: |
|---|---|---|---|---|---|
| 1 | CASP8_NM_001228_human_2821 | TTAAATCATTAGGAATTAAG | 121 | TCTGCTTGGATTATTTTAAATCATTAGGAATTAAGTTATCTTTAA | 141 |
| 2 | CASP8_NM_001228_human_2833 | GAATTAAGTTATCTTTAAAA | 122 | ATTTTAAATCATTAGGAATTAAGTTATCTTTAAAATTTAAGTATC | 142 |
| 3 | CASP8_NM_001228_human_2392 | AACTTTAATTCTCTTTCAAA | 123 | TGTTAATATTCTATTAACTTTAATTCTCTTTCAAAGCTAAATTCC | 143 |
| 4 | CASP8_NM_001228_human_1683 | GACTGAAGTGAACTATGAAG | 124 | TATTCTCACCATCCTGACTGAAGTGAACTATGAAGTAAGCAACAA | 144 |
| 5 | CASP8_NM_001228_human_281 | ATATTCTCCTGCCTTTTAAA | 125 | GGGAATATTGAGATTATATTCTCCTGCCTTTTAAAAAGATGGACT | 145 |
| 6 | CASP8_NM_001228_human_2839 | AGTTATCTTTAAAATTTAAG | 126 | AATCATTAGGAATTAAGTTATCTTTAAAATTTAAGTATCTTTTTT | 146 |
| 7 | CASP8_NM_001228_human_2164 | TAGATTTTCTACTTTATTAA | 127 | TATTTACTAATTTTCTAGATTTTCTACTTTATTAATTGTTTTGCA | 147 |
| 8 | CASP8_NM_001228_human_888 | CTGTGCCCAAATCAACAAGA | 128 | CATCCTGAAAAGAGTCTGTGCCCAAATCAACAAGAGCCTGCTGAA | 148 |
| 9 | CASP8_NM_001228_human_2283 | AGCTGGTGGCAATAAATACC | 129 | TTTGGGAATGTTTTAGCTGGTGGCAATAAATACCAGACACGTAC | 149 |
| 10 | CASP8_NM_001228_human_1585 | TCCTACCGAAACCCTGCAGA | 130 | GTGAATAACTGTGTTCCTACCGAAACCCTGCAGAGGGAACCTGG | 150 |
| 11 | CASP8_NM_001228_human_2200 | TATAAGAGCTAAAGTTAAAT | 131 | TGTTTTGCACTTTTTTATAAGAGCTAAAGTTAAATAGGATATTAA | 151 |
| 12 | CASP8_NM_001228_human_2140 | CACTATGTTTATTTACTAAT | 132 | ACTATTTAGATATAACACTATGTTTATTTACTAATTTTCTAGATT | 152 |
| 13 | CASP8_NM_001228_human_2350 | ATTGTTATCTATCAACTATA | 133 | GGGCTTATGATTCAGATTGTTATCTATCAACTATAAGCCCACTGT | 153 |
| 14 | CASP8_NM_001228_human_1575 | TAACTGTGTTTCCTACCGAA | 134 | GATGGCCACTGTGAATAACTGTGTTTCCTACCGAAACCCTGCAGA | 154 |
| 15 | CASP8_NM_001228_human_2397 | TAATTCTCTTTCAAAGCTAA | 135 | ATATTCTATTAACTTTAATTCTCTTTCAAAGCTAAATTCCACACT | 155 |
| 16 | CASP8_NM_001228_human_2726 | TATATGCTTGGCTAACTATA | 136 | TGCTTTTATGATATATATGCTTGGCTAACTATATTTGCTTTTT | 156 |
| 17 | CASP8_NM_001228_human_2805 | CTCTGCTTGGATTATTTTAA | 137 | CATTTGCTCTTTCATCTCTGCTTGGATTATTTTAAATCATTAGGA | 157 |
| 18 | CASP8_NM_001228_human_2729 | ATGCTTGGCTAACTATATTT | 138 | TTTTATGATATATATGCTTGGCTAACTATATTTGCTTTTTGCT | 158 |
| 19 | CASP8_NM_001228_human_2201 | ATAAGAGCTAAAGTTAAATA | 139 | GTTTTGCACTTTTTTATAAGAGCTAAAGTTAAATAGGATATTAAC | 159 |
| 20 | CASP8_NM_001228_human_2843 | ATCTTTAAAATTTAAGTATC | 140 | ATTAGGAATTAAGTTATCTTTAAAATTTAAGTATCTTTTTTCAAA | 160 |

Accession: NM_000675
HUGO gene symbol: ADORA2A

| Oligo_count | Oligo_ID | targeting sequence | SEQ ID NO: | Gene_region | SEQ ID NO: |
|---|---|---|---|---|---|
| 1 | ADORA2A_NM_000675_human_2482 | TAACTGCCTTTCCTTCTAAA | 161 | GTGAGAGGCCTTGTCTAACTGCCTTTCCTTCTAAAGGGAATGTTT | 181 |

TABLE 1-continued

Targeting sequences and gene regions of genes targeted with sdRNAs to prevent immunosuppression of antigen-presenting cells and T-cells.

| | | | SEQ ID NO: | | SEQ ID NO: |
|---|---|---|---|---|---|
| 2 | ADORA2A_NM_000675_human_2491 | TTCCTTCTAAAGGGAATGTT | 162 | CTTGTCTAACTGCCTTTCCTTCTAA AGGGAATGTTTTTTTCTGAG | 182 |
| 3 | ADORA2A_NM_000675_human_2487 | GCCTTTCCTTCTAAAGGGAA | 163 | AGGCCTTGTCTAACTGCCTTTCCT TCTAAAGGGAATGTTTTTTTC | 183 |
| 4 | ADORA2A_NM_000675_human_2512 | TTTTCTGAGATAAAATAAAA | 164 | CTAAAGGGAATGTTTTTTTCTGAG ATAAAATAAAAACGAGCCACA | 184 |
| 5 | ADORA2A_NM_000675_human_2330 | CATCTCTTGGAGTGACAAAG | 165 | TCTCAGTCCCAGGGCCATCTCTTG GAGTGACAAAGCTGGGATCAA | 185 |
| 6 | ADORA2A_NM_000675_human_987 | CATGGTGTACTTCAACTTCT | 166 | GGTCCCCATGAACTACATGGTGT ACTTCAACTTCTTTGCCTGTGT | 186 |
| 7 | ADORA2A_NM_000675_human_2481 | CTAACTGCCTTTCCTTCTAA | 167 | AGTGAGAGGCCTTGTCTAACTGC CTTTCCTTCTAAAGGGAATGTT | 187 |
| 8 | ADORA2A_NM_000675_human_1695 | CTGATGATTCATGGAGTTTG | 168 | TGGAGCAGGAGTGTCCTGATGAT TCATGGAGTTTGCCCCTTCCTA | 188 |
| 9 | ADORA2A_NM_000675_human_264 | CTCAGAGTCCTCTGTGAAAA | 169 | CCTGGTTTCAGGAGACTCAGAGT CCTCTGTGAAAAGCCCTTGGA | 189 |
| 10 | ADORA2A_NM_000675_human_2531 | AACGAGCCACATCGTGTTTT | 170 | CTGAGATAAAATAAAAACGAGCC ACATCGTGTTTTAAGCTTGTCC | 190 |
| 11 | ADORA2A_NM_000675_human_2492 | TCCTTCTAAAGGGAATGTTT | 171 | TTGTCTAACTGCCTTTCCTTCTAAA GGGAATGTTTTTTTCTGAGA | 191 |
| 12 | ADORA2A_NM_000675_human_978 | CATGAACTACATGGTGTACT | 172 | TGAGGATGTGGTCCCCATGAACT ACATGGTGTACTTCAACTTCTT | 192 |
| 13 | ADORA2A_NM_000675_human_2483 | AACTGCCTTTCCTTCTAAAG | 173 | TGAGAGGCCTTGTCTAACTGCCTT TCCTTCTAAAGGGAATGTTTT | 193 |
| 14 | ADORA2A_NM_000675_human_1894 | CAGATGTTTCATGCTGTGAG | 174 | TGGGTTCTGAGGAAGCAGATGTT TCATGCTGTGAGGCCTTGCACC | 194 |
| 15 | ADORA2A_NM_000675_human_976 | CCCATGAACTACATGGTGTA | 175 | TTTGAGGATGTGGTCCCCATGAA CTACATGGTGTACTTCAACTTC | 195 |
| 16 | ADORA2A_NM_000675_human_1384 | AGGCAGCAAGAACCTTTCAA | 176 | CGCAGCCACGTCCTGAGGCAGCA AGAACCTTTCAAGGCAGCTGGC | 196 |
| 17 | ADORA2A_NM_000675_human_1692 | GTCCTGATGATTCATGGAGT | 177 | GGATGGAGCAGGAGTGTCCTGAT GATTCATGGAGTTTGCCCCTTC | 197 |
| 18 | ADORA2A_NM_000675_human_993 | GTACTTCAACTTCTTTGCCT | 178 | CATGAACTACATGGTGTACTTCAA CTTCTTTGCCTGTGTGCTGGT | 198 |
| 19 | ADORA2A_NM_000675_human_2167 | TGTAAGTGTGAGGAAACCCT | 179 | TTTTTCCAGGAAAATGTAAGTGT GAGGAAACCCTTTTTATTTTA | 199 |
| 20 | ADORA2A_NM_000675_human_1815 | CCTACTTTGGACTGAGAGAA | 180 | TGAGGGCAGCCGGTTCCTACTTT GGACTGAGAGAAGGGAGCCCCA | 200 |

Accession: NM_005214
HUGO gene symbol: CTLA4

| Oligo_count | Oligo_ID | targeting sequence | SEQ ID NO: | Gene_region | SEQ ID NO: |
|---|---|---|---|---|---|
| 1 | CTLA4_NM_005214_human_61 | TGATTCTGTGTGGGTTCAAA | 201 | TCTATATAAAGTCCTTGATTCTGT GTGGGTTCAAACACATTTCAA | 221 |
| 2 | CTLA4_NM_005214_human_909 | TTATTTGTTTGTGCATTTGG | 202 | GCTATCCAGCTATTTTTATTTGTTT GTGCATTTGGGGGGAATTCA | 222 |
| 3 | CTLA4_NM_005214_human_1265 | TGATTACATCAAGGCTTCAA | 203 | TCTTAAACAAATGTATGATTACAT CAAGGCTTCAAAAATACTCAC | 223 |
| 4 | CTLA4_NM_005214_human_1094 | GATGTGGGTCAAGGAATTAA | 204 | GGGATGCAGCATTATGATGTGGG TCAAGGAATTAAGTTAGGGAAT | 224 |

TABLE 1-continued

Targeting sequences and gene regions of genes targeted with sdRNAs to prevent immunosuppression of antigen-presenting cells and T-cells.

| | | | | | |
|---|---|---|---|---|---|
| 5 | CTLA4_NM_005214_human_1241 | CCTTTTATTTCTTAAACAAA | 205 | AAGTTAAATTTTATGCCTTTTATTT CTTAAACAAATGTATGATTA | 225 |
| 6 | CTLA4_NM_005214_human_1266 | GATTACATCAAGGCTTCAAA | 206 | CTTAAACAAATGTATGATTACATC AAGGCTTCAAAAATACTCACA | 226 |
| 7 | CTLA4_NM_005214_human_65 | TCTGTGTGGGTTCAAACACA | 207 | TATAAAGTCCTTGATTCTGTGTGG GTTCAAACACATTTCAAAGCT | 227 |
| 8 | CTLA4_NM_005214_human_1405 | TTGATAGTATTGTGCATAGA | 208 | TATATATATTTTAATTTGATAGTAT TGTGCATAGAGCCACGTATG | 228 |
| 9 | CTLA4_NM_005214_human_1239 | TGCCTTTTATTTCTTAAACA | 209 | TCAAGTTAAATTTTATGCCTTTTAT TTCTTAAACAAATGTATGAT | 229 |
| 10 | CTLA4_NM_005214_human_1912 | TCCATGAAAATGCAACAACA | 210 | TTTAACTCAATATTTTCCATGAAA ATGCAACAACATGTATAATAT | 230 |
| 11 | CTLA4_NM_005214_human_1245 | TTATTTCTTAAACAAATGTA | 211 | TAAATTTTATGCCTTTTATTTCTTA AACAAATGTATGATTACATC | 231 |
| 12 | CTLA4_NM_005214_human_1449 | TTAATGGTTTGAATATAAAC | 212 | GTTTTTGTGTATTTGTTAATGGTT GAATATAAACACTATATGGC | 232 |
| 13 | CTLA4_NM_005214_human_1095 | ATGTGGGTCAAGGAATTAAG | 213 | GGATGCAGCATTATGATGTGGGT CAAGGAATTAAGTTAGGGAATG | 233 |
| 14 | CTLA4_NM_005214_human_1208 | AGCCGAAATGATCTTTTCAA | 214 | GTATGAGACGTTTATAGCCGAAA TGATCTTTTCAAGTTAAATTTT | 234 |
| 15 | CTLA4_NM_005214_human_1455 | GTTTGAATATAAACACTATA | 215 | GTGTATTTGTTAATGGTTTGAATA TAAACACTATATGGCAGTGTC | 235 |
| 16 | CTLA4_NM_005214_human_1237 | TATGCCTTTTATTTCTTAAA | 216 | TTTCAAGTTAAATTTTATGCCTTTT ATTTCTTAAACAAATGTATG | 236 |
| 17 | CTLA4_NM_005214_human_1911 | TTCCATGAAAATGCAACAAC | 217 | TTTTAACTCAATATTTTCCATGAA AATGCAACAACATGTATAATA | 237 |
| 18 | CTLA4_NM_005214_human_937 | CATCTCTCTTTAATATAAAG | 218 | CATTTGGGGGGAATTCATCTCTCT TTAATATAAAGTTGGATGCGG | 238 |
| 19 | CTLA4_NM_005214_human_931 | GGAATTCATCTCTCTTTAAT | 219 | TTTGTGCATTTGGGGGGAATTCAT CTCTCTTTAATATAAAGTTGG | 239 |
| 20 | CTLA4_NM_005214_human_45 | ATCTATATAAAGTCCTTGAT | 220 | TCTGGGATCAAAGCTATCTATATA AAGTCCTTGATTCTGTGTGGG | 240 |

Accession: NM_002286
HUGO gene symbol: LAG3

| Oligo_count | Oligo_ID | targeting sequence | SEQ ID NO: | Gene_region | SEQ ID NO: |
|---|---|---|---|---|---|
| 1 | LAG3_NM_002286_human_1292 | GACTTTACCCTTCGACTAGA | 241 | ACTGGAGACAATGGCGACTTTACC CTTCGACTAGAGGATGTGAGC | 261 |
| 2 | LAG3_NM_002286_human_1096 | CAACGTCTCCATCATGTATA | 242 | CTACAGAGATGGCTTCAACGTCTC CATCATGTATAACCTCACTGT | 262 |
| 3 | LAG3_NM_002286_human_1721 | GTCCTTTCTCTGCTCCTTTT | 243 | TTTCTCATCCTTGGTGTCCTTTCTCT GCTCCTTTTGGTGACTGGA | 263 |
| 4 | LAG3_NM_002286_human_1465 | TCCAGTATCTGGACAAGAAC | 244 | GCTTTGTGAGGTGACTCCAGTATC TGGACAAGAACGCTTTGTGTG | 264 |
| 5 | LAG3_NM_002286_human_1795 | ATTTTCTGCCTTAGAGCAAG | 245 | GTGGCGACCAAGACGATTTTCTGC CTTAGAGCAAGGGATTCACCC | 265 |
| 6 | LAG3_NM_002286_human_1760 | TTTCACCTTTGGAGAAGACA | 246 | ACTGGAGCCTTTGGCTTTCACCTTT GGAGAAGACAGTGGCGACCA | 266 |
| 7 | LAG3_NM_002286_human_904 | CATTTTGAACTGCTCCTTCA | 247 | AGCCTCCGACTGGGTCATTTTGAA CTGCTCCTTCAGCCGCCCTGA | 267 |

TABLE 1-continued

Targeting sequences and gene regions of genes targeted with sdRNAs to prevent immunosuppression of antigen-presenting cells and T-cells.

| | | | | | |
|---|---|---|---|---|---|
| 8 | LAG3_NM_002286_human_1398 | TCATCACAGTGACTCCCAAA | 248 | CTGTCACATTGGCAATCATCACAGT GACTCCCAAATCCTTTGGGT | 268 |
| 9 | LAG3_NM_002286_human_1758 | GCTTTCACCTTTGGAGAAGA | 249 | TGACTGGAGCCTTTGGCTTTCACCT TTGGAGAAGACAGTGGCGAC | 269 |
| 10 | LAG3_NM_002286_human_1753 | CTTTGGCTTTCACCTTTGGA | 250 | TTTGGTGACTGGAGCCTTTGGCTTT CACCTTTGGAGAAGACAGTG | 270 |
| 11 | LAG3_NM_002286_human_905 | ATTTTGAACTGCTCCTTCAG | 251 | GCCTCCGACTGGGTCATTTTGAACT GCTCCTTCAGCCGCCCTGAC | 271 |
| 12 | LAG3_NM_002286_human_1387 | CACATTGGCAATCATCACAG | 252 | GCTCAATGCCACTGTCACATTGGC AATCATCACAGTGACTCCCAA | 272 |
| 13 | LAG3_NM_002286_human_301 | TTTCTGACCTCCTTTTGGAG | 253 | ACTGCCCCCTTTCCTTTTCTGACCTC CTTTTGGAGGGCTCAGCGC | 273 |
| 14 | LAG3_NM_002286_human_895 | CGACTGGGTCATTTTGAACT | 254 | ATCTCTCAGAGCCTCCGACTGGGT CATTTTGAACTGCTCCTTCAG | 274 |
| 15 | LAG3_NM_002286_human_1625 | TACTTCACAGAGCTGTCTAG | 255 | CTTGGAGCAGCAGTGTACTTCACA GAGCTGTCTAGCCCAGGTGCC | 275 |
| 16 | LAG3_NM_002286_human_1390 | ATTGGCAATCATCACAGTGA | 256 | CAATGCCACTGTCACATTGGCAATC ATCACAGTGACTCCCAAATC | 276 |
| 17 | LAG3_NM_002286_human_1703 | CTGTTTCTCATCCTTGGTGT | 257 | GCAGGCCACCTCCTGCTGTTTCTCA TCCTTGGTGTCCTTTCTCTG | 277 |
| 18 | LAG3_NM_002286_human_1453 | TTGTGAGGTGACTCCAGTAT | 258 | CCTGGGGAAGCTGCTTTGTGAGGT GACTCCAGTATCTGGACAAGA | 278 |
| 19 | LAG3_NM_002286_human_1754 | TTTGGCTTTCACCTTTGGAG | 259 | TTGGTGACTGGAGCCTTTGGCTTTC ACCTTTGGAGAAGACAGTGG | 279 |
| 20 | LAG3_NM_002286_human_1279 | TGGAGACAATGGCGACTTTA | 260 | TGACCTCCTGGTGACTGGAGACAA TGGCGACTTTACCCTTCGACT | 280 |

Accession: NM_005018
HUGO gene symbol: PDCD1

| Oligo_count | Oligo_ID | targeting sequence | SEQ ID NO: | Gene_region | SEQ ID NO: |
|---|---|---|---|---|---|
| 1 | PDCDLN1_NM_005018_human_2070 | TATTATATTATAATTATAAT | 281 | CCTTCCCTGTGGTTCTATTATATTAT AATTATAATTAAATATGAG | 301 |
| 2 | PDCDLN1_NM_005018_human_2068 | TCTATTATATTATAATTATA | 282 | CCCCTTCCCTGTGGTTCTATTATATT ATAATTATAATTAAATATG | 302 |
| 3 | PDCDLN1_NM_005018_human_1854 | CATTCCTGAAATTATTTAAA | 283 | GCTCTCCTTGGAACCCATTCCTGAA ATTATTTAAAGGGGTTGGCC | 303 |
| 4 | PDCDLN1_NM_005018_human_2069 | CTATTATATTATAATTATAA | 284 | CCCTTCCCTGTGGTTCTATTATATT ATAATTATAATTAAATATGA | 304 |
| 5 | PDCDLN1_NM_005018_human_1491 | AGTTTCAGGGAAGGTCAGAA | 285 | CTGCAGGCCTAGAGAAGTTTCAGG GAAGGTCAGAAGAGCTCCTGG | 305 |
| 6 | PDCDLN1_NM_005018_human_2062 | TGTGGTTCTATTATATTATA | 286 | GGGATCCCCCTTCCCTGTGGTTCTA TTATATTATAATTATAATTA | 306 |
| 7 | PDCDLN1_NM_005018_human_719 | TGTGTTCTCTGTGGACTATG | 287 | CCCCTCAGCCGTGCCTGTGTTCTCT GTGGACTATGGGGAGCTGGA | 307 |
| 8 | PDCDLN1_NM_005018_human_1852 | CCCATTCCTGAAATTATTTA | 288 | GAGCTCTCCTTGGAACCCATTCCTG AAATTATTTAAAGGGGTTGG | 308 |
| 9 | PDCDLN1_NM_005018_human_1490 | TGCCACCATTGTCTTTCCTA | 289 | TGAGCAGACGGAGTATGCCACCAT TGTCTTTCCTAGCGGAATGGG | 309 |
| 10 | PDCDLN1_NM_005018_human_812 | AAGTTTCAGGGAAGGTCAGA | 290 | CCTGCAGGCCTAGAGAAGTTTCAG GGAAGGTCAGAAGAGCTCCTG | 310 |

… 31 …                                                                                                                             … 32 …

TABLE 1-continued

Targeting sequences and gene regions of genes targeted with sdRNAs to prevent
immunosuppression of antigen-presenting cells and T-cells.

| | | | SEQ ID NO: | | SEQ ID NO: |
|---|---|---|---|---|---|
| 11 | PDCDLN1_NM_005018_human_2061 | CTGTGGTTCTATTATATTAT | 291 | AGGGATCCCCCTTCCCTGTGGTTCT ATTATATTATAATTATAATT | 311 |
| 12 | PDCDLN1_NM_005018_human_2067 | TTCTATTATATTATAATTAT | 292 | CCCCCTTCCCTGTGGTTCTATTATA TTATAATTATAATTAAATAT | 312 |
| 13 | PDCDLN1_NM_005018_human_1493 | TTTCAGGGAAGGTCAGAAGA | 293 | GCAGGCCTAGAGAAGTTTCAGGG AAGGTCAGAAGAGCTCCTGGCT | 313 |
| 14 | PDCDLN1_NM_005018_human_1845 | CTTGGAACCCATTCCTGAAA | 294 | ACCCTGGGAGCTCTCCTTGGAACC CATTCCTGAAATTATTTAAAG | 314 |
| 15 | PDCDLN1_NM_005018_human_2058 | TCCCTGTGGTTCTATTATAT | 295 | ACAAGGGATCCCCCTTCCCTGTGG TTCTATTATATTATAATTATA | 315 |
| 16 | PDCDLN1_NM_005018_human_2060 | CCTGTGGTTCTATTATATTA | 296 | AAGGGATCCCCCTTCCCTGTGGTTC TATTATATTATAATTATAAT | 316 |
| 17 | PDCDLN1_NM_005018_human_1847 | TGGAACCCATTCCTGAAATT | 297 | CCTGGGAGCTCTCCTTGGAACCCA TTCCTGAAATTATTTAAAGGG | 317 |
| 18 | PDCDLN1_NM_005018_human_2055 | CCTTCCCTGTGGTTCTATTA | 298 | GGGACAAGGGATCCCCCTTCCCTG TGGTTCTATTATATTATAATT | 318 |
| 19 | PDCDLN1_NM_005018_human_2057 | TTCCCTGTGGTTCTATTATA | 299 | GACAAGGGATCCCCCTTCCCTGTG GTTCTATTATATTATAATTAT | 319 |
| 20 | PDCDLN1_NM_005018_human_1105 | CACAGGACTCATGTCTCAAT | 300 | CAGGCACAGCCCCACCACAGGACT CATGTCTCAATGCCCACAGTG | 320 |

Accession: NM_004612
HUGO gene symbol: TGFBR1

| Oligo_count | Oligo_ID | targeting sequence | SEQ ID NO: | Gene_region | SEQ ID NO: |
|---|---|---|---|---|---|
| 1 | TGFBRL1_NM_004612_human_5263 | CCTGTTTATTACAACTTAAA | 321 | GTTAATAACATTCAACCTGTTTAT TACAACTTAAAAGGAACTTCA | 341 |
| 2 | TGFBRL1_NM_004612_human_1323 | CCATTGGTGGAATTCATGAA | 322 | TTGCTCGACGATGTTCCATTGGTG GAATTCATGAAGATTACCAAC | 342 |
| 3 | TGFBRL1_NM_004612_human_6389 | TTTTCCTTATAACAAAGACA | 323 | TTTAGGGATTTTTTTTTTCCTTAT AACAAAGACATCACCAGGAT | 343 |
| 4 | TGFBRL1_NM_004612_human_3611 | TGTATTACTTGTTTAATAAT | 324 | TTTTTATAGTTGTGTTGTATTACTT GTTTAATAATAATCTCTAAT | 344 |
| 5 | TGFBRL1_NM_004612_human_3882 | TTATTGAATCAAAGATTGAG | 325 | TGCTGAAGATATTTTTTATTGAAT CAAAGATTGAGTTACAATTAT | 345 |
| 6 | TGFBRL1_NM_004612_human_3916 | TTCTTACCTAAGTGGATAAA | 326 | GTTACAATTATACTTTTCTTACCTA AGTGGATAAAATGTACTTTT | 346 |
| 7 | TGFBRL1_NM_004612_human_5559 | ATGTTGCTCAGTTACTCAAA | 327 | TAAAGTATGGGTATTATGTTGCTC AGTTACTCAAATGGTACTGTA | 347 |
| 8 | TGFBRL1_NM_004612_human_5595 | ATATTTGTACCCCAAATAAC | 328 | GGTACTGTATTGTTTATATTGTA CCCCAAATAACATCGTCTGTA | 348 |
| 9 | TGFBRL1_NM_004612_human_5222 | TGTAAATGTAAACTTCTAAA | 329 | TTATGCAATCTTGTTTGTAAATGT AAACTTCTAAAAATATGGTTA | 349 |
| 10 | TGFBRL1_NM_004612_human_3435 | AGAATGAGTGACATATTACA | 330 | AACCAAAGTAATTTAGAATGAG TGACATATTACATAGGAATTTA | 350 |
| 11 | TGFBRL1_NM_004612_human_3709 | CCATTTCTAAGCCTACCAGA | 331 | GTTGTTGTTTTGGGCCATTTCTA AGCCTACCAGATCTGCTTTAT | 351 |
| 12 | TGFBRL1_NM_004612_human_5826 | ATATTCCAAAAGAATGTAAA | 332 | ATTGTATTTGTAGTAATATTCCAA AAGAATGTAAATAGGAAATAG | 352 |
| 13 | TGFBRL1_NM_004612_human_3146 | TTACTTCCAATGCTATGAAG | 333 | TATAATAACTGGTTTTTACTTCCA ATGCTATGAAGTCTCTGCAGG | 353 |

TABLE 1-continued

Targeting sequences and gene regions of genes targeted with sdRNAs to prevent immunosuppression of antigen-presenting cells and T-cells.

| | | | | | |
|---|---|---|---|---|---|
| 14 | TGFBRL1_NM_004612_human_2675 | TCTTTATCTGTTCAAAGACT | 334 | TGTAAGCCATTTTTTTCTTTATCTG TTCAAAGACTTATTTTTTAA | 354 |
| 15 | TGFBRL1_NM_004612_human_2529 | GTCTAAGTATACTTTTAAAA | 335 | CATTTTAATTGTGTTGTCTAAGTA TACTTTTAAAAAATCAAGTGG | 355 |
| 16 | TGFBRL1_NM_004612_human_5079 | ATCTTTGGACATGTACTGCA | 336 | GAGATACTAAGGATTATCTTTGG ACATGTACTGCAGCTTCTTGTC | 356 |
| 17 | TGFBRL1_NM_004612_human_3607 | GTGTTGTATTACTTGTTTAA | 337 | TTTGTTTTTATAGTTGTGTTGTATT ACTTGTTTAATAATAATCTC | 357 |
| 18 | TGFBRL1_NM_004612_human_5994 | TGCTGTAGATGGCAACTAGA | 338 | CATGCCATATGTAGTTGCTGTAGA TGGCAACTAGAACCTTTGAGT | 358 |
| 19 | TGFBRL1_NM_004612_human_2177 | TCTTTCACTTATTCAGAACA | 339 | GTATACTATTATTGTTCTTTCACTT ATTCAGAACATTACATGCCT | 359 |
| 20 | TGFBRL1_NM_004612_human_5814 | GTATTTGTAGTAATATTCCA | 340 | TTTAAATTGTATATTGTATTTGTA GTAATATTCCAAAAGAATGTA | 360 |

Accession: NM_032782
HUGO gene symbol: HAVCR2

| Oligo_count | Oligo_ID | targeting sequence | SEQ ID NO: | Gene_region | SEQ ID NO: |
|---|---|---|---|---|---|
| 1 | HAVCR2_NM_032782_human_937 | CTCATAGCAAAGAGAAGATA | 361 | TTTTCAAATGGTATTCTCATAGCA AAGAGAAGATACAGAATTTAA | 381 |
| 2 | HAVCR2_NM_032782_human_932 | GTATTCTCATAGCAAAGAGA | 362 | TTTAATTTTCAAATGGTATTCTCAT AGCAAAGAGAAGATACAGAA | 382 |
| 3 | HAVCR2_NM_032782_human_2126 | TTGCTTGTTGTGTGCTTGAA | 363 | TGTATTGGCCAAGTTTTGCTTGTT GTGTGCTTGAAAGAAAATATC | 383 |
| 4 | HAVCR2_NM_032782_human_2171 | TATTCGTGGACCAAACTGAA | 364 | TCTGACCAACTTCTGTATTCGTGG ACCAAACTGAAGCTATATTT | 384 |
| 5 | HAVCR2_NM_032782_human_158 | ATTGTGGAGTAGACAGTTGG | 365 | GCTACTGCTCATGTGATTGTGGA GTAGACAGTTGGAAGAAGTACC | 385 |
| 6 | HAVCR2_NM_032782_human_2132 | GTTGTGTGCTTGAAAGAAAA | 366 | GGCCAAGTTTTGCTTGTTGTGTGC TTGAAAGAAAATATCTCTGAC | 386 |
| 7 | HAVCR2_NM_032782_human_2131 | TGTTGTGTGCTTGAAAGAAA | 367 | TGGCCAAGTTTTGCTTGTTGTGTG CTTGAAAGAAAATATCTCTGA | 387 |
| 8 | HAVCR2_NM_032782_human_2313 | CCCTAAACTTAAATTTCAAG | 368 | TTGACAGAGAGTGGTCCCTAAAC TTAAATTTCAAGACGGTATAGG | 388 |
| 9 | HAVCR2_NM_032782_human_489 | ACATCCAGATACTGGCTAAA | 369 | GATGTGAATTATTGGACATCCAG ATACTGGCTAAATGGGGATTTC | 389 |
| 10 | HAVCR2_NM_032782_human_1272 | CATTTTCAGAAGATAATGAC | 370 | GGAGCAGAGTTTTCCCATTTTCAG AAGATAATGACTCACATGGGA | 390 |
| 11 | HAVCR2_NM_032782_human_785 | CACATTGGCCAATGAGTTAC | 371 | TCTAACACAAATATCCACATTGGC CAATGAGTTACGGGACTCTAG | 391 |
| 12 | HAVCR2_NM_032782_human_2127 | TGCTTGTTGTGTGCTTGAAA | 372 | GTATTGGCCAAGTTTTGCTTGTTG TGTGCTTGAAAGAAAATATCT | 392 |
| 13 | HAVCR2_NM_032782_human_164 | GAGTAGACAGTTGGAAGAAG | 373 | GCTCATGTGATTGTGGAGTAGAC AGTTGGAAGAAGTACCCAGTCC | 393 |
| 14 | HAVCR2_NM_032782_human_2130 | TTGTTGTGTGCTTGAAAGAA | 374 | TTGGCCAAGTTTTGCTTGTTGTGT GCTTGAAAGAAAATATCTCTG | 394 |
| 15 | HAVCR2_NM_032782_human_911 | CGGCGCTTTAATTTTCAAAT | 375 | TCTGGCTCTTATCTTCGGCGCTTT AATTTTCAAATGGTATTCTCA | 395 |
| 16 | HAVCR2_NM_032782_human_1543 | TTTGGCACAGAAAGTCTAAA | 376 | TGAAAGCATAACTTTTTTGGCACA GAAAGTCTAAAGGGGCCACTG | 396 |

TABLE 1-continued

Targeting sequences and gene regions of genes targeted with sdRNAs to prevent immunosuppression of antigen-presenting cells and T-cells.

| | | | SEQ ID NO: | | SEQ ID NO: |
|---|---|---|---|---|---|
| 17 | HAVCR2_NM_032782_human_2346 | GATCTGTCTTGCTTATTGTT | 377 | AGACGGTATAGGCTTGATCTGTC TTGCTTATTGTTGCCCCCTGCG | 397 |
| 18 | HAVCR2_NM_032782_human_2107 | GGTGTGTATTGGCCAAGTTT | 378 | GAAGTGCATTTGATTGGTGTGTA TTGGCCAAGTTTTGCTTGTTGT | 398 |
| 19 | HAVCR2_NM_032782_human_1270 | CCCATTTTCAGAAGATAATG | 379 | ATGGAGCAGAGTTTTCCCATTTTC AGAAGATAATGACTCACATGG | 399 |
| 20 | HAVCR2_NM_032782_human_1545 | TGGCACAGAAAGTCTAAAGG | 380 | AAAGCATAACTTTTTTGGCACAGA AAGTCTAAAGGGGCCACTGAT | 400 |

Accession: NM_002987
HUGO gene symbol: CCL17

| Oligo_count | Oligo_ID | targeting sequence | SEQ ID NO: | Gene_region | SEQ ID NO: |
|---|---|---|---|---|---|
| 1 | CCL17_NM_002987_human_385 | AAATACCTGCAAAGCCTTGA | 401 | GTGAAGAATGCAGTTAAATACCTGC AAAGCCTTGAGAGGTCTTGA | 421 |
| 2 | CCL17_NM_002987_human_318 | TTTTGTAACTGTGCAGGGCA | 402 | CAGGGATGCCATCGTTTTTGTAACT GTGCAGGGCAGGGCCATCTG | 422 |
| 3 | CCL17_NM_002987_human_367 | AGAGTGAAGAATGCAGTTAA | 403 | GACCCCAACAACAAGAGAGTGAAG AATGCAGTTAAATACCTGCAA | 423 |
| 4 | CCL17_NM_002987_human_396 | AAGCCTTGAGAGGTCTTGAA | 404 | AGTTAAATACCTGCAAAGCCTTGAG AGGTCTTGAAGCCTCCTCAC | 424 |
| 5 | CCL17_NM_002987_human_386 | AATACCTGCAAAGCCTTGAG | 405 | TGAAGAATGCAGTTAAATACCTGCA AAGCCTTGAGAGGTCTTGAA | 425 |
| 6 | CCL17_NM_002987_human_378 | TGCAGTTAAATACCTGCAAA | 406 | CAAGAGAGTGAAGAATGCAGTTAA ATACCTGCAAAGCCTTGAGAG | 426 |
| 7 | CCL17_NM_002987_human_357 | CAACAACAAGAGAGTGAAGA | 407 | CATCTGTTCGGACCCCAACAACAAG AGAGTGAAGAATGCAGTTAA | 427 |
| 8 | CCL17_NM_002987_human_55 | CTGAATTCAAAACCAGGGTG | 408 | CTGCTGATGGGAGAGCTGAATTCAA AACCAGGGTGTCTCCCTGAG | 428 |
| 9 | CCL17_NM_002987_human_387 | ATACCTGCAAAGCCTTGAGA | 409 | GAAGAATGCAGTTAAATACCTGCAA AGCCTTGAGAGGTCTTGAAG | 429 |
| 10 | CCL17_NM_002987_human_254 | TTCCCCTTAGAAAGCTGAAG | 410 | ACTTCAAGGGAGCCATTCCCCTTAG AAAGCTGAAGACGTGGTACC | 430 |
| 11 | CCL17_NM_002987_human_49 | GGAGAGCTGAATTCAAAACC | 411 | CACCGCCTGCTGATGGGAGAGCTG AATTCAAAACCAGGGTGTCTC | 431 |
| 12 | CCL17_NM_002987_human_379 | GCAGTTAAATACCTGCAAAG | 412 | AAGAGAGTGAAGAATGCAGTTAAA TACCTGCAAAGCCTTGAGAGG | 432 |
| 13 | CCL17_NM_002987_human_372 | GAAGAATGCAGTTAAATACC | 413 | CAACAACAAGAGAGTGAAGAATGC AGTTAAATACCTGCAAAGCCT | 433 |
| 14 | CCL17_NM_002987_human_377 | ATGCAGTTAAATACCTGCAA | 414 | ACAAGAGAGTGAAGAATGCAGTTA AATACCTGCAAAGCCTTGAGA | 434 |
| 15 | CCL17_NM_002987_human_252 | CATTCCCCTTAGAAAGCTGA | 415 | GTACTTCAAGGGAGCCATTCCCCTT AGAAAGCTGAAGACGTGGTA | 435 |
| 16 | CCL17_NM_002987_human_51 | AGAGCTGAATTCAAAACCAG | 416 | CCGCCTGCTGATGGGAGAGCTGAAT TCAAAACCAGGGTGTCTCCC | 436 |
| 17 | CCL17_NM_002987_human_45 | GATGGGAGAGCTGAATTCAA | 417 | GTGTCACCGCCTGCTGATGGGAGA GCTGAATTCAAAACCAGGGTG | 437 |
| 18 | CCL17_NM_002987_human_44 | TGATGGGAGAGCTGAATTCA | 418 | AGTGTCACCGCCTGCTGATGGGAGA GCTGAATTCAAAACCAGGGT | 438 |

TABLE 1-continued

Targeting sequences and gene regions of genes targeted with sdRNAs to prevent immunosuppression of antigen-presenting cells and T-cells.

| | | | | | |
|---|---|---|---|---|---|
| 19 | CCL17_NM_002987_human_16 | ACTTTGAGCTCACAGTGTCA | 419 | GCTCAGAGAGAAGTGACTTTGAGCTCACAGTGTCACCGCCTGCTG | 439 |
| 20 | CCL17_NM_002987_human_368 | GAGTGAAGAATGCAGTTAAA | 420 | ACCCCAACAACAAGAGAGTGAAGAATGCAGTTAAATACCTGCAAA | 440 |

Accession: NM_002990
HUGO gene symbol: CCL22

| Oligo_count | Oligo_ID | targeting sequence | SEQ ID NO: | Gene_region | SEQ ID NO: |
|---|---|---|---|---|---|
| 1 | CCL22_NM_002990_human_2083 | GTATTTGAAAACAGAGTAAA | 441 | GCTGGAGTTATATATGTATTTGAAAACAGAGTAAATACTTAAGAG | 461 |
| 2 | CCL22_NM_002990_human_298 | CAATAAGCTGAGCCAATGAA | 442 | GGTGAAGATGATTCTCAATAAGCTGAGCCAATGAAGAGCCTACTC | 462 |
| 3 | CCL22_NM_002990_human_2103 | TACTTAAGAGGCCAAATAGA | 443 | TGAAAACAGAGTAAATACTTAAGAGGCCAAATAGATGAATGGAAG | 463 |
| 4 | CCL22_NM_002990_human_2081 | ATGTATTTGAAAACAGAGTA | 444 | AAGCTGGAGTTATATATGTATTTGAAAACAGAGTAAATACTTAAG | 464 |
| 5 | CCL22_NM_002990_human_2496 | TTCATACAGCAAGTATGGGA | 445 | TTGAGAAATATTCTTTTCATACAGCAAGTATGGGACAGCAGTGTC | 465 |
|

TABLE 1-continued

Targeting sequences and gene regions of genes targeted with sdRNAs to prevent immunosuppression of antigen-presenting cells and T-cells.

Accession: NM_005618
HUGO gene symbol: DLL1

| Oligo_count | Oligo_ID | targeting sequence | SEQ ID NO: | Gene_region | SEQ ID NO: |
|---|---|---|---|---|---|
| 1 | DLL1_NM_005618_human_3246 | CTGTTTTGTTAATGAAGAAA | 481 | TATTTGAGTTTTTTACTGTTTTGTTA ATGAAGAAATTCCTTTTTA | 501 |
| 2 | DLL1_NM_005618_human_3193 | TTGTATATAAATGTATTTAT | 482 | TGTGACTATATTTTTTGTATATAAA TGTATTTATGGAATATTGT | 502 |
| 3 | DLL1_NM_005618_human_3247 | TGTTTTGTTAATGAAGAAAT | 483 | ATTTGAGTTTTTTACTGTTTTGTTAA TGAAGAAATTCCTTTTTAA | 503 |
| 4 | DLL1_NM_005618_human_3141 | AATTTTGGTAAATATGTACA | 484 | GTTTTTTATAATTTAAATTTTGGTAA ATATGTACAAAGGCACTTC | 504 |
| 5 | DLL1_NM_005618_human_3293 | AAATTTTATGAATGACAAAA | 485 | ATATTTTTCCAAAATAAATTTTATGA ATGACAAAAAAAAAAAAA | 505 |
| 6 | DLL1_NM_005618_human_3208 | TTTATGGAATATTGTGCAAA | 486 | TTGTATATAAATGTATTTATGGAATA TTGTGCAAATGTTATTTGA | 506 |
| 7 | DLL1_NM_005618_human_3243 | TTACTGTTTTGTTAATGAAG | 487 | TGTTATTTGAGTTTTTTACTGTTTTGT TAATGAAGAAATTCCTTT | 507 |
| 8 | DLL1_NM_005618_human_2977 | TTCTTGAATTAGAAACACAA | 488 | TTATGAGCCAGTCTTTTCTTGAATTA GAAACACAAACACTGCCTT | 508 |
| 9 | DLL1_NM_005618_human_2874 | CAGTTGCTCTTAAGAGAATA | 489 | CCGTTGCACTATGGACAGTTGCTCTT AAGAGAATATATATTTAAA | 509 |
| 10 | DLL1_NM_005618_human_2560 | CAACTTCAAAAGACACCAAG | 490 | CGGACTCGGGCTGTTCAACTTCAAA AGACACCAAGTACCAGTCGG | 510 |
| 11 | DLL1_NM_005618_human_3285 | TCCAAAATAAATTTTATGAA | 491 | TTTTTAAAATATTTTCCAAAATAAA TTTTATGAATGACAAAAAA | 511 |
| 12 | DLL1_NM_005618_human_2909 | GAACTGAATTACGCATAAGA | 492 | TATATTTAAATGGGTGAACTGAATT ACGCATAAGAAGCATGCACT | 512 |
| 13 | DLL1_NM_005618_human_1173 | GGATTTTGTGACAAACCAGG | 493 | TGTGATGAGCAGCATGGATTTTGTG ACAAACCAGGGGAATGCAAG | 513 |
| 14 | DLL1_NM_005618_human_3244 | TACTGTTTTGTTAATGAAGA | 494 | GTTATTTGAGTTTTTTACTGTTTTGTT AATGAAGAAATTCCTTTT | 514 |
| 15 | DLL1_NM_005618_human_3144 | TTTGGTAAATATGTACAAAG | 495 | TTTTATAATTTAAATTTTGGTAAATA TGTACAAAGGCACTTCGGG | 515 |
| 16 | DLL1_NM_005618_human_3286 | CCAAAATAAATTTTATGAAT | 496 | TTTTAAAATATTTTCCAAAATAAAT TTTATGAATGACAAAAAAA | 516 |
| 17 | DLL1_NM_005618_human_3133 | ATAATTTAAATTTTGGTAAA | 497 | TGATGTTCGTTTTTTATAATTTAAAT TTTGGTAAATATGTACAAA | 517 |
| 18 | DLL1_NM_005618_human_2901 | AAATGGGTGAACTGAATTAC | 498 | AGAGAATATATATTTAAATGGGTGA ACTGAATTACGCATAAGAAG | 518 |
| 19 | DLL1_NM_005618_human_3168 | TTCGGGTCTATGTGACTATA | 499 | TATGTACAAAGGCACTTCGGGTCTA TGTGACTATATTTTTTGTA | 519 |
| 20 | DLL1_NM_005618_human_3245 | ACTGTTTTGTTAATGAAGAA | 500 | TTATTTGAGTTTTTTACTGTTTTGTTA ATGAAGAAATTCCTTTTT | 520 |

TABLE 1-continued

Targeting sequences and gene regions of genes targeted with sdRNAs to prevent immunosuppression of antigen-presenting cells and T-cells.

Accession: NM_000639
HUGO gene symbol: FASLG

| Oligo_count | Oligo_ID | targeting sequence | SEQ ID NO: | Gene_region | SEQ ID NO: |
|---|---|---|---|---|---|
| 1 | FASLG_NM_000639_human_1154 | TAGCTCCTCAACTCACCTAA | 521 | GGTTCAAAATGTCTGTAGCTCCTC AACTCACCTAATGTTTATGAG | 541 |
| 2 | FASLG_NM_000639_human_1771 | ATGTTTTCCTATAATATAAT | 522 | TGTCAGCTACTAATGATGTTTTCC TATAATATAATAAATATTTAT | 542 |
| 3 | FASLG_NM_000639_human_1774 | TTTTCCTATAATATAATAAA | 523 | CAGCTACTAATGATGTTTTCCTAT AATATAATAAATATTTATGTA | 543 |
| 4 | FASLG_NM_000639_human_1776 | TTCCTATAATATAATAAATA | 524 | GCTACTAATGATGTTTTCCTATAA TATAATAAATATTTATGTAGA | 544 |
| 5 | FASLG_NM_000639_human_1086 | TGCATTTGAGGTCAAGTAAG | 525 | GAGGGTCTTCTTACATGCATTTGA GGTCAAGTAAGAAGACATGAA | 545 |
| 6 | FASLG_NM_000639_human_1750 | ATTGATTGTCAGCTACTAAT | 526 | TAGTGCTTAAAAATCATTGATTGT CAGCTACTAATGATGTTTTCC | 546 |
| 7 | FASLG_NM_000639_human_1820 | AAATGAAAACATGTAATAAA | 527 | ATGTGCATTTTGTGAAATGAAAA CATGTAATAAAAAGTATATGT | 547 |
| 8 | FASLG_NM_000639_human_1659 | ATTGTGAAGTACATATTAGG | 528 | AGAGAGAATGTAGATATTGTGAA GTACATATTAGGAAAATATGGG | 548 |
| 9 | FASLG_NM_000639_human_667 | GCTTTCTGGAGTGAAGTATA | 529 | CTATGGAATTGTCCTGCTTTCTGG AGTGAAGTATAAGAAGGGTGG | 549 |
| 10 | FASLG_NM_000639_human_1692 | CATTTGGTCAAGATTTTGAA | 530 | GGAAAATATGGGTTGCATTTGGT CAAGATTTTGAATGCTTCCTGA | 550 |
| 11 | FASLG_NM_000639_human_986 | GGCTTATATAAGCTCTAAGA | 531 | TCTCAGACGTTTTTCGGCTTATAT AAGCTCTAAGAAGCACTTT | 551 |
| 12 | FASLG_NM_000639_human_911 | ACCAGTGCTGATCATTTATA | 532 | GCAGTGTTCAATCTTACCAGTGCT GATCATTTATATGTCAACGTA | 552 |
| 13 | FASLG_NM_000639_human_598 | CCATTTAACAGGCAAGTCCA | 533 | GCTGAGGAAAGTGGCCCATTTAA CAGGCAAGTCCAACTCAAGGTC | 553 |
| 14 | FASLG_NM_000639_human_1665 | AAGTACATATTAGGAAAATA | 534 | AATGTAGATATTGTGAAGTACAT ATTAGGAAAATATGGGTTGCAT | 554 |
| 15 | FASLG_NM_000639_human_1625 | TGTGTGTGTGTATGACTAAA | 535 | GTGTGTGTGTGTGTGTGTGTGTG TGTATGACTAAAGAGAGAATGT | 555 |
| 16 | FASLG_NM_000639_human_1238 | AAGAGGGAGAAGCATGAAAA | 536 | CTGGGCTGCCATGTGAAGAGGGA GAAGCATGAAAAAGCAGCTACC | 556 |
| 17 | FASLG_NM_000639_human_1632 | GTGTATGACTAAAGAGAGAA | 537 | TGTGTGTGTGTGTGTGTATGA CTAAAGAGAGAATGTAGATATT | 557 |
| 18 | FASLG_NM_000639_human_1581 | GTATTTCCAGTGCAATTGTA | 538 | CCTAACACAGCATGTGTATTTCCA GTGCAATTGTAGGGGTGTGTG | 558 |
| 19 | FASLG_NM_000639_human_1726 | CAACTCTAATAGTGCTTAAA | 539 | ATGCTTCCTGACAATCAACTCTAA TAGTGCTTAAAAATCATTGAT | 559 |
| 20 | FASLG_NM_000639_human_1626 | GTGTGTGTGTATGACTAAAG | 540 | TGTGTGTGTGTGTGTGTGTGT GTATGACTAAAGAGAGAATGTA | 560 |

TABLE 1-continued

Targeting sequences and gene regions of genes targeted with sdRNAs to prevent immunosuppression of antigen-presenting cells and T-cells.

Accession: NM_001267706
HUGO gene symbol: CD274

| Oligo_count | Oligo_ID | targeting sequence | SEQ ID NO: | Gene_region | SEQ ID NO: |
|---|---|---|---|---|---|
| 1 | CD274_NM_001267706_human_3222 | ACCTGCATTAATTTAATAAA | 561 | ATTGTCACTTTTTGTACCTGCATTAATTTAATAAAATATTCTTAT | 581 |
| 2 | CD274_NM_001267706_human_1538 | AACTTGCCCAAACCAGTAAA | 562 | GCAAACAGATTAAGTAACTTGCCCAAACCAGTAAATAGCAGACCT | 582 |
| 3 | CD274_NM_001267706_human_1218 | ATTTGCTCACATCTAGTAAA | 563 | ACTTGCTGCTTAATGATTTGCTCACATCTAGTAAAACATGGAGTA | 583 |
| 4 | CD274_NM_001267706_human_1996 | CCTTTGCCATATAATCTAAT | 564 | TTTATTCCTGATTTGCCTTTGCCATATAATCTAATGCTTGTTTAT | 584 |
| 5 | CD274_NM_001267706_human_2346 | ATATAGCAGATGGAATGAAT | 565 | ATTTTAGTGTTTCTTATATAGCAGATGGAATGAATTTGAAGTTCC | 585 |
| 6 | CD274_NM_001267706_human_1997 | GCCTTTGCCATATAATCTAA | 566 | ATTTATTCCTGATTTGCCTTTGCCATATAATCTAATGCTTGTTTA | 586 |
| 7 | CD274_NM_001267706_human_1992 | GATTTGCCTTTGCCATATAA | 567 | ATTATATTTATTCCTGATTTGCCTTTGCCATATAATCTAATGCTT | 587 |
| 8 | CD274_NM_001267706_human_1905 | ATTTTCATTTACAAAGAGA | 568 | CTTAATAATCAGAGTAATTTTCATTTACAAAGAGAGGTCGGTACT | 588 |
| 9 | CD274_NM_001267706_human_2336 | AGTGTTTCTTATATAGCAGA | 569 | ATTTTATTTATTTTAGTGTTTCTTATATAGCAGATGGAATGAAT | 589 |
| 10 | CD274_NM_001267706_human_2656 | CTTTCTGTCAAGTATAAAC | 570 | GAACTTTTGTTTTCTGCTTTCTGTCAAGTATAAACTTCACTTTGA | 590 |
| 11 | CD274_NM_001267706_human_2235 | CATTTGGAAATGTATGTTAA | 571 | TCTAAAGATAGTCTACATTTGGAAATGTATGTTAAAAGCACGTAT | 591 |
| 12 | CD274_NM_001267706_human_2329 | TTATTTAGTGTTTCTTATA | 572 | CTTTGCTATTTTATTTATTTTAGTGTTTCTTATATAGCAGATGG | 592 |
| 13 | CD274_NM_001267706_human_1436 | GTGGTAGCCTACACACATAA | 573 | CAGCTTTACAATTATGTGGTAGCCTACACACATAATCTCATTTCA | 593 |
| 14 | CD274_NM_001267706_human_1745 | ATGAGGAGATTAACAAGAAA | 574 | GGAGCTCATAGTATAATGAGGAGATTAACAAGAAATGTATTATT | 594 |
| 15 | CD274_NM_001267706_human_1180 | CAATTTTGTCGCCAAACTAA | 575 | TTGTAGTAGATGTTACAATTTTGTCGCCAAACTAAACTTGCTGCT | 595 |
| 16 | CD274_NM_001267706_human_2345 | TATATAGCAGATGGAATGAA | 576 | TATTTTAGTGTTTCTTATATAGCAGATGGAATGAATTTGAAGTTC | 596 |
| 17 | CD274_NM_001267706_human_2069 | AAATGCCACTAAATTTTAAA | 577 | CTGTCTTTTCTATTTAAATGCCACTAAATTTTAAATTCATACCTT | 597 |
| 18 | CD274_NM_001267706_human_2414 | CTTTCCCATAGCTTTTCAT | 578 | TTTGTTTCTAAGTTATCTTTCCCATAGCTTTTCATTATCTTTCAT | 598 |
| 19 | CD274_NM_001267706_human_129 | TATATTCATGACCTACTGGC | 579 | GATATTGCTGTCTTTATATTCATGACCTACTGGCATTTGCTGAA | 599 |
| 20 | CD274_NM_001267706_human_1783 | GTCCAGTGTCATAGCATAAG | 580 | TATTATTACAATTTAGTCCAGTGTCATAGCATAAGGATGATGCGA | 600 |

TABLE 1-continued

Targeting sequences and gene regions of genes targeted with sdRNAs to prevent immunosuppression of antigen-presenting cells and T-cells.

Accession: NM_002164
HUGO gene symbol: IDO1

| Oligo_count | Oligo_ID | targeting sequence | SEQ ID NO: | Gene_region | SEQ ID NO: |
|---|---|---|---|---|---|
| 1 | IDO1_NM_002164_human_1896 | ATTCTGTCATAATAAATAAA | 601 | AAAAAAAAAGATATATTCTGTCA TAATAAATAAAAATGCATAAG | 621 |
| 2 | IDO1_NM_002164_human_1532 | TATCTTATCATTGGAATAAA | 602 | AAGTTTTGTAATCTGTATCTTATCA TTGGAATAAAATGACATTCA | 622 |
| 3 | IDO1_NM_002164_human_578 | GTGATGGAGACTGCAGTAAA | 603 | TTTTGTTCTCATTTCGTGATGGAGA CTGCAGTAAAGGATTCTTCC | 623 |
| 4 | IDO1_NM_002164_human_1897 | TTCTGTCATAATAAATAAA | 604 | AAAAAAAAGATATATTCTGTCAT AATAAATAAAAATGCATAAGA | 624 |
| 5 | IDO1_NM_002164_human_1473 | CTTGTAGGAAAACAACAAA | 605 | AATACCTGTGCATTTCTTGTAGGAA AACAACAAAAGGTAATTATG | 625 |
| 6 | IDO1_NM_002164_human_1547 | ATAAAATGACATTCAATAAA | 606 | TATCTTATCATTGGAATAAAATGAC ATTCAATAAATAAAAATGCA | 626 |
| 7 | IDO1_NM_002164_human_412 | CGTAAGGTCTTGCCAAGAAA | 607 | GGTCATGGAGATGTCCGTAAGGTC TTGCCAAGAAATATTGCTGTT | 627 |
| 8 | IDO1_NM_002164_human_1472 | TCTTGTAGGAAAACAACAAA | 608 | AAATACCTGTGCATTTCTTGTAGGA AAACAACAAAAGGTAATTAT | 628 |
| 9 | IDO1_NM_002164_human_1248 | AACTGGAGGCACTGATTTAA | 609 | ACTGGAAGCCAAAGGAACTGGAG GCACTGATTTAATGAATTTCCT | 629 |
| 10 | IDO1_NM_002164_human_1440 | CAATACAAAAGACCTCAAAA | 610 | GTTTTACCAATAATGCAATACAAAA GACCTCAAAATACCTGTGCA | 630 |
| 11 | IDO1_NM_002164_human_636 | TGCTTCTGCAATCAAAGTAA | 611 | GGTGGAAATAGCAGCTGCTTCTGC AATCAAAGTAATTCCTACTGT | 631 |
| 12 | IDO1_NM_002164_human_1551 | AATGACATTCAATAAATAAA | 612 | TTATCATTGGAATAAAATGACATTC AATAAATAAAAATGCATAAG | 632 |
| 13 | IDO1_NM_002164_human_1538 | ATCATTGGAATAAAATGACA | 613 | TGTAATCTGTATCTTATCATTGGAA TAAAATGACATTCAATAAAT | 633 |
| 14 | IDO1_NM_002164_human_1430 | ACCAATAATGCAATACAAAA | 614 | ACTATGCAATGTTTTACCAATAATG CAATACAAAAGACCTCAAAA | 634 |
| 15 | IDO1_NM_002164_human_1527 | ATCTGTATCTTATCATTGGA | 615 | ACTAGAAGTTTTGTAATCTGTATCT TATCATTGGAATAAAATGAC | 635 |
| 16 | IDO1_NM_002164_human_1533 | ATCTTATCATTGGAATAAAA | 616 | AGTTTTGTAATCTGTATCTTATCAT TGGAATAAAATGACATTCAA | 636 |
| 17 | IDO1_NM_002164_human_632 | CAGCTGCTTCTGCAATCAAA | 617 | TATTGGTGGAAATAGCAGCTGCTT CTGCAATCAAAGTAATTCCTA | 637 |
| 18 | IDO1_NM_002164_human_1439 | GCAATACAAAAGACCTCAAA | 618 | TGTTTTACCAATAATGCAATACAAA AGACCTCAAAATACCTGTGC | 638 |
| 19 | IDO1_NM_002164_human_657 | TCCTACTGTATTCAAGGCAA | 619 | TGCAATCAAAGTAATTCCTACTGTA TTCAAGGCAATGCAAATGCA | 639 |
| 20 | IDO1_NM_002164_human_1398 | CAGAGCCACAAACTAATACT | 620 | CATTACCCATTGTAACAGAGCCAC AAACTAATACTATGCAATGTT | 640 |

Accession: NM_001558
HUGO gene symbol: IL10RA

| Oligo_count | Oligo_ID | targeting sequence | SEQ ID NO: | Gene_region | SEQ ID NO: |
|---|---|---|---|---|---|
| 1 | IL10RA_NM_001558_human_3364 | TTGTTCATTTATTTATTGGA | 641 | CTTTATTTATTTATTTTGTTCATTT ATTTATTGGAGAGGCAGCAT | 661 |

TABLE 1-continued

Targeting sequences and gene regions of genes targeted with sdRNAs to prevent immunosuppression of antigen-presenting cells and T-cells.

| | | | SEQ ID NO: | | SEQ ID NO: |
|---|---|---|---|---|---|
| 2 | IL10RA_NM_001558_human_3626 | TTATTCCAATAAATTGTCAA | 642 | AGTGATACATGTTTTTATTCCAA TAAATTGTCAAGACCACAGGA | 662 |
| 3 | IL10RA_NM_001558_human_2395 | TATTTTCTGGACACTCAAAC | 643 | AGATCTTAAGGTATATATTTTCTG GACACTCAAACACATCATAAT | 663 |
| 4 | IL10RA_NM_001558_human_3375 | TTTATTGGAGAGGCAGCATT | 644 | TATTTGTTCATTTATTTATTGGAG AGGCAGCATTGCACAGTGAA | 664 |
| 5 | IL10RA_NM_001558_human_3469 | ACCTTGGAGAAGTCACTTAT | 645 | GTTTCCAGTGGTATGACCTTGGA GAAGTCACTTATCCTCTTGGAG | 665 |
| 6 | IL10RA_NM_001558_human_3351 | TTATTTATTTATTTTGTTCA | 646 | GTTCCCTTGAAAGCTTTATTTATTT ATTTTGTTCATTTATTTATT | 666 |
| 7 | IL10RA_NM_001558_human_2108 | CTCTTTCCTGTATCATAAAG | 647 | TCTCCCTCCTAGGAACTCTTTCCT GTATCATAAAGGATTATTTGC | 667 |
| 8 | IL10RA_NM_001558_human_3563 | CTGAGGAAATGGGTATGAAT | 648 | GGATGTGAGGTTCTGCTGAGGAA ATGGGTATGAATGTGCCTTGAA | 668 |
| 9 | IL10RA_NM_001558_human_3579 | GAATGTGCCTTGAACACAAA | 649 | TGAGGAAATGGGTATGAATGTGC CTTGAACACAAAGCTCTGTCAA | 669 |
| 10 | IL10RA_NM_001558_human_2403 | GGACACTCAAACACATCATA | 650 | AGGTATATATTTTCTGGACACTCA AACACATCATAATGGATTCAC | 670 |
| 11 | IL10RA_NM_001558_human_2115 | CTGTATCATAAAGGATTATT | 651 | CCTAGGAACTCTTTCCTGTATCAT AAAGGATTATTTGCTCAGGGG | 671 |
| 12 | IL10RA_NM_001558_human_563 | TCACTTCCGAGAGTATGAGA | 652 | TGAAAGCATCTTCAGTCACTTCCG AGAGTATGAGATTGCCATTCG | 672 |
| 13 | IL10RA_NM_001558_human_3197 | TCTCTGGAGCATTCTGAAAA | 653 | TCTCAGCCCTGCCTTTCTCTGGAG CATTCTGAAAACAGATATTCT | 673 |
| 14 | IL10RA_NM_001558_human_2987 | TTATGCCAGAGGCTAACAGA | 654 | AAGCTGGCTTGTTTCTTATGCCAG AGGCTAACAGATCCAATGGGA | 674 |
| 15 | IL10RA_NM_001558_human_1278 | AGTGGCATTGACTTAGTTCA | 655 | AGGGGCCAGGATGACAGTGGCA TTGACTTAGTTCAAAACTCTGAG | 675 |
| 16 | IL10RA_NM_001558_human_2398 | TTTCTGGACACTCAAACACA | 656 | TCTTAAGGTATATATTTTCTGGAC ACTCAAACACATCATAATGGA | 676 |
| 17 | IL10RA_NM_001558_human_3390 | GCATTGCACAGTGAAAGAAT | 657 | TTTATTGGAGAGGCAGCATTGCA CAGTGAAAGAATTCTGGATATC | 677 |
| 18 | IL10RA_NM_001558_human_3468 | GACCTTGGAGAAGTCACTTA | 658 | TGTTTCCAGTGGTATGACCTTGGA GAAGTCACTTATCCTCTTGGA | 678 |
| 19 | IL10RA_NM_001558_human_610 | TCACGTTCACACACAAGAAA | 659 | AGGTGCCGGGAAACTTCACGTTC ACACACAAGAAAGTAAAACATG | 679 |
| 20 | IL10RA_NM_001558_human_3446 | ACTTTGCTGTTTCCAGTGGT | 660 | GAAATTCTAGCTCTGACTTTGCTG TTTCCAGTGGTATGACCTTGG | 680 |

Accession: NM_000214
HUGO gene symbol: JAG1

| Oligo_count | Oligo_ID | targeting sequence | SEQ ID NO: | Gene_region | SEQ ID NO: |
|---|---|---|---|---|---|
| 1 | JAG1_NM_000214_human_4799 | TATTTGATTTATTAACTTAA | 681 | ATTAATCACTGTGTATATTTGATTT ATTAACTTAATAATCAAGAG | 701 |
| 2 | JAG1_NM_000214_human_5658 | GAAAGTAATATTTATTAAA | 682 | TTGGCAATAAATTTTGAAAAGTAA TATTTATTAAATTTTTTTGTA | 702 |
| 3 | JAG1_NM_000214_human_4752 | ACTTTGTATAGTTATGTAAA | 683 | AATGTCAAAAGTAGAACTTTGTAT AGTTATGTAAATAATTCTTTT | 703 |
| 4 | JAG1_NM_000214_human_5418 | GAATACTTGAACCATAAAAT | 684 | TCTAATAAGCTAGTTGAATACTTGA ACCATAAAATGTCCAGTAAG | 704 |

TABLE 1-continued

Targeting sequences and gene regions of genes targeted with sdRNAs to prevent immunosuppression of antigen-presenting cells and T-cells.

| | | | SEQ ID NO: | | SEQ ID NO: |
|---|---|---|---|---|---|
| 5 | JAG1_NM_000214_human_5641 | TCTTGGCAATAAATTTTGAA | 685 | TCTTTGATGTGTTGTTCTTGGCAATAAATTTTGAAAAGTAATATT | 705 |
| 6 | JAG1_NM_000214_human_5150 | TTTCTGCTTTAGACTTGAAA | 686 | TGTTTGTTTTTGTTTTTCTGCTTTAGACTTGAAAAGAGACAGGC | 706 |
| 7 | JAG1_NM_000214_human_4526 | TATATTTATTGACTCTTGAG | 687 | GATCATAGTTTTATTTATATTTATTGACTCTTGAGTTGTTTTTGT | 707 |
| 8 | JAG1_NM_000214_human_4566 | TATGATGACGTACAAGTAGT | 688 | TTTGTATATTGGTTTTATGATGACGTACAAGTAGTTCTGTATTTG | 708 |
| 9 | JAG1_NM_000214_human_5634 | GTGTTGTTCTTGGCAATAAA | 689 | AAATGCATCTTTGATGTGTTGTTCTTGGCAATAAATTTTGAAAAG | 709 |
| 10 | JAG1_NM_000214_human_173 | CTGATCTAAAAGGGAATAAA | 690 | CCTTTTTCCATGCAGCTGATCTAAAAGGGAATAAAAGGCTGCGCA | 710 |
| 11 | JAG1_NM_000214_human_5031 | TACGACGTCAGATGTTTAAA | 691 | GATGGAATTTTTTGTACGACGTCAGATGTTTAAAACACCTTCTA | 711 |
| 12 | JAG1_NM_000214_human_4817 | AATAATCAAGAGCCTTAAAA | 692 | TTGATTTATTAACTTAATAATCAAGAGCCTTAAAACATCATTCCT | 712 |
| 13 | JAG1_NM_000214_human_5685 | GTATGAAAACATGGAACAGT | 693 | TTATTAAATTTTTTTGTATGAAAACATGGAACAGTGTGGCCTCTT | 713 |
| 14 | JAG1_NM_000214_human_4560 | TGGTTTTATGATGACGTACA | 694 | GTTGTTTTTGTATATTGGTTTTATGATGACGTACAAGTAGTTCTG | 714 |
| 15 | JAG1_NM_000214_human_5151 | TTCTGCTTTAGACTTGAAAA | 695 | GTTTGTTTTTGTTTTTCTGCTTTAGACTTGAAAAGAGACAGGCA | 715 |
| 16 | JAG1_NM_000214_human_5642 | CTTGGCAATAAATTTTGAAA | 696 | CTTTGATGTGTTGTTCTTGGCAATAAATTTTGAAAAGTAATATTT | 716 |
| 17 | JAG1_NM_000214_human_5377 | TTTAATCTACTGCATTTAGG | 697 | GATTTGATTTTTTTTTAATCTACTGCATTTAGGGAGTATTCTA | 717 |
| 18 | JAG1_NM_000214_human_4756 | TGTATAGTTATGTAAATAAT | 698 | TCAAAAGTAGAACTTTGTATAGTTATGTAAATAATTCTTTTTAT | 718 |
| 19 | JAG1_NM_000214_human_4523 | ATTTATATTTATTGACTCTT | 699 | TTAGATCATAGTTTTATTTATATTTATTGACTCTTGAGTTGTTTT | 719 |
| 20 | JAG1_NM_000214_human_5325 | CTTTTCACCATTCGTACATA | 700 | TGTAAATTCTGATTTCTTTTCACCATTCGTACATAATACTGAACC | 720 |

Accession: NM_002226
HUGO gene symbol: JAG2

| Oligo_count | Oligo_ID | targeting sequence | SEQ ID NO: | Gene_region | SEQ ID NO: |
|---|---|---|---|---|---|
| 1 | JAG2_NM_002226_human_4266 | CGTTTCTTTAACCTTGTATA | 721 | AATGTTTATTTCTACGTTTCTTTAACCTTGTATAAATTATTCAG | 741 |
| 2 | JAG2_NM_002226_human_5800 | TAAATGAATGAACGAATAAA | 722 | GGCAGAACAAATGAATAAATGAATGAACGAATAAAAATTTGACC | 742 |
| 3 | JAG2_NM_002226_human_5450 | TCATTCATTTATTCCTTTGT | 723 | GGTCAAAATTTTTATTCATTCATTTATTCCTTTGTTTTGCTTGGT | 743 |
| 4 | JAG2_NM_002226_human_5021 | GTAAATGTGTACATATTAAA | 724 | TGAAAGTGCATTTTTGTAAATGTGTACATATTAAAGGAAGCACTC | 744 |
| 5 | JAG2_NM_002226_human_5398 | ACCCACGAATACGTATCAAG | 725 | AGTATAAAATTGCTTACCCACGAATACGTATCAAGGTCTTAAGGA | 745 |
| 6 | JAG2_NM_002226_human_5371 | GTTTTATAAAATAGTATAAA | 726 | AAACAGCTGAAAACAGTTTTATAAAATAGTATAAAATTGCTTACC | 746 |
| 7 | JAG2_NM_002226_human_5691 | CAACTGAGTCAAGGAGCAAA | 727 | TGAGGGGTAGGAGGTCAACTGAGTCAAGGAGCAAAGCCAAGAACC | 747 |

TABLE 1-continued

Targeting sequences and gene regions of genes targeted with sdRNAs to prevent immunosuppression of antigen-presenting cells and T-cells.

| | | | | | |
|---|---|---|---|---|---|
| 8 | JAG2_NM_002226_human_5025 | ATGTGTACATATTAAAGGAA | 728 | AGTGCATTTTTGTAAATGTGTACAT ATTAAAGGAAGCACTCTGTA | 748 |
| 9 | JAG2_NM_002226_human_4269 | TTCTTTAACCTTGTATAAAT | 729 | GTTTATTTTCTACGTTTCTTTAACCT TGTATAAATTATTCAGTAA | 749 |
| 10 | JAG2_NM_002226_human_4258 | ATTTTCTACGTTTCTTTAAC | 730 | AAAAACCAAATGTTTATTTTCTACG TTTCTTTAACCTTGTATAAA | 750 |
| 11 | JAG2_NM_002226_human_5369 | CAGTTTTATAAAATAGTATA | 731 | TAAAACAGCTGAAAACAGTTTTAT AAAATAGTATAAAATTGCTTA | 751 |
| 12 | JAG2_NM_002226_human_5780 | GCACAGGCAGAACAAATGAA | 732 | GAGTGAGGCTGCCTTGCACAGGCA GAACAAATGAATAAATGAATG | 752 |
| 13 | JAG2_NM_002226_human_4302 | TCAGGCTGAAAACAATGGAG | 733 | ATTATTCAGTAACTGTCAGGCTGA AAACAATGGAGTATTCTCGGA | 753 |
| 14 | JAG2_NM_002226_human_5387 | TAAAATTGCTTACCCACGAA | 734 | TTTTATAAAATAGTATAAAATTGCT TACCCACGAATACGTATCAA | 754 |
| 15 | JAG2_NM_002226_human_4301 | GTCAGGCTGAAAACAATGGA | 735 | AATTATTCAGTAACTGTCAGGCTG AAAACAATGGAGTATTCTCGG | 755 |
| 16 | JAG2_NM_002226_human_5023 | AAATGTGTACATATTAAAGG | 736 | AAAGTGCATTTTTGTAAATGTGTAC ATATTAAAGGAAGCACTCTG | 756 |
| 17 | JAG2_NM_002226_human_4293 | CAGTAACTGTCAGGCTGAAA | 737 | CTTGTATAAATTATTCAGTAACTGT CAGGCTGAAAACAATGGAGT | 757 |
| 18 | JAG2_NM_002226_human_4321 | GTATTCTCGGATAGTTGCTA | 738 | GCTGAAAACAATGGAGTATTCTCG GATAGTTGCTATTTTTGTAAA | 758 |
| 19 | JAG2_NM_002226_human_3994 | TCTCACACAAATTCACCAAA | 739 | AGGCGGAGAAGTTCCTCTCACACA AATTCACCAAAGATCCTGGCC | 759 |
| 20 | JAG2_NM_002226_human_5466 | TTGTTTTGCTTGGTCATTCA | 740 | CATTCATTTATTCCTTTGTTTTGCTT GGTCATTCAGAGGCAAGGT | 760 |

Accession: NM_001315
HUGO gene symbol: MAPK14

| Oligo_count | Oligo_ID | targeting sequence | SEQ ID NO: | Gene_region | SEQ ID NO: |
|---|---|---|---|---|---|
| 1 | MAPK14_NM_001315_human_670 | TCATGCGAAAAGAACCTACA | 761 | ATTTCAGTCCATCATTCATGCGAAAA GAACCTACAGAGAACTGCG | 781 |
| 2 | MAPK14_NM_001315_human_833 | AAATGTCAGAAGCTTACAGA | 762 | CTGAACAACATTGTGAAATGTCAGA AGCTTACAGATGACCATGTT | 782 |
| 3 | MAPK14_NM_001315_human_707 | AAACATATGAAACATGAAAA | 763 | GAACTGCGGTTACTTAAACATATGA AACATGAAAATGTGATTGGT | 783 |
| 4 | MAPK14_NM_001315_human_863 | CAGTTCCTTATCTACCAAAT | 764 | ACAGATGACCATGTTCAGTTCCTTAT CTACCAAATTCTCCGAGGT | 784 |
| 5 | MAPK14_NM_001315_human_1150 | TCCTGGTACAGACCATATTA | 765 | TGGAAGAACATTGTTTCCTGGTACA GACCATATTAACCAGCTTCA | 785 |
| 6 | MAPK14_NM_001315_human_866 | TTCCTTATCTACCAAATTCT | 766 | GATGACCATGTTCAGTTCCTTATCTA CCAAATTCTCCGAGGTCTA | 786 |
| 7 | MAPK14_NM_001315_human_1149 | TTCCTGGTACAGACCATATT | 767 | CTGGAAGAACATTGTTTCCTGGTAC AGACCATATTAACCAGCTTC | 787 |
| 8 | MAPK14_NM_001315_human_896 | AAGTATATACATTCAGCTGA | 768 | ATTCTCCGAGGTCTAAAGTATATAC ATTCAGCTGACATAATTCAC | 788 |
| 9 | MAPK14_NM_001315_human_1076 | CATTACAACCAGACAGTTGA | 769 | ATGCTGAACTGGATGCATTACAACC AGACAGTTGATATTTGGTCA | 789 |
| 10 | MAPK14_NM_001315_human_926 | AGGGACCTAAAACCTAGTAA | 770 | GCTGACATAATTCACAGGGACCTAA AACCTAGTAATCTAGCTGTG | 790 |

TABLE 1-continued

Targeting sequences and gene regions of genes targeted with sdRNAs to prevent immunosuppression of antigen-presenting cells and T-cells.

| | | | SEQ ID NO: | | SEQ ID NO: |
|---|---|---|---|---|---|
| 11 | MAPK14_NM_001315_human_765 | CTCTGGAGGAATTCAATGAT | 771 | TTACACCTGCAAGGTCTCTGGAGGA ATTCAATGATGTGTATCTGG | 791 |
| 12 | MAPK14_NM_001315_human_706 | TAAACATATGAAACATGAAA | 772 | AGAACTGCGGTTACTTAAACATATG AAACATGAAAATGTGATTGG | 792 |
| 13 | MAPK14_NM_001315_human_815 | GATCTGAACAACATTGTGAA | 773 | CATCTCATGGGGCAGATCTGAACA ACATTGTGAAATGTCAGAAG | 793 |
| 14 | MAPK14_NM_001315_human_862 | TCAGTTCCTTATCTACCAAA | 774 | TACAGATGACCATGTTCAGTTCCTTA TCTACCAAATTCTCCGAGG | 794 |
| 15 | MAPK14_NM_001315_human_917 | ATAATTCACAGGGACCTAAA | 775 | ATACATTCAGCTGACATAATTCACA GGGACCTAAAACCTAGTAAT | 795 |
| 16 | MAPK14_NM_001315_human_887 | CGAGGTCTAAAGTATATACA | 776 | ATCTACCAAATTCTCCGAGGTCTAA AGTATATACATTCAGCTGAC | 796 |
| 17 | MAPK14_NM_001315_human_832 | GAAATGTCAGAAGCTTACAG | 777 | TCTGAACAACATTGTGAAATGTCAG AAGCTTACAGATGACCATGT | 797 |
| 18 | MAPK14_NM_001315_human_1125 | AGCTGTTGACTGGAAGAACA | 778 | GATGCATAATGGCCGAGCTGTTGAC TGGAAGAACATTGTTTCCTG | 798 |
| 19 | MAPK14_NM_001315_human_879 | AAATTCTCCGAGGTCTAAAG | 779 | AGTTCCTTATCTACCAAATTCTCCGA GGTCTAAAGTATATACATT | 799 |
| 20 | MAPK14_NM_001315_human_725 | AATGTGATTGGTCTGTTGGA | 780 | CATATGAAACATGAAAATGTGATTG GTCTGTTGGACGTTTTTACA | 800 |

Accession: NM_003745
HUGO gene symbol: SOCS1

| Oligo_count | Oligo_ID | targeting sequence | SEQ ID NO: | Gene_region | SEQ ID NO: |
|---|---|---|---|---|---|
| 1 | SOCS1_NM_003745_human_1141 | CTGCTGTGCAGAATCCTATT | 801 | TCTGGCTTTATTTTCTGCTGTGCA GAATCCTATTTTATATTTTT | 821 |
| 2 | SOCS1_NM_003745_human_1143 | GCTGTGCAGAATCCTATTTT | 802 | TGGCTTTATTTTCTGCTGTGCAGA ATCCTATTTTATATTTTTTA | 822 |
| 3 | SOCS1_NM_003745_human_1170 | TTAAAGTCAGTTTAGGTAAT | 803 | CCTATTTTATATTTTTAAAGTCAG TTTAGGTAATAAACTTTATT | 823 |
| 4 | SOCS1_NM_003745_human_1144 | CTGTGCAGAATCCTATTTTA | 804 | GGCTTTATTTTCTGCTGTGCAGAA TCCTATTTTATATTTTTTAA | 824 |
| 5 | SOCS1_NM_003745_human_1076 | GTTTACATATACCCAGTATC | 805 | CTCCTACCTCTTCATGTTTACATAT ACCCAGTATCTTTGCACAAA | 825 |
| 6 | SOCS1_NM_003745_human_837 | ATTTGTTATTACTTGCCTG | 806 | CTGGGATGCCGTGTTATTTTGTTA TTACTTGCCTGGAACCATGTG | 826 |
| 7 | SOCS1_NM_003745_human_819 | TAACTGGGATGCCGTGTTAT | 807 | CCGTGCACGCAGCATTAACTGGGATG CCGTGTTATTTTGTTATTA | 827 |
| 8 | SOCS1_NM_003745_human_841 | TGTTATTACTTGCCTGGAAC | 808 | GATGCCGTGTTATTTTGTTATTACT TGCCTGGAACCATGTGGGTA | 828 |
| 9 | SOCS1_NM_003745_human_1138 | TTTCTGCTGTGCAGAATCCT | 809 | GTCTCTGGCTTTATTTTCTGCTGT GCAGAATCCTATTTTATATT | 829 |
| 10 | SOCS1_NM_003745_human_831 | CGTGTTATTTTGTTATTACT | 810 | CATTAACTGGGATGCCGTGTTATTTTG TTATTACTTGCCTGGAAC | 830 |
| 11 | SOCS1_NM_003745_human_1168 | TTTTAAAGTCAGTTTAGGTA | 811 | ATCCTATTTTATATTTTTAAAGTC AGTTTAGGTAATAAACTTTA | 831 |
| 12 | SOCS1_NM_003745_human_1142 | TGCTGTGCAGAATCCTATTT | 812 | CTGGCTTTATTTTCTGCTGTGCAG AATCCTATTTTATATTTTTT | 832 |
| 13 | SOCS1_NM_003745_human_825 | GGATGCCGTGTTATTTTGTT | 813 | ACGCAGCATTAACTGGGATGCCGTGTT ATTTTGTTATTACTTGCC | 833 |

TABLE 1-continued

Targeting sequences and gene regions of genes targeted with sdRNAs to prevent immunosuppression of antigen-presenting cells and T-cells.

| Oligo_count | Oligo_ID | targeting sequence | SEQ ID NO: | Gene_region | SEQ ID NO: |
|---|---|---|---|---|---|
| 14 | SOCS1_NM_003745_human_1169 | TTTAAAGTCAGTTTAGGTAA | 814 | TCCTATTTTATATTTTTAAAGTCAGTTTAGGTAATAAACTTTAT | 834 |
| 15 | SOCS1_NM_003745_human_1171 | TAAAGTCAGTTTAGGTAATA | 815 | CTATTTTATATTTTTAAAGTCAGTTTAGGTAATAAACTTTATTA | 835 |
| 16 | SOCS1_NM_003745_human_1140 | TCTGCTGTGCAGAATCCTAT | 816 | CTCTGGCTTTATTTTCTGCTGTGCAGAATCCTATTTTATATTTT | 836 |
| 17 | SOCS1_NM_003745_human_1082 | ATATACCCAGTATCTTTGCA | 817 | CCTCTTCATGTTTACATATACCCAGTATCTTTGCACAAACCAGGG | 837 |
| 18 | SOCS1_NM_003745_human_1150 | AGAATCCTATTTTATATTTT | 818 | ATTTTTCTGCTGTGCAGAATCCTATTTTATATTTTTAAAGTCAG | 838 |
| 19 | SOCS1_NM_003745_human_1011 | GGTTGTTGTAGCAGCTTAAC | 819 | CCTCTGGGTCCCCCTGGTTGTTGTAGCAGCTTAACTGTATCTGGA | 839 |
| 20 | SOCS1_NM_003745_human_1087 | CCCAGTATCTTTGCACAAAC | 820 | TCATGTTTACATATACCCAGTATCTTTGCACAAACCAGGGGTTGG | 840 |

Accession: NM_003150
HUGO gene symbol: STAT3

| Oligo_count | Oligo_ID | targeting sequence | SEQ ID NO: | Gene_region | SEQ ID NO: |
|---|---|---|---|---|---|
| 1 | STAT3_NM_003150_human_4897 | ATATTGCTGTATCTACTTTA | 841 | TTTTTTTTTTTGGTATATTGCTGTATCTACTTTAACTTCCAGAA | 861 |
| 2 | STAT3_NM_003150_human_4325 | TGTTTGTTAAATCAAATTAG | 842 | GTTTCTGTGGAATTCTGTTTGTTAAATCAAATTAGCTGGTCTCTG | 862 |
| 3 | STAT3_NM_003150_human_2730 | TTTATCTAAATGCAAATAAG | 843 | TGTGGGTGATCTGCTTTTATCTAAATGCAAATAAGGATGTGTTCT | 863 |
| 4 | STAT3_NM_003150_human_3615 | ATTTTCCTTTGTAATGTATT | 844 | TTTATAAATAGACTTATTTTCCTTTGTAATGTATTGGCCTTTTAG | 864 |
| 5 | STAT3_NM_003150_human_453 | TATCAGCACAATCTACGAAG | 845 | GAGTCGAATGTTCTCTATCAGCACAATCTACGAAGAATCAAGCAG | 865 |
| 6 | STAT3_NM_003150_human_4477 | AGCTTAACTGATAAACAGAA | 846 | CTTCAGTACATAATAAGCTTAACTGATAAACAGAATATTTAGAAA | 866 |
| 7 | STAT3_NM_003150_human_2870 | GTTGTTGTTGTTCTTAGACA | 847 | CAGCTTTTGTTATTGTTGTTGTTGTTCTTAGACAAGTGCCTCCT | 867 |
| 8 | STAT3_NM_003150_human_2873 | GTTGTTGTTCTTAGACAAGT | 848 | CTTTTTGTTATTGTTGTTGTTGTTCTTAGACAAGTGCCTCCTGGT | 868 |
| 9 | STAT3_NM_003150_human_3096 | TCTGTATTTAAGAAACTTAA | 849 | TATCAGCATAGCCTTTCTGTATTTAAGAAACTTAAGCAGCCGGGC | 869 |
| 10 | STAT3_NM_003150_human_3613 | TTATTTTCCTTTGTAATGTA | 850 | TTTTTATAAATAGACTTATTTTCCTTTGTAATGTATTGGCTTTT | 870 |
| 11 | STAT3_NM_003150_human_4481 | TAACTGATAAACAGAATATT | 851 | AGTACATAATAAGCTTAACTGATAAACAGAATATTTAGAAAGGTG | 871 |
| 12 | STAT3_NM_003150_human_1372 | ACATTCTGGGCACAAACACA | 852 | GATCCCGGAAATTTAACATTCTGGGCACAAACACAAAAGTGATGA | 872 |
| 13 | STAT3_NM_003150_human_2720 | GTGATCTGCTTTTATCTAAA | 853 | AATGAGTGAATGTGGGTGATCTGCTTTTATCTAAATGCAAATAAG | 873 |
| 14 | STAT3_NM_003150_human_1044 | CAGACCCGTCAACAAATTAA | 854 | GCAGAATCTCAACTTCAGACCCGTCAACAAATTAAGAAACTGGAG | 874 |
| 15 | STAT3_NM_003150_human_1148 | GGAGCTGTTTAGAAACTTAA | 855 | GGAGGAGAGAATCGTGGAGCTGTTTAGAAACTTAATGAAAAGTGC | 875 |
| 16 | STAT3_NM_003150_human_4523 | ACCATTGGGTTTAAATCATA | 856 | GTGAGACTTGGGCTTACCATTGGGTTTAAATCATAGGGACCTAGG | 876 |

TABLE 1-continued

Targeting sequences and gene regions of genes targeted with sdRNAs to prevent immunosuppression of antigen-presenting cells and T-cells.

| | | | SEQ ID NO: | | SEQ ID NO: |
|---|---|---|---|---|---|
| 17 | STAT3_NM_003150_human_3573 | GGAGAATCTAAGCATTTTAG | 857 | AATAGGAAGGTTTAAGGAGAATC TAAGCATTTTAGACTTTTTTTT | 877 |
| 18 | STAT3_NM_003150_human_2987 | CCTTGCTGACATCCAAATAG | 858 | CATTGCACTTTTTAACCTTGCTGA CATCCAAATAGAAGATAGGAC | 878 |
| 19 | STAT3_NM_003150_human_3041 | AAATTAAGAAATAATAACAA | 859 | CCTAGGTTTCTTTTTAAATTAAGA AATAATAACAATTAAAGGGCA | 879 |
| 20 | STAT3_NM_003150_human_3037 | TTTTAAATTAAGAAATAATA | 860 | AAGCCCTAGGTTTCTTTTTAAATT AAGAAATAATAACAATTAAAG | 880 |

Accession: NM_006290
HUGO gene symbol: TNFAIP3

| Oligo_count | Oligo_ID | targeting sequence | SEQ ID NO: | Gene_region | SEQ ID NO: |
|---|---|---|---|---|---|
| 1 | TNFAIP3_NM_006290_human_3451 | AGCTTGAACTGAGGAGTAAA | 881 | ACTTCTAAAGAAGTTAGCTTGAAC TGAGGAGTAAAAGTGTGTACA | 901 |
| 2 | TNFAIP3_NM_006290_human_916 | CCTTTGCAACATCCTCAGAA | 882 | AATACACATATTTGTCCTTTGCAA CATCCTCAGAAGGCCAATCAT | 902 |
| 3 | TNFAIP3_NM_006290_human_4422 | TTCTTTCCAAAGATACCAAA | 883 | ACGAATCTTTATAATTTCTTCCAA AGATACCAAATAAACTTCAG | 903 |
| 4 | TNFAIP3_NM_006290_human_3688 | TTATTTTATTACAAACTTCA | 884 | TGTAATTCACTTTATTTATTTTATT ACAAACTTCAAGATTATTTA | 904 |
| 5 | TNFAIP3_NM_006290_human_4536 | TATTTATACTTATTATAAAA | 885 | GTGAAAAAAGTAATTATTTATAC TTATTATAAAAAGTATTTGAA | 905 |
| 6 | TNFAIP3_NM_006290_human_949 | CATTTCAGACAAAATGCTAA | 886 | AAGGCCAATCATTGTCATTTCAGA CAAAATGCTAAGAAGTTTGGA | 906 |
| 7 | TNFAIP3_NM_006290_human_1214 | ATGAAGGAGAAGCTCTTAAA | 887 | GATCCTGAAAATGAGATGAAGGA GAAGCTCTTAAAAGAGTACTTA | 907 |
| 8 | TNFAIP3_NM_006290_human_4489 | ATTTTGTGTTGATCATTATT | 888 | AGTTGATATCTTAATATTTTGTGT TGATCATTATTTCCATTCTTA | 908 |
| 9 | TNFAIP3_NM_006290_human_2204 | TTCATCGAGTACAGAGAAAA | 889 | TTTTGCACACTGTGTTTCATCGAG TACAGAGAAAACAAACATTTT | 909 |
| 10 | TNFAIP3_NM_006290_human_3394 | TTACTGGGAAGACGTGTAAC | 890 | AAAAATTAGAATATTTTACTGGGA AGACGTGTAACTCTTTGGGTT | 910 |
| 11 | TNFAIP3_NM_006290_human_2355 | TCATTGAAGCTCAGAATCAG | 891 | ACTGCCAGAAGTGTTTCATTGAA GCTCAGAATCAGAGATTTCATG | 911 |
| 12 | TNFAIP3_NM_006290_human_4508 | TTCCATTCTTAATGTGAAAA | 892 | TGTGTTGATCATTATTTCCATTCTT AATGTGAAAAAAGTAATTA | 912 |
| 13 | TNFAIP3_NM_006290_human_2332 | TGAAGGATACTGCCAGAAGT | 893 | TGGAAGCACCATGTTTGAAGGAT ACTGCCAGAAGTGTTTCATTGA | 913 |
| 14 | TNFAIP3_NM_006290_human_4650 | CACAAGAGTCAACATTAAAA | 894 | ATAAATGTAACTTTTCACAAGAGT CAACATTAAAAAATAAATTAT | 914 |
| 15 | TNFAIP3_NM_006290_human_4533 | AATTATTTATACTTATTATA | 895 | AATGTGAAAAAAGTAATTATTTA TACTTATTATAAAAAGTATTT | 915 |
| 16 | TNFAIP3_NM_006290_human_3907 | TTCGTGCTTCTCCTTATGAA | 896 | CATATTCATCGATGTTTCGTGCTT CTCCTTATGAAACTCCAGCTA | 916 |
| 17 | TNFAIP3_NM_006290_human_3689 | TATTTTATTACAAACTTCAA | 897 | GTAATTCACTTTATTTATTTTATTA CAAACTTCAAGATTATTTAA | 917 |
| 18 | TNFAIP3_NM_006290_human_3694 | TATTACAAACTTCAAGATTA | 898 | TCACTTTATTTATTTTATTACAAAC TTCAAGATTATTTAAGTGAA | 918 |
| 19 | TNFAIP3_NM_006290_human_4467 | CTCTTAAAGTTGATATCTTA | 899 | TGTTTTCATCTAATTCTCTTAAAGT TGATATCTTAATATTTTGTG | 919 |

TABLE 1-continued

Targeting sequences and gene regions of genes targeted with sdRNAs to prevent immunosuppression of antigen-presenting cells and T-cells.

| | | | SEQ ID NO: | | SEQ ID NO: |
|---|---|---|---|---|---|
| 20 | TNFAIP3_NM_006290_human_4426 | TTCCAAAGATACCAAATAAA | 900 | ATCTTTATAATTTCTTTCCAAAGAT ACCAAATAAACTTCAGTGTT | 920 |

Accession: NM_003326
HUGO gene symbol: TNFSF4

| Oligo_count | Oligo_ID | targeting sequence | SEQ ID NO: | Gene_region | SEQ ID NO: |
|---|---|---|---|---|---|
| 1 | TNFSF4_NM_003326_human_2984 | AATTTGACTTAGCCACTAAC | 921 | GAGATCAGAATTTTAAATTTGACT TAGCCACTAACTAGCCATGTA | 941 |
| 2 | TNFSF4_NM_003326__human_3422 | GATATTAATAATATAGTTAA | 922 | GAGAGTATTAATATTGATATTAAT AATATAGTTAATAGTAATATT | 942 |
| 3 | TNFSF4_NM_003326_human_3119 | CTGTGAATGCACATATTAAA | 923 | TGCTTACAGTGTTATCTGTGAATG CACATATTAAATGTCTATGTT | 943 |
| 4 | TNFSF4_NM_003326_human_2208 | GTTTTCTATTTCCTCTTAAG | 924 | GGATTTTTTTTCCTGTTTTCTATT TCCTCTTAAGTACACCTTCA | 944 |
| 5 | TNFSF4_NM_003326_human_1727 | AAATAGCACTAAGAAGTTAT | 925 | ATTCAATCTGATGTCAAATAGCAC TAAGAAGTTATTGTGCCTTAT | 945 |
| 6 | TNFSF4_NM_003326_human_3311 | CCAATCCCGATCCAAATCAT | 926 | AATGCTTAAGGGATTCCAATCCC GATCCAAATCATAATTTGTTCT | 946 |
| 7 | TNFSF4_NM_003326_human_3286 | CTATTTAGAGAATGCTTAAG | 927 | TTAGTTAGATATTTTCTATTTAGA GAATGCTTAAGGGATTCCAAT | 947 |
| 8 | TNFSF4_NM_003326_human_1222 | CAGTTTGCATATTGCCTAAA | 928 | AGGTTAAATTGATTGCAGTTTGCA TATTGCCTAAATTTAAACTTT | 948 |
| 9 | TNFSF4_NM_003326_human_326 | CTCGAATTCAAAGTATCAAA | 929 | TATCACATCGGTATCCTCGAATTC AAAGTATCAAAGTACAATTTA | 949 |
| 10 | TNFSF4_NM_003326_human_3117 | ATCTGTGAATGCACATATTA | 930 | TATGCTTACAGTGTTATCTGTGAA TGCACATATTAAATGTCTATG | 950 |
| 11 | TNFSF4_NM_003326_human_2938 | TTTGTGGGAAAAGAATTGAA | 931 | TATACATGGCAGAGTTTTGTGGG AAAAGAATTGAATGAAAAGTCA | 951 |
| 12 | TNFSF4_NM_003326_human_2537 | ATTGACCATGTTCTGCAAAA | 932 | ATTTCACTTTTTGTTATTGACCATG TTCTGCAAAATTGCAGTTAC | 952 |
| 13 | TNFSF4_NM_003326_human_776 | GATTCTTCATTGCAAGTGAA | 933 | GGTGGACAGGGCATGGATTCTTC ATTGCAAGTGAAGGAGCCTCCC | 953 |
| 14 | TNFSF4_NM_003326_human_1721 | GATGTCAAATAGCACTAAGA | 934 | TATCAAATTCAATCTGATGTCAAA TAGCACTAAGAAGTTATTGTG | 954 |
| 15 | TNFSF4_NM_003326_human_1459 | GTATACAGGGAGAGTGAGAT | 935 | AAGAGAGATTTTCTTGTATACAG GGAGAGTGAGATAACTTATTGT | 955 |
| 16 | TNFSF4_NM_003326_human_3152 | GTTGCTATGAGTCAAGGAGT | 936 | AATGTCTATGTTCTTGTTGCTATG AGTCAAGGAGTGTAACCTTCT | 956 |
| 17 | TNFSF4_NM_003326_human_1882 | TAGTTGAAATGTCCCCTTAA | 937 | GTATCCCCTTATGTTTAGTTGAAA TGTCCCCTTAACTTGATATAA | 957 |
| 18 | TNFSF4_NM_003326_human_1980 | CTCTGTGCCAAACCTTTTAT | 938 | GATGATTTGTAACTTCTCTGTGCC AAACCTTTTATAAACATAAAT | 958 |
| 19 | TNFSF4_NM_003326_human_1770 | CTCTGTCTAGAAATACCATA | 939 | ATGAAAAATAATGATCTCTGTCTA GAAATACCATAGACCATATAT | 959 |
| 20 | TNFSF4_NM_003326_human_1680 | GGTTTCAAGAAATGAGGTGA | 940 | CACAGAAACATTGCTGGTTTCAA GAAATGAGGTGATCCTATTATC | 960 |

TABLE 1-continued

Targeting sequences and gene regions of genes targeted with sdRNAs to prevent immunosuppression of antigen-presenting cells and T-cells.

Accession: NM_006293
HUGO gene symbol: TYRO3

| Oligo_count | Oligo_ID | targeting sequence | SEQ ID NO: | Gene_region | SEQ ID NO: |
|---|---|---|---|---|---|
| 1 | TYRO3_NM_006293_human_3927 | AGTTGCTGTTTAAAATAGAA | 961 | CATTTCCAAGCTGTTAGTTGCTGTT TAAAATAGAAATAAAATTGA | 981 |
| 2 | TYRO3_NM_006293_human_3932 | CTGTTTAAAATAGAAATAAA | 962 | CCAAGCTGTTAGTTGCTGTTTAAAA TAGAAATAAAATTGAAGACT | 982 |
| 3 | TYRO3_NM_006293_human_1731 | GGCATCAGCGATGAACTAAA | 963 | ACATTGGACAGCTTGGGCATCAGC GATGAACTAAAGGAAAAACTG | 983 |
| 4 | TYRO3_NM_006293_human_3699 | AATATCCTAAGACTAACAAA | 964 | GCTACCAAATCTCAAAATATCCTAA GACTAACAAAGGCAGCTGTG | 984 |
| 5 | TYRO3_NM_006293_human_3928 | GTTGCTGTTTAAAATAGAAA | 965 | ATTTCCAAGCTGTTAGTTGCTGTTT AAAATAGAAATAAAATTGAA | 985 |
| 6 | TYRO3_NM_006293_human_3938 | AAAATAGAAATAAAATTGAA | 966 | TGTTAGTTGCTGTTTAAAATAGAAA TAAAATTGAAGACTAAAGAC | 986 |
| 7 | TYRO3_NM_006293_human_842 | CTGTGAAGCTCACAACCTAA | 967 | GAGCACCATGTTTTCCTGTGAAGC TCACAACCTAAAAGGCCTGGC | 987 |
| 8 | TYRO3_NM_006293_human_3953 | TTGAAGACTAAAGACCTAAA | 968 | AAAATAGAAATAAAATTGAAGACT AAAGACCTAAAAAAAAAAAA | 988 |
| 9 | TYRO3_NM_006293_human_3703 | TCCTAAGACTAACAAAGGCA | 969 | CCAAATCTCAAAATATCCTAAGACT AACAAAGGCAGCTGTGTCTG | 989 |
| 10 | TYRO3_NM_006293_human_3909 | GGACATTTCCAAGCTGTTAG | 970 | GGTCCTAGCTGTTAGGGACATTTC CAAGCTGTTAGTTGCTGTTTA | 990 |
| 11 | TYRO3_NM_006293_human_3190 | ATGTTTCCATGGTTACCATG | 971 | AGGAGTGGGGTGGTTATGTTTCCA TGGTTACCATGGGTGTGGATG | 991 |
| 12 | TYRO3_NM_006293_human_3926 | TAGTTGCTGTTTAAAATAGA | 972 | ACATTTCCAAGCTGTTAGTTGCTGT TTAAAATAGAAATAAAATTG | 992 |
| 13 | TYRO3_NM_006293_human_3949 | AAAATTGAAGACTAAAGACC | 973 | GTTTAAAATAGAAATAAAATTGAA GACTAAAGACCTAAAAAAAAA | 993 |
| 14 | TYRO3_NM_006293_human_3900 | AGCTGTTAGGGACATTTCCA | 974 | CATGGGGCGGGTCCTAGCTGTTAG GGACATTTCCAAGCTGTTAGT | 994 |
| 15 | TYRO3_NM_006293_human_2511 | GAGGACGTGTATGATCTCAT | 975 | CCTCCGGAGTGTATGGAGGACGTG TATGATCTCATGTACCAGTGC | 995 |
| 16 | TYRO3_NM_006293_human_3400 | TTTTAGGTGAGGGTTGGTAA | 976 | CCTTGTAATATTCCCTTTTAGGTGA GGGTTGGTAAGGGGTTGGTA | 996 |
| 17 | TYRO3_NM_006293_human_1895 | AGCTGACATCATTGCCTCAA | 977 | TGTGAAGATGCTGAAAGCTGACAT CATTGCCTCAAGCGACATTGA | 997 |
| 18 | TYRO3_NM_006293_human_3690 | AAATCTCAAAATATCCTAAG | 978 | TCTGAGCACGCTACCAAATCTCAA AATATCCTAAGACTAACAAAG | 998 |
| 19 | TYRO3_NM_006293_human_3919 | AAGCTGTTAGTTGCTGTTTA | 979 | GTTAGGGACATTTCCAAGCTGTTA GTTGCTGTTTAAAATAGAAAT | 999 |
| 20 | TYRO3_NM_006293_human_3384 | TCCTTGTAATATTCCCTTTT | 980 | AGTCACAAAGAGATGTCCTTGTAA TATTCCCTTTTAGGTGAGGGT | 1000 |

TABLE 1-continued

Targeting sequences and gene regions of genes targeted with sdRNAs to prevent immunosuppression of antigen-presenting cells and T-cells.

Accession: NM_000546
HUGO gene symbol: TP53

| Oligo_count | Oligo_ID | targeting sequence | SEQ ID NO: | Gene_region | SEQ ID NO: |
| --- | --- | --- | --- | --- | --- |
| 1 | TP53_NM_000546_human_1630 | TGTTTGGGAGATGTAAGAAA | 81 | TTTTACTGTGAGGGATGTTTGGG AGATGTAAGAAATGTTCTTGCA | 101 |
| 2 | TP53_NM_000546_human_1808 | GCATTGTGAGGGTTAATGAA | 82 | CCTACCTCACAGAGTGCATTGTGA GGGTTAATGAAATAATGTACA | 102 |
| 3 | TP53_NM_000546_human_2538 | TCGATCTCTTATTTTACAAT | 83 | TATCCCATTTTTATATCGATCTCTT ATTTTACAATAAAACTTTGC | 103 |
| 4 | TP53_NM_000546_human_1812 | TGTGAGGGTTAATGAAATAA | 84 | CCTCACAGAGTGCATTGTGAGGG TTAATGAAATAATGTACATCTG | 104 |
| 5 | TP53_NM_000546_human_812 | GAGTATTTGGATGACAGAAA | 85 | GGAAATTTGCGTGTGGAGTATTT GGATGACAGAAACACTTTTCGA | 105 |
| 6 | TP53_NM_000546_human_1627 | GGATGTTTGGGAGATGTAAG | 86 | GGTTTTTACTGTGAGGGATGTTTG GGAGATGTAAGAAATGTTCTT | 106 |
| 7 | TP53_NM_000546_human_1646 | GAAATGTTCTTGCAGTTAAG | 87 | GTTTGGGAGATGTAAGAAATGTT CTTGCAGTTAAGGGTTAGTTTA | 107 |
| 8 | TP53_NM_000546_human_1831 | ATGTACATCTGGCCTTGAAA | 88 | AGGGTTAATGAAATAATGTACAT CTGGCCTTGAAACCACCTTTTA | 108 |
| 9 | TP53_NM_000546_human_1645 | AGAAATGTTCTTGCAGTTAA | 89 | TGTTTGGGAGATGTAAGAAATGT TCTTGCAGTTAAGGGTTAGTTT | 109 |
| 10 | TP53_NM_000546_human_2015 | GGTGAACCTTAGTACCTAAA | 90 | GTCTGACAACCTCTTGGTGAACCT TAGTACCTAAAAGGAAATCTC | 110 |
| 11 | TP53_NM_000546_human_1753 | TAACTTCAAGGCCCATATCT | 91 | CTGTTGAATTTTCTCTAACTTCAA GGCCCATATCTGTGAAATGCT | 111 |
| 12 | TP53_NM_000546_human_782 | CTTATCCGAGTGGAAGGAAA | 92 | GCCCCTCCTCAGCATCTTATCCGA GTGGAAGGAAATTTGCGTGTG | 112 |
| 13 | TP53_NM_000546_human_2086 | ATGATCTGGATCCACCAAGA | 93 | CATCTCTTGTATATGATGATCTGG ATCCACCAAGACTTGTTTTAT | 113 |
| 14 | TP53_NM_000546_human_1744 | AATTTTCTCTAACTTCAAGG | 94 | TGTCCCTCACTGTTGAATTTTCTCT AACTTCAAGGCCCATATCTG | 114 |
| 15 | TP53_NM_000546_human_2542 | TCTCTTATTTTACAATAAAA | 95 | CCATTTTTATATCGATCTCTTATTT TACAATAAAACTTTGCTGCC | 115 |
| 16 | TP53_NM_000546_human_2546 | TTATTTTACAATAAAACTTT | 96 | TTTTATATCGATCTCTTATTTTACA ATAAAACTTTGCTGCCACCT | 116 |
| 17 | TP53_NM_000546_human_1842 | GCCTTGAAACCACCTTTTAT | 97 | AATAATGTACATCTGGCCTTGAAA CCACCTTTTATTACATGGGGT | 117 |
| 18 | TP53_NM_000546_human_2534 | TATATCGATCTCTTATTTTA | 98 | TTTATATCCCATTTTTATATCGATC TCTTATTTTACAATAAAACT | 118 |
| 19 | TP53_NM_000546_human_2021 | CCTTAGTACCTAAAAGGAAA | 99 | CAACCTCTTGGTGAACCTTAGTAC CTAAAAGGAAATCTCACCCCA | 119 |
| 20 | TP53_NM_000546_human_1809 | CATTGTGAGGGTTAATGAAA | 100 | CTACCTCACAGAGTGCATTGTGA GGGTTAATGAAATAATGTACAT | 120 |

What is claimed is:

1. An immune modulator comprising an sdRNA, wherein the sdRNA comprises a guide strand and a passenger strand, wherein the guide strand is about 19-25 nucleotides long, and the passenger strand is about 10-19 nucleotides long, wherein the sdRNA includes a double stranded region and a single stranded region, wherein the single stranded region includes 5-9 phosphorothioate modifications, wherein the sdRNA is chemically modified, including at least one 2'-O-methyl modification or 2'-fluoro modification, wherein the sdRNA targets a sequence selected from SEQ ID NOs: 281-300, and wherein the sdRNA is capable of suppressing expression of PD1.

2. An immunogenic composition comprising an sdRNA, wherein the sdRNA comprises a guide strand and a passenger strand, wherein the guide strand is about 19-25 nucleotides long, and the passenger strand is about 10-19 nucleotides long, wherein the sdRNA includes a double stranded region and a single stranded region, wherein the single stranded region includes 5-9 phosphorothioate modifications, wherein the sdRNA is chemically modified, including at least one 2'-O-methyl modification or 2'-fluoro modification, wherein the sdRNA targets a sequence selected from SEQ ID NOs: 281-300, wherein the sdRNA is capable of suppressing expression of PD1, and wherein the immunogenic composition further comprises immune cells modified by the sdRNA to suppress expression of PD1.

3. The immunogenic composition of claim 2, wherein the immune cells within the composition are further modified to suppress expression of a different immune checkpoint gene.

4. The immunogenic composition of claim 3, wherein said cells are modified to suppress expression of at least one immune checkpoint gene, and at least one anti-apoptosis gene.

5. The immunogenic composition of claim 2, wherein the immune cells within the composition are further modified to suppress expression of at least one cytokine receptor gene.

6. The immunogenic composition of claim 3, wherein said cells are modified to suppress expression of at least one immune checkpoint gene and at least one regulator gene.

7. The immunogenic composition of claim 3, wherein the different immune checkpoint gene is HAVCR2, wherein the composition further comprises an sdRNA capable of suppressing expression of HAVCR2, wherein the sdRNA comprises a guide strand and a passenger strand, wherein the guide strand is about 19-25 nucleotides long, and the passenger strand is about 10-19 nucleotides long, wherein the sdRNA includes a double stranded region and a single stranded region, wherein the single stranded region includes 5-9 phosphorothioate modifications, and wherein the sdRNA is chemically modified, including at least one 2'-O-methyl modification or 2'-fluoro modification.

8. The immunogenic composition of claim 2, wherein said cells are selected from the group consisting of T-cells, NK-cells, antigen-presenting cells, dendritic cells, stem cells, induced pluripotent stem cells, and/or stem central memory T-cells.

9. The immunogenic composition of claim 8, wherein said cells are T-cells comprising one or more transgene expressing high affinity T-cell receptors (TCR) and/or chimeric antibody-T-cell receptors (CAR).

10. The immunogenic composition of claim 7, wherein said cells further comprise one or more sdRNA agent targeting TP53.

11. The immunogenic composition of claim 2, wherein the sdRNA induces at least 50% inhibition of expression of PD1.

12. The immunogenic composition of claim 2, wherein the sdRNA comprises at least one hydrophobic modification.

13. The immunogenic composition of claim 2, wherein the sdRNA is modified to comprises at least one cholesterol molecule.

14. The immunogenic composition of claim 7, wherein the sdRNA capable of suppressing expression of HAVCR2 targets a sequence selected from SEQ ID NOs: 361-380.

15. A method of producing the immunogenic composition of claim 2, said method comprising transforming an immune cell with an sdRNA, wherein the sdRNA targets a sequence selected from SEQ ID NOs: 281-300, and wherein the sdRNA is capable of suppressing expression of PD1.

16. The method of claim 15, wherein the cell further comprises an sdRNA that inhibits expression of HAVCR2, wherein the sdRNA that inhibits expression of HAVCR2 comprises a guide strand and a passenger strand, wherein the guide strand is about 19-25 nucleotides long, and the passenger strand is about 10-19 nucleotides long, wherein the sdRNA includes a double stranded region and a single stranded region, wherein the single stranded region includes 5-9 phosphorothioate modifications, wherein the sdRNA is chemically modified, including at least one 2'-O-methyl modification or 2'-fluoro modification and wherein the sdRNA targets a sequence selected from SEQ ID NOs: 361-380.

17. The method of claim 15, wherein said cells are selected from the group consisting of T-cells, NK-cells, antigen-presenting cells, dendritic cells, stem cells, induced pluripotent stem cells, and/or stem central memory T-cells.

18. The method of claim 15, wherein said cells are T-cells comprising a transgene expressing high affinity T-cell receptors (TCR) and/or chimeric antibody-T-cell receptors (CAR).

* * * * *